US008912318B2

(12) United States Patent
Hrdlicka et al.

(10) Patent No.: US 8,912,318 B2
(45) Date of Patent: Dec. 16, 2014

(54) NUCLEOBASE-FUNCTIONALIZED CONFORMATIONALLY RESTRICTED NUCLEOTIDES AND OLIGONUCLEOTIDES FOR TARGETING NUCLEIC ACIDS

(71) Applicant: University of Idaho, Moscow, ID (US)

(72) Inventors: Patrick Jerzy Hrdlicka, Moscow, ID (US); Pawan Kumar, Kurukshetra (IN); Michael E. Østergaard, Vista, CA (US)

(73) Assignee: University of Idaho, Moscow, ID (US)

( * ) Notice: Subject to any disclaimer, the term of this patent is extended or adjusted under 35 U.S.C. 154(b) by 0 days.

(21) Appl. No.: 13/922,068

(22) Filed: Jun. 19, 2013

(65) Prior Publication Data

US 2013/0337581 A1 Dec. 19, 2013

Related U.S. Application Data

(63) Continuation of application No. 13/416,906, filed on Mar. 9, 2012, now Pat. No. 8,518,908, which is a continuation of application No. PCT/US2010/048520, filed on Sep. 10, 2010.

(60) Provisional application No. 61/241,292, filed on Sep. 10, 2009.

(51) Int. Cl.
*C07H 19/00* (2006.01)
*C07H 19/06* (2006.01)
*C12Q 1/68* (2006.01)
*C07H 19/16* (2006.01)
*C07H 19/10* (2006.01)

(52) U.S. Cl.
CPC .............. *C12Q 1/6883* (2013.01); *C07H 19/06* (2013.01); *C07H 19/16* (2013.01); *C07H 19/10* (2013.01)
USPC ..................... 536/27.13; 536/27.1; 536/27.14

(58) Field of Classification Search
None
See application file for complete search history.

(56) References Cited

U.S. PATENT DOCUMENTS

| | | | |
|---|---|---|---|
| 5,514,786 A | 5/1996 | Cook et al. | |
| 5,623,068 A | 4/1997 | Reddy et al. | |
| 5,892,024 A | 4/1999 | Chaturvedula et al. | |
| 7,002,006 B2 | 2/2006 | Song et al. | |
| 7,037,654 B2 | 5/2006 | Chenna et al. | |
| 7,053,207 B2 | 5/2006 | Wengel | |
| 7,084,125 B2 | 8/2006 | Wengel | |
| 7,202,036 B2 | 4/2007 | Cai et al. | |
| 7,276,599 B2 | 10/2007 | Moore et al. | |
| 7,282,575 B2 | 10/2007 | Ikeda et al. | |
| 7,572,582 B2 | 8/2009 | Wengel et al. | |
| 7,575,863 B2 | 8/2009 | Chen et al. | |
| 7,741,294 B1 | 6/2010 | Benner | |
| 7,803,580 B2 | 9/2010 | Millar | |
| 8,057,997 B2 | 11/2011 | Seela et al. | |
| 8,153,365 B2 | 4/2012 | Wengel et al. | |
| 2003/0032794 A1 | 2/2003 | Koch et al. | |
| 2003/0087230 A1 | 5/2003 | Wengel | |
| 2003/0198982 A1 | 10/2003 | Seela et al. | |
| 2003/0224377 A1 | 12/2003 | Wengel et al. | |
| 2004/0142946 A1 | 7/2004 | Chattopadhyaya | |
| 2004/0219565 A1 | 11/2004 | Kauppinen et al. | |
| 2005/0026192 A1 | 2/2005 | Moore et al. | |
| 2005/0053939 A1 | 3/2005 | Chenna et al. | |
| 2005/0266418 A1 | 12/2005 | Chen et al. | |
| 2005/0287566 A1 | 12/2005 | Wengel et al. | |
| 2007/0117144 A1 | 5/2007 | Kauppinen et al. | |
| 2010/0210712 A1 | 8/2010 | Hansen et al. | |
| 2010/0223691 A1 | 9/2010 | Bundock | |
| 2010/0273999 A1 | 10/2010 | Jung et al. | |
| 2010/0311059 A1 | 12/2010 | Didion et al. | |
| 2010/0317004 A1 | 12/2010 | Bunce et al. | |
| 2011/0021365 A1 | 1/2011 | Seela et al. | |
| 2011/0137010 A1 | 6/2011 | Srivastava et al. | |
| 2011/0287415 A1 | 11/2011 | Fan et al. | |
| 2012/0040857 A1 | 2/2012 | Kingston et al. | |

FOREIGN PATENT DOCUMENTS

| | | |
|---|---|---|
| EP | 1 334 109 | 5/2006 |
| EP | 2 149 605 | 2/2010 |
| JP | 2000-32999 | 2/2000 |
| WO | WO 00/56748 | 9/2000 |
| WO | WO 02/12263 | 2/2002 |
| WO | WO 03/039523 | 5/2003 |
| WO | WO 03/052132 | 6/2003 |
| WO | WO 03/052133 | 6/2003 |
| WO | WO 03/052134 | 6/2003 |
| WO | WO 2007/104318 | 9/2007 |
| WO | WO 2008/061311 | 5/2008 |
| WO | WO 2009/064115 | 5/2009 |
| WO | WO 2009/079456 | 6/2009 |

(Continued)

OTHER PUBLICATIONS

Fonvielle et al., "Decoding the Logic of the tRNA Regiospecificity of Nonribosomal FemX$_{Wv}$ Aminoacyl Transferase," *Angew. Chem. Int. Ed.* 49:5115-5119, 2010.

(Continued)

*Primary Examiner* — Patrick Lewis
(74) *Attorney, Agent, or Firm* — Klarquist Sparkman, LLP

(57) ABSTRACT

Embodiments are disclosed herein that involve C5-functionalized nucleic acids, which can be used for detecting a target in a nucleic acid. Particular embodiments disclose methods for making these compounds, wherein the compounds can be formed by coupling of an intermediate with a linker. Certain embodiments disclose the use of these compounds for detecting single nucleotide polymorphisms, and for increasing the thermal affinity of nucleic acid complements as compared to unmodified nucleic acid complements. In addition, the disclosed compounds can decrease enzymatic degradation of nucleic acids.

20 Claims, 31 Drawing Sheets

(56) References Cited

FOREIGN PATENT DOCUMENTS

| WO | WO 2010/003420 | 1/2010 |
|---|---|---|
| WO | WO 2011/103468 | 8/2011 |
| WO | WO 2011/117353 | 9/2011 |

OTHER PUBLICATIONS

Fukuda et al., "Duplex formation of multiple pyrene-modified RNAs," *Nucleic Acid Symposium Series* 53(1):133-134, Sep. 27, 2009.

Gupta et al., "Synthesis and Biophysical Studies of Coronene Functionalized 2'-Amino-LNA: A Novel Class of Fluorescent Nucleic Acids," *Bioconjugate Chem.* 21:513-520, 2010.

Kalra et al., "Conformationally controlled high-affinity targeting of RNA or DNA by novel 2'-amino-DNA/LNA mixmers and pyrenyl-functionalized 2'-amino-DNA," *Org. Biomol. Chem.* 2(20:2885-2887, Oct. 21, 2004.

Kumar et al., "Synthesis and Biophysical Studies of N2'-Functionalized 2'-Amino-α-L-LNA," *Nucleosides, Nucleotides and Nucleic Acids* 26:1403-1405, 2007.

Kumar et al., "2'-N-(Pyren-1-yl)acetyl-2'-Amino-α-L-LNA: Synthesis and Detection of Single Nucleotide Mismatches in DNA and RNA Targets," *ChemBioChem* 8:122-1125, 2007.

Kumar et al., "Nucleic Acid Structural Engineering Using Pyrene-Functionalized 2'-Amino-α-L-LNA Monomers and Abasic Sites," *Journal of Organic Chemistry* 73:7060-7066, 2008.

Kumar et al., "Functionalized 2'-Amino-α-L-LNA: Directed Positioning of Intercalators for DNA Targeting," *Journal of Organic Chemistry* 74:1070-1081, 2009.

Kumar et al., "Parallel RNA-strand recognition by 2'-Amino-β-L-LNA," *Bioorganic & Medicinal Chemistry Letters* 19:2396-2399, 2009.

Mahara et al., "Detection of acceptor sites for antisense oligonucleotides on native folded RNA by fluorescence-labeled oligonucleotide," *Nucleic Acids Research Supplement No. 3*, pp. 73-43, 2003.

Mahara et al., "Detection of Acceptor Sites for Antisense Oligonucleotides on Native Folded RNA by Fluorescence Spectroscopy," *Bioorganic & Medicinal Chemistry Letters* 11:2783-2790, 2003.

Mayer-Enthart et al., "Helical self-assembled chromophore clusters based on DNA-like architecture," *Tetrahedron* 63:3434-3439, 2007.

Nakamura et al., "Pyrene aromatic arrays on RNA duplexes as helical templates," *Org. Biomol. Chem.* 5:1945-1951, 2007.

Oeda et al., "Microwave-Assisted Synthesis of 2'O-Aryluridine Derivatives," *Organic Letters* 11(24):5582-5585, 2009.

Østergaard et al., "Novel insights into the use of Glowing LNA as nucleic acid detection probes—Influence of labeling density and nucleobases," *Bioorganic & Medicinal Chemistry Letters* 20:7265-7268, 2010.

Sakamoto et al., "Solid-phase detection of RNA using bispyrene-modified RNA probe," *Nucleic Acids Symposium Series No. 50*, pp. 215-216, 2006.

Sakamoto et al., "Microarray-based label-free detection of RNA using bispyrene-modified 2'-O-methyl oligoribonucleotide as capture and detection probe," *Bioorganic & Medicinal Chemistry Letters* 18:2590-2593, 2008.

Sekine et al., "Synthesis and hybridization properties of 2'-O-methylated oligoribonucleotides incorporating 2'-O-naphthyluridines," *Organic & Biomolecular Chemistry* 9:210-218, 2011.

Yamana et al., "Synthesis of Oligonucleotide Derivatives with Pyrene Group at sugar Fragment," *Tetrahedron Letters* 32(44):6347-6350, 1991.

Yamana et al., "2'-Pyrene-modified oligonucleotide provides a highly sensitive fluorescent probe of RNA," *Nucleic Acids Research* 27(11):2387-2392, 1999.

Hrdlicka et al. "Targeting of mixed sequence double-stranded DNA using pyrenefunctionalized 2'-amino-alpha-L-LNA," *Chem. Commun.*, p. 4279-4281, 2005.

GenBank CT030234 (retrieved from http://www.ncbi.nlm.nih.gov/nuccore/89145300 on Oct. 7, 2012), Mar. 2, 2006.

Umemoto et al. "Sensitive SNP Dual-Probe Assays Based on Pyrene-Functionalized 2'-Amino-LNA: Lessons to Be Learned," *Chem. BioChem.* vol. 8, 2240-2248, 2007.

International Search Report dated May 26, 2011, from International Application No. PCT/US2010/048520.

International Search Report dated Jan. 25, 2013, from International Application No. PCT/US2012/047442.

Written Opinion dated Jan. 25, 2013, from International Application No. PCT/US2012/047442.

SEQUENCE LISTING

```
<160> NUMBER OF SEQ ID NOS: 48

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine
```

```
<400> SEQUENCE: 1
tttttntttn tntnt                                                        15

<210> SEQ ID NO 2
<211> LENGTH: 21
<212> TYPE: DNA
<213> ORGANISM: Artificial sequence
<220> FEATURE:
<223> OTHER INFORMATION: synthesized dsDNA sequence (5')

<400> SEQUENCE: 2
gctaaaaaga aagagagatc g                                                 21

<210> SEQ ID NO 3
<211> LENGTH: 21
<212> TYPE: DNA
<213> ORGANISM: Artificial sequence
<220> FEATURE:
<223> OTHER INFORMATION: synthesized dsDNA target (3')

<400> SEQUENCE: 3 cgattttttct ttctctctac g                                                21

<210> SEQ ID NO 4
<211> LENGTH: 21
<212> TYPE: DNA
<213> ORGANISM: Artificial sequence
<220> FEATURE:
<223> OTHER INFORMATION: synthesized mismatched DNA target5'
<220> FEATURE:
<221> NAME/KEY: misc_feature
<222> LOCATION: (7)..(7)
<223> OTHER INFORMATION: n is a, t, c, or g

<400> SEQUENCE: 4
gctaaanaga aagagagatc g                                                 21

<210> SEQ ID NO 5
<211> LENGTH: 21
<212> TYPE: DNA
<213> ORGANISM: Artificial sequence
<220> FEATURE:
<223> OTHER INFORMATION: modified dsDNA target3'
<220> FEATURE:
<221> NAME/KEY: misc_feature
<222> LOCATION: (11)..(11)
<223> OTHER INFORMATION: n is t, a, or c

<400> SEQUENCE: 5 cgattttttct ntctctctac g                                                21

<210> SEQ ID NO 6
<211> LENGTH: 13
<212> TYPE: DNA
<213> ORGANISM: Artificial sequence
<220> FEATURE:
<223> OTHER INFORMATION: unmodified DNA target for fluorescence studies

<400> SEQUENCE: 6
cgcaactcaa cgc                                                          13

<210> SEQ ID NO 7
<211> LENGTH: 13
<212> TYPE: DNA
<213> ORGANISM: Artificial sequence
<220> FEATURE:
<223> OTHER INFORMATION: synthezied DNA sequence modified with compound
```

```
            P
<220> FEATURE:
<221> NAME/KEY: misc_feature
<222> LOCATION: (7)..(7)
<223> OTHER INFORMATION: n is
      Beta-D-3-(2,4-dioxo-5-(3-(pyrene-1-carboxamido)prop-1-ynyl)-3,4-
      dihydropyrimidin-1(2H)-yl)-1-((hydrogen
      phosphonatooxy)methyl)-2,5-dioxabicyclo[2.2.1]heptan-7-yl

<400> SEQUENCE: 7
cgcaacncaa cgc                                                          13

<210> SEQ ID NO 8
<211> LENGTH: 13
<212> TYPE: DNA
<213> ORGANISM: Artificial sequence
<220> FEATURE:
<223> OTHER INFORMATION: synthesized DNA sequence modified with compound
      P'
<220> FEATURE:
<221> NAME/KEY: misc_feature
<222> LOCATION: (7)..(7)
<223> OTHER INFORMATION: n is
      Alpha-L-3-(2,4-dioxo-5-(3-(pyrene-1-carboxamido)prop-1-ynyl)-3,4-
      dihydropyrimidin-1(2H)-yl)-1-((hydrogen
      phosphonatooxy)methyl)-2,5-dioxabicyclo[2.2.1]heptan-7-yl

<400> SEQUENCE: 8
cgcaacncaa cgc                                                          13

<210> SEQ ID NO 9
<211> LENGTH: 13
<212> TYPE: DNA
<213> ORGANISM: Artificial sequence
<220> FEATURE:
<223> OTHER INFORMATION: synthesized DNA sequence modified with compound
      Beta
<220> FEATURE:
<221> NAME/KEY: misc_feature
<222> LOCATION: (7)..(7)
<223> OTHER INFORMATION: n is
      Beta-D-3-(2,4-dioxo-5-(1-(pyren-1-ylmethyl)-1H-1,2,3-triazol-4-
      yl)-3,4-dihydropyrimidin-1(2H)-yl)-1-((hydrogen
      phosphonatooxy)methyl)-2,5-dioxabicyclo[2.2.1]heptan-7-yl

<400> SEQUENCE: 9
cgcaacncaa cgc                                                          13

<210> SEQ ID NO 10
<211> LENGTH: 13
<212> TYPE: DNA
<213> ORGANISM: Artificial sequence
<220> FEATURE:
<223> OTHER INFORMATION: synthesized  DNA sequence modified with
      compound gamma
<220> FEATURE:
<221> NAME/KEY: misc_feature
<222> LOCATION: (7)..(7)
<223> OTHER INFORMATION: n is
      3-(2,4-dioxo-5-(1-(pyren-1-yl)-1H-1,2,3-triazol-4-yl)-3,4-dihydro-
      pyrimidin-1(2H)-yl)-1-((hydrogen
      phosphonatooxy)methyl)-2,5-dioxabicyclo[2.2.1]heptan-7-yl
<220> FEATURE:
<221> NAME/KEY: misc_feature
<222> LOCATION: (7)..(7)
<223> OTHER INFORMATION: n is
      Beta-D-3-(2,4-dioxo-5-(1-(pyren-1-yl)-1H-1,2,3-triazol-4-yl)-3,4-
      dihydropyrimidin-1(2H)-yl)-1-((hydrogen
      phosphonatooxy)methyl)-2,5-dioxabicyclo[2.2.1]heptan-7-yl

<400> SEQUENCE: 10
cgcaacncaa cgc                                                          13
```

<210> SEQ ID NO 11
<211> LENGTH: 13
<212> TYPE: DNA
<213> ORGANISM: Artificial sequence
<220> FEATURE:
<223> OTHER INFORMATION: synthesized DNA sequence modified with compound
      Alpha
<220> FEATURE:
<221> NAME/KEY: misc_feature
<222> LOCATION: (7)..(7)
<223> OTHER INFORMATION: n is
      3-(2,4-dioxo-5-(perylen-3-ylethynyl)-3,4-dihydropyrimidin-1(2H)-
      yl)-1-((hydrogen phosphonatooxy)methyl)-2,5-
      dioxabicyclo[2.2.1]heptan-7-yl

<400> SEQUENCE: 11
cgcaacncaa cgc                                                    13

<210> SEQ ID NO 12
<211> LENGTH: 15
<212> TYPE: DNA
<213> ORGANISM: artificial sequence
<220> FEATURE:
<223> OTHER INFORMATION: synthesized oligonucleotide for dsDNA target
      modified with compound Y
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (8)..(8)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-
      dioxabicyclo[2.2.1]heptan-7-yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine

<400> SEQUENCE: 12
tttttntntn tntnt                                                  15

<210> SEQ ID NO 13
<211> LENGTH: 15
<212> TYPE: DNA
<213> ORGANISM: artificial sequence
<220> FEATURE:
<223> OTHER INFORMATION: synthesized oligonucleotide for dsDNA target
      modified with compound Y
<220> FEATURE:
<221> NAME/KEY: misc_feature
<222> LOCATION: (5)..(5)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (9)..(9)

```
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (14)..(14)
<223> OTHER INFORMATION: n is 5-methyldeoxycytidine

<400> SEQUENCE: 13
ttttnnttnn tnnnt                                                    15

<210> SEQ ID NO 14
<211> LENGTH: 15
<212> TYPE: DNA
<213> ORGANISM: artificial sequence
<220> FEATURE:
<223> OTHER INFORMATION: synthesized oligonucleotide for dsDNA target
      modified with compound Y
<220> FEATURE:
<221> NAME/KEY: misc_feature
<222> LOCATION: (5)..(5)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (8)..(8)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (11)..(11)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine

<400> SEQUENCE: 14
ttttnntntn nntnt                                                    15
```

```
<210> SEQ ID NO 15
<211> LENGTH: 15
<212> TYPE: DNA
<213> ORGANISM: artificial sequence
<220> FEATURE:
<223> OTHER INFORMATION: synthesized oligonucleotide
<220> FEATURE:
<221> NAME/KEY: misc_feature
<222> LOCATION: (3)..(3)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (5)..(5)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (7)..(7)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (9)..(9)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (11)..(11)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is
      Beta-D-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (14)..(14)
<223> OTHER INFORMATION: n is 5-methyldeoxycytidine

<400> SEQUENCE: 15
ttntnnntnn nnnnt                                                15

<210> SEQ ID NO 16
<211> LENGTH: 15
<212> TYPE: DNA
<213> ORGANISM: artificial sequence
<220> FEATURE:
<223> OTHER INFORMATION: synthesized oligonucleotide for dsDNA target
      modified with compound V
<220> FEATURE:
<221> NAME/KEY: misc_feature
```

```
<222> LOCATION: (6)..(6)
<223> OTHER INFORMATION: n is 5-methyldeoxycytidine
<220> FEATURE:
<221> NAME/KEY: misc_feature
<222> LOCATION: (8)..(8)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine

<400> SEQUENCE: 16 ttttntntn tntnt                                                          15

<210> SEQ ID NO 17
<211> LENGTH: 15
<212> TYPE: DNA
<213> ORGANISM: artificial sequence
<220> FEATURE:
<223> OTHER INFORMATION: synthesized oligonucleotide for dsDNA target
      modified with compound V
<220> FEATURE:
<221> NAME/KEY: misc_feature
<222> LOCATION: (5)..(5)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (9)..(9)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (14)..(14)
<223> OTHER INFORMATION: n is 5-methyldeoxycytidine

<400> SEQUENCE: 17
ttttnnttnn tnnnt                                                         15

<210> SEQ ID NO 18
<211> LENGTH: 15
```

<212> TYPE: DNA
<213> ORGANISM: artificial sequence
<220> FEATURE:
<223> OTHER INFORMATION: synthesized oligonucleotide for dsDNA target
      modified with compound V
<220> FEATURE:
<221> NAME/KEY: misc_feature
<222> LOCATION: (5)..(5)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (8)..(8)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (11)..(11)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine

<400> SEQUENCE: 18
ttttnntntn nntnt                                                      15

<210> SEQ ID NO 19
<211> LENGTH: 15
<212> TYPE: DNA
<213> ORGANISM: artificial sequence
<220> FEATURE:
<223> OTHER INFORMATION: synthesized oligonucleotide for dsDNA target
      modified with compound V
<220> FEATURE:
<221> NAME/KEY: misc_feature
<222> LOCATION: (3)..(3)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (5)..(5)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (7)..(7)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-

```
              dioxabicyclo[2.2.1]heptan-7-yl
<220> FEATURE:
<221> NAME/KEY: misc_feature
<222> LOCATION: (9)..(9)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (11)..(11)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is
      Beta-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (14)..(14)
<223> OTHER INFORMATION: n is 5-methyldeoxycytidine

<400> SEQUENCE: 19
ttntnnntnn nnnnt                                                       15

<210> SEQ ID NO 20
<211> LENGTH: 15
<212> TYPE: DNA
<213> ORGANISM: artificial sequence
<220> FEATURE:
<223> OTHER INFORMATION: synthesized oligonucleotide for dsDNA target
      modified with compound X
<220> FEATURE:
<221> NAME/KEY: misc_feature
<222> LOCATION: (5)..(5)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (9)..(9)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
```

```
<222> LOCATION: (14)..(14)
<223> OTHER INFORMATION: n is 5-methyldeoxycytidine

<400> SEQUENCE: 20
ttttnnttnn tnnnt                                                    15

<210> SEQ ID NO 21
<211> LENGTH: 15
<212> TYPE: DNA
<213> ORGANISM: artificial sequence
<220> FEATURE:
<223> OTHER INFORMATION: synthesized oligonucleotide for dsDNA target
      modified with compound X
<220> FEATURE:
<221> NAME/KEY: misc_feature
<222> LOCATION: (5)..(5)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (6)..(6)
<223> OTHER INFORMATION: n is  5-methyldeoxycytidine
<220> FEATURE:
<221> NAME/KEY: misc_feature
<222> LOCATION: (8)..(8)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (10)..(10)
<223> OTHER INFORMATION: n is  5-methyldeoxycytidine
<220> FEATURE:
<221> NAME/KEY: misc_feature
<222> LOCATION: (11)..(11)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (12)..(12)
<223> OTHER INFORMATION: n is  5-methyldeoxycytidine
<220> FEATURE:
<221> NAME/KEY: misc_feature
<222> LOCATION: (14)..(14)
<223> OTHER INFORMATION: n is  5-methyldeoxycytidine

<400> SEQUENCE: 21
ttttnntntn nntnt                                                    15

<210> SEQ ID NO 22
<211> LENGTH: 15
<212> TYPE: DNA
<213> ORGANISM: artificial sequence
<220> FEATURE:
<223> OTHER INFORMATION: synthesized oligonucleotide for dsDNA target
      modified with compound X
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (7)..(7)
```

```
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (9)..(9)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (11)..(11)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (14)..(14)
<223> OTHER INFORMATION: n is 5-methyldeoxycytidine

<400> SEQUENCE: 22
ttntnnntnn nnnnt                                                    15

<210> SEQ ID NO 23
<211> LENGTH: 15
<212> TYPE: DNA
<213> ORGANISM: artificial sequence
<220> FEATURE:
<223> OTHER INFORMATION: synthesized oligonucleotide for dsDNA target
      modified with compound X
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (8)..(8)
<223> OTHER INFORMATION: n is Beta-D-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine

<400> SEQUENCE: 23
tttttntntn tntnt                                                    15

<210> SEQ ID NO 24
<211> LENGTH: 13
<212> TYPE: DNA
<213> ORGANISM: artificial sequence
<220> FEATURE:
```

```
<223> OTHER INFORMATION: synthesized oligonucleotide for fluorescence
      studies

<400> SEQUENCE: 24
cgcaaataaa cgc                                                            13

<210> SEQ ID NO 25
<211> LENGTH: 13
<212> TYPE: DNA
<213> ORGANISM: artificial sequence
<220> FEATURE:
<223> OTHER INFORMATION: synthesized oligonucleotide for fluorescence
      studies

<400> SEQUENCE: 25
cgcaagtgaa cgc                                                            13

<210> SEQ ID NO 26
<211> LENGTH: 13
<212> TYPE: DNA
<213> ORGANISM: artificial sequence
<220> FEATURE:
<223> OTHER INFORMATION: synthesized oligonucleotide for fluorescence
      studies

<400> SEQUENCE: 26
cgcaatttaa cgc                                                            13

<210> SEQ ID NO 27
<211> LENGTH: 13
<212> TYPE: DNA
<213> ORGANISM: artificial sequence
<220> FEATURE:
<223> OTHER INFORMATION: synthesized oligonucleotide modified with
      compound P''
<220> FEATURE:
<221> NAME/KEY: misc_feature
<222> LOCATION: (7)..(7)
<223> OTHER INFORMATION: n is
      5-(2,4-dioxo-5-(3-(pyrene-1-carboxamido)prop-1-ynyl)-3,4-
      dihydropyrimidin-1(2H)-yl)-2-((hydrogen
      phosphonatooxy)methyl)tetrahydrofuran-3-yl phosphate

<400> SEQUENCE: 27
cgcaaanaaa cgc                                                            13

<210> SEQ ID NO 28
<211> LENGTH: 13
<212> TYPE: DNA
<213> ORGANISM: artificial sequence
<220> FEATURE:
<223> OTHER INFORMATION: synthesized oligonucleotide modified with
      compound P''
<220> FEATURE:
<221> NAME/KEY: misc_feature
<222> LOCATION: (7)..(7)
<223> OTHER INFORMATION: n is
      5-(2,4-dioxo-5-(3-(pyrene-1-carboxamido)prop-1-ynyl)-3,4-
      dihydropyrimidin-1(2H)-yl)-2-((hydrogen
      phosphonatooxy)methyl)tetrahydrofuran-3-yl phosphate

<400> SEQUENCE: 28
cgcaacncaa cgc                                                            13

<210> SEQ ID NO 29
<211> LENGTH: 13
<212> TYPE: DNA
<213> ORGANISM: artificial sequence
<220> FEATURE:
```

```
<223> OTHER INFORMATION: synthesized oligonucleotide modified with
      compound P''
<220> FEATURE:
<221> NAME/KEY: misc_feature
<222> LOCATION: (7)..(7)
<223> OTHER INFORMATION: n is
      5-(2,4-dioxo-5-(3-(pyrene-1-carboxamido)prop-1-ynyl)-3,4-
      dihydropyrimidin-1(2H)-yl)-2-((hydrogen
      phosphonatooxy)methyl)tetrahydrofuran-3-yl phosphate

<400> SEQUENCE: 29
cgcaagngaa cgc                                                    13

<210> SEQ ID NO 30
<211> LENGTH: 13
<212> TYPE: DNA
<213> ORGANISM: artificial sequence
<220> FEATURE:
<223> OTHER INFORMATION: synthesized oligonucleotide modified with
      compound P''
<220> FEATURE:
<221> NAME/KEY: misc_feature
<222> LOCATION: (7)..(7)
<223> OTHER INFORMATION: n is
      5-(2,4-dioxo-5-(3-(pyrene-1-carboxamido)prop-1-ynyl)-3,4-
      dihydropyrimidin-1(2H)-yl)-2-((hydrogen
      phosphonatooxy)methyl)tetrahydrofuran-3-yl phosphate

<400> SEQUENCE: 30
cgcaatntaa cgc                                                    13

<210> SEQ ID NO 31
<211> LENGTH: 13
<212> TYPE: DNA
<213> ORGANISM: artificial sequence
<220> FEATURE:
<223> OTHER INFORMATION: synthesized oligonucleotide modified with
      compound P
<220> FEATURE:
<221> NAME/KEY: misc_feature
<222> LOCATION: (7)..(7)
<223> OTHER INFORMATION: n is
      Beta-D-3-(2,4-dioxo-5-(3-(pyrene-1-carboxamido)prop-1-ynyl)-3,4-
      dihydropyrimidin-1(2H)-yl)-1-((hydrogen phosphonatooxy)methyl)-
      2,5-dioxabicyclo[2.2.1]heptan-7-yl

<400> SEQUENCE: 31
cgcaaanaaa cgc                                                    13

<210> SEQ ID NO 32
<211> LENGTH: 13
<212> TYPE: DNA
<213> ORGANISM: artificial sequence
<220> FEATURE:
<223> OTHER INFORMATION: synthesized oligonucleotide modified with
      compound P
<220> FEATURE:
<221> NAME/KEY: misc_feature
<222> LOCATION: (7)..(7)
<223> OTHER INFORMATION: n is
      Beta-D-3-(2,4-dioxo-5-(3-(pyrene-1-carboxamido)prop-1-ynyl)-3,4-
      dihydropyrimidin-1(2H)-yl)-1-((hydrogen phosphonatooxy)methyl)-
      2,5-dioxabicyclo[2.2.1]heptan-7-yl

<400> SEQUENCE: 32
cgcaagngaa cgc                                                    13

<210> SEQ ID NO 33
<211> LENGTH: 13
<212> TYPE: DNA
<213> ORGANISM: artificial sequence
```

```
<220> FEATURE:
<223> OTHER INFORMATION: synthesized oligonucleotide modified with
      compound P
<220> FEATURE:
<221> NAME/KEY: misc_feature
<222> LOCATION: (7)..(7)
<223> OTHER INFORMATION: n is
      Beta-D-3-(2,4-dioxo-5-(3-(pyrene-1-carboxamido)prop-1-ynyl)-3,4-
      dihydropyrimidin-1(2H)-yl)-1-((hydrogen phosphonatooxy)methyl)-
      2,5-dioxabicyclo[2.2.1]heptan-7-yl

<400> SEQUENCE: 33
cgcaatntaa cgc                                                          13

<210> SEQ ID NO 34
<211> LENGTH: 13
<212> TYPE: DNA
<213> ORGANISM: artificial sequence
<220> FEATURE:
<223> OTHER INFORMATION: synthesized oligonucleotide modified with
      compound P'
<220> FEATURE:
<221> NAME/KEY: misc_feature
<222> LOCATION: (7)..(7)
<223> OTHER INFORMATION: n is
      Alpha-L-3-(2,4-dioxo-5-(3-(pyrene-1-carboxamido)prop-1-ynyl)-3,4-
      dihydropyrimidin-1(2H)-yl)-1-((hydrogen
      phosphonatooxy)methyl)-2,5-dioxabicyclo[2.2.1]heptan-7-yl

<400> SEQUENCE: 34
cgcaaanaaa cgc                                                          13

<210> SEQ ID NO 35
<211> LENGTH: 13
<212> TYPE: DNA
<213> ORGANISM: artificial sequence
<220> FEATURE:
<223> OTHER INFORMATION: synthesized oligonucleotide modified with
      compound P'
<220> FEATURE:
<221> NAME/KEY: misc_feature
<222> LOCATION: (7)..(7)
<223> OTHER INFORMATION: n is
      Alpha-L3-(2,4-dioxo-5-(3-(pyrene-1-carboxamido)prop-1-ynyl)-3,4-
      dihydropyrimidin-1(2H)-yl)-1-((hydrogen
      phosphonatooxy)methyl)-2,5-dioxabicyclo[2.2.1]heptan-7-yl

<400> SEQUENCE: 35
cgcaagngaa cgc                                                          13

<210> SEQ ID NO 36
<211> LENGTH: 13
<212> TYPE: DNA
<213> ORGANISM: artificial sequence
<220> FEATURE:
<223> OTHER INFORMATION: synthesized oligonucleotide modified with
      compound P'
<220> FEATURE:
<221> NAME/KEY: misc_feature
<222> LOCATION: (7)..(7)
<223> OTHER INFORMATION: n is
      Alpha-L3-(2,4-dioxo-5-(3-(pyrene-1-carboxamido)prop-1-ynyl)-3,4-
      dihydropyrimidin-1(2H)-yl)-1-((hydrogen phosphonatooxy)methyl)-
      2,5-dioxabicyclo[2.2.1]heptan-7-yl

<400> SEQUENCE: 36
cgcaatntaa cgc                                                          13

<210> SEQ ID NO 37
<211> LENGTH: 15
<212> TYPE: DNA
```

```
<213> ORGANISM: Artificial sequence
<220> FEATURE:
<223> OTHER INFORMATION: synthesized oligonucleotide modified with
      compound X'
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (8)..(8)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine

<400> SEQUENCE: 37
tttttntntn tntnt                                                        15

<210> SEQ ID NO 38
<211> LENGTH: 15
<212> TYPE: DNA
<213> ORGANISM: Artificial sequence
<220> FEATURE:
<223> OTHER INFORMATION: synthesized oligonucleotide modified with
      compound Y'
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (8)..(8)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine

<400> SEQUENCE: 38
tttttntntn tntnt                                                        15

<210> SEQ ID NO 39
<211> LENGTH: 15
<212> TYPE: DNA
<213> ORGANISM: Artificial sequence
<220> FEATURE:
<223> OTHER INFORMATION: synthesized oligonucleotide modified with
      compound V'
<220> FEATURE:
<221> NAME/KEY: misc_feature
<222> LOCATION: (6)..(6)
<223> OTHER INFORMATION: n is 5-methyldeoxycytidine
```

```
<220> FEATURE:
<221> NAME/KEY: misc_feature
<222> LOCATION: (8)..(8)
<223> OTHER INFORMATION: n is
      Alpha-D-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine

<400> SEQUENCE: 39
tttttntntn tntnt                                                  15

<210> SEQ ID NO 40
<211> LENGTH: 15
<212> TYPE: DNA
<213> ORGANISM: Artificial Sequence
<220> FEATURE:
<223> OTHER INFORMATION: synthetic oligonucleotide modified with
      compound X'
<220> FEATURE:
<221> NAME/KEY: misc_feature
<222> LOCATION: (5)..(5)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (9)..(9)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (14)..(14)
<223> OTHER INFORMATION: n is 5-methyldeoxycytidine

<400> SEQUENCE: 40
ttttnnttnn tnnnt                                                  15

<210> SEQ ID NO 41
<211> LENGTH: 15
<212> TYPE: DNA
<213> ORGANISM: artificial sequence
<220> FEATURE:
<223> OTHER INFORMATION: synthetic oligonucleotide modified with
      compound X'
```

```
<220> FEATURE:
<221> NAME/KEY: misc_feature
<222> LOCATION: (5)..(5)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (6)..(6)
<223> OTHER INFORMATION: n is  5-methyldeoxycytidine
<220> FEATURE:
<221> NAME/KEY: misc_feature
<222> LOCATION: (8)..(8)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (10)..(10)
<223> OTHER INFORMATION: n is  5-methyldeoxycytidine
<220> FEATURE:
<221> NAME/KEY: misc_feature
<222> LOCATION: (11)..(11)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (12)..(12)
<223> OTHER INFORMATION: n is  5-methyldeoxycytidine
<220> FEATURE:
<221> NAME/KEY: misc_feature
<222> LOCATION: (14)..(14)
<223> OTHER INFORMATION: n is  5-methyldeoxycytidine

<400> SEQUENCE: 41
ttttnntntn nntnt                                                   15

<210> SEQ ID NO 42
<211> LENGTH: 15
<212> TYPE: DNA
<213> ORGANISM: artificial sequence
<220> FEATURE:
<223> OTHER INFORMATION: synthetic oligonucleotide modified with
      compound X'
<220> FEATURE:
<221> NAME/KEY: misc_feature
<222> LOCATION: (3)..(3)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (5)..(5)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (7)..(7)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (9)..(9)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (10)..(10)
<223> OTHER INFORMATION: n is 5-methyldeoxycytidine
```

```
<220> FEATURE:
<221> NAME/KEY: misc_feature
<222> LOCATION: (11)..(11)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is Alpha-L-1-((hydrogen
      phosphonatooxy)methyl)-3-(5-methyl-2,4-dioxo-3,4-dihydropyrimidin-
      1(2H)-yl)-2,5-dioxabicyclo[2.2.1]heptan-7-yl phosphate
<220> FEATURE:
<221> NAME/KEY: misc_feature
<222> LOCATION: (14)..(14)
<223> OTHER INFORMATION: n is 5-methyldeoxycytidine

<400> SEQUENCE: 42
ttntnnntnn nnnnt                                                        15

<210> SEQ ID NO 43
<211> LENGTH: 15
<212> TYPE: DNA
<213> ORGANISM: artificial sequence
<220> FEATURE:
<223> OTHER INFORMATION: synthetic oligonucleotide modified with
      compound Y'
<220> FEATURE:
<221> NAME/KEY: misc_feature
<222> LOCATION: (5)..(5)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (9)..(9)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (14)..(14)
<223> OTHER INFORMATION: n is 5-methyldeoxycytidine

<400> SEQUENCE: 43
ttttnnttnn tnnnt                                                        15

<210> SEQ ID NO 44
<211> LENGTH: 15
<212> TYPE: DNA
```

```
<213> ORGANISM: artificial sequence
<220> FEATURE:
<223> OTHER INFORMATION: synthetic oligonucleotide modified with
      compound Y'
<220> FEATURE:
<221> NAME/KEY: misc_feature
<222> LOCATION: (5)..(5)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (8)..(8)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (11)..(11)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine

<400> SEQUENCE: 44
ttttnntntn nntnt                                                    15

<210> SEQ ID NO 45
<211> LENGTH: 15
<212> TYPE: DNA
<213> ORGANISM: artificial sequence
<220> FEATURE:
<223> OTHER INFORMATION: synthetic oligonucleotide modified with
      compound Y'
<220> FEATURE:
<221> NAME/KEY: misc_feature
<222> LOCATION: (3)..(3)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (5)..(5)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (7)..(7)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
```

-continued

```
<220> FEATURE:
<221> NAME/KEY: misc_feature
<222> LOCATION: (9)..(9)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (11)..(11)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is
      Alpha-L-3-(5-ethynyl-2,4-dioxo-3,4-dihydropyrimidin-1(2H)-yl)-1-
      ((hydrogen phosphonatooxy)methyl)-2,5-dioxabicyclo[2.2.1]heptan-7-
      yl
<220> FEATURE:
<221> NAME/KEY: misc_feature
<222> LOCATION: (14)..(14)
<223> OTHER INFORMATION: n is 5-methyldeoxycytidine

<400> SEQUENCE: 45
ttntnnntnn nnnnt                                                      15

<210> SEQ ID NO 46
<211> LENGTH: 15
<212> TYPE: DNA
<213> ORGANISM: artificial sequence
<220> FEATURE:
<223> OTHER INFORMATION: synthetic oligonucleotide modified with
      compound V'
<220> FEATURE:
<221> NAME/KEY: misc_feature
<222> LOCATION: (5)..(5)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (9)..(9)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
```

```
<220> FEATURE:
<221> NAME/KEY: misc_feature
<222> LOCATION: (14)..(14)
<223> OTHER INFORMATION: n is 5-methyldeoxycytidine

<400> SEQUENCE: 46
ttttnnttnn tnnnt                                                          15

<210> SEQ ID NO 47
<211> LENGTH: 15
<212> TYPE: DNA
<213> ORGANISM: artificial sequence
<220> FEATURE:
<223> OTHER INFORMATION: synthetic oligonucleotide modified with
      compound V'
<220> FEATURE:
<221> NAME/KEY: misc_feature
<222> LOCATION: (5)..(5)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (8)..(8)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (11)..(11)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (14)..(14)
<223> OTHER INFORMATION: n is 5-methyldeoxycytidine

<400> SEQUENCE: 47
ttttnntntn nntnt                                                          15

<210> SEQ ID NO 48
<211> LENGTH: 15
<212> TYPE: DNA
<213> ORGANISM: artificial sequence
<220> FEATURE:
<223> OTHER INFORMATION: synthetic oligonucleotide modified with
      compound V'
<220> FEATURE:
<221> NAME/KEY: misc_feature
<222> LOCATION: (3)..(3)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (5)..(5)
<223> OTHER INFORMATION: n is
      Alpha-L-3-(5-(3-aminoprop-1-ynyl)-2,4-dioxo-3,4-dihydropyrimidin-
```

```
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (6)..(6)
<223> OTHER INFORMATION: n is 5-methyldeoxycytidine
<220> FEATURE:
<221> NAME/KEY: misc_feature
<222> LOCATION: (7)..(7)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (9)..(9)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (10)..(10)
<223> OTHER INFORMATION: n is 5-methyldeoxycytidine
<220> FEATURE:
<221> NAME/KEY: misc_feature
<222> LOCATION: (11)..(11)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (12)..(12)
<223> OTHER INFORMATION: n is 5-methyldeoxycytidine
<220> FEATURE:
<221> NAME/KEY: misc_feature
<222> LOCATION: (13)..(13)
<223> OTHER INFORMATION: n is
      Alpha-L-3-(5-(3-aminoprop-1-ynyl)-2,4-dioxo-3,4-dihydropyrimidin-
      1(2H)-yl)-1-((hydrogen phosphonatooxy)methyl)-2,5-
      dioxabicyclo[2.2.1]heptan-7-yl
<220> FEATURE:
<221> NAME/KEY: misc_feature
<222> LOCATION: (14)..(14)
<223> OTHER INFORMATION: n is 5-methyldeoxycytidine

<400> SEQUENCE: 48
ttntnnntnn nnnnt                                               15
```

NUCLEOBASE-FUNCTIONALIZED CONFORMATIONALLY RESTRICTED NUCLEOTIDES AND OLIGONUCLEOTIDES FOR TARGETING NUCLEIC ACIDS

CROSS REFERENCE TO RELATED APPLICATION

This is a continuation application of U.S. patent application Ser. No. 13/416,906, filed Mar. 9, 2012, which is a continuation application under 35 U.S.C. §120 of International Patent Application No. PCT/US2010/048520, filed Sep. 10, 2010, which claims the benefit of the earlier filing date of U.S. Provisional Application No. 61/241,292, filed Sep. 10, 2009. Each of these prior applications is incorporated herein by reference.

ACKNOWLEDGMENT OF GOVERNMENT SUPPORT

This invention was made with government support from an Idaho NSF EPSCoR Research Infrastructure Improvement (RII) Startup Augmentation grant. The government has certain rights in the invention.

FIELD

This invention concerns the synthesis and use of oligonucleotides modified with one or more conformationally restricted nucleotides, such as C5- or C8-functionalized Locked Nucleic Acid (LNA) and/or C5- or C8-functionalized α-L-LNA building blocks, for nucleic-acid-based therapeutics, diagnostics and material science applications that target nucleic acids.

BACKGROUND

Chemically modified exogenous oligonucleotides (ONs) can bind to specific nucleic acid sequences (i.e., double stranded DNA, single stranded DNA, single stranded RNA), which has enabled their use as fundamental research tools, diagnostic probes and therapeutic agents. For example, modulation of gene expression via the antigene [Duca et al., *Nucleic Acids Res.* 36:5123 (2008)], antisense [Kurreck, *J. Eur. J. Biochem.* 270:1628-1644 (2003)] and/or siRNA [Bumcrot et al., *Nat Chem Biol* 2:711-719 (2006)] strategies are very useful approaches to establish the function of specific genes or transcripts (fundamental research tool), and to develop agents against diseases of genetic origin (therapeutics).

Introduction of chemically modified nucleotides into ONs has been investigated for increasing binding affinity toward double stranded DNA (via Hoogsteen base-pairing), single stranded DNA (via Watson-Crick base-pairing), and single stranded RNA targets (via Watson-Crick base-pairing); b) improving discrimination of mismatched nucleic acid targets to minimize false positives and non-target specific effects in diagnostic and biological applications; and/or c) enhancing stability against degradation by enzymes including nucleases. The use of conformationally restricted nucleotides [Meldgaard et al., *J. Chem. Soc., Perkin Trans.* 1:3539-3554 (2000); Leumann, *J. Bioorg. Med. Chem.* 10:841-854 (2002)] such as Locked Nucleic Acid (LNA, also called bridged nucleic, BNA) [Singh et al., *Chem. Commun.* 455-456 (1998); Koshkin et al., *Tetrahedron* 54:3607-3630 (1998); Obika et al., *Tetrahedron Lett.* 39:5401-5404 (1998); Obika et al., *Bioorg. Med. Chem.* 9:1001-1011 (2001)] or α-L-LNA, [Sørensen et al., *J. Am. Chem. Soc.* 124:2164-2176 (2002)] have partially addressed these challenges. LNA and α-L-LNA exhibit increased thermal affinity toward complementary single stranded DNA/RNA strands of up to +10° C. per modification, along with markedly improved mismatch discrimination and enzymatic stability relative to unmodified oligodeoxyribonucleotides [Petersen et. al., *Trends Biotechnol.* 21:74-81 (2003)]. Similarly, introducing LNA or α-L-LNA monomers into triplex forming oligonucleotides may result in markedly improved thermal affinity toward double stranded DNA targets [Torigoe et al., *J. Biol. Chem.* 276:2354 (2001); Obika et al., *Chem. Pharm. Bull.* 52:1399 (2004); Sun et al., *Biochemistry* 43:4160 (2004); Brunet et al., *J. Biol. Chem.* 280:20076 (2005); Kumar et al., *J. Am. Chem. Soc.,* 128:14 (2006)]. These properties render LNA and α-L-LNA with considerable therapeutic and diagnostic potential [Petersen et. al., *Trends Biotechnol.* 21:74-81 (2003); Frieden et al., *IDrugs* 9:706-711 (2006); Jepsen et al., *Curr. Opin. Drug Discovery Dev.* 7:188-194 (2004); Grünweller et al., *Biodrugs* 21:235-243 (2007); Stenvang et al., *Sem. Cancer Biol.* 18:89-102 (2008)].

Substantial efforts have been invested to develop LNA analogs with more desirable biophysical properties, i.e., improved thermal affinity toward single stranded DNA/RNA targets or double stranded DNA targets, improved thermal mismatch discrimination and enhanced enzymatic stability [representative examples: Koizumi et al., *Nucleic Acids Res.* 31:3267 (2003); Morita et al., *Bioorg. Med. Chem.* 11:2211-2226 (2003); Sørensen et al., *Chem. Commun.* 2130-2131 (2003); Fluiter et al., *ChemBioChem.* 1104-1109 (2005); Albæk et al., *J. Org. Chem.* 71:7731-7740 (2006); Varghese et al., *J. Am. Chem. Soc.* 128:15173-15187 (2006); Højland et al., *Org. Biomol. Chem.* 5:2375 (2007); Rahman et al., *Angew. Chem., Int. Ed.,* 46:4306 (2007); Rahman et al., *J. Am. Chem. Soc.* 130:4886-4896 (2008); Mitsuoka et al., *Nucleic Acids Res.* 37:1225-1238 (2009); Kumar et al., *J. Org. Chem.* 1070-1081 (2009); Seth et al., *J. Med. Chem.* 52:10-13 (2009); Zhou et al., *J. Org. Chem.* 74:118-134 (2009)]. These studies have primarily focused on using stereoisomers of LNA, modification of the oxymethylene bridge spanning the C2'- and C4'-positions and/or introducing minor-groove oriented substituents into the bridge. Improved enzymatic stability [Morita et al. (2003), Varghese et al. (2006), Rahman et al. (2008), Zhou et al. (2009)], altered biodistribution [Fluiter et al. (2005)], or reduced hepatotoxicity [Seth (2009)], has been reported for some of the analogs, but improvements in hybridization properties relative to LNA were generally not observed. Thus, the significantly increased synthetic complexity of these conformationally restricted nucleotide analogs does not appear to be justified.

SUMMARY

Certain disclosed embodiments concern compounds having a first general formula

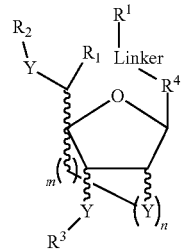

With reference to this first general formula, $R^1$ may be selected from hydrogen, hydroxyl, thiol, aliphatic, heteroaliphatic, aryl, heteroaryl, charged moieties, and metal complexes. $R^1$ typically is selected from ether, carbonyl, nitrile, disulfide, thioether, amine, amino acid, aminoglycoside, carbohydrate, fluorophores, nucleosides, nucleotides, oligonucleotides, peptides, intercalators, lipidoids, porphyrins, proteins, and vitamins, and even more typically from amide, amine, ester, carboxylic acid, aldehyde, ketone, spermine derivatives, guanidine groups, spin labels, electrochemical probes, fatty acids, glycerols, sterols, glycols, alkylene glycol, redox active FRET labels, nuclear localization signals, transportan, and ferrocene derivatives. Particular species of the $R^1$ substituent include, but are not limited to, lauric acid, palmitic acid, stearic acid, fluorescein, rhodamine, cyanine, pyrene, perylene, coronene, adamantane, acridine, phenantroline, diphenylphosphorylazide, HIV Tat fragment, cholesterol, lithocolic-oleyl, myristoyl, lauroyl, docosanyl, palmitoyl, stearoyl, oleoyl, linoleoyl, dihydrotestosterone, lithocholic acid, folic acid, and vitamin E.

$R^2$ may be selected from hydrogen, aliphatic, heteroaliphatic, aryl, heteroaryl, and functional group protecting groups. Particular species of the $R^2$ substituent include, but are not limited to, carbonyl, sulfonyl, benzyl, benzoyl, and alkyl. $R^2$ is typically selected from hydrogen, 4,4'-dimethoxytrityl, trityl, 9-arylthioxanthenyl, mesyl (Ms), tosyl (Ts), besoyl (Bs), and trifluormethanesulonyl. $R^2$ can also be selected to include an oligonucleotide.

$R^3$ typically may be selected from a phosphorous-containing compound, a sulfur-containing compound, a nitrogen-containing compound, an oxygen-containing compound, a metal-containing compound, and a selenium-containing compound. Certain disclosed embodiments utilize $R^3$ substituents having a formula

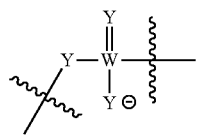

where Y is selected from oxygen, sulfur, $N(R^5)$ where $R^5$ is selected from hydrogen, aliphatic, aryl, heteroaliphatic, heteroaryl, and any combination thereof, and W is selected from phosphorus, SH, or SeH. Certain species of $R^3$ substituents include, without limitation,

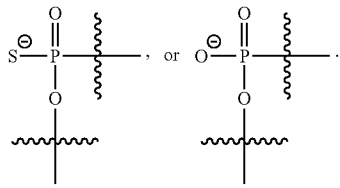 [SMILES: *OP(*)(=O)[S-] ; "," ; "or" ; *OP(*)(=O)[O-] ; "."]

In other disclosed embodiments, $R^3$ has a formula

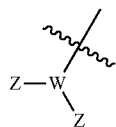

where W is phosphorus, and Z independently is selected from ether, thioether, hydroxyl, and $N(R^5)_2$ where $R^5$ is selected from hydrogen, aliphatic, aryl, heteroaliphatic, and heteroaryl, sulfhydryl, and any combination thereof. A particular example of an $R^3$ substituent is

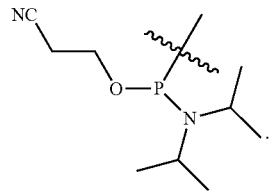 [SMILES: *P(OCCC#N)N(C(C)C)C(C)C ; "."]

$R^4$ is a natural or non-natural nucleobase. For example, $R^4$ may have a formula

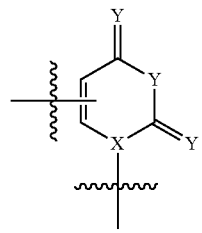

and particular species of such compounds have the regiochemistry shown below:

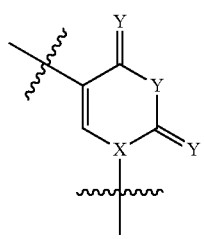

where X is nitrogen or carbon; Y is selected from oxygen, sulfur and $N(R^5)$ where $R^5$ is selected from hydrogen, aliphatic, aryl, heteroaliphatic, and heteroaryl. A particular species of the $R^4$ substituent is

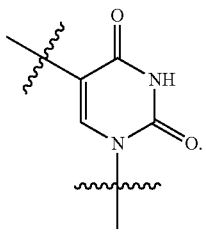 [SMILES: *c1cn(*)c(=O)[nH]c1=O]

Additional examples of disclosed compounds may have an $R^4$ substituent having a formula

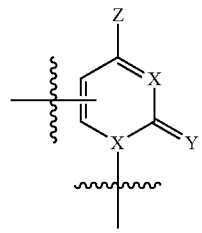

with specific $R^4$ substituents having the following regiochemistry

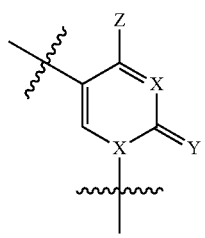

where X is nitrogen, carbon, or any combination thereof; Y is selected from oxygen, sulfur, and $N(R^5)$ where $R^5$ is selected from hydrogen, aliphatic, aryl, heteroaliphatic, and heteroaryl; Z is selected from ether, thioether, hydroxyl, sulfhydryl and $N(R^5)_2$ where $R^5$ is selected from hydrogen, aliphatic, aryl, heteroaliphatic, heteroaryl, and any combination thereof. A particular species of the $R^4$ substituent has a formula

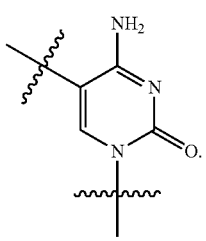 [SMILES: *c1cn(*)c(=O)nc1N]

Additional examples of disclosed compounds may have an $R^4$ substituent having a formula

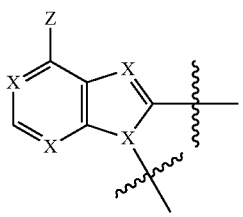

where X is nitrogen, carbon, or any combination thereof; Z is selected from ether, thioether, hydroxyl, sulfhydryl, $N(R^5)_2$ where $R^5$ is selected from hydrogen, aliphatic, aryl, heteroaliphatic, heteroaryl, and any combination thereof. A particular example of such an $R^4$ substituent is

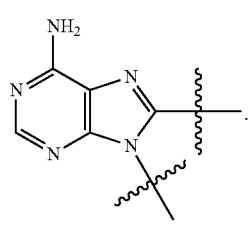 [SMILES: *c1nc2c(N)ncnc2n1*]

Still another example of an $R^4$ substituent has a formula

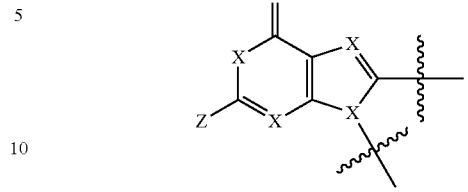

where X is nitrogen, carbon, or any combination thereof; Y is selected from oxygen, sulfur, and $N(R^5)$ where $R^5$ is selected from hydrogen, aliphatic, aryl, heteroaliphatic, and heteroaryl; Z is selected from ether, thioether, hydroxyl, sulfhydryl and $N(R^5)_2$ where $R^5$ is selected from hydrogen, aliphatic, aryl, heteroaliphatic, heteroaryl, and any combination thereof. A particular example of such an $R^4$ substituent is

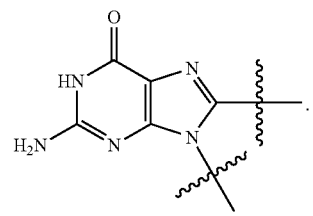

With reference to the first general formula, the linker typically is selected from aliphatic, aryl, heteroaliphatic, and heteroaryl, and even more particularly is alkyl (other than methyl), alkenyl, alkynyl, or heterocyclic. Particular examples of linkers include, without limitation, (E isomer) —CH=CH—, (Z isomer) —CH=CH—, 1,2,3-triazole, or 1,2,4-triazole.

Again with reference to the first general formula, Y is a heteroatom selected from oxygen, sulfur, or $NR^5$ where $R^5$ is selected from hydrogen, aliphatic, aryl, heteroaliphatic, and heteroaryl. M and n are used to designate the size of a bridge in the compounds wherein m+n is from 2 to at least 4.

Certain disclosed embodiments may satisfy a second general formula

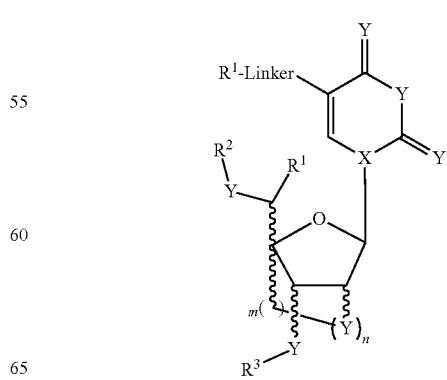

a third general formula
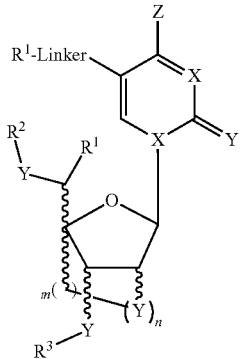
a fourth general formula
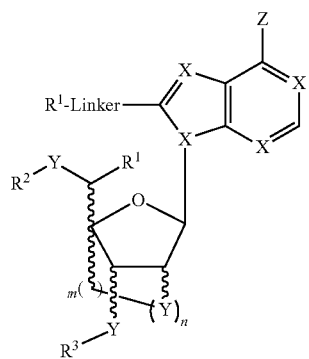
a fifth general formula
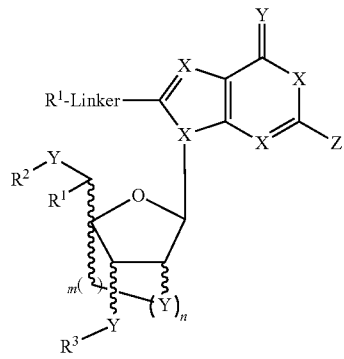
where the various substituents are as stated above with reference to the first general formula.
Certain disclosed embodiments have an R$^1$-linker moiety selected from
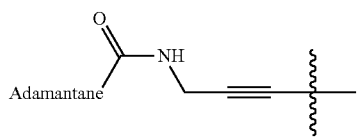
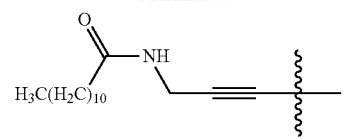
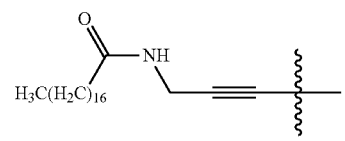
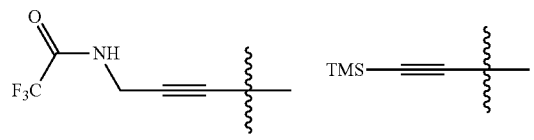
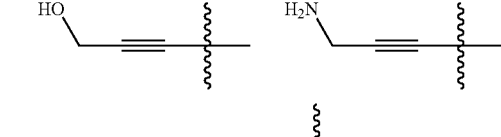
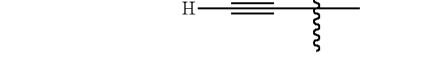
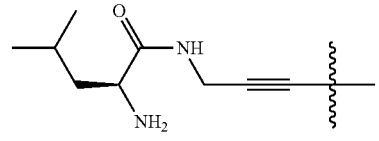
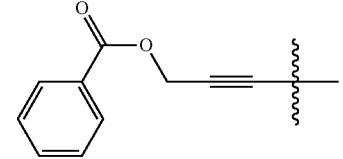
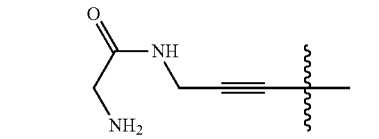
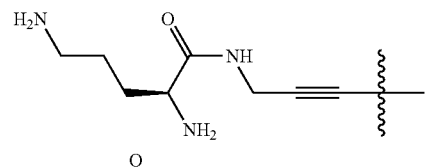
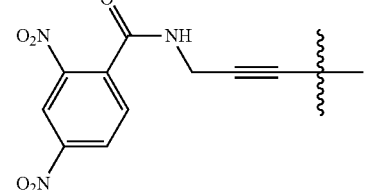
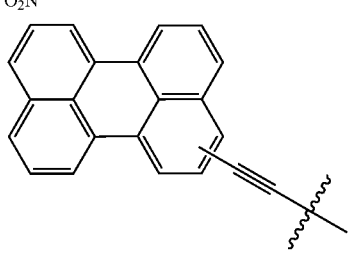

-continued
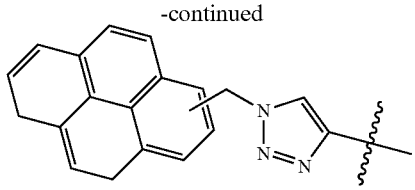
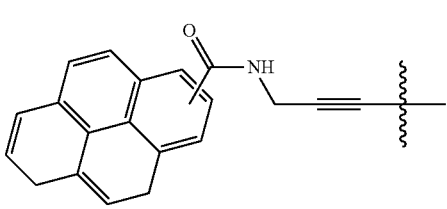
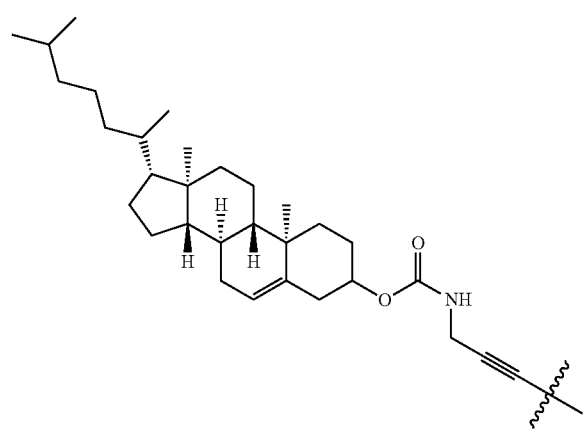
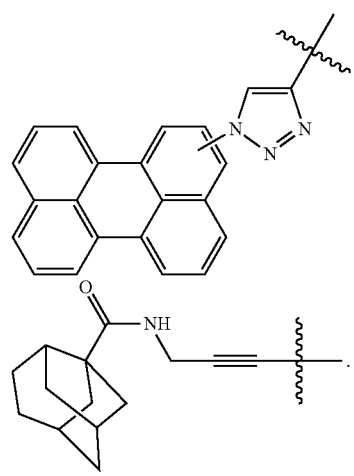
Particular examples of disclosed compounds include
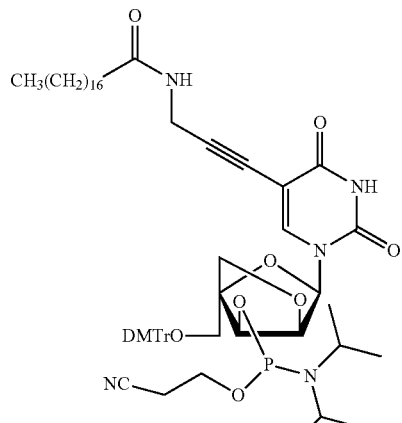
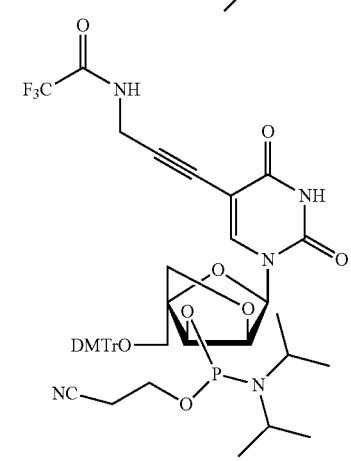
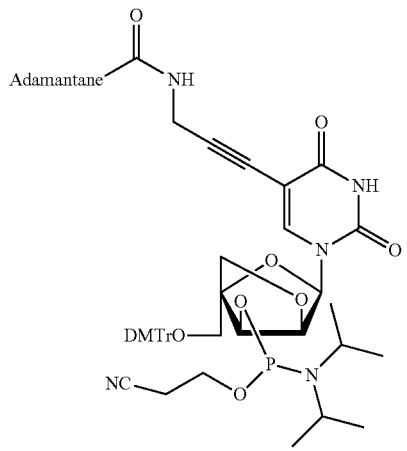

11
-continued
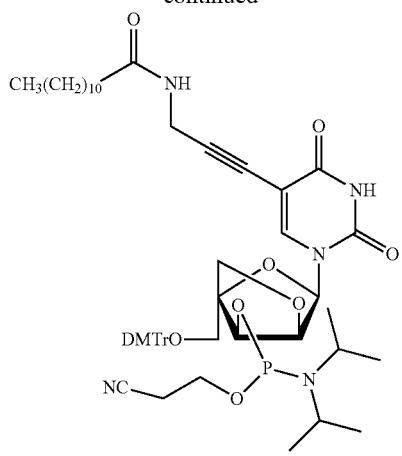
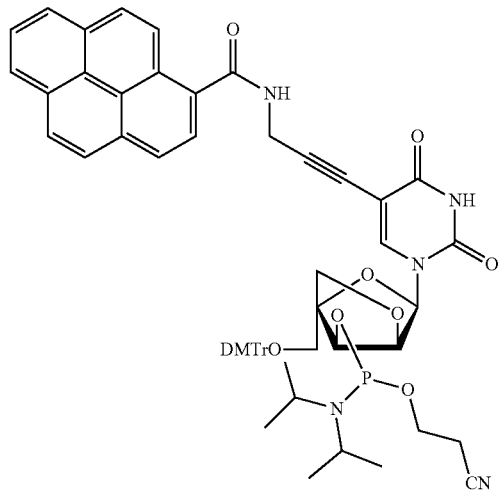
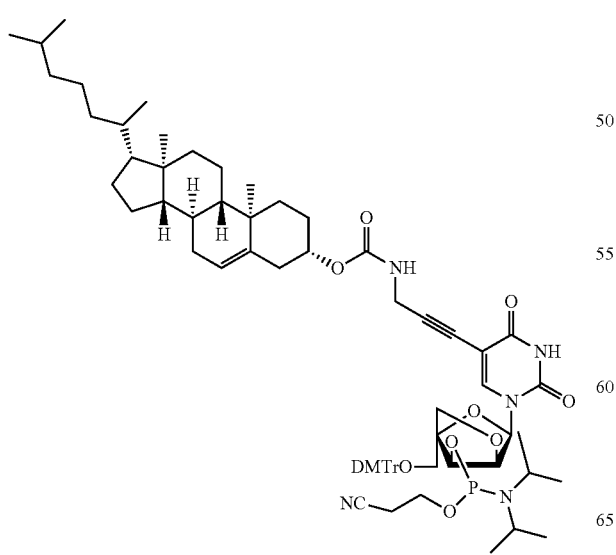
12
-continued
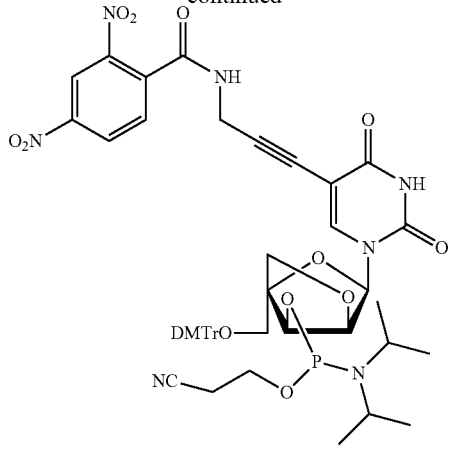
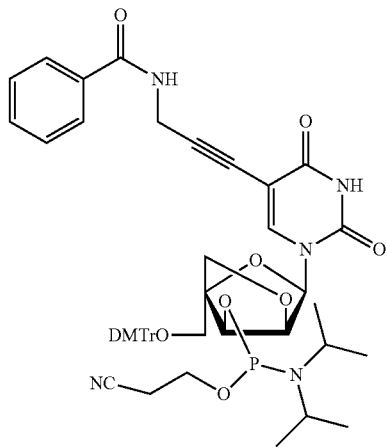
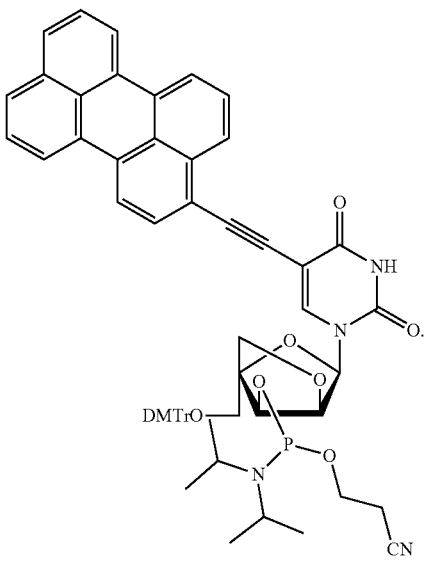

Certain disclosed compound concern α-L-locked nucleotides having a formula

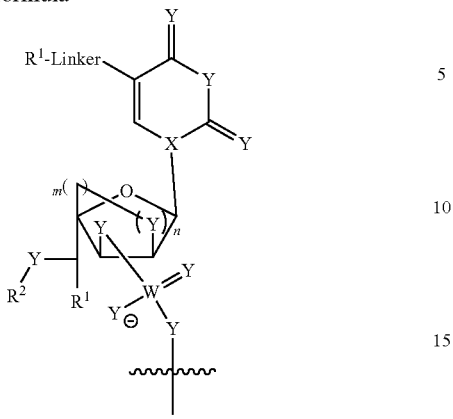

where $R^1$ is selected from aliphatic, heteroaliphatic, aryl, heteroaryl, charged moieties, and metal complexes; $R^2$ is selected from hydrogen, aliphatic, heteroaliphatic, aryl, heteroaryl, functional group protecting groups, oligonucleotides, a phosphorous-containing compound, a sulfur-containing compound, a nitrogen-containing compound, an oxygen-containing compound, a metal-containing compound, and a selenium-containing compound; linker is selected from aliphatic, aryl, heteroaliphatic, and heteroaryl; X is nitrogen or carbon; Y is selected from oxygen, sulfur, $N(R^5)$ where $R^5$ is selected from hydrogen, aliphatic, aryl, heteroaliphatic, heteroaryl, and any combination thereof; W is selected from phosphorus, SH, and SeH; and m+n=2 to at least 4. Particular examples of such compounds include

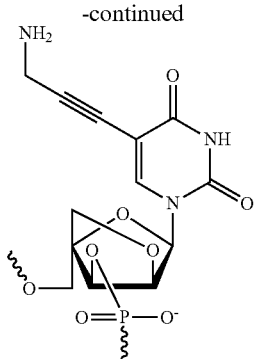

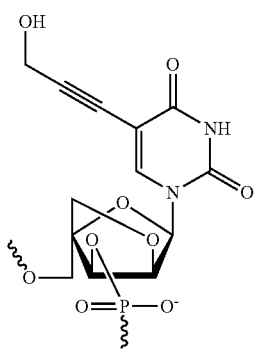

-continued

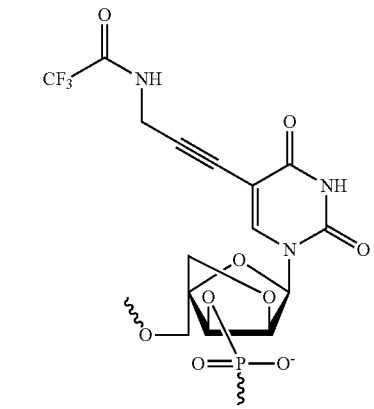

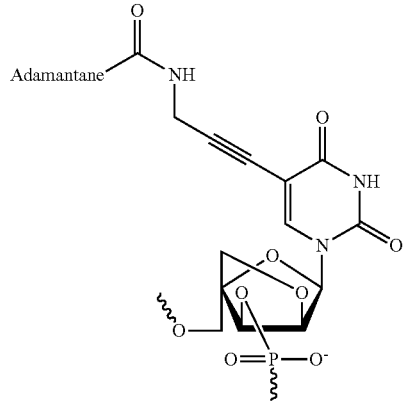

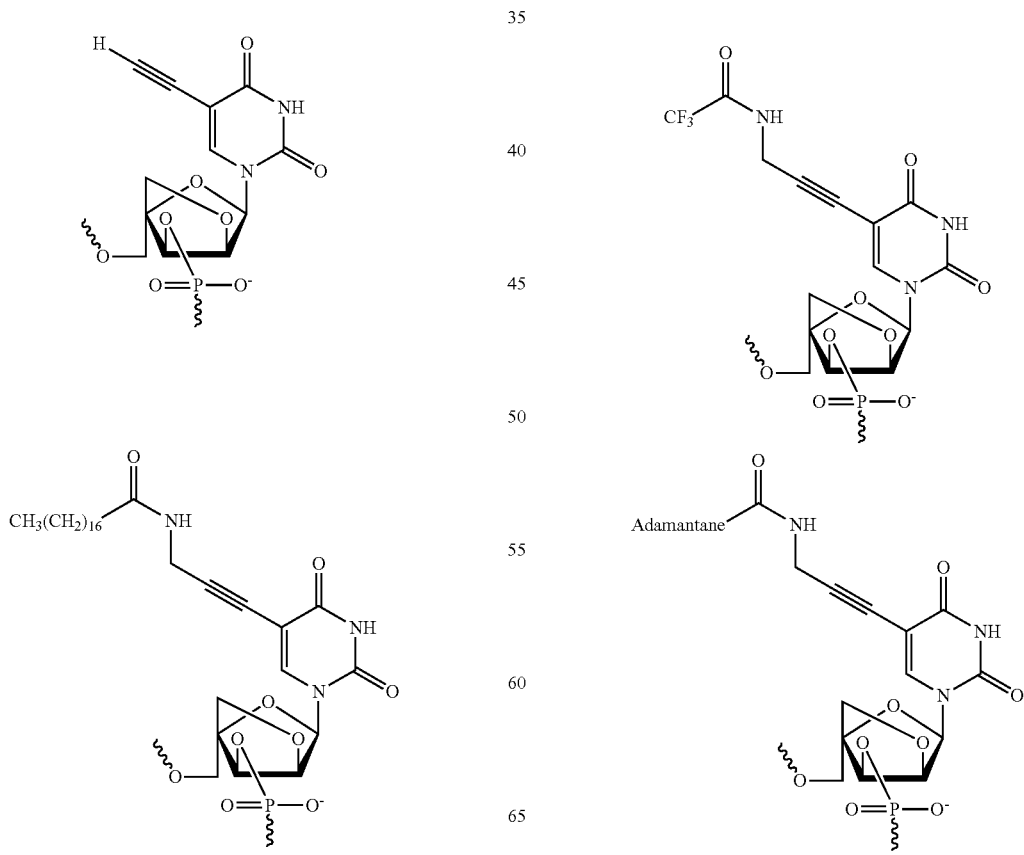

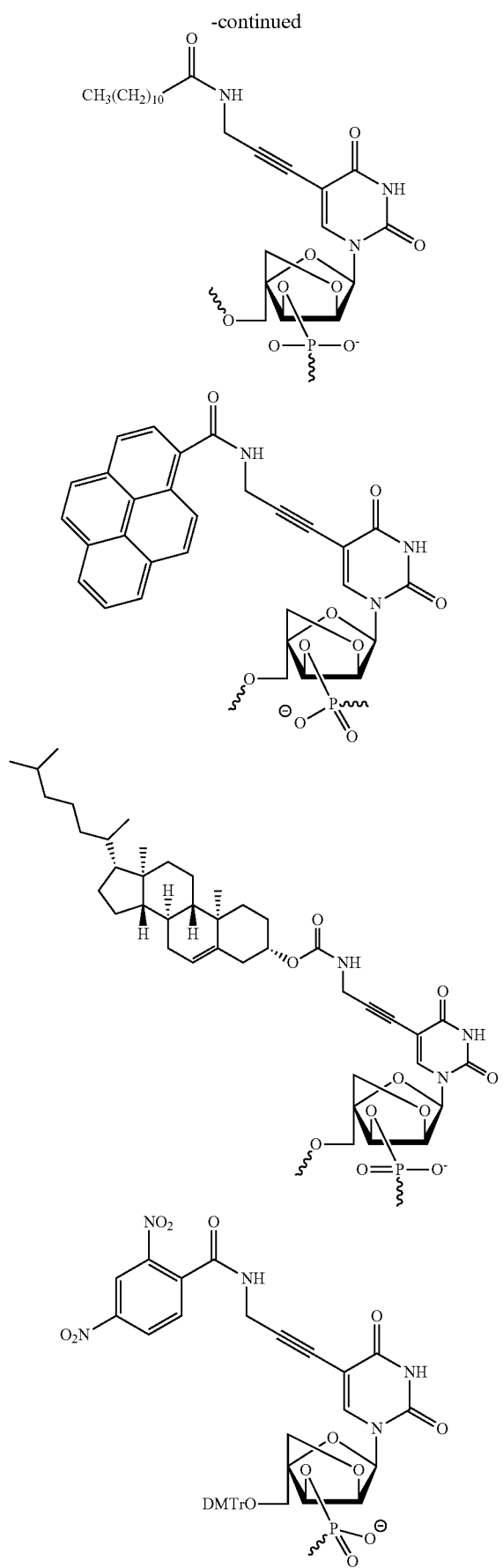

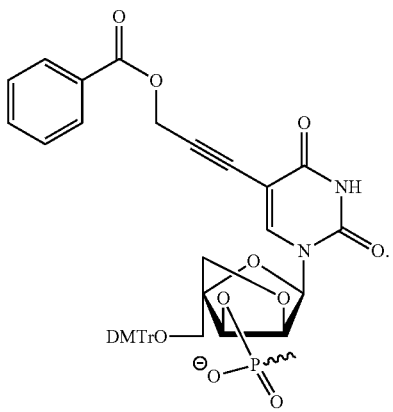

Certain disclosed compounds comprise β-D-locked nucleotides having a formula

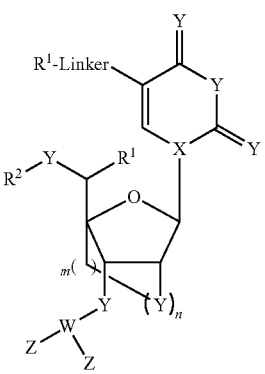

where $R^1$ is selected from aliphatic, heteroaliphatic, aryl, heteroaryl, charged moieties, and metal complexes; $R^2$ is selected from hydrogen, aliphatic, heteroaliphatic, aryl, heteroaryl, functional group protecting groups, oligonucleotides, a phosphorous-containing compound, a sulfur-containing compound, a nitrogen-containing compound, an oxygen-containing compound, a metal-containing compound, and a selenium-containing compound; linker is selected from aliphatic, aryl, heteroaliphatic, and heteroaryl; X is nitrogen, carbon, or any combination thereof; Y is selected from oxygen, sulfur, $N(R^5)$ where $R^5$ is selected from hydrogen, aliphatic, aryl, heteroaliphatic, heteroaryl, and any combination thereof; W is phosphorus; Z independently is selected from ether, thioether, hydroxyl, and $N(R^5)_2$ where $R^5$ is selected from hydrogen, aliphatic, aryl, heteroaliphatic, and heteroaryl, sulfhydryl, and any combination thereof; and m+n=2 to at least 4. Particular examples of such nucleotides include 17
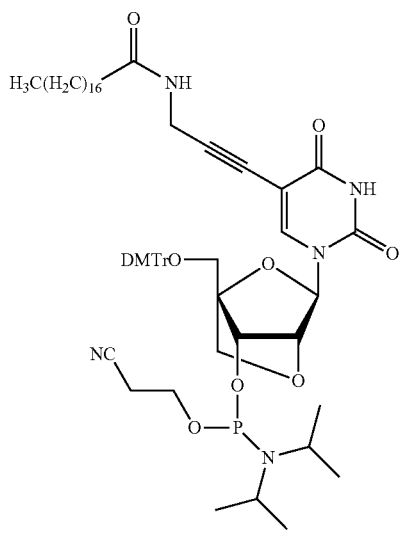
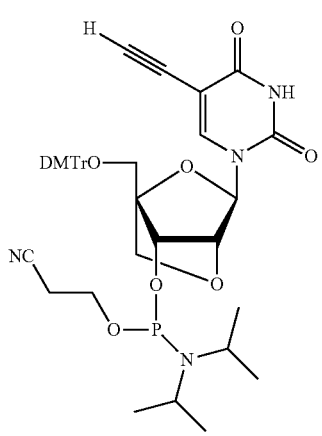
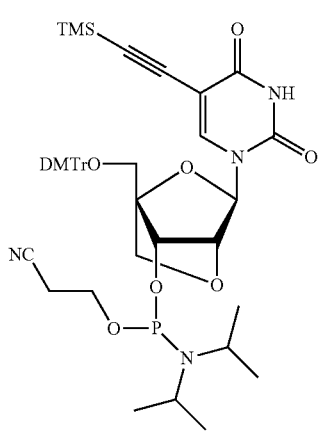
18
-continued
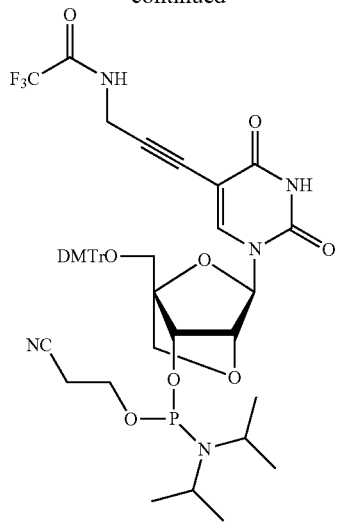
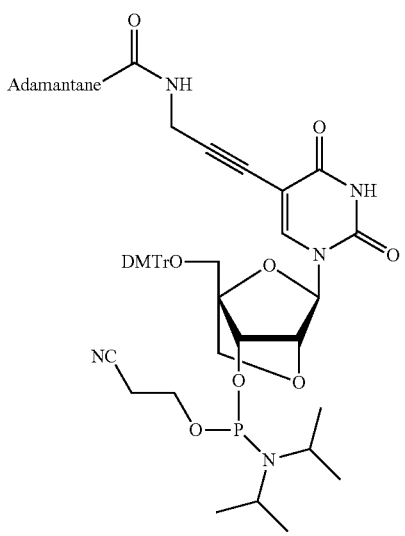
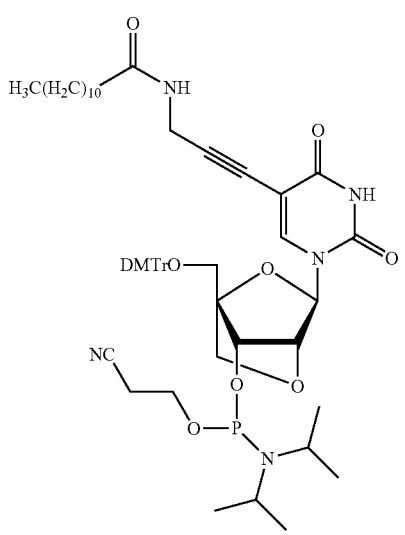

-continued
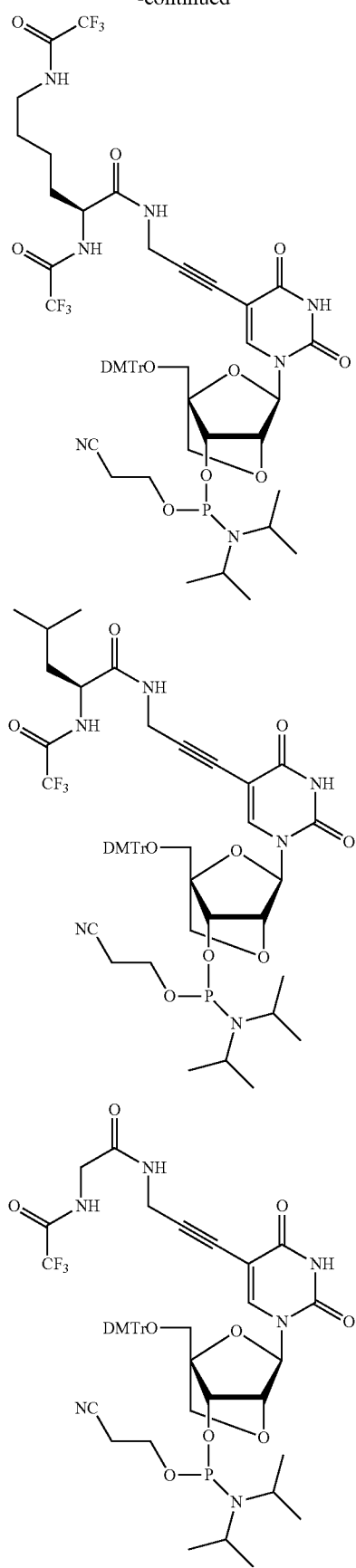
-continued
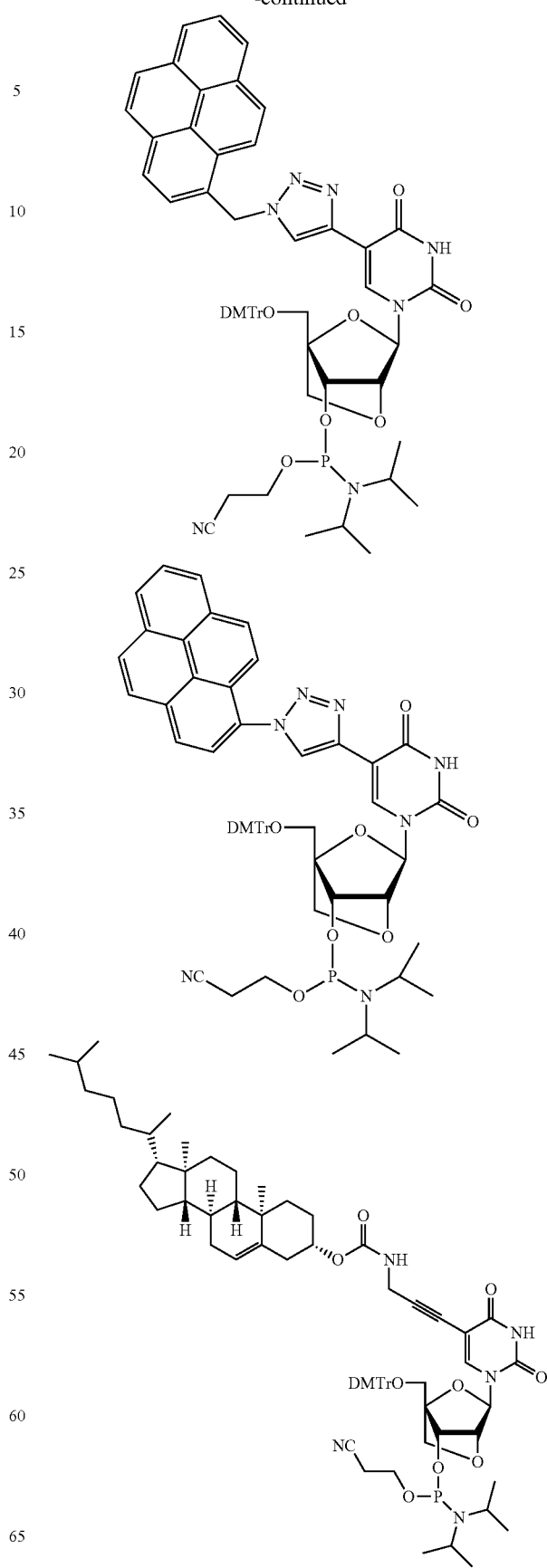

21
-continued

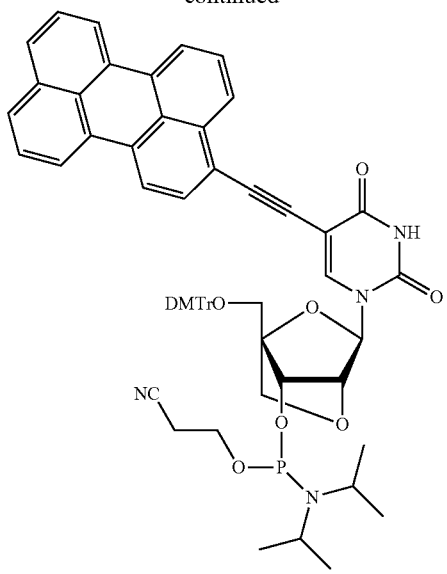

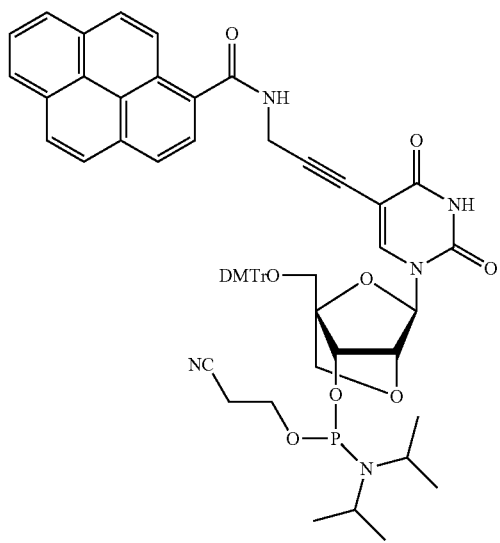

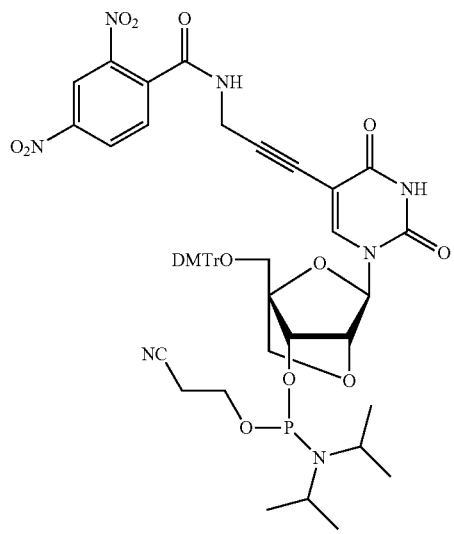

22
-continued

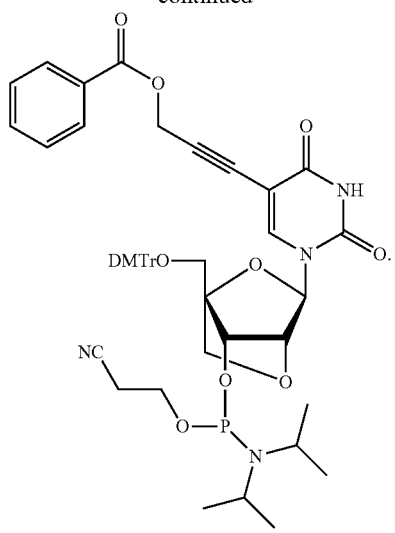

Yet additional disclosed compounds concern β-D-locked nucleotides having a formula

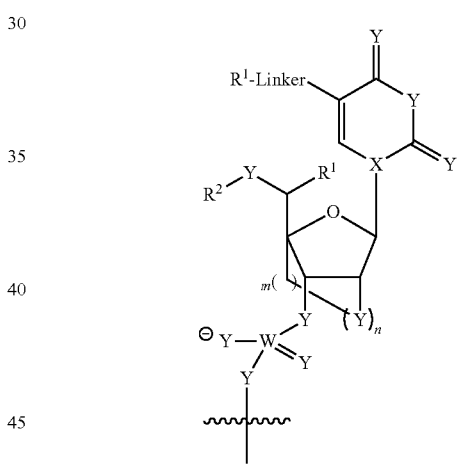

where $R^1$ is selected from aliphatic, heteroaliphatic, aryl, heteroaryl, charged moieties, and metal complexes; $R^2$ is selected from hydrogen, aliphatic, heteroaliphatic, aryl, heteroaryl, functional group protecting groups, oligonucleotides, a phosphorous-containing compound, a sulfur-containing compound, a nitrogen-containing compound, an oxygen-containing compound, a metal-containing compound, and a selenium-containing compound; linker is selected from aliphatic, aryl, heteroaliphatic, and heteroaryl; X is nitrogen or carbon; Y is selected from oxygen, sulfur, $N(R^5)$ where $R^5$ is selected from hydrogen, aliphatic, aryl, heteroaliphatic, heteroaryl, and any combination thereof; W is selected from phosphorus, SH, and SeH; and m+n=2 to at least 4. Particular examples of such nucleotides include

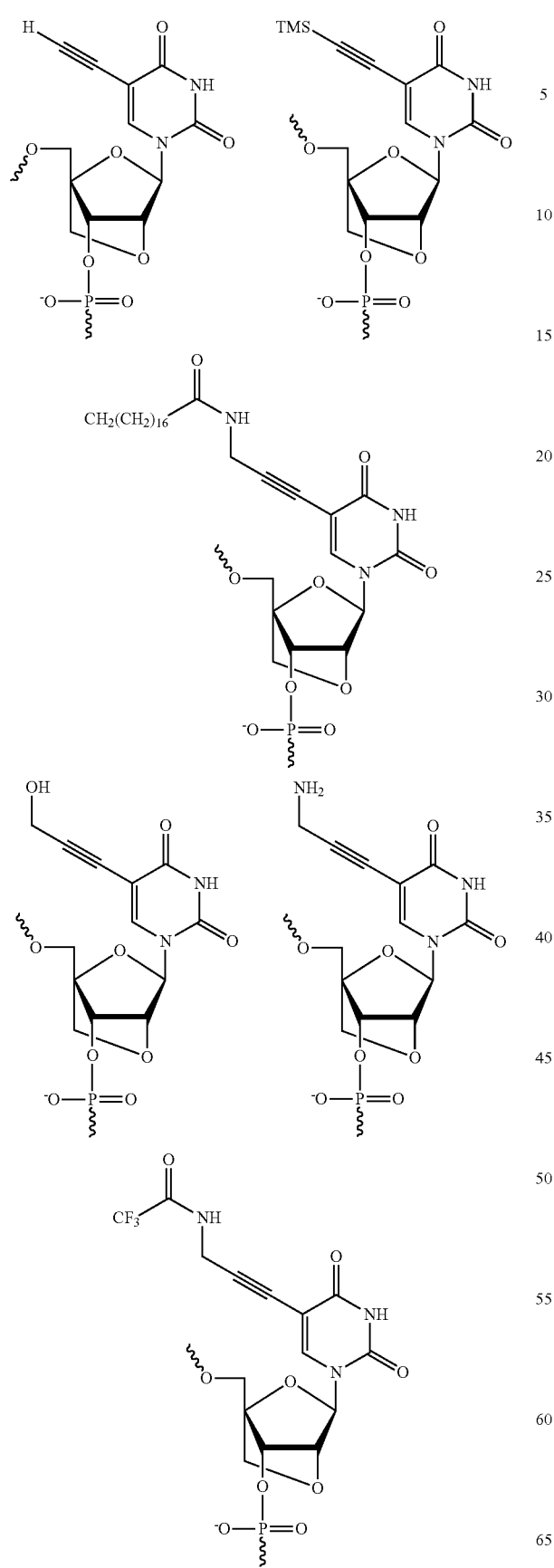
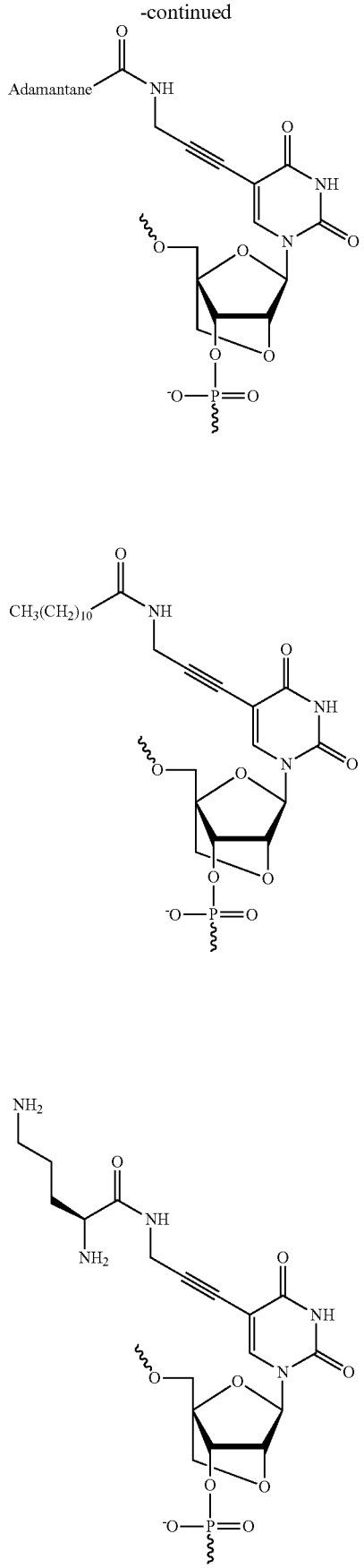

25
-continued
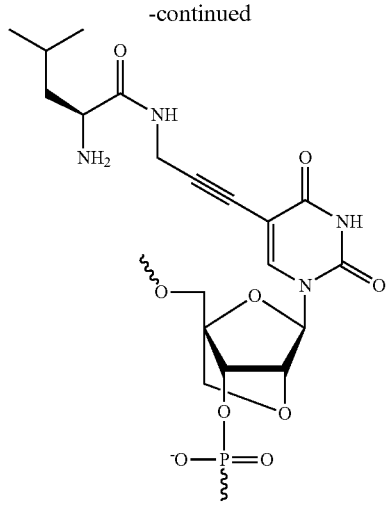
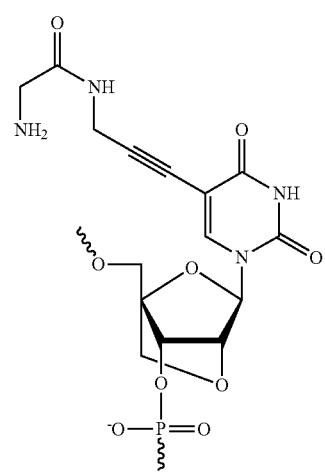
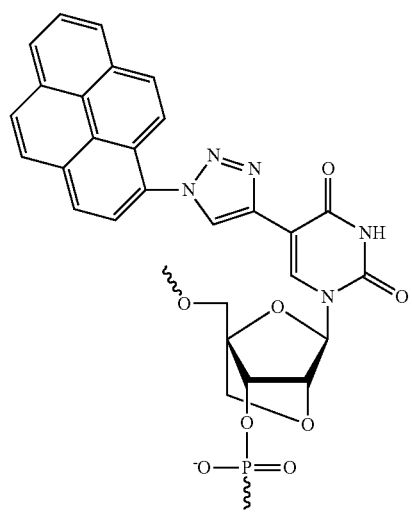
26
-continued
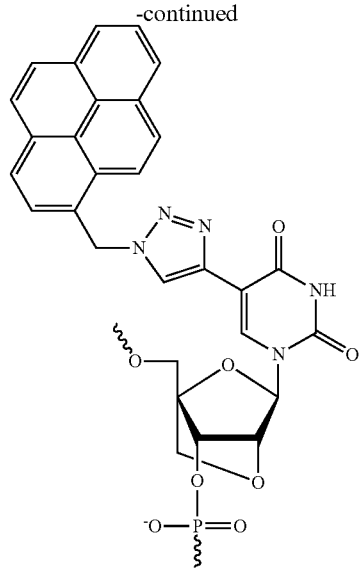
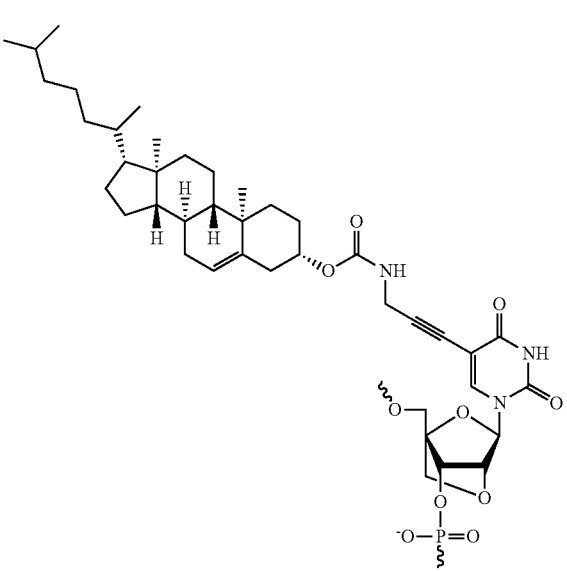
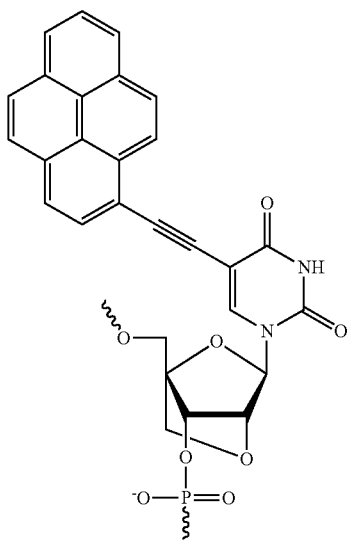

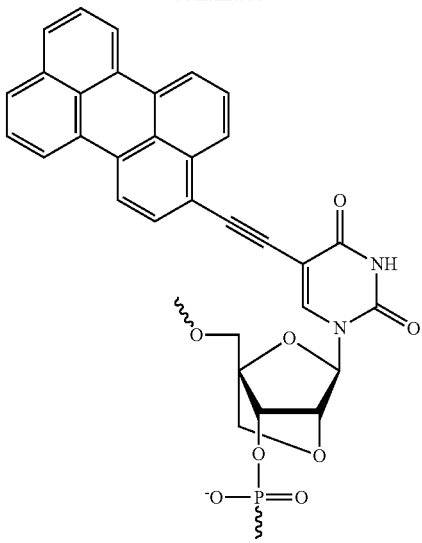

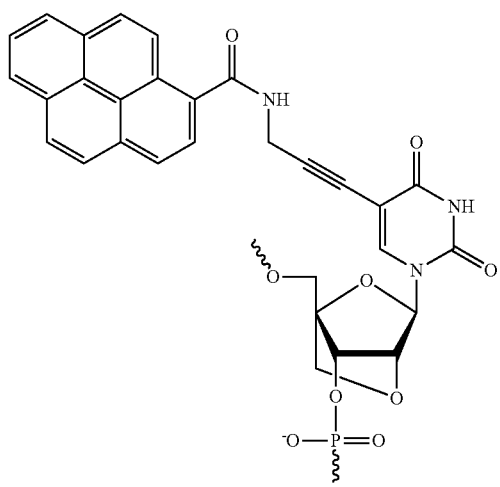

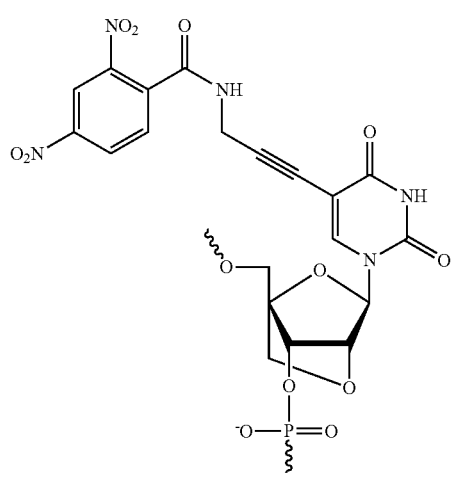

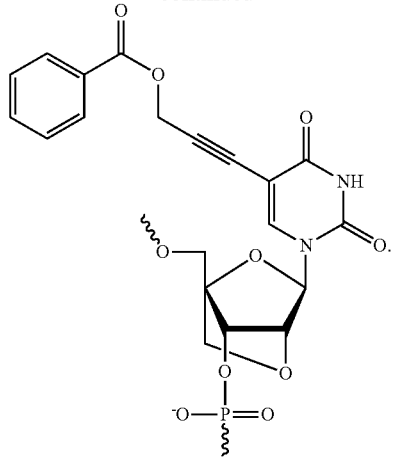

Yet additional disclosed compounds concern β-D-locked nucleotides having a formula

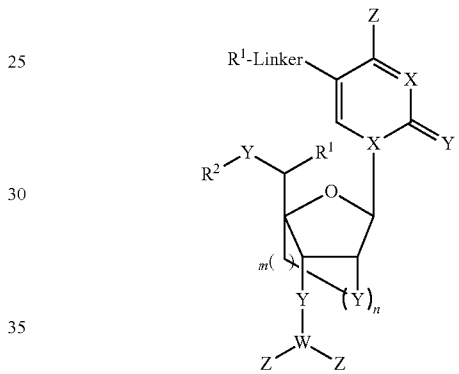

where $R^1$ is selected from aliphatic, heteroaliphatic, aryl, heteroaryl, charged moieties, and metal complexes; $R^2$ is selected from hydrogen, aliphatic, heteroaliphatic, aryl, heteroaryl, functional group protecting groups, oligonucleotides, a phosphorous-containing compound, a sulfur-containing compound, a nitrogen-containing compound, an oxygen-containing compound, a metal-containing compound, and a selenium-containing compound; linker is selected from aliphatic, aryl, heteroaliphatic, and heteroaryl; X is nitrogen, carbon, or any combination thereof; Y is selected from oxygen, sulfur, $N(R^5)$ where $R^5$ is selected from hydrogen, aliphatic, aryl, heteroaliphatic, heteroaryl, and any combination thereof; W is phosphorus; and Z independently is selected from ether, thioether, hydroxyl, and $N(R^5)_2$ where $R^5$ is selected from hydrogen, aliphatic, aryl, heteroaliphatic, and heteroaryl, sulfhydryl, and any combination thereof; and m+n=2 to at least 4.

Yet additional disclosed compounds alpha locked nucleotides having a formula

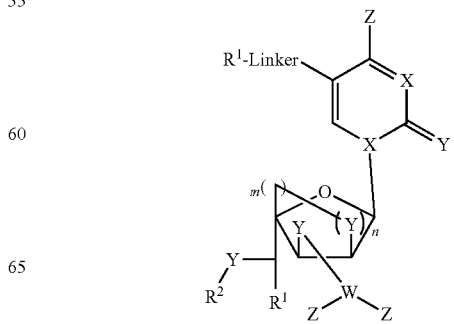

where $R^1$ is selected from aliphatic, heteroaliphatic, aryl, heteroaryl, charged moieties, and metal complexes; $R^2$ is selected from hydrogen, aliphatic, heteroaliphatic, aryl, heteroaryl, functional group protecting groups, oligonucleotides, a phosphorous-containing compound, a sulfur-containing compound, a nitrogen-containing compound, an oxygen-containing compound, a metal-containing compound, and a selenium-containing compound; linker is selected from aliphatic, aryl, heteroaliphatic, and heteroaryl; X is nitrogen, carbon, or any combination thereof; Y is selected from oxygen, sulfur, $N(R^5)$ where $R^5$ is selected from hydrogen, aliphatic, aryl, heteroaliphatic, heteroaryl, and any combination thereof; W is phosphorus; and Z independently is selected from ether, thioether, hydroxyl, and $N(R^5)_2$ where $R^5$ is selected from hydrogen, aliphatic, aryl, heteroaliphatic, and heteroaryl, sulfhydryl, and any combination thereof; and m+n=2 to at least 4.

A person of ordinary skill in the art will appreciate that disclosed compounds can be formulated as a pharmaceutically acceptable salt, a hydrate, a solvate, or combinations thereof.

Oligonucleotides comprising the compound/nucleotides/ nucleosides described above also are disclosed. For example, certain disclosed oligonucleotides have a first formula

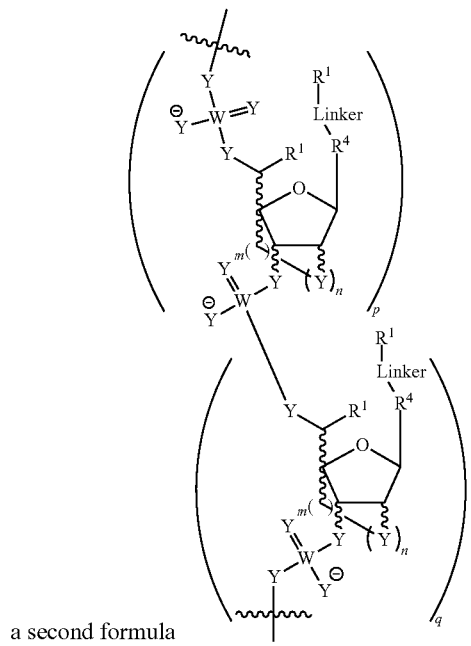

a second formula

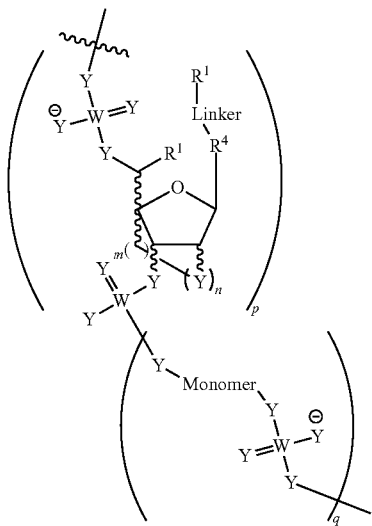

a third formula

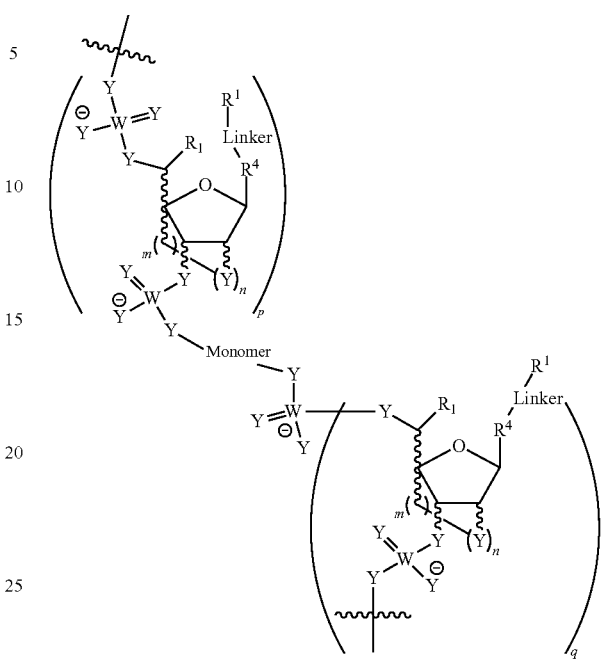

or a fourth formula.

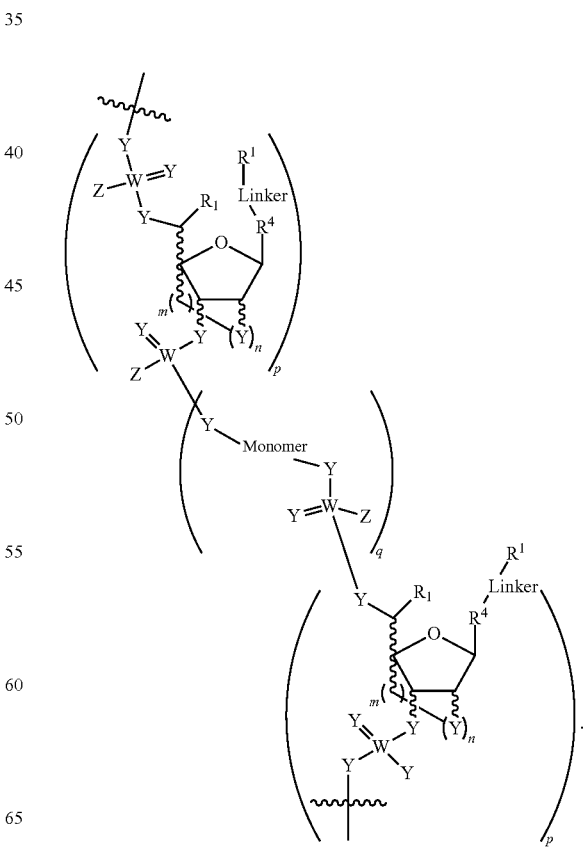

With reference to these general oligonucleotide formulas, $R^1$ is selected from aliphatic, heteroaliphatic, aryl, heteroaryl, charged moieties, and metal complexes; $R^4$ is a natural or non-natural nucleobase; linker is selected from aliphatic, aryl, heteroaliphatic, and heteroaryl; Y is selected from oxygen, sulfur, $N(R^5)$ where $R^5$ is selected from hydrogen, aliphatic, aryl, heteroaliphatic, heteroaryl, and any combination thereof; W is selected from phosphorus, SH, and SeH; the monomer can be selected from deoxyribonucleotides, ribonucleotides, O2'-alkylated ribonucleotides, β-locked nucleic acids, α-L-locked nucleic acids, and other conformationally-restricted nucleotides; m+n=2 to at least 4; and p+q is from 2 to about 50.

A person of ordinary skill in the art will appreciate that the disclosed compounds/nucleotides/nucleosides, or oligonucleotides comprising one or more of the disclosed compounds can be used as probes. For example, disclosed probes comprise at least one compound having a formula

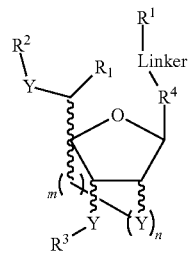

where $R^1$ is aliphatic, heteroaliphatic, aryl, heteroaryl, charged moieties, or metal complexes; $R^2$ is selected from hydrogen, aliphatic, heteroaliphatic, aryl, heteroaryl, functional group protecting groups, oligonucleotides, a phosphorous-containing compound, a sulfur-containing compound, a nitrogen-containing compound, an oxygen-containing compound, a metal-containing compound, and a selenium-containing compound; $R^3$ is selected from a phosphorous-containing compound, a sulfur-containing compound, a nitrogen-containing compound, an oxygen-containing compound, a metal-containing compound, and a selenium-containing compound, or an oligonucleotide; $R^4$ is a nucleobase; the linker is aliphatic, aryl, heteroaliphatic, or heteroaryl; and Y is oxygen, sulfur, or $NR^5$ where $R^5$ is selected from hydrogen aliphatic, heteroaliphatic, aryl, heteroaryl, and any combination thereof; and m+n=2 to at least 4.

Pharmaceutical compositions also are disclosed. Certain disclosed pharmaceutical compositions include a compound, or an oligonucleotide comprising the compound, having the first general formula

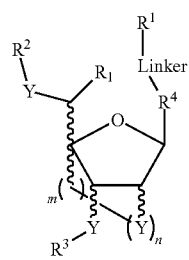

where the substituents are as stated above. The pharmaceutical composition includes at least a second material selected from carriers, thickeners, diluents, buffers, preservatives, surface active agents, one or more additional active ingredients, bulking agents, disintegrating agents, anti-adherents and glidants, lubricants, binding agents, flavoring agents, and combinations thereof.

Embodiments of a method for making disclosed compounds also are described. One disclosed embodiment for making a first compound having a formula

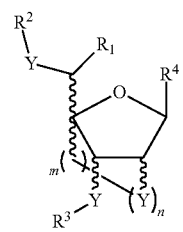

comprises providing a compound having a formula

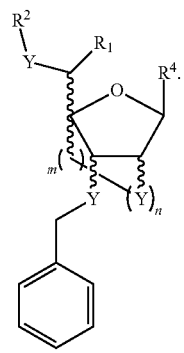

This compound is subjected to debenzylation conditions to provide greater than a 98:2 ratio of the debenzylated compound to a second compound. The debenzylation conditions may comprise using a transition metal, such as $Pd(OH)_2$, an acid, such as acetic acid or formic acid, a solvent, such as a mixture of tetrahydrofuran and methanol, and heat. The method also can include making a second compound having a formula

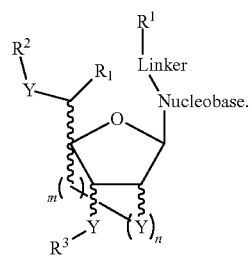

The method comprises providing the first compound, above. A vinyl substituent is coupled to the nucleobase where the vinyl substituent comprises a

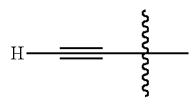

moiety or an $R^1$-linker moiety. For certain disclosed embodiments the $R^1$-linker comprises an alkenyl linker, or an alkyne linker. For certain embodiments the vinyl substituent is a vinyl halide (i.e. vinyl iodide, vinyl bromide, vinyl fluoride, and vinyl chloride) or a vinyl triflate. For certain embodiments, coupling the vinyl substituent with the

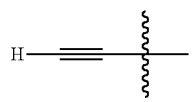 [SMILES: *C#C]

moiety or the $R^1$-linker moiety comprises performing a coupling reaction using a transition metal, such as palladium, and in certain embodiments the reaction is a Sonogashira coupling reaction (Sonogoshira, et al. *Tetrahedron Lett.* 1975, 4467-4470).

The alkyne moiety can be converted to a triazole linker. For example, the method may further comprise reacting the alkyne with $R^1$—$N_3$ to form a triazole having a formula

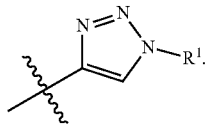

Embodiments of a method for detecting a target in a nucleic acid also are disclosed. Certain disclosed embodiments comprise providing a compound having a formula

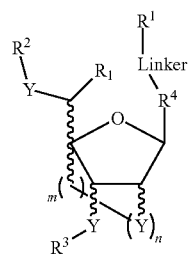

and contacting a nucleic acid, such as a genomic nucleic acid, a ribonucleic acid, a deoxyribonucleic acid, either single stranded or double stranded, with the compound in a manner effective to detect the target. The method is useful, amongst other things, for detecting a single nucleotide polymorphism. Certain disclosed embodiments include modifying a nucleic acid with the compound, thereby increasing thermal affinity of the nucleic acid, such as increasing the thermal affinity of the nucleic acid by greater than 0° C. to about 15° C., compared to the thermal affinity of an unmodified nucleic acid. Coupling the compound to the target can also decrease enzymatic degradation relative to an unmodified nucleic acid. Certain examples of targets include, without limitation, $HER^2$, EGFR gene, MET gene, CMYC gene, IGF1R, D5S271, KRAS, TYMS, lipoprotein lipase gene, RB1, p53, N-MYC, CHOP, FUS, FKHR, ALK, Ig heavy chain, CCND1, BCL2, BCL6, AP1, TOP2A, TMPRSS2, ERG, ETV1, EWS, FLI1, PAX3, PAX7, PTEN, AKT2, MYCL1, REL, and CSF1R.

Embodiments of a kit for isolating, purifying, amplifying, detecting, identifying or quantifying a nucleic acid also are disclosed. Such kits typically comprise at least one nucleoside unit having a formula

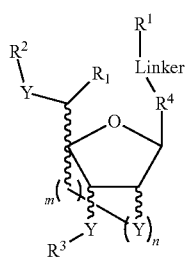

where the substituents are as stated above. For particular embodiments, the kit comprises disclosed oligonucleotides.

The foregoing and other objects, features, and advantages of the disclosed embodiments will become more apparent from the following detailed description, which proceeds with reference to the accompanying figures.

SEQUENCE LISTING

Figure 1:
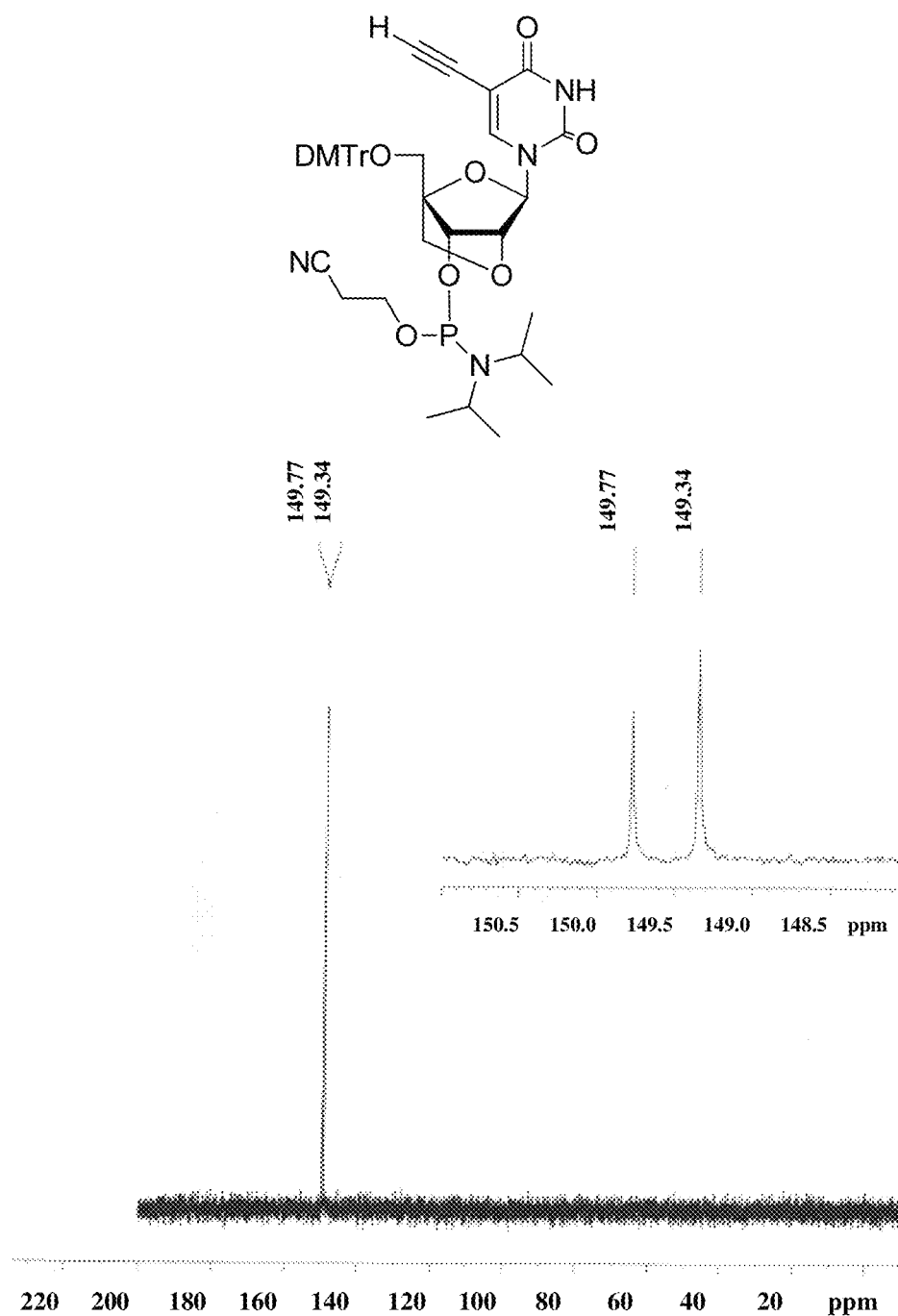
FIG. 1 is a nuclear magnetic resonance (NMR) spectrum of a disclosed embodiment of a β-D-LNA phosphoramidite.

The nucleic acid sequences listed in the accompanying sequence listing are shown using standard letter abbreviations for nucleotide bases, as defined in 37 C.F.R. 1.822.

The Sequence Listing is submitted as an ASCII text file, Annex C/St.25 text file, created on Sep. 10, 2010, 41 KB, which is incorporated by reference herein.

In the accompanying sequence listing:

SEQ ID NO: 1 is a synthesized nucleic acid sequence.

SEQ ID NO: 2 and 3 are complementary synthesized nucleic acid sequences.

SEQ ID NO: 4 and 5 are complementary synthesized nucleic acid sequences.

SEQ ID NO: 6 is a synthesized nucleic acid sequence used as a target for fluorescence studies.

SEQ ID NO: 7-11 are synthesized nucleic acid sequences modified with disclosed embodiments of β-D- and α-L-LNA compounds.

SEQ ID NO: 12-19 are synthesized nucleic acid sequences modified with disclosed embodiments of β-D-LNA compounds.

SEQ ID NO: 20-23 are synthesized nucleic acid sequences modified with conventional LNA compound X.

SEQ ID NO: 24-26 are synthesized nucleic acid sequences used for fluorescence studies.

SEQ ID NO: 27-30 are synthesized nucleic acid sequences modified with compound SEQ ID NO: 31-33 are synthesized nucleic acid sequences modified with compound P.

SEQ ID NO: 34-36 are synthesized nucleic acid sequences modified with compound P'.

SEQ ID NO: 37-48 are synthesized nucleic acid sequences modified with disclosed embodiments of α-L-LNA compounds and conventional LNA compound X'.

DETAILED DESCRIPTION

I. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

A wavy line ("〰") indicates a bond disconnection. A dashed line (" - - - ") illustrates that a bond may be formed at a particular position.

All nucleotide sizes or amino acid sizes, and all molecular weight or molecular mass values, given for nucleic acids or polypeptides or other compounds are approximate, and are provided for description.

Although methods and materials similar or equivalent to those described herein can be used in the practice or testing of the present disclosure, suitable methods and materials are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

Aliphatic:

Any open or closed chain molecule, excluding aromatic compounds, containing only carbon and hydrogen atoms which are joined by single bonds (alkanes), double bonds (alkenes), or triple bonds (alkynes). This term encompasses substituted aliphatic compounds, saturated aliphatic compounds, and unsaturated aliphatic compounds.

Analog, Derivative or Mimetic:

An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Aromatic:

A term describing conjugated rings having unsaturated bonds, lone pairs, or empty orbitals, which exhibit a stabilization stronger than would be expected by the stabilization of conjugation alone. It can also be considered a manifestation of cyclic delocalization and of resonance.

Aryl:

A substantially hydrocarbon-based aromatic compound, or a radical thereof (e.g. $C_6H_5$) as a substituent bonded to another group, particularly other organic groups, having a ring structure as exemplified by benzene, naphthalene, phenanthrene, anthracene, etc. This term also encompasses substituted aryl compounds.

Aryl Alkyl:

A compound, or a radical thereof ($C_7H_7$ for toluene) as a substituent bonded to another group, particularly other organic groups, containing both aliphatic and aromatic structures.

Complementary:

The natural binding of polynucleotides under permissive salt and temperature conditions by base-pairing. Complementarity may exist when only some of the nucleic acids bind, or when total complementarity exists between the nucleic acids.

Conjugating, Joining, Bonding or Linking:

Joining one molecule to another molecule to make a larger molecule. For example, making two polypeptides into one contiguous polypeptide molecule, or covalently attaching a hapten or other molecule to a polypeptide, such as an sCFv antibody. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Coupled:

The term "coupled" means joined together, either directly or indirectly. A first atom or molecule can be directly coupled or indirectly coupled to a second atom or molecule. A secondary antibody provides an example of indirect coupling. Coupling can occur via covalent, non-covalent, and ionic bond formation.

Derivative:

In chemistry, a derivative is a compound that is derived from a similar compound or a compound that can be imagined to arise from another compound, for example, if one atom is replaced with another atom or group of atoms. The latter definition is common in organic chemistry. In biochemistry, the word is used for compounds that at least theoretically can be formed from the precursor compound.

Displace(ment)(ed):

A reaction in which an atom, radical, or molecule (anionic or neutral) replaces another in a compound.

Double Stranded Nucleic Acid:

An oligonucleotide containing a region of two or more nucleotides having a double stranded motif.

Epitope:

An antigenic determinant. These are particular chemical groups or contiguous or non-contiguous peptide sequences on a molecule that are antigenic, that is, that elicit a specific immune response.

Fluorescence:

The emission of light by a substance that has absorbed light or other electromagnetic radiation of a different wavelength.

Fluorophore:

A functional group of a molecule which causes the molecule to be fluorescent. Typically, the functional group can absorb energy of a specific wavelength and re-emit energy at a different (but equally specific) wavelength.

Heteroaliphatic:

An aliphatic group, which contains one or more atoms other than carbon and hydrogen, such as, but not limited to, oxygen, sulfur, nitrogen, phosphorus, chlorine, fluorine, bromine, iodine, and selenium.

Homology:

As used herein, "homology" refers to a degree of complementarity. Partial homology or complete homology can exist. Partial homology involves a nucleic acid sequence that at least partially inhibits an identical sequence from hybridizing to a target nucleic acid.

Homopolymer:

This term refers to a polymer formed by the bonding together of multiple units of a single type of molecular species, such as a single monomer (for example, an amino acid).

Isolated:

An "isolated" microorganism (such as a virus, bacterium, fungus, or protozoan) has been substantially separated or purified away from microorganisms of different types, strains, or species. Microorganisms can be isolated by a variety of techniques, including serial dilution and culturing.

An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Leaving Group:

A molecular fragment that departs with a pair of electrons after heterolytic bond cleavage. Leaving groups can be anions or neutral molecules. Common anionic leaving groups can include halides, such as $Cl^-$, $Br^-$, and $I^-$, and sulfonate esters, such as para-toluenesulfonate ($TsO^-$), trifluoromethane-sulfonate ($TfO^-$), Common neutral molecule leaving groups can include $H_2O$, $NH_3$, alcohols, and gases ($N_2$, $O_2$, $CO_2$, CO, and $SO_2$).

Lewis Acid:

A chemical substance that can accept a pair of electrons from a Lewis base, B, which acts as an electron-pair donor, forming an adduct, AB as given by the following: $A+:B \rightarrow A-B$.

Linker:

As used herein, a linker is a molecule or group of atoms positioned between two moieties.

Lower Alkyl:

Any aliphatic chain that contains 1-10 carbon atoms.

Modified:

As used herein, "modified" refers to an oligonucleotide that has a non-natural composition, in that it comprises one or more synthetic nucleobases which can pair with a natural base.

Molecule of interest or Target:

A molecule for which the presence, location and/or concentration is to be determined. Examples of molecules of interest include proteins and nucleic acid sequences tagged with C5-functionalized locked nucleic acids.

Nucleobase:

As used herein, "nucleobase" includes naturally occurring nucleobases as well as non-natural nucleobases. A person of ordinary skill in the art will recognize that nucleobase encompases purine and pyrimidine derivatives, as well as heterocyclic and tautomers thereof.

Nucleophile:

A reagent that forms a chemical bond to its reaction partner (the electrophile) by donating both bonding electrons. A molecule or ion with a free pair of electrons can act as nucleophile.

Nucleotide:

Phosphorylated nucleosides are "nucleotides," which are the molecular building-blocks of DNA and RNA.

Nucleoside:

A glycoside of a heterocyclic base. The term "nucleoside" is used broadly as to include non-naturally occurring nucleosides, naturally occurring nucleosides as well as other nucleoside analogues. Illustrative examples of nucleosides are ribonucleosides comprising a ribose moiety as well as deoxyribonucleosides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

Oligonucleotide:

A plurality of joined nucleotides joined by native phosphodiester bonds. An oligonucleotide is a polynucleotide of between at least 2 and about 300 nucleotides in length. Typically, an oligonucleotide is a polynucleotide of between about 5 and about 50 nucleotides. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Pharmaceutically Acceptable Salt:

Pharmaceutically acceptable salts are more soluble in aqueous solutions than the corresponding free acids and bases from which the salts are produced; however, salts having lower solubility than the corresponding free acids and bases from which the salts are produced may also be formed. Pharmaceutically acceptable salts are typically counterbalanced with an inorganic base, organic base, or basic amino acid if the salts are positively charged; or the salt is counterbalanced with an inorganic acid, organic acid, or acidic amino acid if they are negatively charged. Pharmaceutically acceptable salts can also be zwitterionic in form. Salts can be formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, and tetramethylammonium hydroxide. Other elements capable of forming salts are well-known to those of ordinary skill in the art, e.g. all elements from the main groups I to V of the Periodic Table of the Elements, as well as the elements from the subgroups I to VIII. Any chemical compound recited in this specification may alternatively be administered as a pharmaceutically acceptable salt thereof. "Pharmaceutically acceptable salts" are also inclusive of the free acid, base, and, Descriptions of suitable pharmaceutically acceptable salts can be found in *Handbook of Pharmaceutical Salts, Properties, Selection and Use*, Wiley VCH (2002), which we herein incorporate by reference.

Polypeptide:

A polymer in which the monomers are amino acid residues that are joined together through amide bonds. When the amino acids are α-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Protecting Group:

A moiety that can be introduced into a molecule by chemical modification of a functional group. Protecting groups often are used to protect one functional group in order to obtain chemoselectivity in a chemical reaction with a different functional group. Suitable protecting groups are well known to those of ordinary skill in the art and can include aryl groups, aliphatic groups, heteroaliphatic groups, heteroaryl groups.

Protein:

A molecule, particularly a polypeptide, comprised of amino acids.

Purified:

The term "purified" does not require absolute purity; rather, it is intended as a relative term. Thus, for example, a purified compound is one that is isolated in whole or in part from other contaminants. Generally, substantially purified peptides, proteins, conjugates, or other active compounds for use within the disclosure comprise more than 80% of all macromolecular species present in a preparation prior to admixture or formulation of the peptide, protein, conjugate or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Quantum Yield:

A measure of the efficiency of the fluorescence process. The "quantum yield" of a radiation-induced process indicates the number of times that a defined event occurs per photon absorbed by the system.

Reactive Groups:

Formulas throughout this application refer to "reactive groups," which can be any of a variety of groups suitable for undergoing a chemical transformation as described herein. For example, the reactive group might be an amine-reactive group, such as an isothiocyanate, an isocyanate, an acyl azide, an NHS ester, an acid chloride, such as sulfonyl chloride, aldehydes and glyoxals, epoxides and oxiranes, carbonates, arylating agents, imidoesters, carbodiimides, anhydrides, and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Suitable carboxylate-reactive functional groups include diazoalkanes, diazoacetyl compounds, carbonyldiimidazole compounds, and carbodiimides. Suitable hydroxyl-reactive functional groups include epoxides and oxiranes, carbonyldiimidazole, N,N'-disuccinimidyl carbonates or N-hydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, Mannich condensation products, iodination reaction products, and combinations thereof. Photoreactive chemical functional groups include aryl azides, halogenated aryl azides, benzophonones, diazo compounds, diazirine derivatives, and combinations thereof.

Sample:

A biological specimen from a subject, such as might contain genomic DNA, RNA (including mRNA), protein, or combinations thereof. Examples include, but are not limited to, peripheral blood, urine, saliva, tissue biopsy, surgical specimen, amniocentesis samples and autopsy material.

Single Nucleotide Polymorphism:

A nucleic acid sequence variation occurring when a single nucleotide in the genome (or other shared sequence) differs between members of a species or paired chromosomes in an individual. For example, two sequenced nucleic acid fragments from different individuals, AAGCCTA to AAGCTTA, contain a difference in a single nucleotide.

Substantially Complementary:

As used herein, "substantially complementary refers to the oligonucleotides of the disclosed methods that are at least about 50% homologous to target nucleic acid sequence they are designed to detect, more preferably at least about 60%, more preferably at least about 70%, more preferably at least about 80%, more preferably at least about 90%, more preferably at least about 90%, more preferably at least about 95%, most preferably at least about 99%.

Transition Metal:

Any of the metallic elements within Groups 3 to 12 in the Periodic Table that have an incomplete inner electron shell and that serve as transitional links between the most and the least electropositive in a series of elements.

II. Introduction

Disclosed embodiments concern the synthesis and use of oligonucleotides modified with one or more C5- or C8-functionalized pyrimidine β-D-Locked Nucleic Acids (LNA) or C5- or C8-functionalized pyrimidine α-L-LNA building blocks. These modified oligonucleotides have a variety of applications, including applications within nucleic acid based therapeutics, diagnostics and nanosciences, particulary for applications that target single stranded DNA, single stranded RNA or double stranded DNA. These oligonucleotides exhibit high thermal affinity toward complementary single stranded DNA, single stranded DNA or double stranded DNA strands, along with high mismatch discrimination and/or significantly improved stability against nucleases. The nature of the C5-substituent of these building blocks influences cellular uptake of the oligonucleotide probes and their pharmacokinetics. These oligonucleotide probes are useful for modulating gene expression via the antisense/antigene/siRNA strategies or as miRNA antagonists/decoy oligonucleotides/DNAzymes/ribozymes, and for specific and sensitive detection of nucleic acid targets. Furthermore, when the functional moiety at the C5- or C8-position of C5- or C8-functionalized LNA or α-L-LNA building blocks is a chromophore, such as a fluorescent group, pronounced changes in output signals are observed upon hybridization to complementary single stranded DNA/RNA targets, with excellent discrimination of single nucleotide polymorphisms. Oligonucleotides modified with one or more C5- or C8-functionalized LNA and α-L-LNA compounds allow the generation of isolated/grouped/patterned/arrayed moieties in the grooves of nucleic acid complexes, for applications in material science.

III. C5-Functionalized Locked Nucleic Acid Compounds

A variety of conformationally restricted C5-functionalized nucleotides are presented. Disclosed embodiments have a general formula illustrated below.

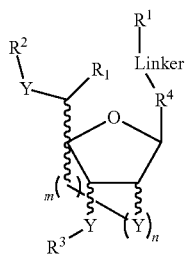

Formula 1

With respect to Formula 1, $R^1$ can be selected from hydrogen, hydroxyl, thiol, aliphatic, heteroaliphatic, aryl, heteroaryl, charged moieties, and metal complexes. $R^2$ can be selected from hydrogen, aliphatic, heteroaliphatic, aryl, heteroaryl, functional group protecting groups, a heteroatom-containing compound, such as a phosphorus-containing compound, a nitrogen-containing compound, an oxygen-containing compound, a sulfur-containing compound, and a selenium-containing compound. $R^3$ can be selected from hydrogen, a heteroatom-containing compound, such as a phosphorus-containing compound, a nitrogen-containing compound, an oxygen-containing compound, a sulfur-containing compound, and a selenium-containing compound. $R^4$ is a nucleobase selected from natural or non-natural nucleobases. The linker moiety can be selected from aliphatic, aryl, heteroaliphatic, and heteroaryl. Y can be selected from oxygen, sulfur, or $NR^5$ where $R^5$ is selected from hydrogen, aliphatic, aryl, heteroaliphatic, and heteroaryl; and m+n=2 to 4.

In certain embodiments, $R^1$ can be selected from ether, carbonyl, nitrile, disulfide, thioether, amine, amino acid, aminoglycoside, carbohydrate, fluorophores, nucleosides, nucleotides, oligonucleotides, peptides, intercalators, lipidoids, sterols, porphyrins, proteins, and vitamins. In particular embodiments, $R^1$ can be selected from amide, ester, carboxylic acid, aldehyde, ketone, spermine derivatives, guanidine groups, spin labels, electrochemical probes, fatty acids, glycerols, glycols, polyethylene glycol, redox active FRET labels, and ferrocene derivatives. Even more typically, $R^1$ can be selected from hydrogen, hydroxyl, thiol, primary amine, biotin, lauric acid, palmitic acid, stearic acid, fluorescein, rhodamine, cyanine, pyrene, perylene, coronene, adamantine, acridine, phenantroline, diphenylphosphorylazide, HIV Tat fragment, transportan, cholesterol, lithocolic-oleyl, myristoyl, docosanyl, lauroyl, stearoyl, palmitoyl, oleoyl, and linoleoyl, dihydrotestosterone, lithocholic acid, folic acid, and vitamin E.

Particular embodiments concern compounds satisfying one or more of general Formulas 2-5 provided below.

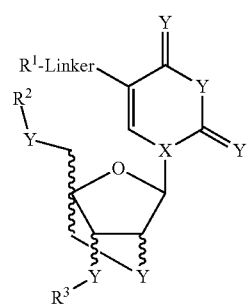

Formula 2

Formula 3

Formula 4

Formula 5

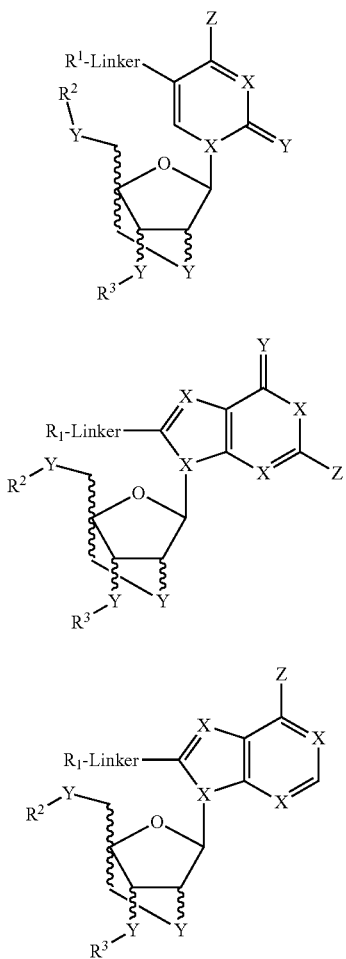

With reference to Formulas 2-5, $R^1$-$R^3$ are as recited above. X is nitrogen or carbon (with reference to Formula 2), or X is nitrogen, carbon or any combination thereof (with reference to Formulas 3-5), and Y is selected from oxygen, sulfur, and $N(R^5)$ where $R^5$ is selected from hydrogen, aliphatic, aryl, heteroaliphatic, and heteroaryl. Z is selected from ether, thioether, hydroxyl, sulfhydryl and $N(R^5)_2$ where $R^5$ is selected from hydrogen, aliphatic, aryl, heteroaliphatic, heteroaryl, and any combination thereof.

Formula 6

Formula 7

Formula 8

Formula 9

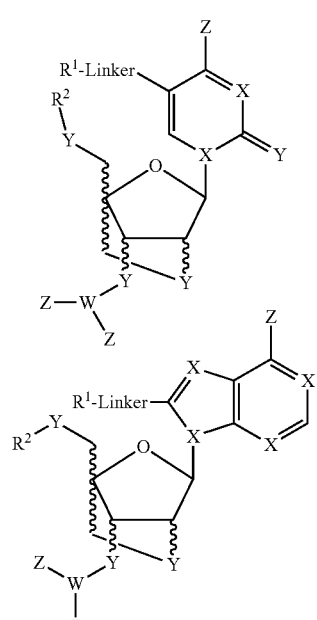

With reference to Formulas 6-9, $R^1$, $R^2$, X, Y, Z, and W are as recited above. Particular working embodiments include phosphoramidite compounds. A person of ordinary skill in the art will understand that the disclosed phosphoramidite compounds can be converted to nucleosides, and these compounds are claimed herein. Particular working embodiments are illustrated below.

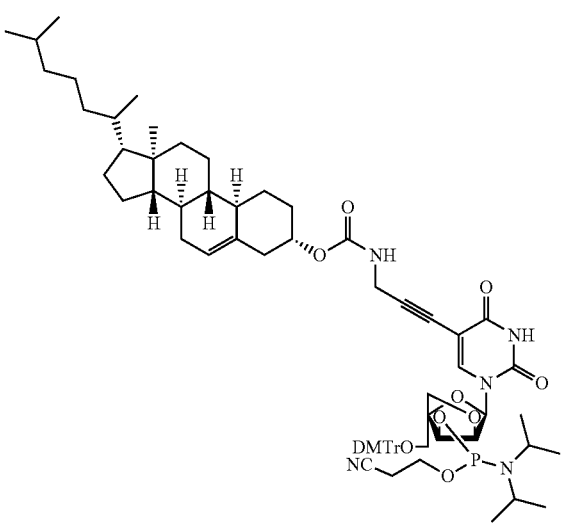

47
-continued
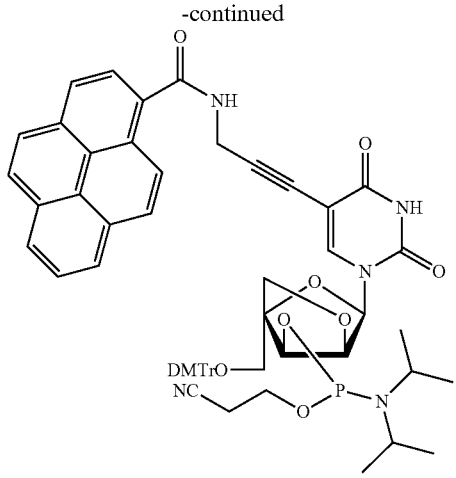
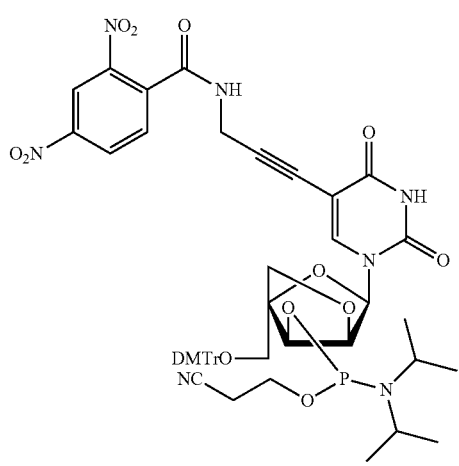
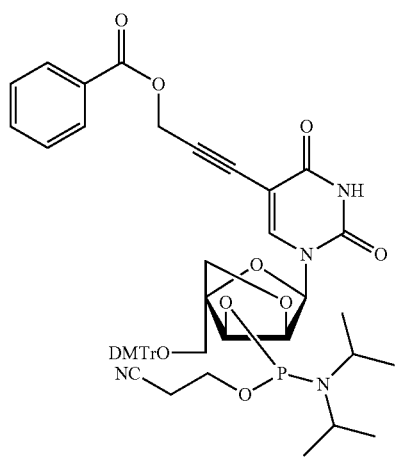
48
-continued
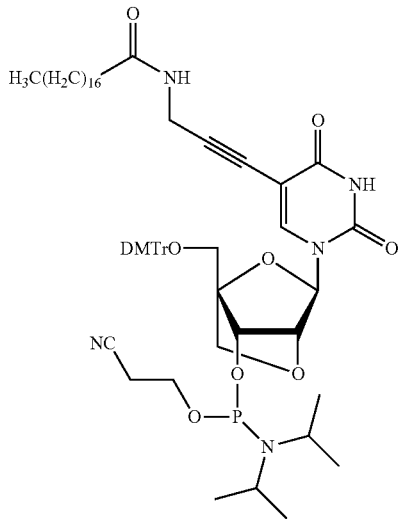
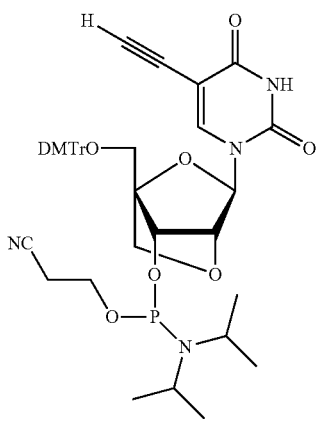
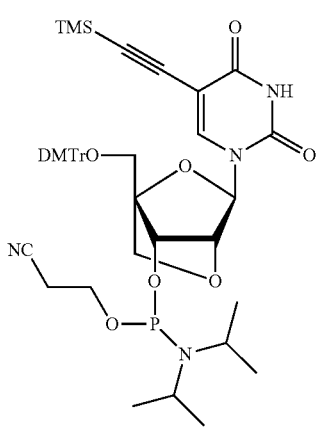

49
-continued
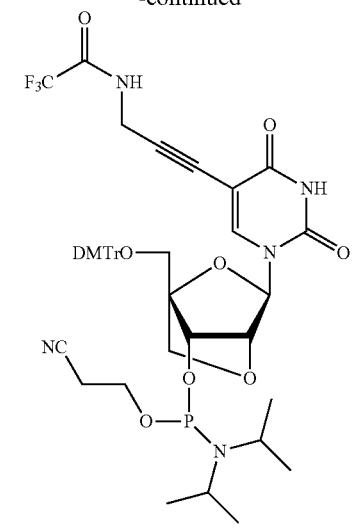
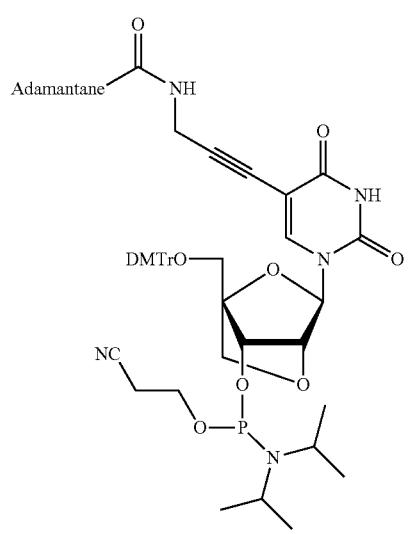
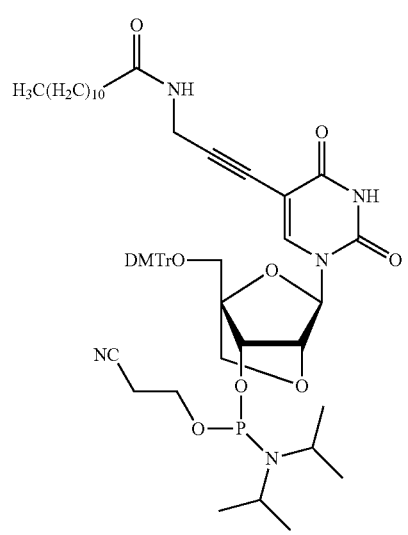
50
-continued
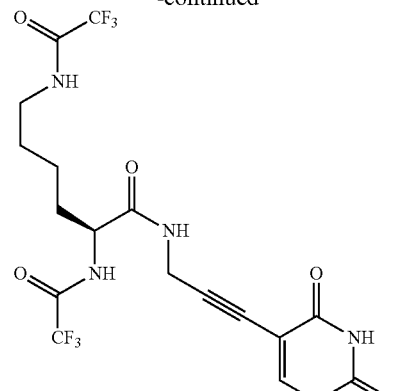
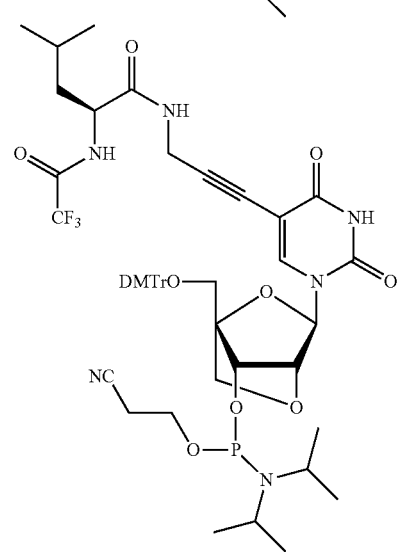

-continued

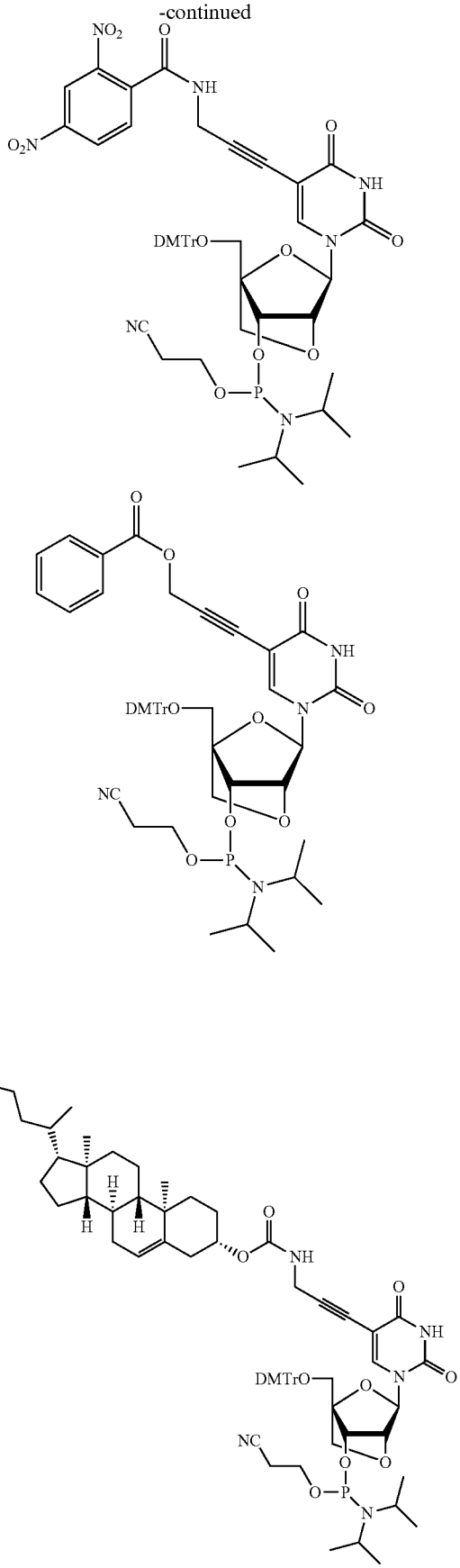

Particular embodiments have structures illustrated below.

Formula 10

Formula 11

Formula 12

Formula 13

With reference to Formulas 10-13, $R^1$, $R^2$, X, Y, and Z are as recited above. W can be selected from phosphorus, SH, and SeH. Particular working embodiments are phosphorylated compounds. A person of ordinary skill in the art will understand that the disclosed phosphorylated compounds can be converted to nucleosides, and these compounds are claimed herein. Particular embodiments are illustrated below.
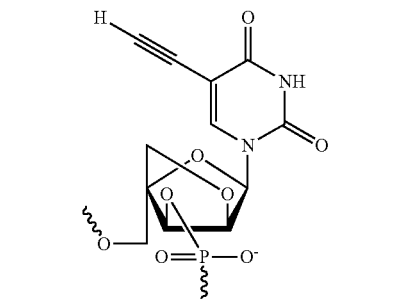
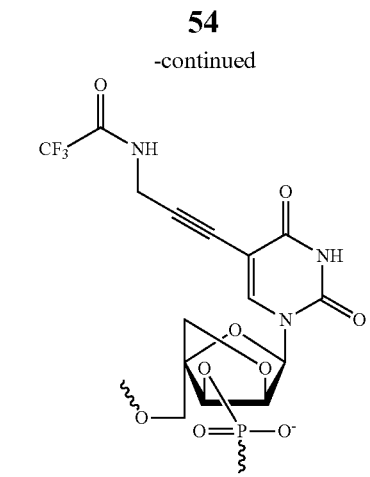
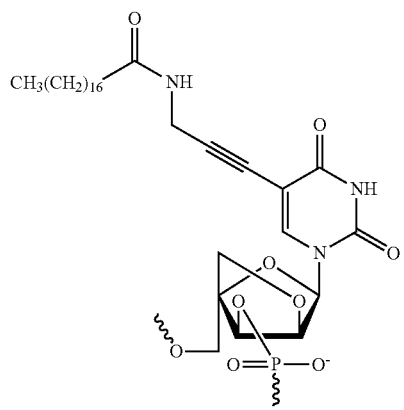
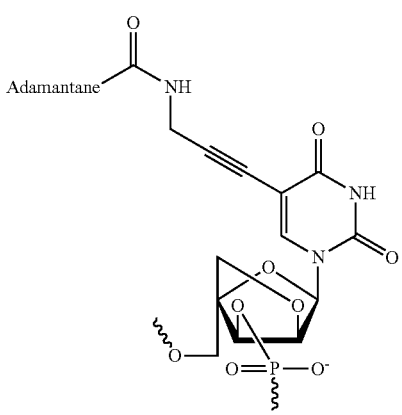
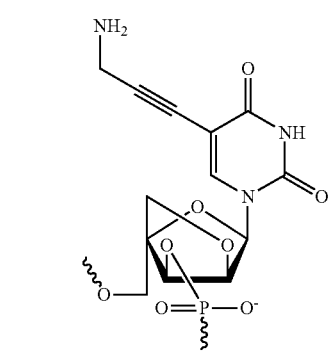
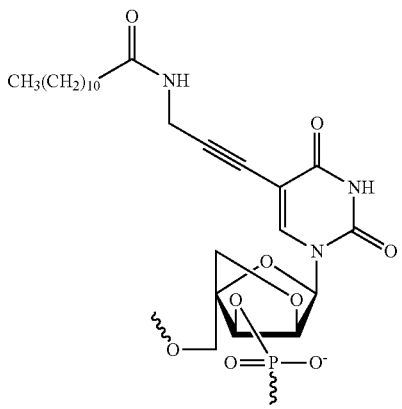
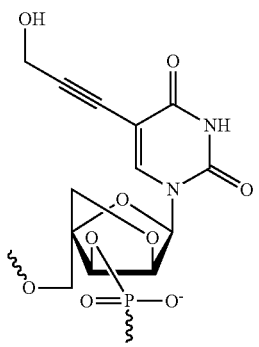
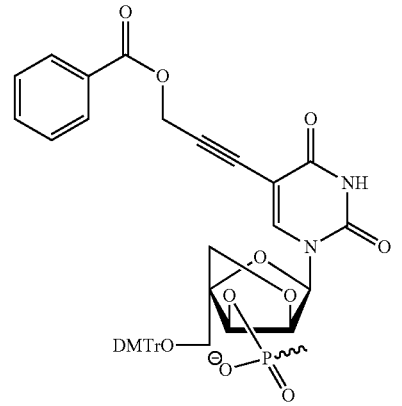

55
-continued
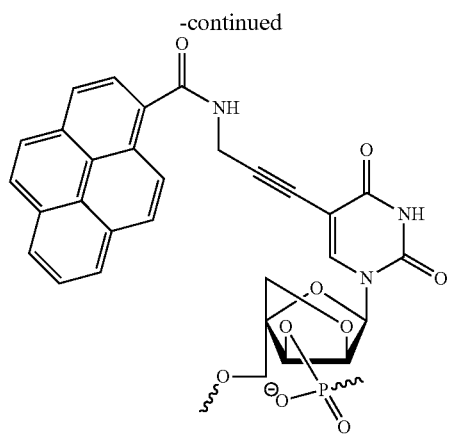
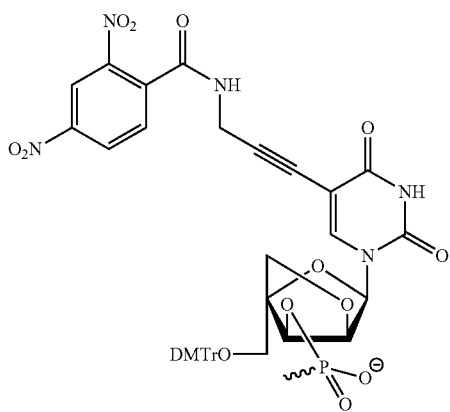
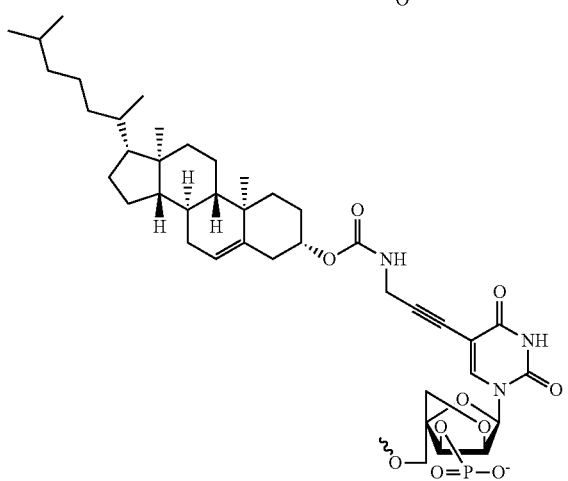
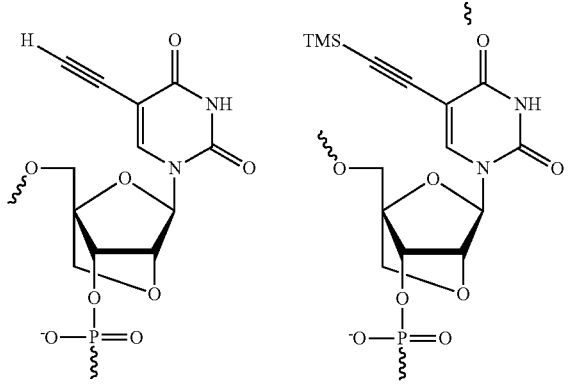
56
-continued
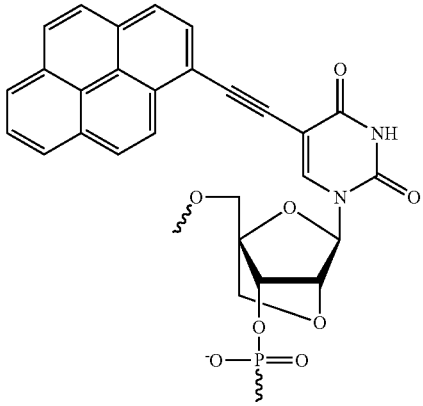
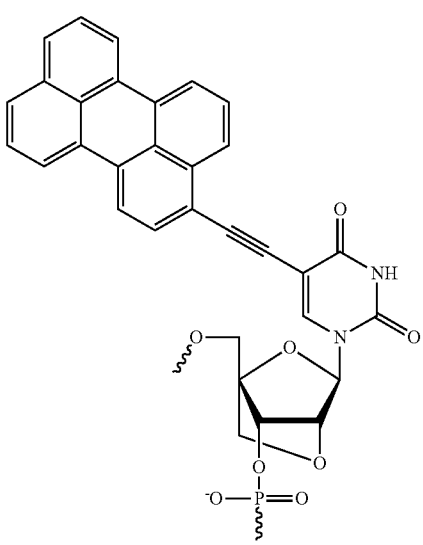
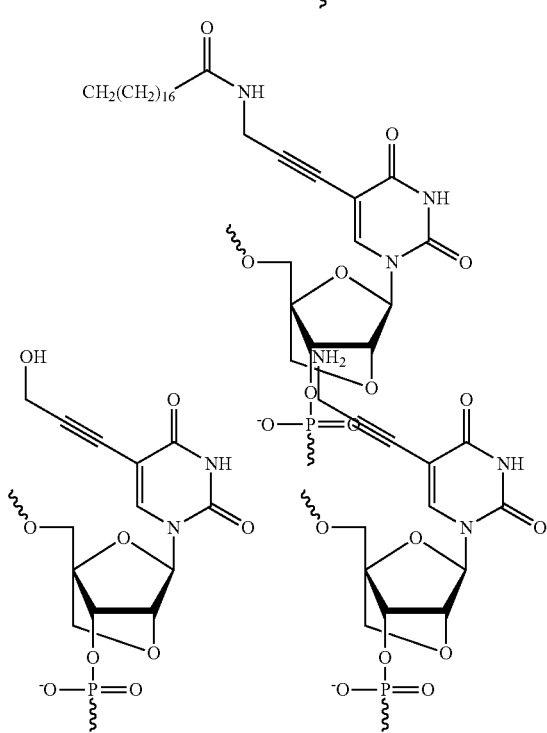

57
-continued
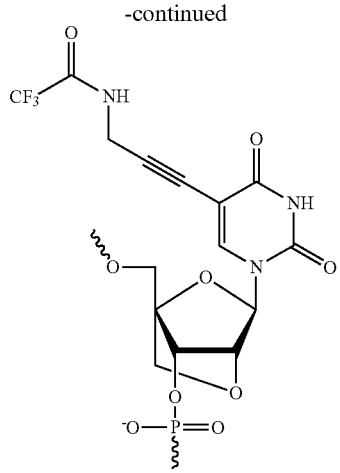
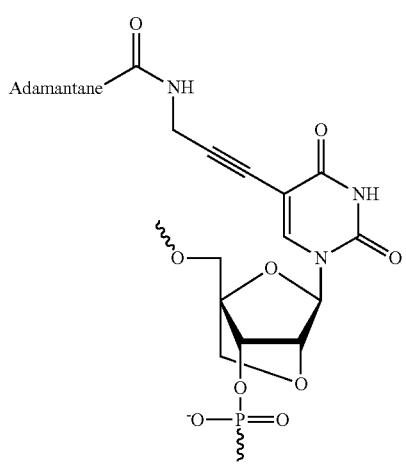
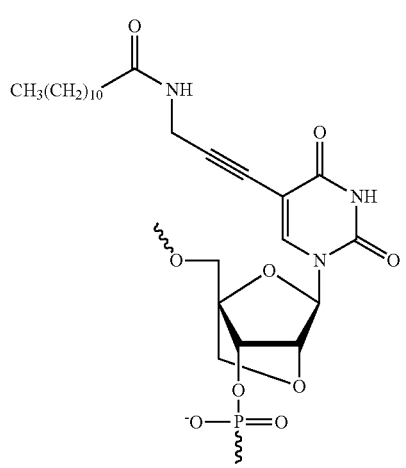
58
-continued
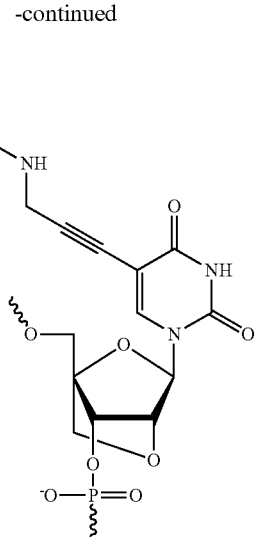
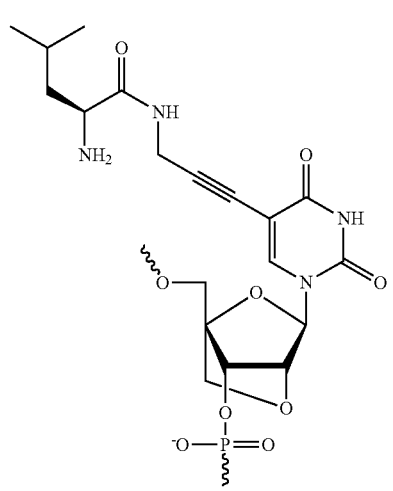
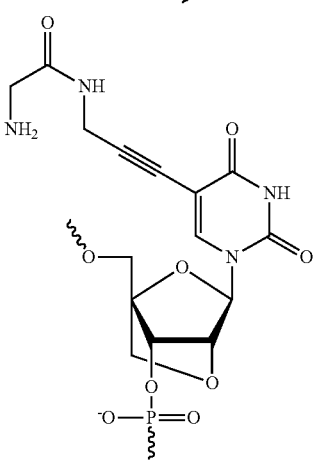
Certain embodiments concern compounds having an alkyne moiety as a linker, which binds the nucleobase to the $R^1$ moiety. Compounds having an alkyne have a general formula illustrated below. With reference to Formulas 14-17, $R^1$, $R^2$, $R^3$, X, Y, and Z are as recited above.

Formula 14
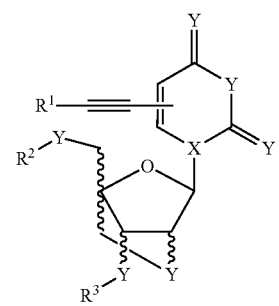

Formula 15
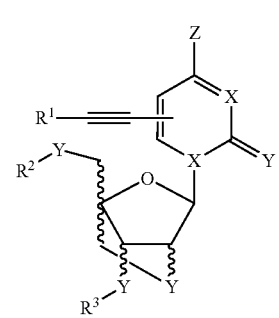

Formula 16
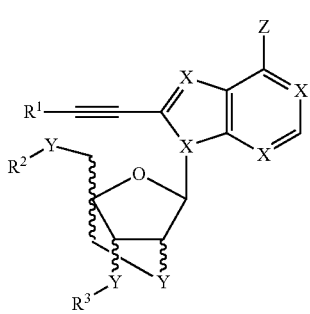

Formula 17
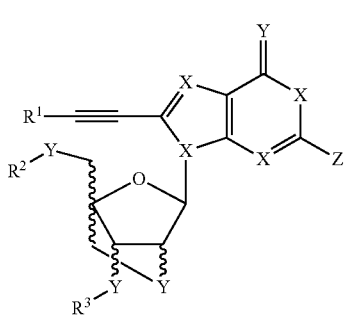

Formula 18
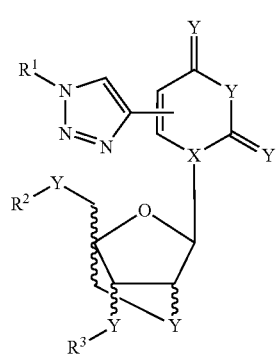

Formula 19
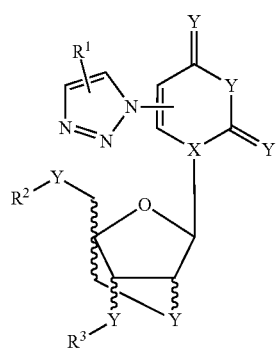

Formula 20
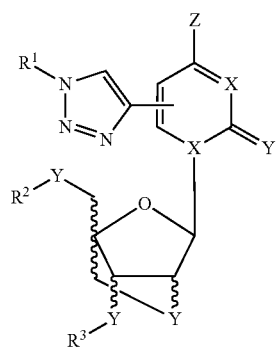

Formula 21
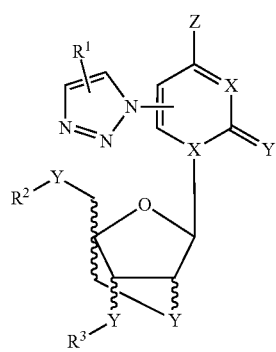

Other embodiments concern compounds having a triazole moiety as a linker. The triazole moiety may be formed from reacting an alkyne precursor with an azide-containing compound. In certain embodiments, the azide-containing compound can be attached to the nucleobase, in which case it undergoes intermolecular reaction with a separate alkyne moiety. Particular embodiments have the alkyne attached to the nucleobase, in which case the alkyne will undergo an intermolecular reaction with a separate azide moiety. Compounds containing triazole linkers have general formulas 18-25, illustrated below. With reference to Formulas 14-17, $R^1$, $R^2$, $R^3$, X, Y, and Z are as recited above.

Formula 22
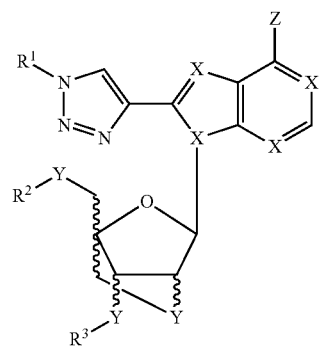

Formula 23
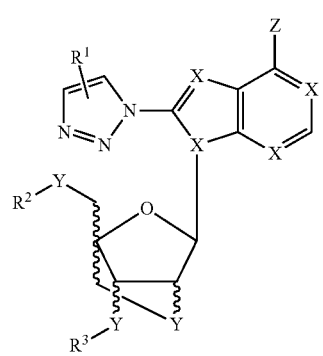

Formula 24
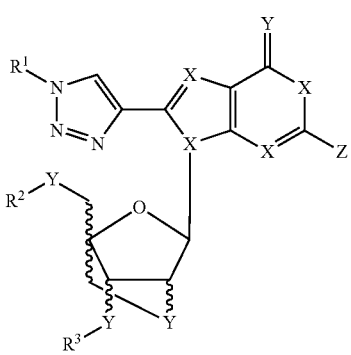

Formula 25
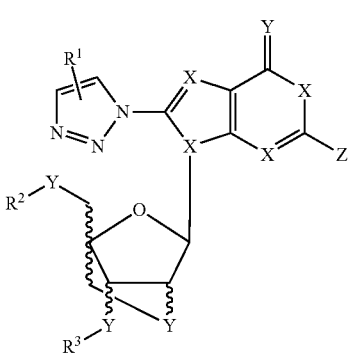

Particular working embodiments are phosphoramidite compounds or phosphorylated compounds. A person of ordinary skill in the art will understand that the disclosed phosphoramidite compounds and/or phosphorylated compounds can be converted to nucleosides, and these compounds are claimed herein. Particular working embodiments are illustrated below.

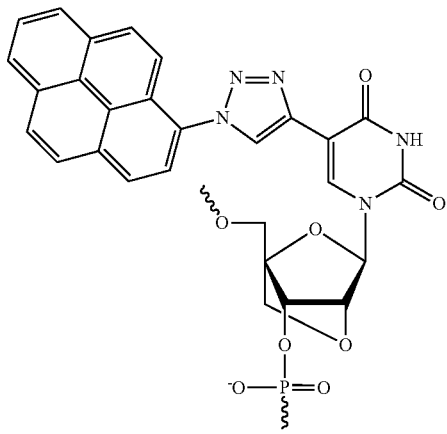

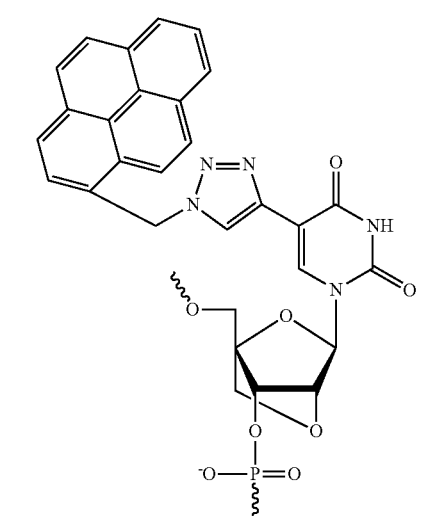

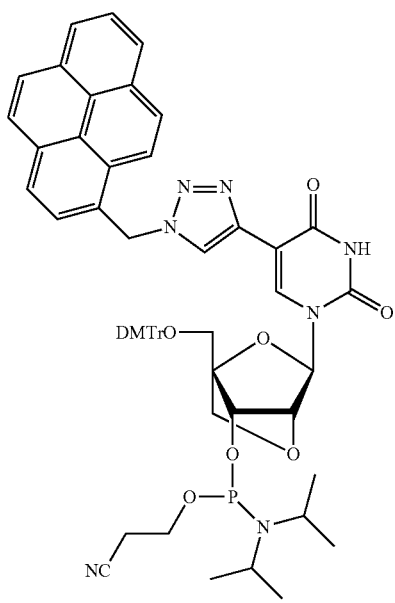

-continued

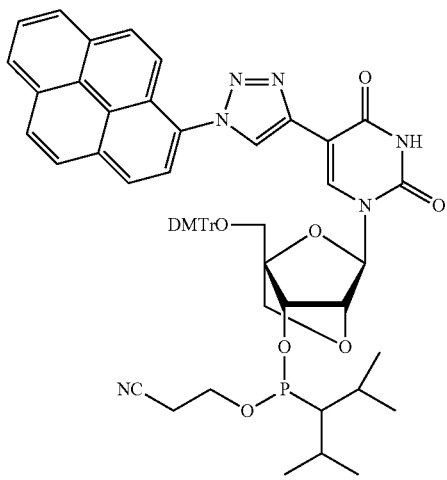

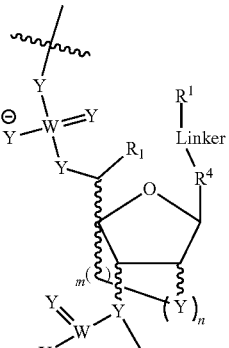

Formula 27

Disclosed embodiments concern the use of C5- or C8-functionalized LNA and α-L-LNA compounds to form oligonucleotides. Particular embodiments can be incorporated into a sequence containing at least two nucleotides to about 50 nucleotides. More typically, the C5- or C8-functionalized LNA and α-L-LNA compounds will be combined with at least one unmodified nucleotide to about 49 unmodified nucleotides or with at least one C5- or C8-functionalized LNA and/or C5- or C8-functionalized α-L-LNA nucleotide to 100 percent of the number nucleotides present in the oligonucleotide. Oligonucleotides comprising particular embodiments of C5- or C8-functionalized LNA and α-L-LNA have the following general formulas.

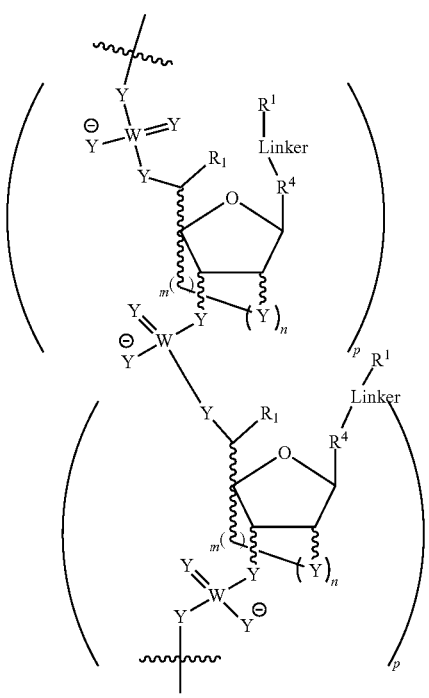

Formula 26

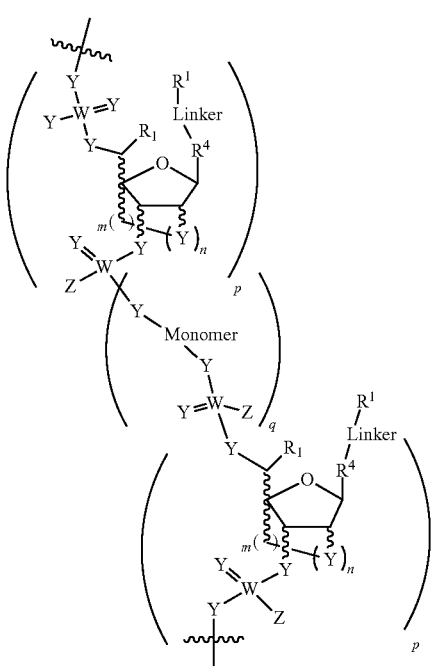

Formula 28

-continued

Formula 29

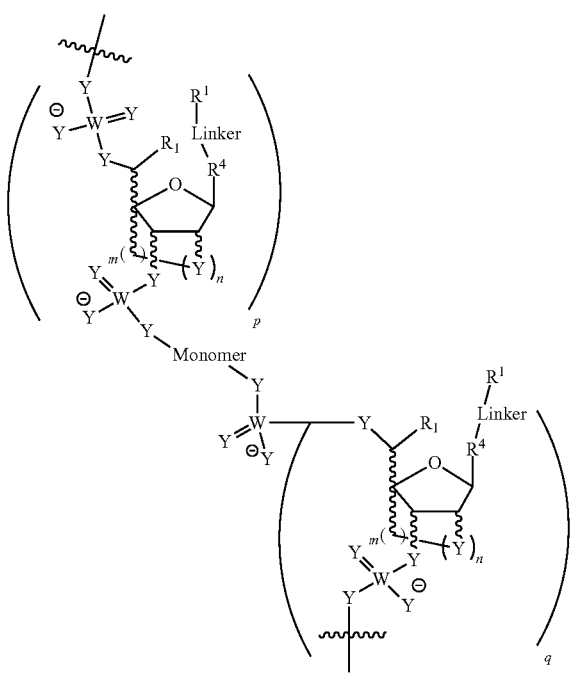

With reference to Formulas 26-29, $R^1$, $R^4$, W, Y, m, and n are as defined above, Z is selected from ether, thioether, hydroxyl (an anions thereof), sulfhydryl (and anions thereof), and $N(R^5)_2$ where $R^5$ independently is selected from hydrogen, aliphatic, aryl, heteroaliphatic, heteroaryl; p can be from 1 to about 50 percent of the value of q, and q can be from 1 to about 49. More typically, the value of q+p ranges from about 9 to about 35. Even more particularly, q+p ranges from about 8 to about 25. The monomer can be selected from deoxyribonucleotides, ribonucleotides, O2'-alkylated ribonucleotides, locked nucleic acids, α-L-locked nucleic acids, and other conformationally-restricted nucleotides.

IV. Method for Making Locked Nucleic Acid Analogs

Disclosed embodiments concern the synthesis of C5- or C8-functionalized locked nucleic acids. The disclosed methods can be used to synthesize a variety of C5- or C8-functionalized locked nucleic acids.

A. C5- or C8-Functionalized α-L-LNA Compounds

Scheme 1

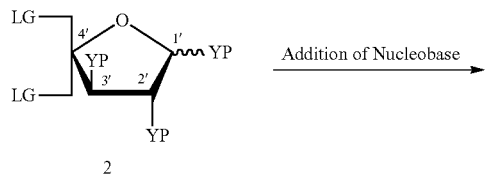

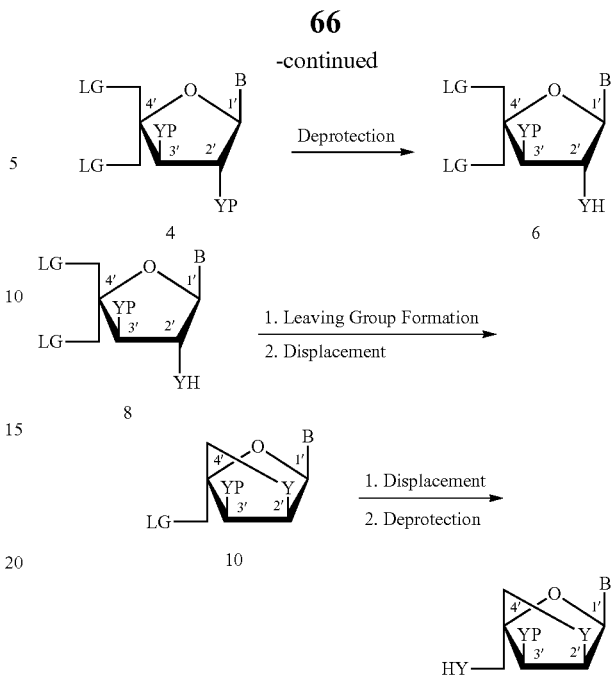

Scheme 1 illustrates the synthesis of α-L-locked nucleic acids. With reference to Scheme 1, Y is a heteroatom moiety; P is a heteroatom protecting group; B is a nucleobase, and LG is a leaving group capable of being displaced by a nucleophile. In particular embodiments, Y is selected from oxygen, sulfur, or $NR^5$ where $R^5$ is selected from hydrogen, aliphatic, aryl, heteroaliphatic, and heteroaryl. P is selected from aliphatic, aryl, heteroaliphatic and heteroaryl (more typically, P is selected from, but is not limited to, acetyl, benzyl, benzoyl, methoxyethoxymethyl ether, methoxymethyl ether, p-methoxybenzyl, methylthiomethyl ether, pivaloyl, tetrahydropyranyl, trityl, and silyl ether). B can be selected from natural and non-natural nucleobases, with particular examples including adenosine, cytosine, guanine, thymine, and uracil. LG can be selected from halides, sulfonyls, carbonyls, amides, sulfonates, and phosphonates; more typically, LG is selected from mesyl (Ms), tosyl (Ts), besoyl (Bs), and triflate (OTf).

According to Scheme 1, furanose 2 (which can be obtained from commercially available material) is transformed to a nucleobase-substituted furanose 4 by reaction with a nucleobase and a Lewis acid. The Lewis acid can be selected from, but is not limited to, TMSOTf, $BF_3 \cdot OEt_2$, $AlCl_3$, $SnCl_4$, and $Ti(OiPr)_4$.

Upon addition of the nucleobase, the furanose ring can be further manipulated to form a locked nucleic acid. The Y2' protecting group can be removed using methods known to a person of ordinary skill in the art, such as those disclosed in Greene ("Greene's Protective Groups in Organic Synthesis", Wiley-Interscience; $4^{th}$ edition, Oct. 30, 2006), which is incorporated herein by reference. Particular embodiments use an acid in a protonated solvent, such as HCl in MeOH. The deprotected Y2' group can then be converted to a leaving group using methods known to a person of ordinary skill in the art, such as a sulfonate-containing reagent and a base. For example, the sulfonate-containing reagent can be methanesulfonate, tosyl chloride, or trifluoromethylsulfonyl anhydride. The base can be selected from hydroxide bases selected from, but not limited to, sodium hydroxide, lithium hydroxide, potassium hydroxide, and cesium hydroxide. Once the bicycle has been formed, the remaining leaving group at C4' is displaced and subsequently deprotected to provide bicycle 12.

Scheme 2

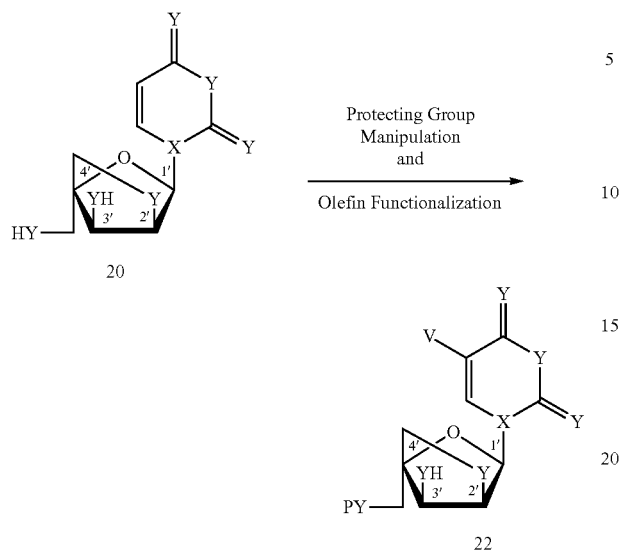

Scheme 2 illustrates the formation of a C5-functionalized, locked nucleic acid precursor 22. With reference to Scheme 2, X is nitrogen or carbon and Y is selected from oxygen, sulfur, and $N(R^5)$ where $R^5$ is selected from hydrogen, aliphatic, aryl, heteroaliphatic, and heteroaryl. P is a heteroatom protecting group and V is selected from halogen (such as Cl, Br, F, and I) or a triflate (OTf).

As illustrated in Scheme 2, Y3' deprotection, followed by Y4' protection can provide an intermediate capable of undergoing olefin functionalization. An olefin of the nucleobase can be functionalized using any reagents known to a person of ordinary skill in the art to elicit halogenation or oxygenation, such as electrophilic halogenation and/or oxidation reagents. Examples of halogenation reagents include, but are not limited to, $I_2$, n-iodosuccinimide, $Cl_2$, oxalyl chloride, thionyl chloride, n-chlorosuccinimide, n-chlorophthalimide, $Br_2$, n-bromoacetamide, n-bromophthalimide, n-bromosuccinimide, n-fluorobenznesulfonimide, 1-1'-difluoro-2,2'-bipyridinium bis(tetrafluoroborate), 1-fluoro-2,4,6-trimethylpyridinium tetrafluoroborate, 1-fluoro-2,4,6-trimethylpyridinium trifluoromethanesulfonate, 1-fluoro-2,6-dichloropyridinium tetrafluoroborate, 1-fluoropyridinium pyridine heptafluorodiborate, 1-fluoropyridinium trifluoromethanesulfonate, and 2,6-dichloro-1-fluoro-pyridinium trifluoromethanesulfonate. Examples of oxygenation reagents include m-chloroperbenzoic acid, dimethyldioxirane, titanium isopropoxide or vanadium acetyl acetonate in combination with tert-butyl hydrogen peroxide. The functionalized olefin 22 is an intermediate that can be functionalized with various substituents to provide a wide number of C5-functionalized locked nucleic acids.

Scheme 3

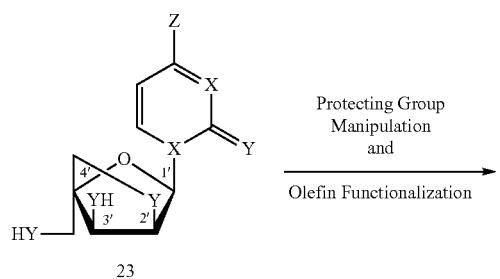

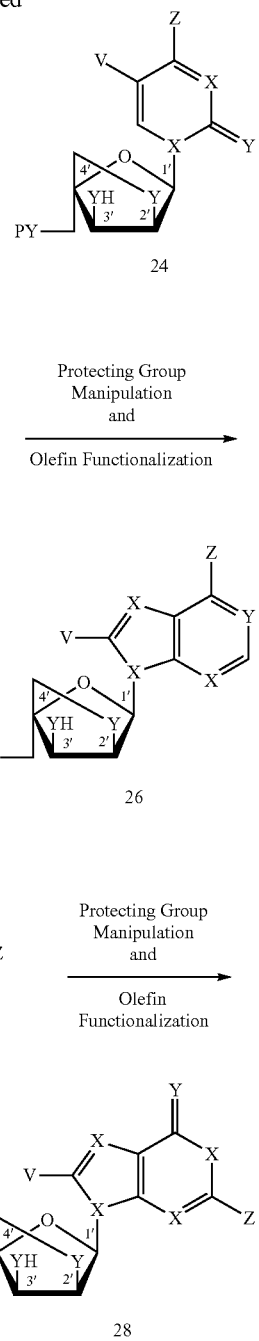

Scheme 3 illustrates particular embodiments in which the nucleobase can be selected from a purine, a purine analog, a pyrimidine, or a pyrimidine analog, thus forming additional intermediates for the formation of C5- or C8-functionalized locked nucleic acids. With reference to Scheme 3, X is nitrogen, carbon or any combination thereof, and Y is selected from oxygen, sulfur, and $N(R^5)$ where $R^5$ is selected from hydrogen, aliphatic, aryl, heteroaliphatic, and heteroaryl. Z is selected from ether, thioether, hydroxyl, sulfhydryl and $N(R^5)_2$ where $R^5$ is selected from hydrogen, aliphatic, aryl, heteroaliphatic, heteroaryl, and any combination thereof. P is a heteroatom protecting group and V is selected from halogen (such as Cl, Br, F, and I) or a triflate (OTf). A person of ordinary skill in the art will recognize that similar conditions

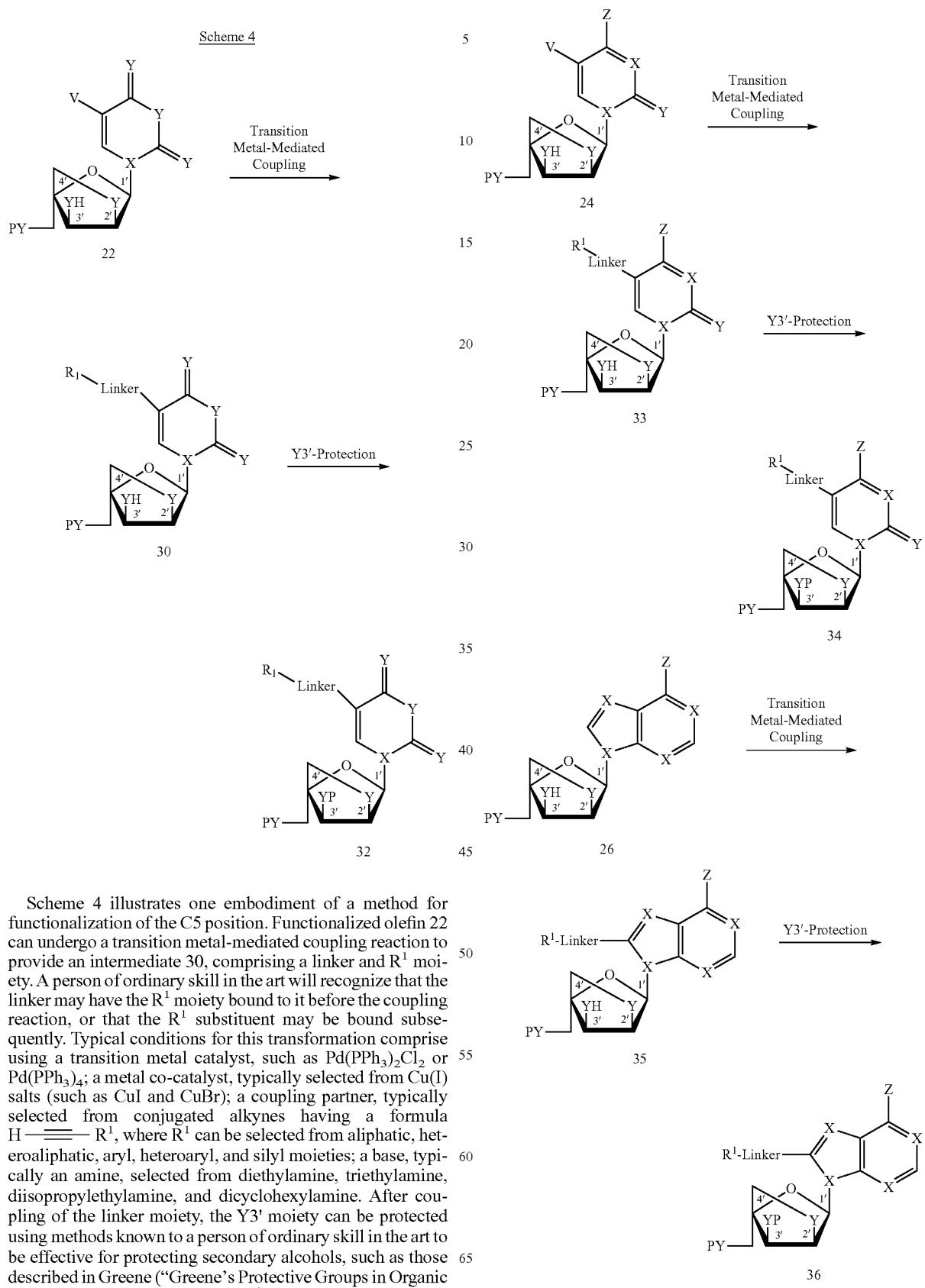

Scheme 4 illustrates one embodiment of a method for functionalization of the C5 position. Functionalized olefin 22 can undergo a transition metal-mediated coupling reaction to provide an intermediate 30, comprising a linker and $R^1$ moiety. A person of ordinary skill in the art will recognize that the linker may have the $R^1$ moiety bound to it before the coupling reaction, or that the $R^1$ substituent may be bound subsequently. Typical conditions for this transformation comprise using a transition metal catalyst, such as $Pd(PPh_3)_2Cl_2$ or $Pd(PPh_3)_4$; a metal co-catalyst, typically selected from Cu(I) salts (such as CuI and CuBr); a coupling partner, typically selected from conjugated alkynes having a formula H≡≡≡—$R^1$, where $R^1$ can be selected from aliphatic, heteroaliphatic, aryl, heteroaryl, and silyl moieties; a base, typically an amine, selected from diethylamine, triethylamine, diisopropylethylamine, and dicyclohexylamine. After coupling of the linker moiety, the Y3' moiety can be protected using methods known to a person of ordinary skill in the art to be effective for protecting secondary alcohols, such as those described in Greene ("Greene's Protective Groups in Organic Synthesis", Wiley-Interscience; 4$^{th}$ edition, Oct. 30, 2006).

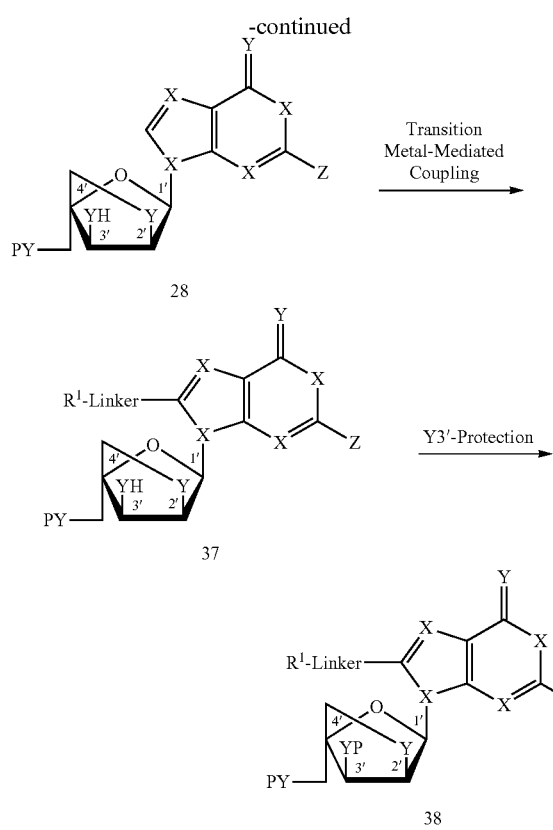

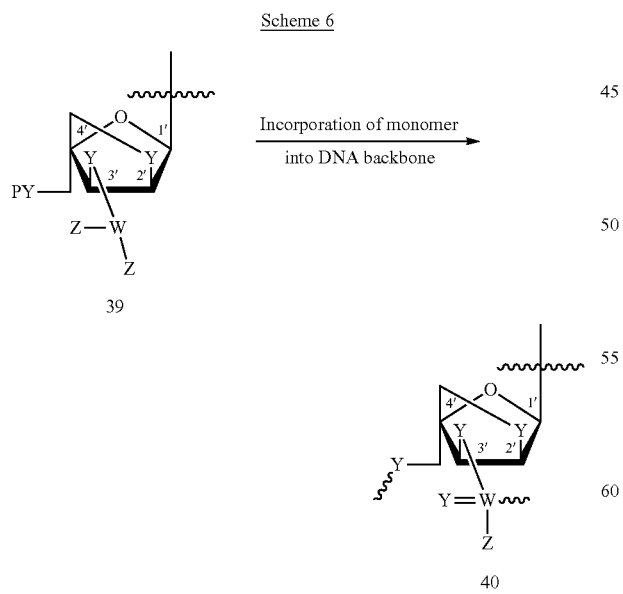

Scheme 5 illustrates particular embodiments in which the nucleobase can be selected from a purine, a purine analog, a pyrimidine, or a pyrimidine analog, thus forming additional C5- or C8-functionalized locked nucleic acids. A person of ordinary skill in the art will recognize that similar conditions to those described for Scheme 4 can be utilized with the compounds illustrated in Scheme 5.

Scheme 6 illustrates the incorporation of C5- or C8-modified α-L-LNA compounds into a DNA backbone. The wavy line indicates that W is bound to other monomers of the particular sequence. A person of ordinary skill in the art will recognize that compounds 39 can be coupled with another C5- or C8-modified LNA compound, an unmodified monomer or any combination thereof. The C5- or C8-functionalized locked nucleic acid compounds unit 39 can be converted to oligomers by removing the Y3' protecting group and converting it to a phosphate backbone which connects compounds 39 with other monomers in the sequence. In addition, the protecting group of Y4' can be removed to provide another location to which other monomers of the sequence can attach. Standard conditions for this transformation were employed, such as those known to a person of ordinary skill in the art, including using a DNA synthesizer. Conditions used for the conversion of particular embodiments can include using an activator, such as an imidazole, triazole, or tetrazole compound and an oxidant, such as a peroxide compound. Particular embodiments utilize dicyanoimidazole as the activator. Examples of peroxide compounds include, but are not limited to, hydrogen peroxide or tert-butyl hydrogen peroxide.

A working embodiment of the current method is illustrated below in Scheme 7.

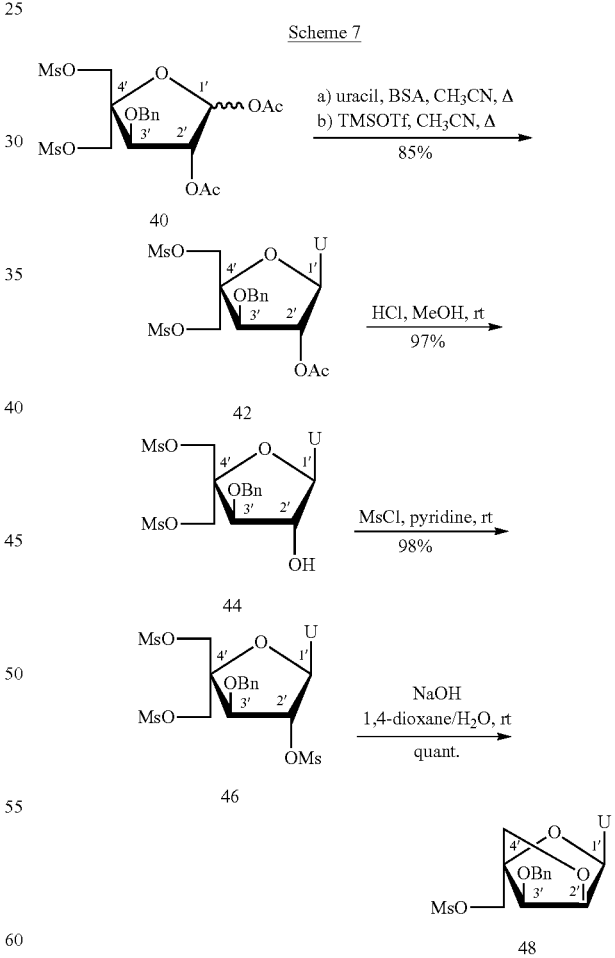

Following the procedure described by Wengel et al. (*J. Am. Chem. Soc.*, 2002, 124, 2164-2176), compound 40 was converted to nucleoside 42 in 85% yield. The O2' acetate protecting group is removed under acidic conditions using hydrochloric acid in methanol to provide the free hydroxyl moiety 44 in 97%. O2' mesylate formation and subsequent displacement using sodium hydroxide provides the desired bicycle 48 in quantitative yield.

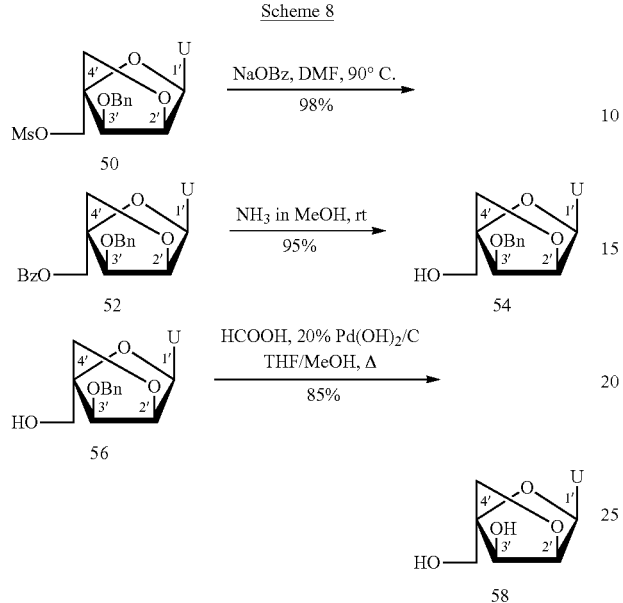

Scheme 8 illustrates the formation of a particular embodiment. The mesylate moiety of bicycle 50 can be displaced using sodium benzoate in dimethylformamide to afford benzoyl-protected 52. The benzoate protecting group can then subsequently be removed using ammonia in methanol to provide 54. The O3' benzyl protecting group can also be removed using acetic acid with palladium hydroxide on carbon to provide compound 58. These conditions provide the desired diol in good yield, with minimal formation of undesired by-products.

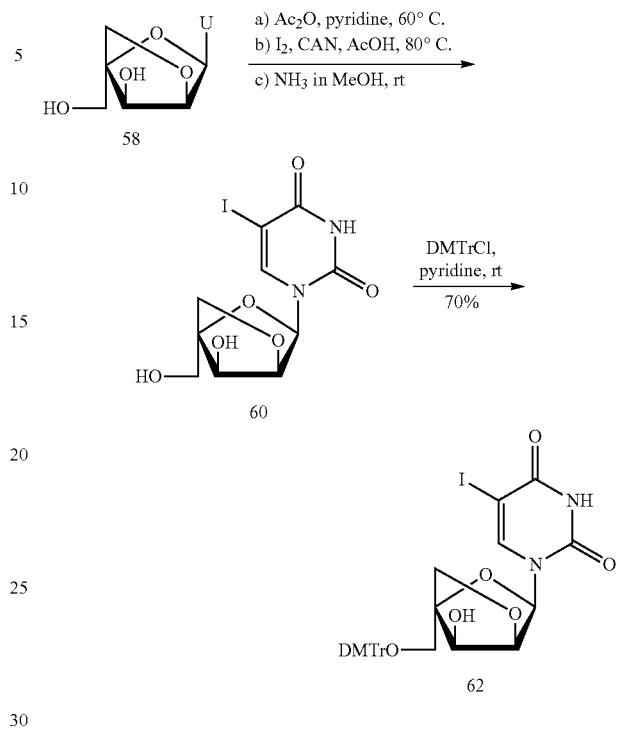

Scheme 9 represents one embodiment wherein the nucleobase can be halogenated in preparation for further C5 functionalization. Bicycle 58 can be protected, such as with as an acetate moiety using acetic anhydride and pyridine. The uracil moiety may be subsequently iodinated using I₂, ceric ammonium nitrate and acetic acid, providing iodide 62 in 80% yield. After deprotection of the acetate moiety using ammonia in methanol, the primary hydroxyl group of iodide 62 can be protected, such as with a dimethoxytrityl protecting group.

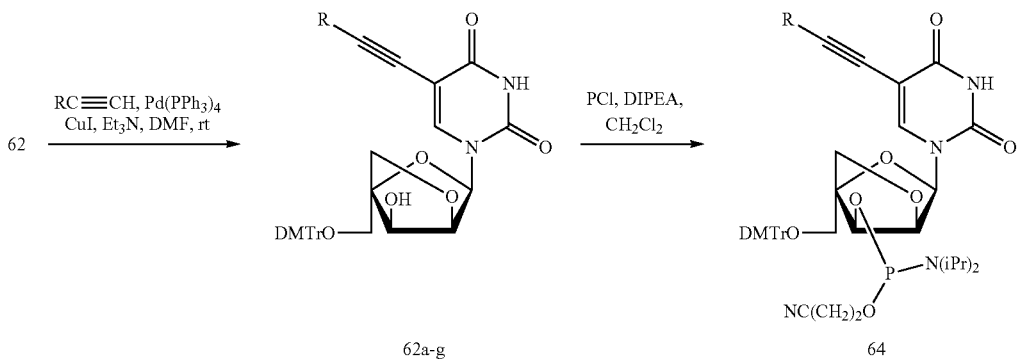

62a R = SiMe₃ (84%)
62b R = H
62c R = CH₂OBz (76%)
62d R = CH₂NHCOCF₃ (84%)
62e R = CH₂NHC(O)(CH₂)₁₆CH₃ (55%)
62f R = CH₂NHC(O)Chol (76%)
62g R = CH₂NHC(O)Py (79%)

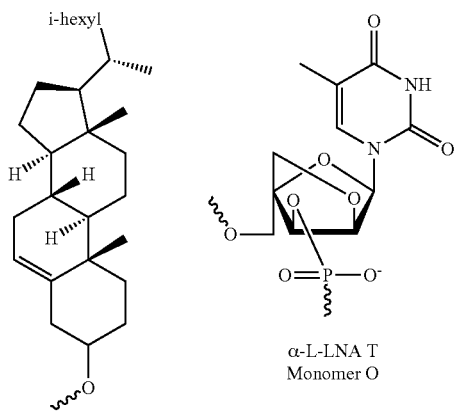

α-L-LNA T
Monomer O

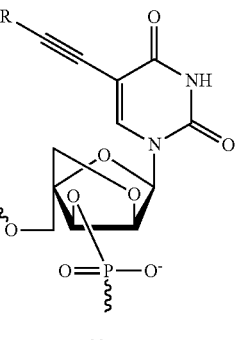

66

C5-functionalized α-L-LNA

Monomer S: R = H
Monomer V: R = CH$_2$OH
Monomer W: R = CH$_2$NH$_2$
Monomer X: R = CH$_2$NHC(O)(CH$_2$)$_{16}$CH$_3$
Monomer Y: R = CH$_2$NHC(O)Chol
Monomer Z: R = CH$_2$NHC(O)Py Scheme 10 illustrates manipulation of vinyl iodide 62 to append a variety of R$^1$-functionalized alkyne linkers, thus providing an efficient route to a variety of C5-functionalized, locked nucleic acids. The vinyl iodide undergoes a Sonogashira coupling reaction using palladium tetrakis, a functionalized alkyne, copper iodide, and triethylamine in dimethylformamide at room temperature. In particular embodiments, the alkyne is functionalized with a trimethyl silyl group (62a), which can subsequently be removed to provide a terminal alkyne 62b. Once the alkyne linker has been attached to the nucleobase, the free C3' hydroxyl group can be protected with a protecting group, such as a phosphoramidite moiety. The phosphoramidite protecting group can be converted to a phosphate group and/or phosphate backbone through the use of a DNA synthesizer. Typical conditions for this transformation include using 4,5-dicyanoimidazole as an activator, followed by oxidation to provide stepwise coupling yields of greater that 95%. Scheme 10 illustrates the synthesis of a number of C5-functionalized, locked nucleic acids.

B. C5- or C8-Functionalized β-D-LNA Compounds

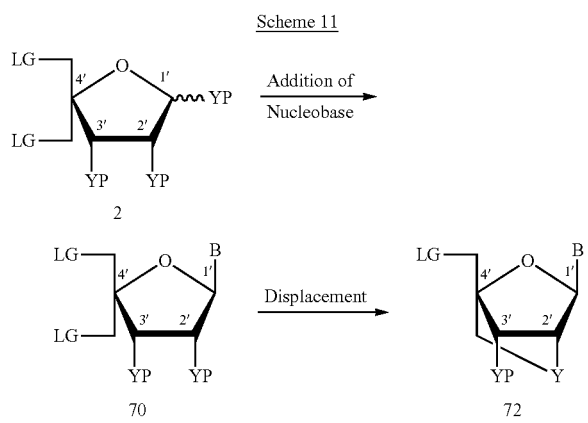

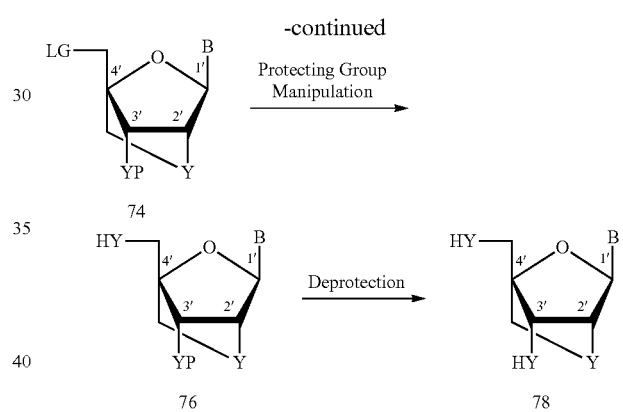

Scheme 11 illustrates the synthesis of β-D-locked nucleic acids. With reference to Scheme 11, Y is a heteroatom moiety; P is a heteroatom protecting group; B is a nucleobase, and LG is a leaving group capable of being displaced by a nucleophile. In particular embodiments, Y is selected from oxygen, sulfur, or NR$^5$ where R$^5$ is selected from hydrogen, aliphatic, aryl, heteroaliphatic, and heteroaryl. P is selected from aliphatic, aryl, heteroaliphatic and heteroaryl (more typically, P is selected from, but is not limited to, acetyl, benzyl, benzoyl, methoxyethoxymethyl ether, methoxymethyl ether, p-methoxybenzyl, methylthiomethyl ether, pivaloyl, tetrahydropyranyl, trityl, and silyl ether). B can be selected from non-natural and natural nucleobases, including adenosine, cytosine, guanine, thymine, and uracil. LG can be selected from sulfonyls, carbonyls, amides, sulfonates, and phosphonates; more typically, LG is selected from mesyl (Ms), tosyl (Ts), besoyl (Bs), triflate (OTO, and halides (Cl, F, Br, I).

According to Scheme 11, furanose 2 (which can be obtained from commercially available material) is transformed to a nucleobase-substituted furanose 4 by reaction with a nucleobase and a Lewis acid. The Lewis acid can be selected from, but is not limited to, TMSOTf, BF$_3$.OEt$_2$, AlCl$_3$, and Ti(OiPr)$_4$.

Upon addition of the nucleobase, the furanose ring can be further manipulated to form a locked nucleic acid. Tandem deprotection and cyclization to produce bicycle 74 can be accomplished using basic conditions, wherein the base typically is a metal hydroxide, such as, but not limited to, sodium hydroxide, lithium hydroxide, potassium hydroxide, and cesium hydroxide. Once the bicycle has been formed, the remaining C4' substituent can be manipulated to provide a deprotected moiety, followed by subsequent deprotection of the C3' functional group.

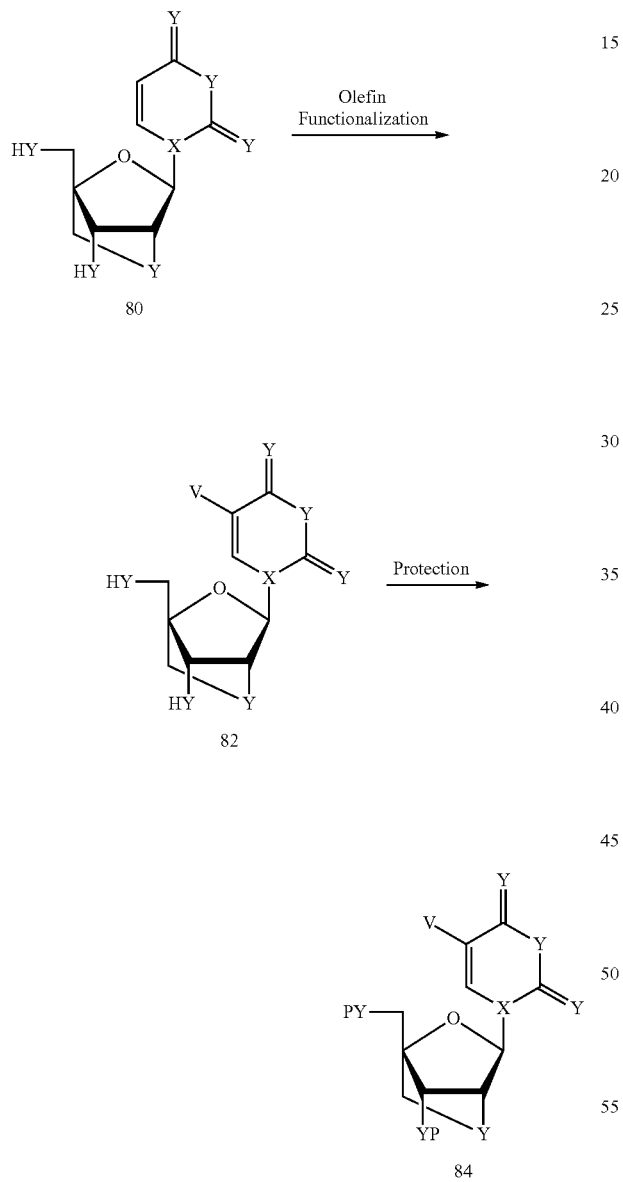

Scheme 12

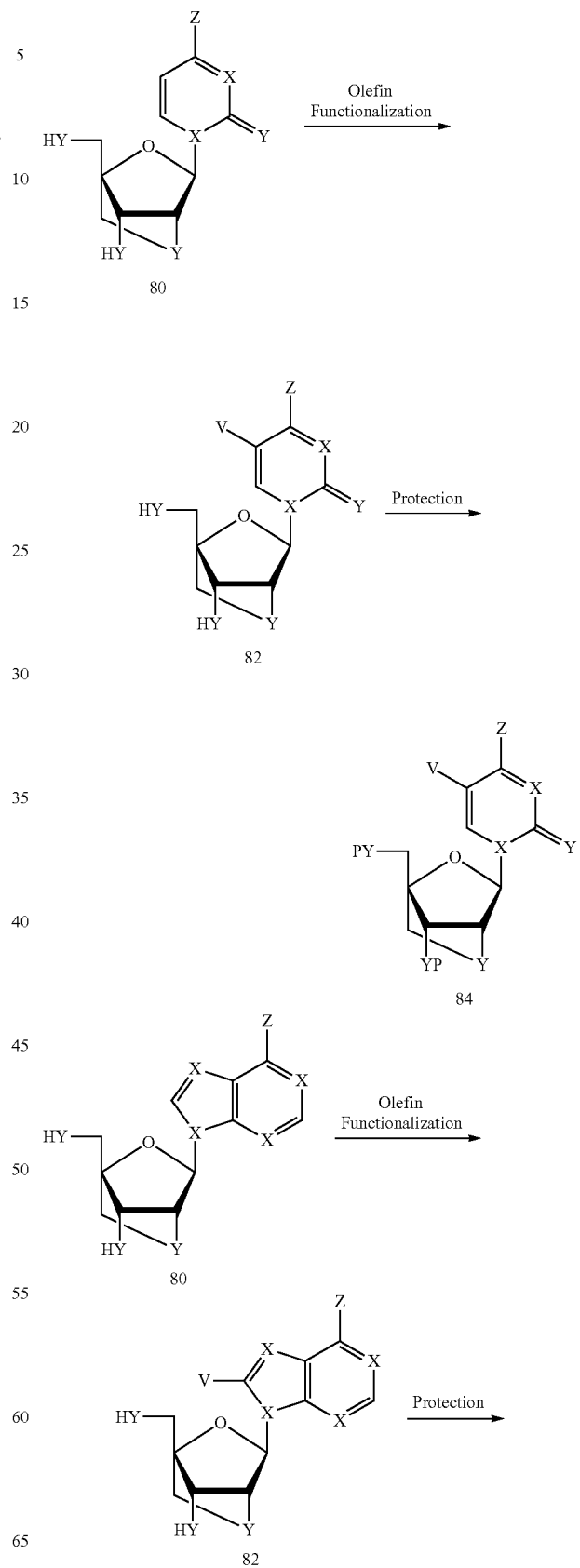

Scheme 13

Scheme 12 illustrates the formation of a C5-functionalized locked nucleic acid precursor. The olefin of the nucleobase can be functionalized using methods described for the α-series. After functionalization, the remaining C4' functional group can be protected in order to produce functionalized olefin 82. The vinyl halide 84 is an intermediate that can be functionalized with various substituents to provide a wide number of C5-functionalized locked nucleic acids.

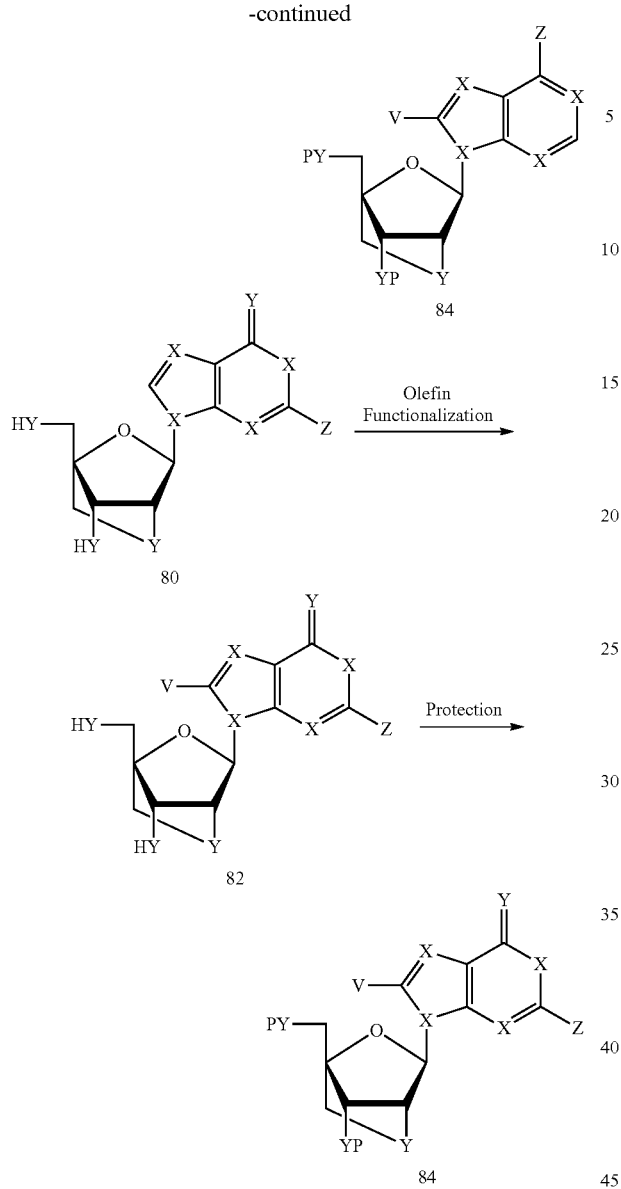

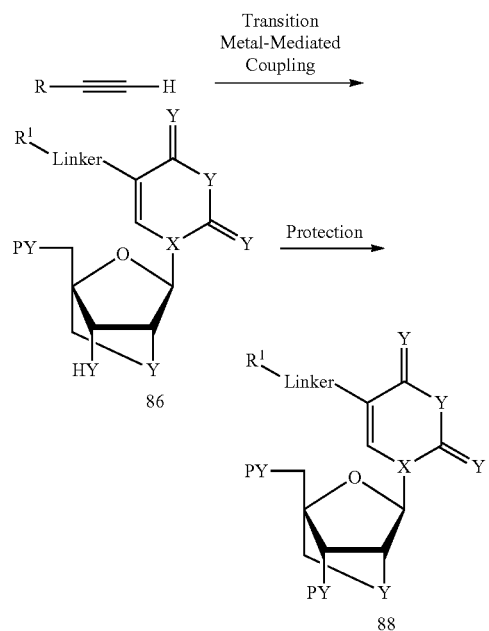

Scheme 13 illustrates particular embodiments in which the nucleobase can be selected from a purine, a purine analog, a pyrimidine, or a pyrimidine analog, thus producing intermediates for forming additional C5- or C8-functionalized locked nucleic acids. A person of ordinary skill in the art will recognize that similar conditions to those described for Scheme 12 can be utilized with the compounds illustrated in Scheme 13.

Scheme 14 illustrates the further functionalization of the C5 position. Nucleoside 84 can undergo a transition metal-mediated coupling reaction to provide a functionalized intermediate 86, comprising a linker and an $R^1$ moiety. A person of ordinary skill in the art will recognize that the linker may have the $R^1$ moiety bound to it before the coupling reaction, or that the $R^1$ substituent may be bound subsequently. Typical conditions for this metal-mediated coupling reaction comprise a transition metals catalyst; typically, $Pd(PPh_3)_2Cl_2$ or $Pd(PPh_3)_4$; a metal co-catalyst, typically selected from Cu(I) salts (such as CuI and CuBr); a coupling partner, typically selected from conjugated alkynes having a formula H≡≡≡$R^1$, where $R^1$ can be selected from aliphatic, heteroaliphatic, aryl, heteroaryl, and silyl moieties; a base selected from diethylamine, triethylamine, diisopropylethylamine, and dicyclohexylamine. After appendage of the linker moiety, the O3' can be protected using methods known to a person of ordinary skill in the art to be effective for protecting secondary alcohols, such as those described in Greene ("Greene's Protective Groups in Organic Synthesis", Wiley-Interscience; 4th edition, Oct. 30, 2006). Particular embodiments having different nucleobases are illustrated below.

Scheme 14

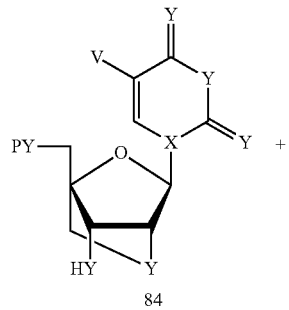

Scheme 15

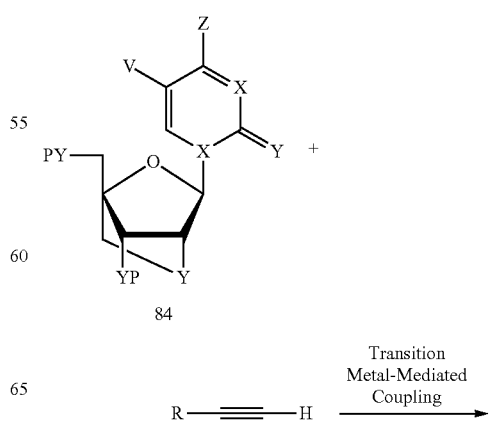

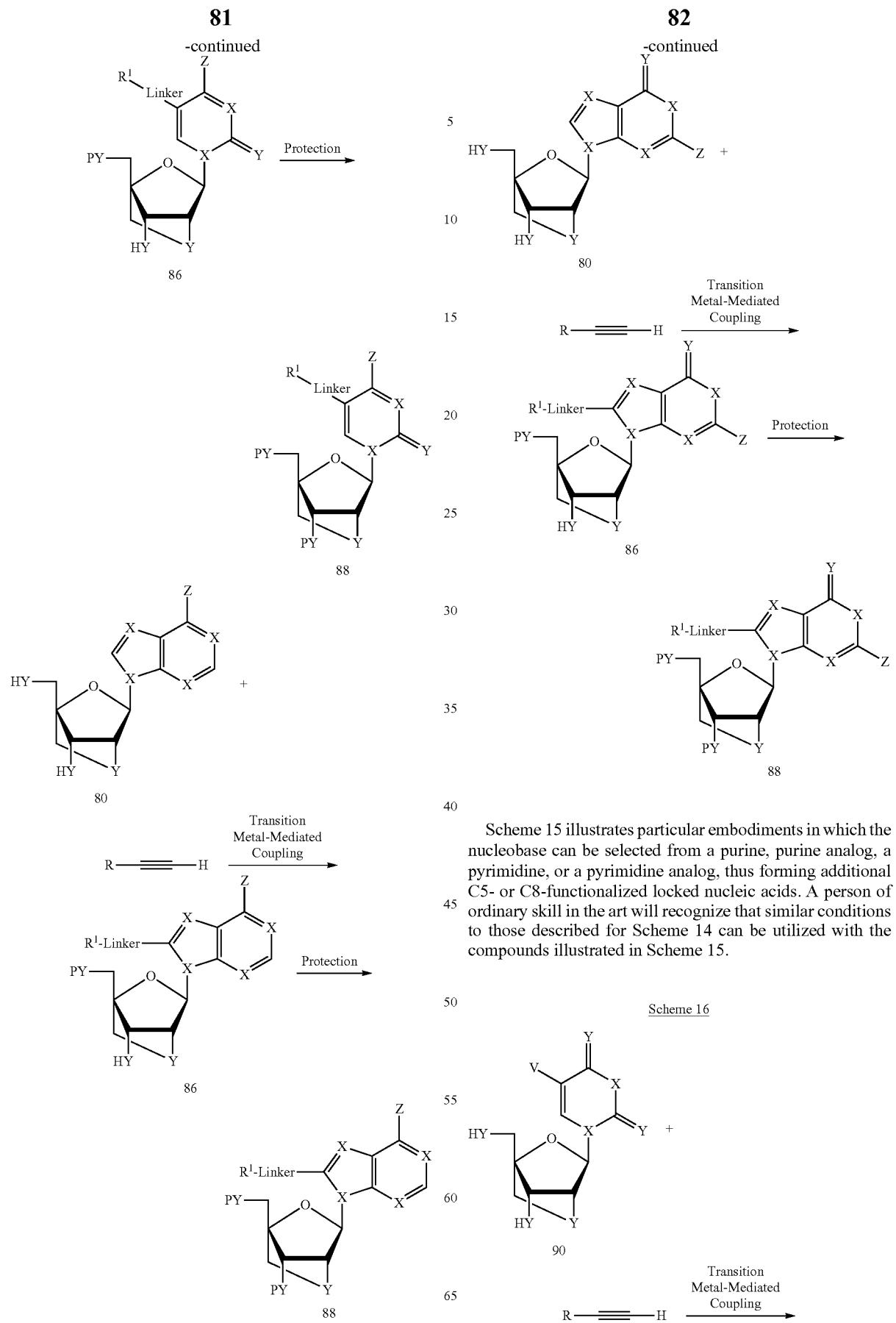

Scheme 15 illustrates particular embodiments in which the nucleobase can be selected from a purine, purine analog, a pyrimidine, or a pyrimidine analog, thus forming additional C5- or C8-functionalized locked nucleic acids. A person of ordinary skill in the art will recognize that similar conditions to those described for Scheme 14 can be utilized with the compounds illustrated in Scheme 15.

Scheme 16

-continued

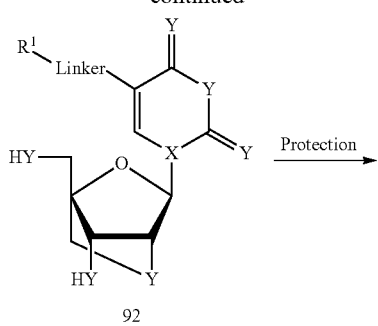

92

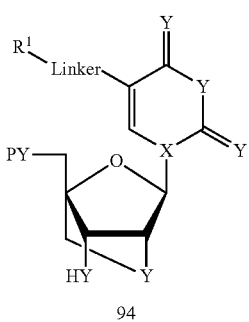

94

Scheme 16 illustrates an alternate route that can also be utilized to form C5-functionalized locked nucleic acids. This synthetic route begins with an unprotected moiety at C4'. Functionalized olefin 90 can undergo a transition metal-mediated coupling with a functionalized alkyne to give the coupled product 92, as described above. Subsequently, the C4' and the C3' functional groups can be protected with appropriate protecting groups. This alternate route can be utilized with the purine and pyrimidine analogs illustrated in Scheme 15. The C5- or C8-functionalized locked nucleic acid compounds can be converted to oligomers, such as by using a DNA synthesizer, where the O3' protecting group is removed and converted to a phosphate backbone.

Scheme 17

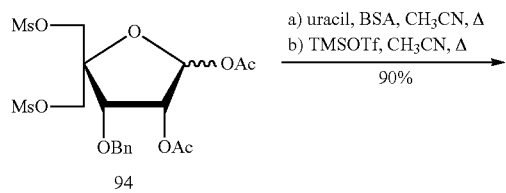

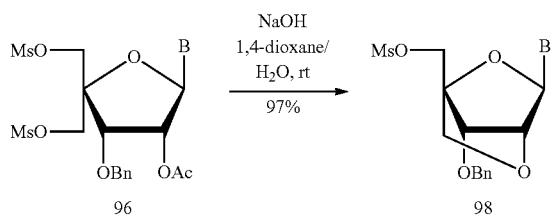

-continued

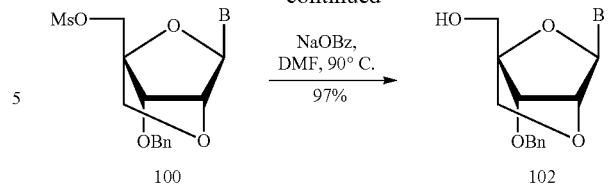

Scheme 17 illustrates a particular embodiment of the current method. Following Koshkin's general route (Koshkin et al. *J. Org. Chem.* 2001, 66, 8504-8512) treatment of the anomeric mixture of furanose 94 (obtained using the procedure described by Lomholt, et. al., *Curr. Protoc. Nucleic Acid Chem.* 2002, 4.12.1-4.12.16) with persilylated uracil and trimethylsilyl triflate in refluxing acetonitrile initially afforded desired β-nucleoside 96 via anchimeric assistance in a moderate 65% yield. Decreasing the reaction temperature to 60° C. improved the reaction yield to 90% after purification by column chromatography. Treatment of β-nucleoside 96 with aqueous sodium hydroxide in 1,4-dioxane resulted in efficient tandem O2'-deacylation and O2',C4'-ring closure to afford bicycle 98 in 97% yield. Treatment of bicycle 98 with sodium benzoate in DMF at 90° C. resulted in nucleophilic displacement of the O5'-mesylate group to furnish O5'-benzoate 100 (97%), which was hydrolyzed using ammonia in methanol to provide alcohol 102 in 95% yield.

Scheme 18

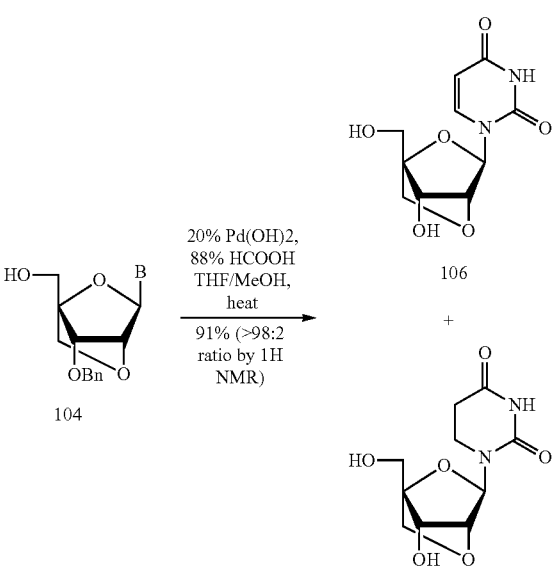

Scheme 18 illustrates the removal of the O3' benzyl group. Utilization of previously established hydrogenolysis conditions from Imanishi, T. et. al. (*Bioorg. Med. Chem.* 2001, 9, 1001-1011) to remove the benzyl protecting group repeatedly afforded mixtures (30:70 ratio by 1H NMR) of desired LNA uracil nucleoside 106 and by-product 108 in which the C5-C6 double bond of the nucleobase was reduced. The tentative assignment of the reduced by-product was based on mass spectra (FAB-HRMS m/z 259.0945 ([M+H]$^+$, C$_{10}$H$_{14}$N$_2$O$_6$ H+, calcd 259.0925)) and on key signals in 1H and COSY NMR spectra including an internally coupling multiplet at 3.26-3.51 ppm (integration of four) arising from H5/H6-protons and a broad exchangeable singlet at 10.26 ppm from the nucleobase imino proton. Numerous debenzylation conditions, summarized in Table 1, were accordingly screened to prevent nucleobase reduction. Debenzylation under strongly acidic conditions, such as 1 M boron trichloride in $CH_2Cl_2$ (entry 2), or methanesulfonic acid 18 (entry 3), was anticipated to render the C5-C6 olefin bond of the uracil moiety unharmed. These conditions failed to afford desired diol 106, most likely as a consequence of ether bond cleavage between O2'-O5' and/or cleavage of the glycosidic bond as very polar products were observed (results not shown). Although a change of catalyst to Pearlman's catalyst (20% $Pd(OH)_2/C$) afforded a remarkably improved ratio in favor of desired diol 106 relative to the original conditions, unacceptable levels of reduced by-product were still observed (entry 4). Catalyst poisoning with pyridine did not improve yield and selectivity (entry 5), nor did the use of catalytic transfer hydrogenation conditions with ammonium formate as hydrogen donor (entry 6). Gratifyingly, changing to 88% formic acid as a hydrogen donor in concert with 20% $Pd(OH)_2/C$ as catalyst and THF/MeOH (9:1, v/v) as reaction solvent, in addition to desired diol 106, only resulted in traces of by-product 108 in the crude. After separation of the by-product during column chromatography, desired LNA uracil diol 106 was afforded in 91% yield, pure by $^1H$ NMR.

TABLE 1

Debenzylation conditions for conversion of 5 into desired LNA uracil diol 6

| Entry | Conditions | Ratio (106:108)[a] |
|---|---|---|
| 1 | 10% Pd/C, H2, MeOH, rt | 30:70 |
| 2 | 1M BCl3 (5 equiv), CH2Cl2, −78° C. for 3 h, then rt | — |
| 3 | MeSO3H, CHCl3, rt | — |
| 4 | 20% Pd(OH)2/C, H2, THF/MeOH (9:1, v/v), rt | 85:15 |
| 5 | 20% Pd(OH)2/C, H2, pyridine (0.5 equiv), THF/MeOH (9:1, v/v), rt | 5:95 |
| 6 | 20% Pd(OH)2/C, HCOONH4 (3.5 equiv), MeOH, heat | 60:40 |
| 7 | 20% Pd(OH)2/C, 88% HCOOH, THF/MeOH (9:1, v/v), heat | >98:2 |

[a]Estimated from 1H NMR of crude products

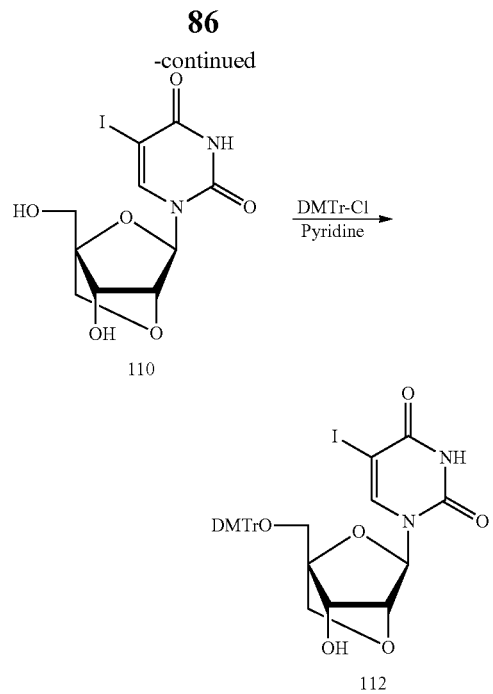

Scheme 19 represents one embodiment wherein the nucleobase can be halogenated in preparation for further C5 functionalization. Bicycle 106 can be protected as an acetate moiety, such as by using acetic anhydride and pyridine. In a particular embodiment, the uracil moiety of compound 106 may be subsequently iodinated using $I_2$, ceric ammonium nitrate and acetic acid, providing iodide 110 in 80% yield. Upon iodination, the primary hydroxyl group of iodide 110 can be protected, such as with a dimethoxytrityl protecting group using dimethoxytrityl chloride (DMT-Cl) and pyridine, providing compound 112.

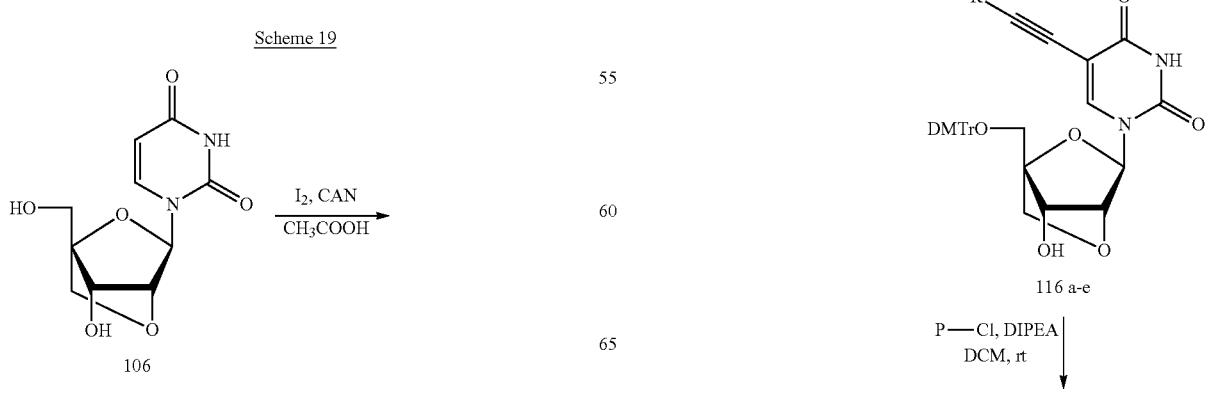

purity (>80%) was verified by MALDI-TOF MS analysis (FIGS. 2-5) and RPHPLC, respectively.

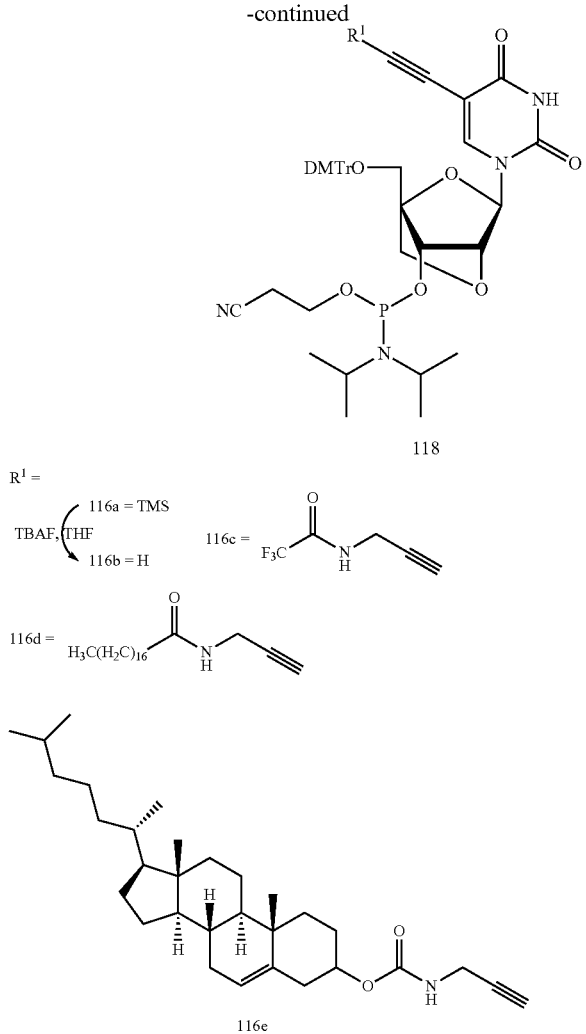

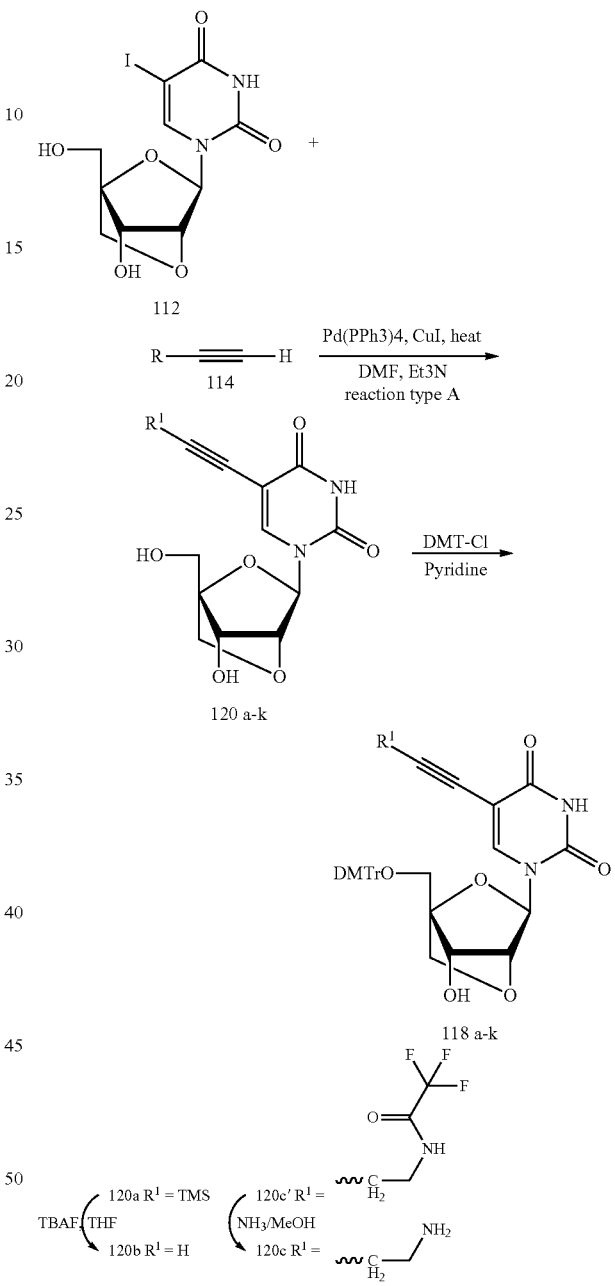

Figure 2:
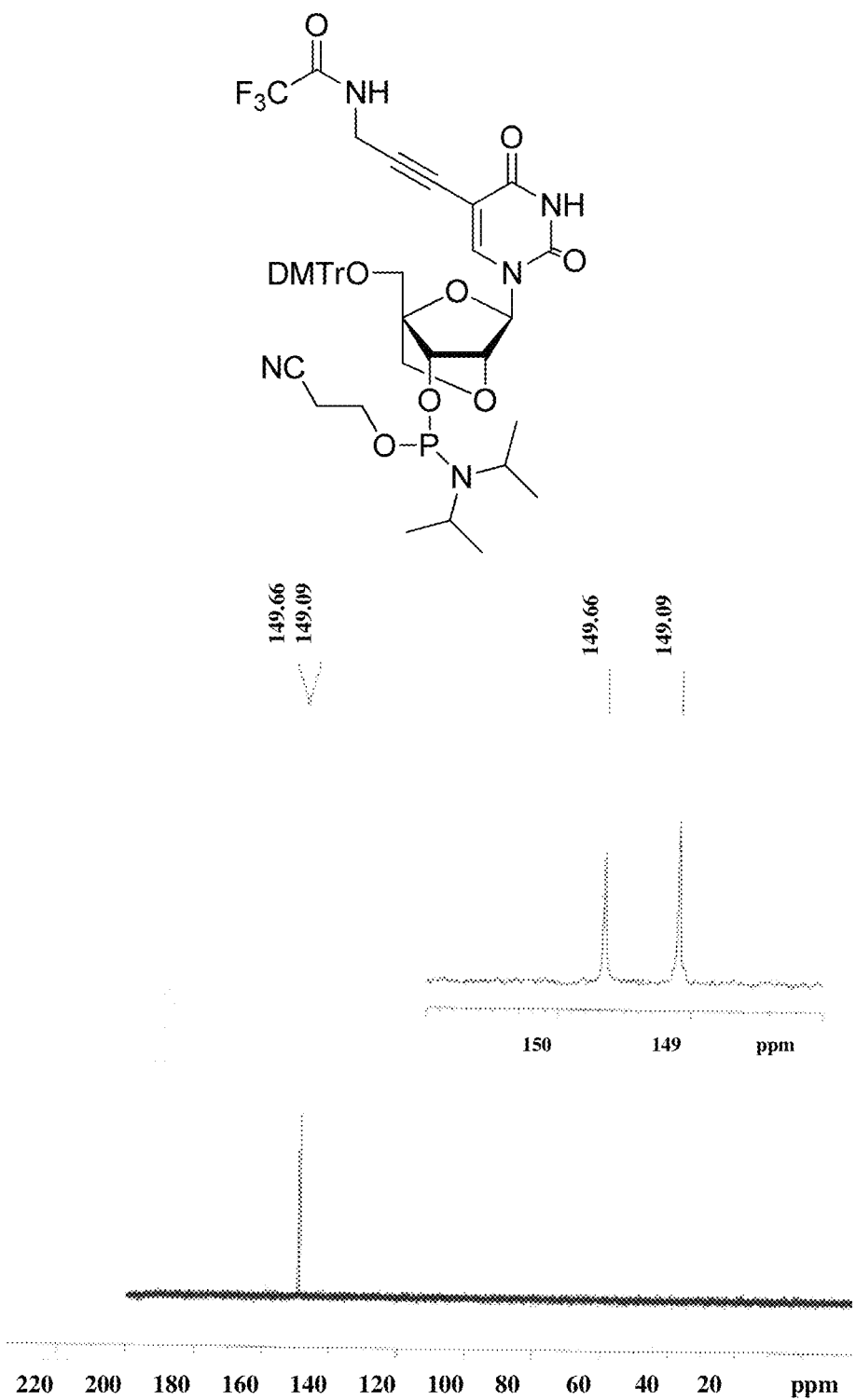
FIG. 2 is a NMR spectrum of a disclosed embodiment of a β-D-LNA phosphoramidite.
Figure 3:
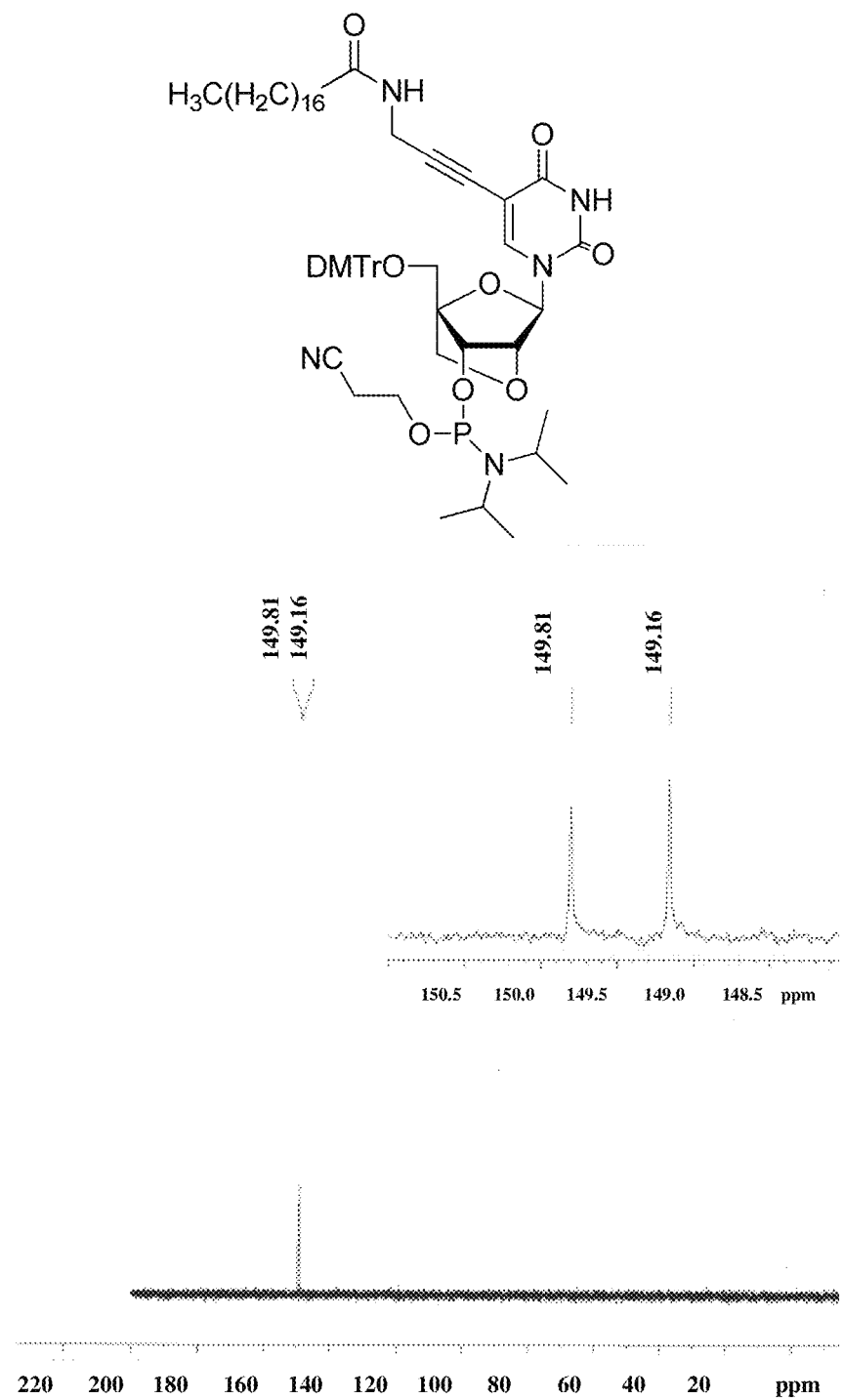
FIG. 3 is a NMR spectrum of a disclosed embodiment of a β-D-LNA phosphoramidite.
Figure 4:
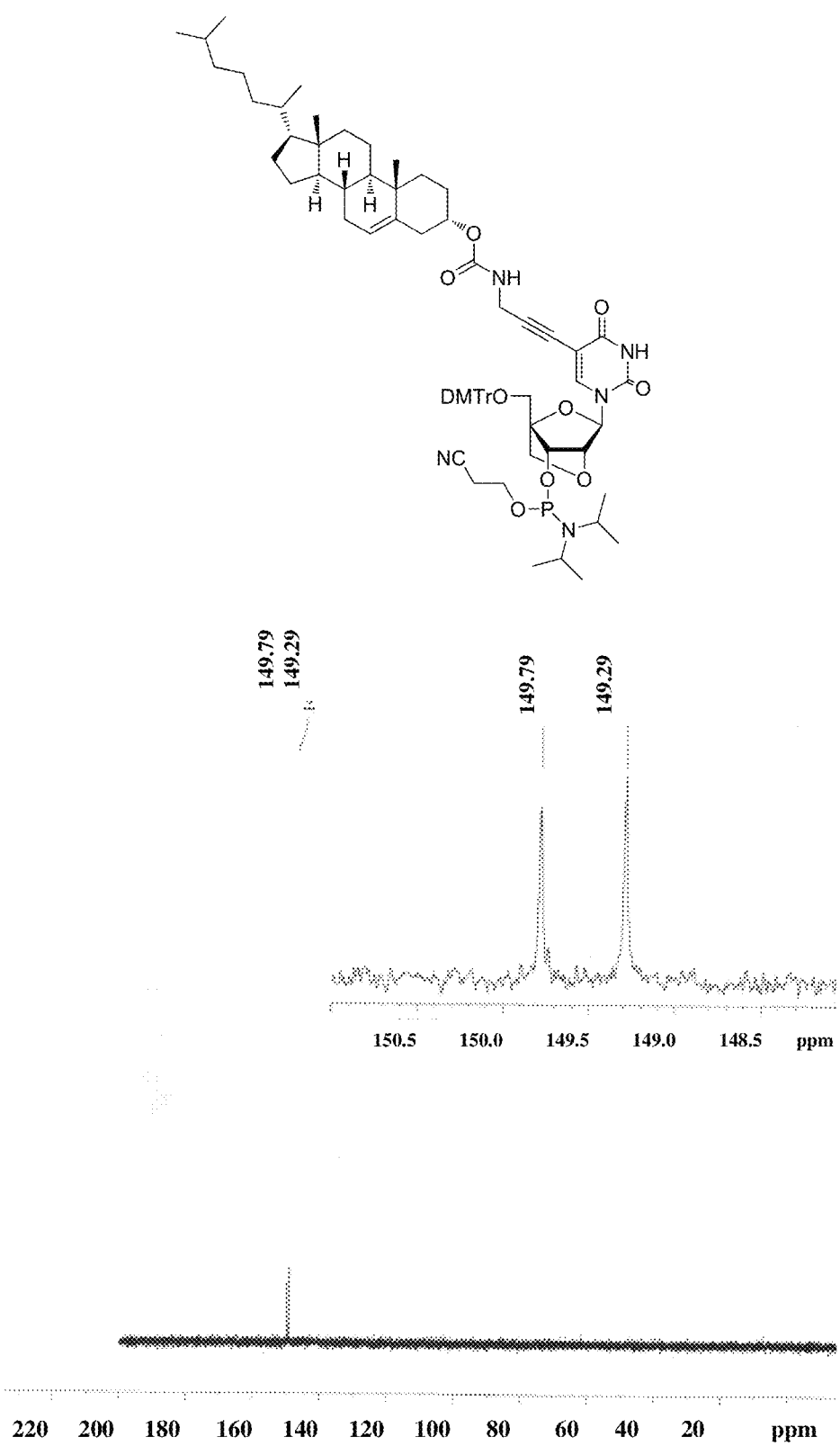
FIG. 4 is a NMR spectrum of a disclosed embodiment of a β-D-LNA phosphoramidite.
Figure 5:
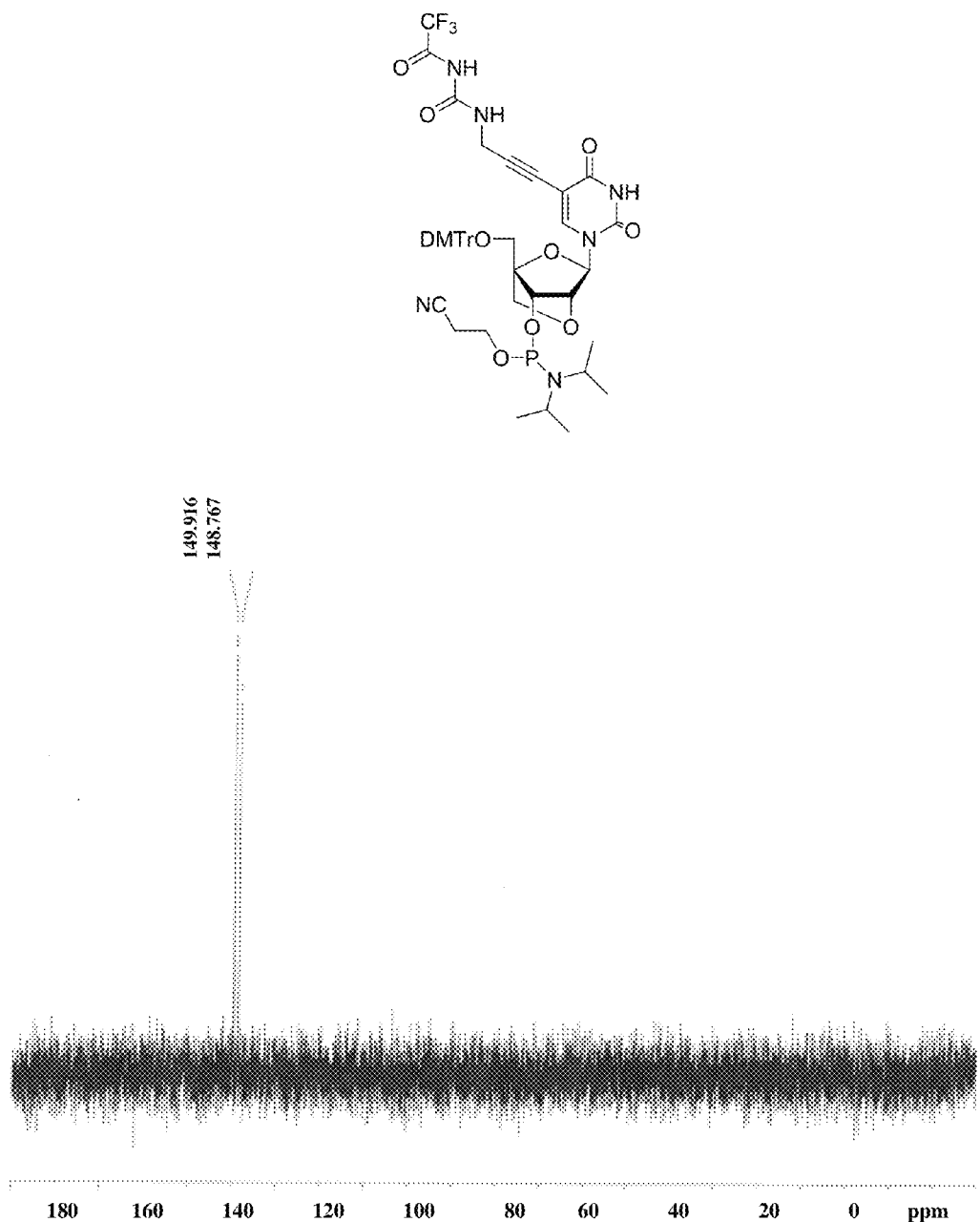
FIG. 5 is a NMR spectrum of a disclosed embodiment of a β-D-LNA phosphoramidite.
Figure 6:
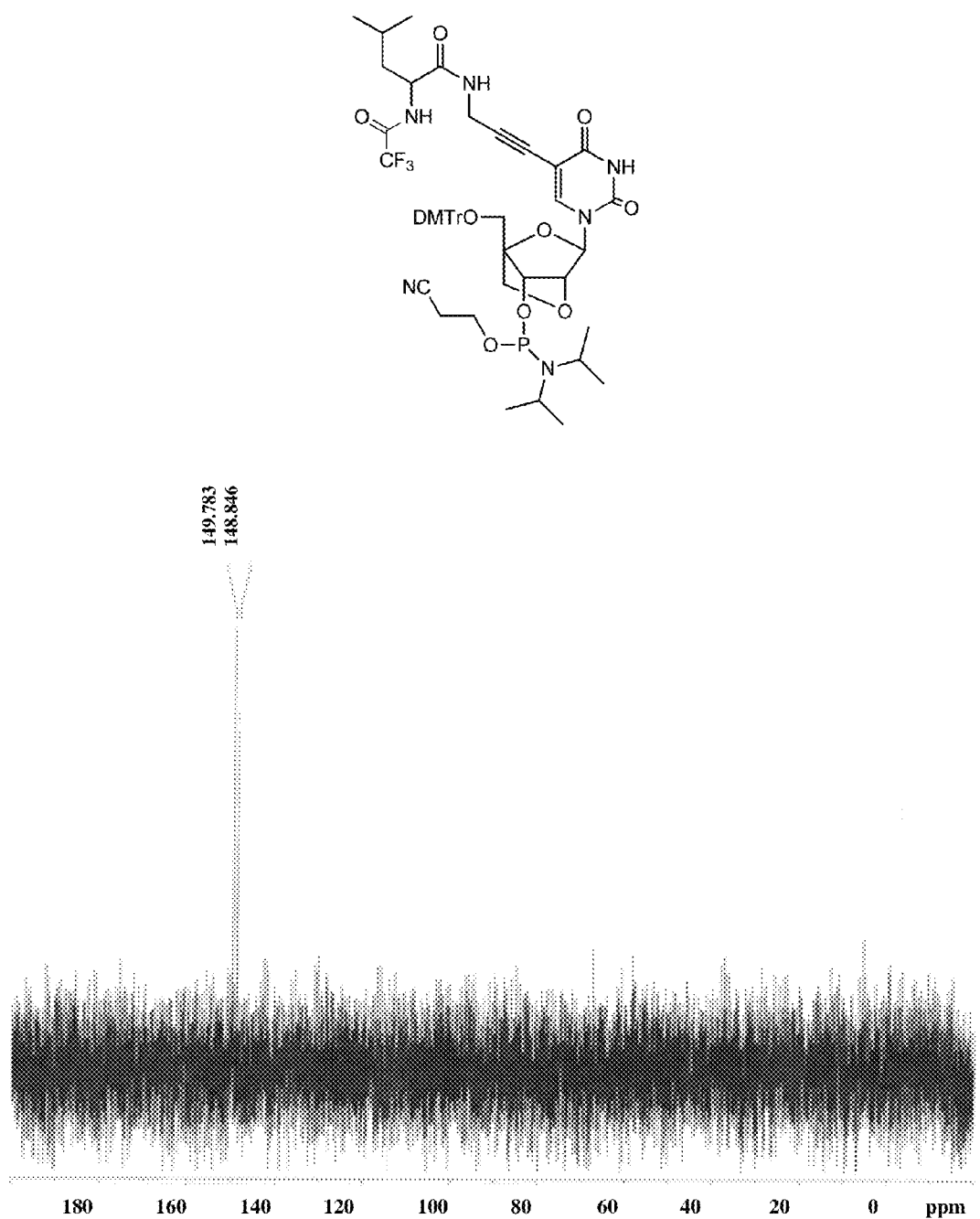
FIG. 6 is a NMR spectrum of a disclosed embodiment of a β-D-LNA phosphoramidite.
Figure 7:
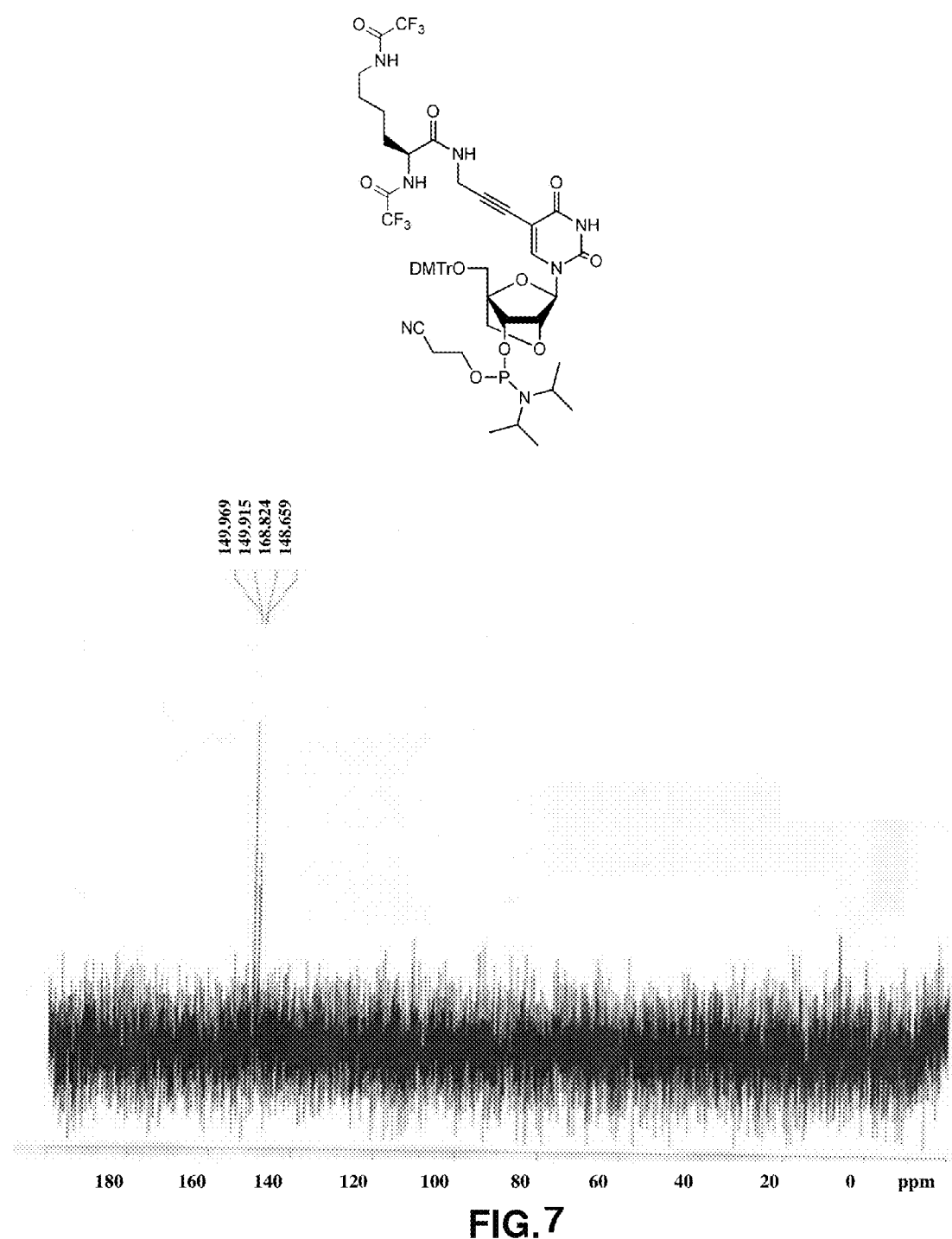
FIG. 7 is a NMR spectrum of a disclosed embodiment of a β-D-LNA phosphoramidite.
Figure 8:
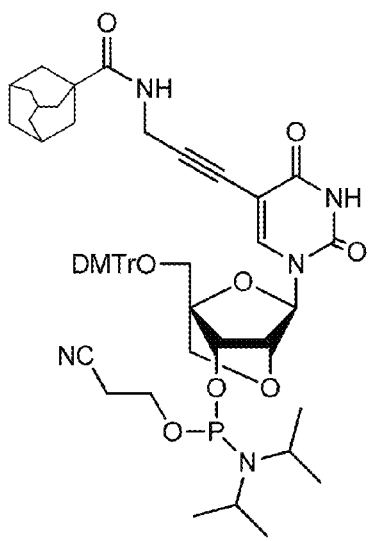
FIG. 8 is a NMR spectrum of a disclosed embodiment of a β-D-LNA phosphoramidite.
Figure 8:
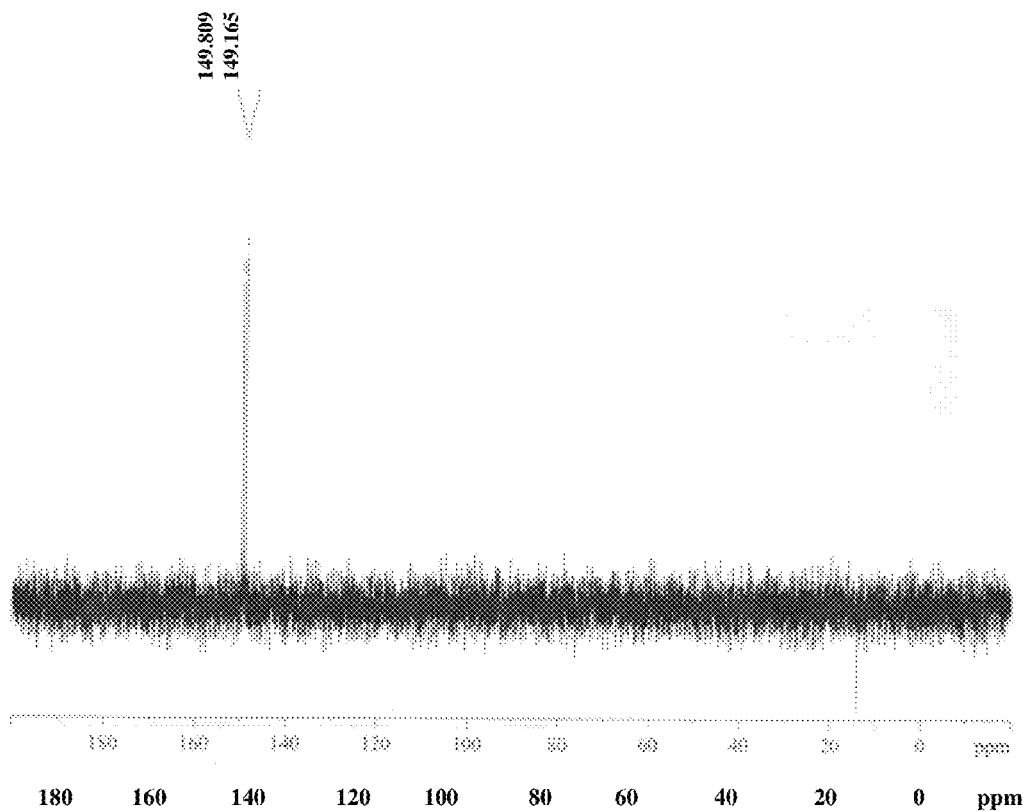

Scheme 20 illustrates manipulation of vinyl iodide 112 to couple a variety of alkyne linkers, thus providing an efficient route to a variety of C5-functionalized locked nucleic acids. The vinyl iodide can undergo a Sonogashira coupling reaction using palladium tetrakis [Pd(PPh$_3$)$_4$], a functionalized alkyne, copper iodide (CuI), and triethyl amine (Et$_3$N) in dimethylformamide (DMF) at room temperature. In particular embodiments, the alkyne is functionalized with a trimethyl silyl group, which can subsequently be removed to provide a terminal alkyne. FIG. 1 illustrates the mass spectrum obtained for the desilylated LNA compound. Other exemplary R$^1$ groups are illustrated in Scheme 20 and their corresponding nuclear magnetic resonance (NMR) spectra are illustrated in FIGS. 2-4. FIGS. 5-8 are additional NMR spectra of other working embodiments disclosed herein. Once the alkyne linker has been attached to the nucleobase, the free C3' hydroxyl group can be protected with a protecting group, such as a phosphoramidite moiety, providing compound 118. The phosphoramidite protecting group can be converted to a phosphate group and/or phosphate backbone, such as by using a DNA synthesizer. Standard conditions for this transformation were employed, except for extended coupling (15 min, using 4,5-dicyanoimidazole as activator) and oxidation times (45 sec), resulting in stepwise coupling yields of >95% for the LNA compounds. The composition and Scheme 21 illustrates an alternative route that can be used to synthesize C5-functionalized locked nucleic acids. The vinyl iodide 112 is first coupled to the alkyne linker 114 using Sonogashira coupling conditions, followed by subsequent protection of the O4' hydroxyl group with DMT-Cl, providing compound 118.

V. Biological Properties of C5- or C8-Functionalized LNA and α-L-LNA

Antisense oligonucleotides (ONs) are useful as fundamental research tools and therapeutic agents against diseases of genetic origin due to their ability to modulate gene expression by interfering with target RNA (S. T. Crooke, "*Antisense Drug Technology—Principles, Strategies, and Applications,*" 2nd ed; CRC Press, Boca Raton, 2008, pp. 3-46). Introduction of chemically modified nucleotides into antisense ONs is crucial to increase binding affinity toward RNA targets, improve discrimination of mismatched RNA to avoid off-target effects, and enhance stability against nucleases to slow down degradation. The use of conformationally restricted nucleotides, Locked Nucleic Acids (LNAs) in particular, has to some extent addressed these challenges. Substantial efforts have been invested to develop LNA analogs with even more desirable biophysical properties and reduced hepatotoxicity (Imanishi et. al. *Bioorg. Med. Chem.* 2003, 11, 2211-2226). These studies have primarily focused on modification of the oxymethylene bridge spanning the C2'- and C4'-positions and/or introduction of minor-groove oriented substituents into the bridge. In general, improvements in hybridization properties relative to LNA have not yet been observed. The working embodiments disclosed herein overcome this shortcoming.

A. Modulation of Thermal Affinity Toward Matched, Single Stranded DNA/RNA Targets or Double Stranded DNA Targets.

Certain embodiments can be used to modify oligonucleotides and modulate affinity towards single stranded DNA/RNA targets or double stranded DNA targets (dsDNA). Compounds of C5- or C8-functionalized locked nucleic acids can be incorporated into oligonucleotides using a DNA synthesizer, as previously described. A person of ordinary skill in the art will understand that oligonucleotides can contain from two nucleotides to at least 300 of nucleotides. Particular embodiments utilize oligonucleotides having from about 5 to about 50 nucleotides; more typically from about 8 to 35 nucleotides. Particular embodiments can be tested against unmodified reference strands, as well as reference strands modified with commercially available LNA thymidine phosphoramidite (Wengel et. al. *Tetrahedron*, 1998, 54, 3607-3630).

1. Single Stranded DNA/RNA Targets

Particular embodiments of the disclosed method concern determining the thermal affinity of modified nucleic acids with complementary nucleic acid strands. Strong thermal affinity can be an indication of strong binding between the modified and complementary strands, which can be a valuable property exploited in biological applications. These applications are discussed subsequently. One or more C5- or C8-functionalized LNA and α-L-LNA compounds can be incorporated into an oligonucleotide, and changes in thermal affinity can be determined. For example, the thermal affinity of these modified oligonucleotides can be compared with thermal affinity values obtained from oligonucleotides comprising one or more reference DNA monomers and/or one or more conventional LNA monomers. Thermal affinity can be determined by any method known to a person of ordinary skill in the art to involve denaturation of an unmodified or modified nucleic acid and its complement DNA or RNA strand.

Figure 9:
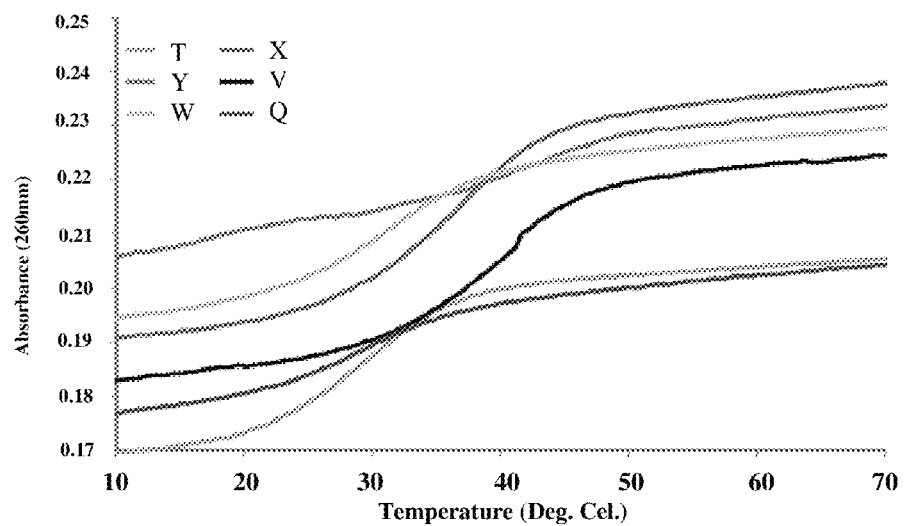
FIG. 9 is a graph of temperature in ° C. (x-axis) versus absorbance (y-axis) illustrating thermal denaturation curves of duplexes between complementary RNA and reference DNA strand (T), a conventional LNA-containing strand (X), and strands containing disclosed embodiments of β-D-LNA compounds (Y, W, V, and Q).

Particular embodiments of the disclosed method concern using UV thermal denaturation experiments, which can be used to determine the stability of the secondary structure of nucleic acids. The modified and reference DNA/RNA duplexes are heated to a temperature effective to cause dissociation of 50% of the duplex into the respective single strands, which is herein referred to as $T_m$. $T_m$ values for (C5- or C8-functionalized LNA or α-L-LNA)-modified DNA/RNA strands can range from greater than 0° C. to about 95° C.; more typically the $T_m$ ranges from about 15° C. to about 60° C. Particular embodiments exhibited increased $T_m$ values as compared to the $T_m$ for unmodified DNA/RNA. A person of ordinary skill in the art will recognize that this increase in $T_m$ values for modified DNA/RNA is likely to be sequence specific; however, certain embodiments of (C5- or C8-functionalized LNA or α-L-LNA)-modified DNA strands, comprising from about 5 to about 50 nucleotides, can exhibit an increase in $T_m$ ranging from greater than 0° C. to about 15° C. as compared to unmodified DNA strands. Representative thermal denaturation curves of particular embodiments are illustrated in FIG. 9, which illustrates denaturation curves of duplexes formed between C5- or C8-functionalized LNA compounds Q, V, W, Y and complementary RNA, as well as duplexes formed between complementary RNA and conventional LNA monomer X and reference DNA monomer T. FIG. 9 illustrates that increases in temperature will result in increases (and ultimate leveling-off) of absorbance, therefore indicating the progressive and denaturation of the duplexes.

Table 2 provides data obtained from particular embodiments utilized in UV thermal denaturation experiments. According to Table 2, C5-LNA compounds Y, O, and V illustrated increased $T_m$ values as compared to unmodified DNA $T_m$ values. Particular embodiments include C5-LNAs wherein the alkynyl linker is attached to a hydrogen atom or $CH_2X$, where X is selected from hydroxyl, sulfhydryl, phosphine, or amine. Incorporation of particular embodiments, such as C5-acetylene or C5-propargylamine-functionalized LNA uridine compounds, resulted in dramatic duplex stabilization with RNA complements with increases in thermal denaturation temperatures ($T_m$-values) ranging from 8.5° C. to 13.0° C. relative to the unmodified DNA strand (Table 2). Introduction of the C5-propargylamine LNA compound, therefore, results in approximately a 3° C. additional increase in thermal affinity relative to the corresponding LNA strands (Table 2).

Particular embodiments utilize C5-LNAs comprising a hydrophobic moiety at the C5 position. Certain embodiments comprise steroidal components, such as cholesterol or stearic acid appended to the C5 position via a functionalized alkyne linker. Introduction of hydrophobic units, such as steroids and fatty acids, into ONs has been demonstrated to improve cellular uptake of ONs (Unverzagt, et. al. *Bioorg. Med. Chem. Lett.* 2004, 14, 4975-4977; Stoffel, et. al. *Nat. Biotechnol.* 2007, 25, 1149-1157). Considering the bulk of the substituent, singly modified C5-stearic acid functionalized LNA results in remarkable stabilization of duplexes with RNA complements ($\Delta T_m$=+2.5 to +4.0° C., Table 2). While these $T_m$ values are less than those obtained from conventional LNA-functionalized strands, the values are increased as compared to unmodified DNA, which a person of ordinary skill in the art will recognize as a commercially important difference. The even bulkier C5-cholesterol LNA exhibits slightly decreased thermal affinity relative to unmodified DNA ($\Delta T_m$=-2.0 to 0° C., Table 2). These data suggest that the LNA-skeleton is partially compensating for the energetic penalty arising from positioning hydrophobic substituents in the polar major groove. Conversely, introduction of two hydrophobic C5-functionalized LNA compounds as next-nearest neighbors into ONs is detrimental for duplex formation, presumably due to steric crowding and/or unfavorable hydrophobic interactions; however, a person of ordinary skill in the art will recognize that does not preclude duplex formation of oligonucleotides comprising two or more hydrophobic compounds that are not next-nearest neighbors.

91
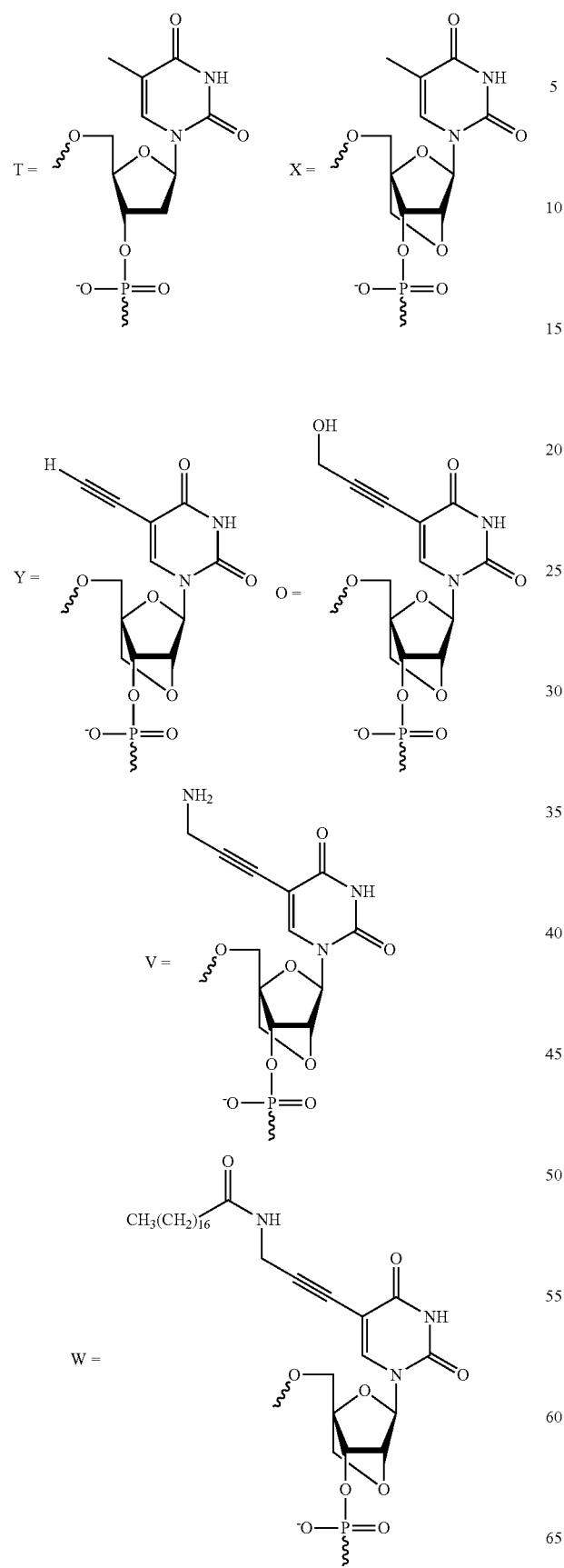
92
-continued
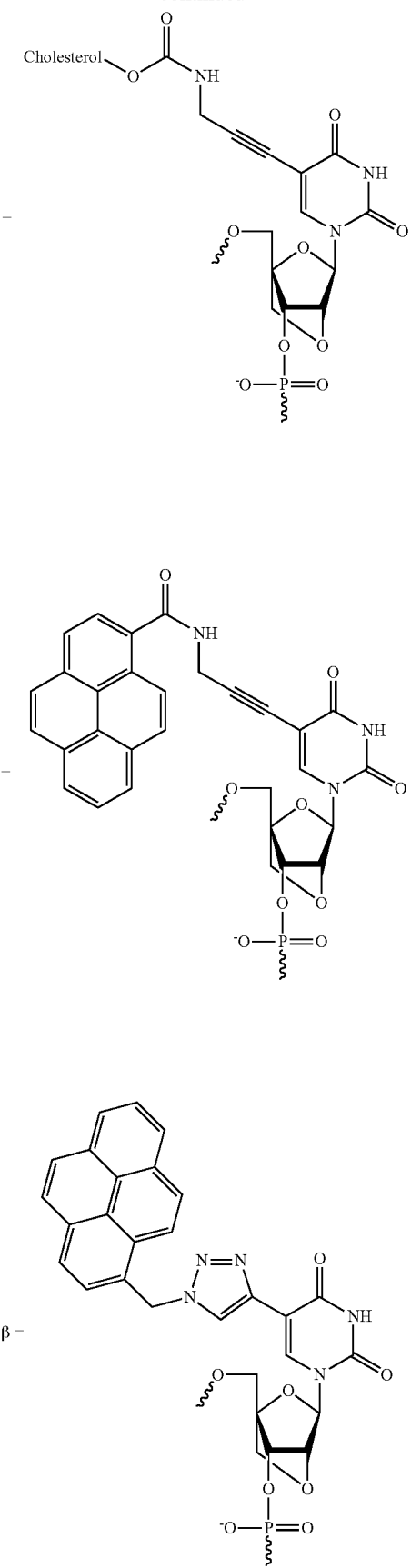

γ = 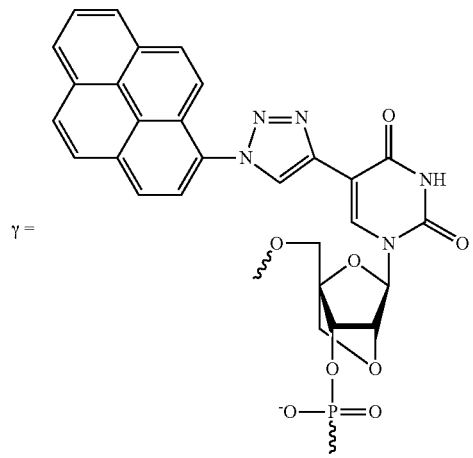

α = 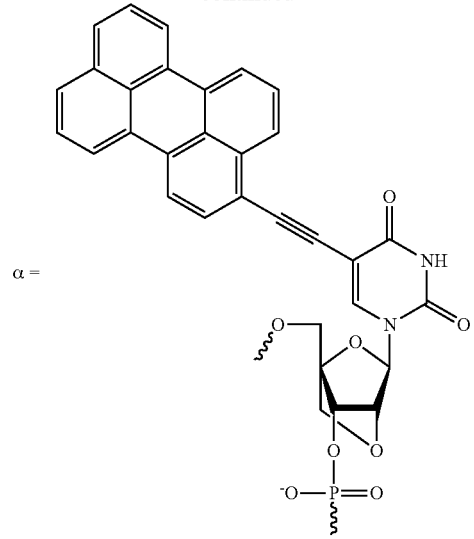

Legend for β-D-LNA Compounds of Tables 2, 3, 6-8, and 10-13.

TABLE 2

Thermal affinity values for LNA against complementary DNA and RNA

| Duplex | B = T | X | Y | O | V | W | Q |
|---|---|---|---|---|---|---|---|
| 5'-d(GCA TAT CAC) 3'-d(CGT ABA GTG) | 29.5 | 34.5 (+5.0) | 36.5 (+7.0) | 36.0 (+6.5) | 37.5 (+8.0) | 30.5 (+1.0) | 24.0 (−5.5) |
| 5'-d(GCA TAB CAC) 3'-d(CGT ATA GTG) | 29.5 | 33.5 (+4.0) | 35.0 (+5.5) | 35.0 (+5.5) | 36.0 (+6.5) | 30.0 (+0.5) | 24.5 (−5.0) |
| 5'-d(GCA BAT CAC) 3'-d(CGT ATA GTG) | 29.5 | 36.0 (+6.5) | — | 35.0 (+5.5) | 39.0 (+9.5) | 30.5 (+1.0) | 26.0 (−3.5) |
| 5'-d(GCA BAB CAC) 3'-d(CGT ATA GTG) | 29.5 | 40.0 (+5.5) | 40.5 (+5.5) | 40.5 (+5.5) | 45.5 (+8.0) | nt | nt |
| 5'-r(GCA UAU CAC) 3'-d(CGT ABA GTG) | 27.0 | 36.5 (+9.5) | 38.0 (+11.0) | 37.0 (+10.0) | 40.0 (+13.0) | 31.0 (+4.0) | 25.0 (−2.0) |
| 5'-d(GCA TAB CAC) 3'-r(CGU AUA GUG) | 27.0 | 33.5 (+6.5) | 35.5 (+8.5) | 35.0 (+8.0) | 37.0 (+10.0) | 30.5 (+3.5) | 27.0 (0) |
| 5'-d(GCA BAT CAC) 3'-r(CGU AUA GUG) | 27.0 | 36.5 (+9.5) | — | 35.0 (+8.0) | 39.5 (+12.5) | 29.5 (+2.5) | 26.0 (−1.0) |
| 5'-d(GCA BAB CAC) 3'-r(CGU AUA GUG) | 27.0 | 43.0 (+8.0) | 44.0 (+8.5) | 43.5 (+8.5) | 49.0 (+11.0) | nt | nt |

Table 3 illustrates the $T_m$ values for other embodiments of the current method. Particular embodiments illustrated in Table 3 have C5-functionalization wherein the linker is either an alkyne moiety or a triazole moiety substituted with a fluorophore. Exemplary fluorophores include pyrene and perylene, but a person of ordinary skill in the art will recognize that any fluorophore moiety can potentially be used. The values disclosed in Table 3 illustrate that the fluorophore-functionalized LNA compounds destabilize duplexes formed between the modified oligonucleotide and complementary nucleic acid strand.

TABLE 3

Thermal affinity values for fluorophore-functionalzed LNA against complementary DNA and RNA

| Duplex | B = T | X | P | β | γ | α |
|---|---|---|---|---|---|---|
| 5'-d(GCA TAT CAC) | 29.5 | 34.5 | 23.0 | 24.0 | 19.0 | 17.0 |
| 3'-d(CGT ABA GTG) | | (+5.0) | (−6.0) | (−5.5) | (−10.5) | (−12.5) |
| 5'-d(GCA TAB CAC) | 29.5 | 33.5 | 22.0 | 23.0 | 16.0 | <10 |
| 3'-d(CGT ATA GTG) | | (+4.0) | (−7.5) | (−6.5) | (−13.5) | (<−19.5) |
| 5'-d(GCA BAT CAC) | 29.5 | 36.0 | 25.5 | 24.0 | 17.0 | 18.0 |
| 3'-d(CGT ATA GTG) | | (+6.5) | (−4.0) | (−5.0) | (−12.0) | (−11.5) |
| 5'-d(GCA BAB CAC) | 29.5 | 40.0 | 30.5 | 25.0 | 21.5 | <10 |
| 3'-d(CGT ATA GTG) | | (+5.5) | (+0.5) | (−2.0) | (−4.0) | (<−19.5) |
| 5'-r(GCA UAU CAC) | 27.0 | 36.5 | 23.0 | 25.5 | 25.0 | 15.0 |
| 3'-d(CGT ABA GTG) | | (+9.5) | (−4.0) | (−1.5) | (−2.0) | (−12.0) |
| 5'-d(GCA TAB CAC) | 27.0 | 33.5 | 21.0 | 22.0 | 17.0 | 15.0 |
| 3'-r(CGU AUA GUG) | | (+6.5) | (−6.0) | (−5.0) | (−10.0) | (−12.0) |
| 5'-d(GCA BAT CAC) | 27.0 | 36.5 | 27.0 | 26.0 | 18.0 | 16.0 |
| 3'-r(CGU AUA GUG) | | (+9.5) | (0) | (−1.0) | (−9.0) | (−11.0) |
| 5'-d(GCA BAB CAC) | 27.0 | 43.0 | 30.5 | 26.0 | 23.0 | <10 |
| 3'-r(CGU AUA GUG) | | (+8.0) | (+2.0) | (−0.5) | (−2.0) | (<−19.5) |

The thermal affinity of oligonucleotides modified with C5-α-L-LNA compounds can also be examined using the disclosed methods. In particular embodiments, oligonucleotides comprising compounds Y', O' or V' result in dramatic increases in thermal affinity toward complementary single stranded DNA ($\Delta T_m$/modification range between +2.0° C. and +9.5° C.) and RNA ($\Delta T_m$/modification generally between +5.0° C. and +12.5° C.) targets. Table 4 illustrates the results obtained from thermal affinity studies of certain embodiments.

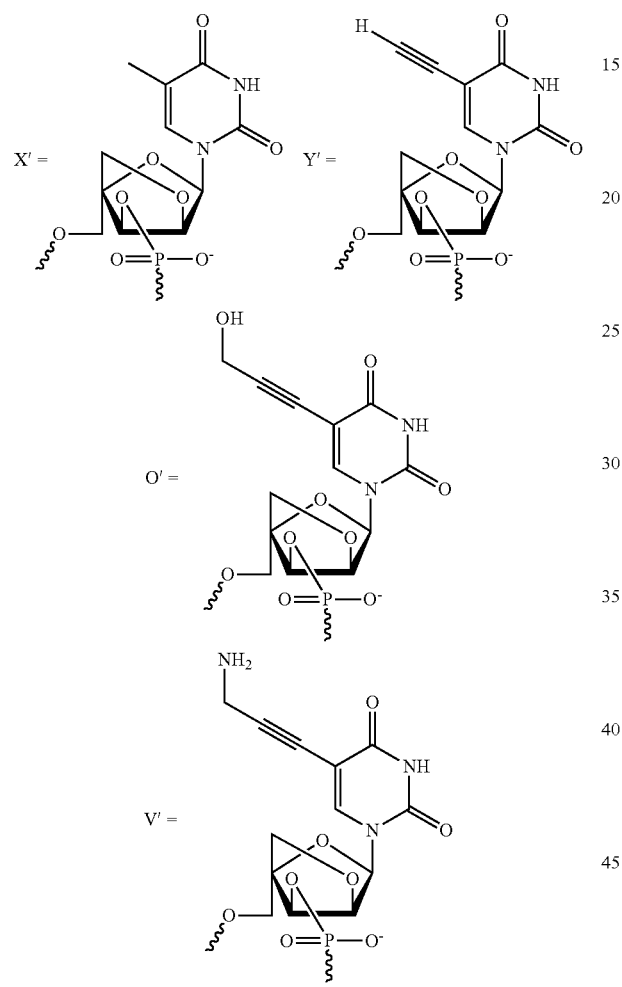
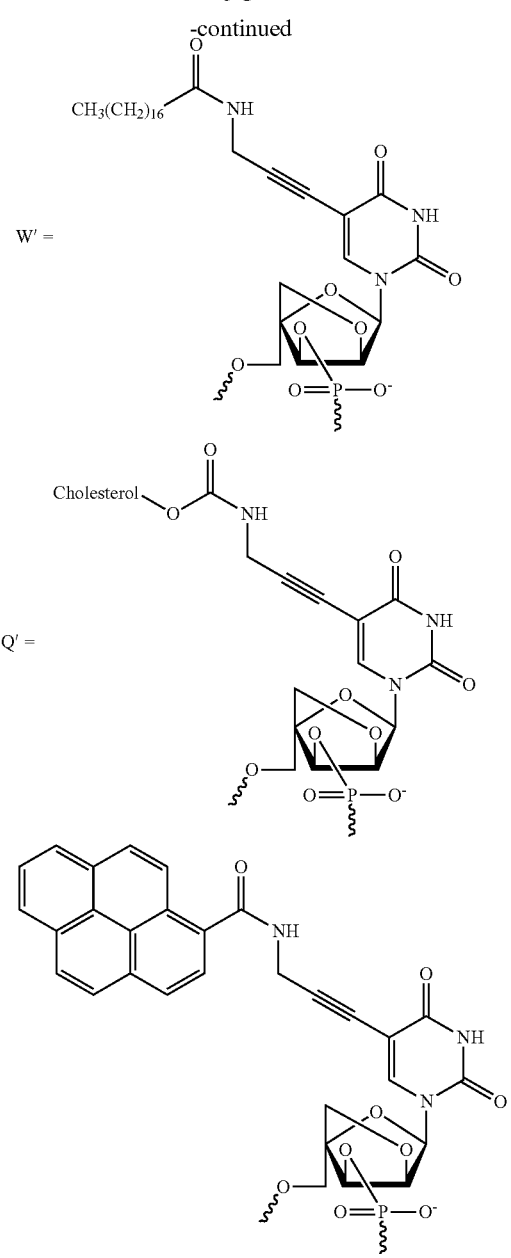

Legend for α-L-LNA Compounds of Tables 4, 5, 9, and 14-17.

TABLE 4

Thermal affinity values for α-L-LNA against complementary DNA and RNA

| Duplex | B = | T | X' | Y' | O' | V' |
|---|---|---|---|---|---|---|
| 5'-d(GCA TAT CAC) 3'-d(CGT ABA GTG) | | 29.5 | 33.5 (+4.0) | 37.0 (+7.5) | 36.5 (+7.0) | 39.0 (+9.5) |
| 5'-d(GCA TAB CAC) 3'-d(CGT ATA GTG) | | 29.5 | 31.5 (+2.0) | 33.0 (+3.5) | 33.5 (+2.0) | 35.0 (+5.5) |
| 5'-d(GCA BAT CAC) 3'-d(CGT ATA GTG) | | 29.5 | 38.0 (+8.5) | 38.0 (+8.5) | 36.5 (+7.0) | 39.0 (+9.5) |
| 5'-d(GCA BAB CAC) 3'-d(CGT ATA GTG) | | 29.5 | 37.0 (+4.0) | 37.0 (+4.0) | 37.5 (+4.0) | 42.0 (+6.0) |

TABLE 4-continued

Thermal affinity values for α-L-LNA against complementary DNA and RNA

| Duplex | B = T | X' | Y' | O' | V' |
|---|---|---|---|---|---|
| 5'-r(GCA UAU CAC)<br>3'-d(CGT ABA GTG) | 27.0 | 36.5<br>(+9.5) | 38.0<br>(+11.0) | 35.5<br>(+8.5) | 39.5<br>(+12.5) |
| 5'-d(GCA TAB CAC)<br>3'-r(CGU AUA GUG) | 27.0 | 31.0<br>(+4.0) | 32.0<br>(+5.0) | 32.0<br>(+5.0) | 34.0<br>(+7.0) |
| 5'-d(GCA BAT CAC)<br>3'-r(CGU AUA GUG) | 27.0 | 36.0<br>(+9.0) | 36.0<br>(+9.0) | 35.5<br>(+8.5) | 39.0<br>(+12.0) |
| 5'-d(GCA BAB CAC)<br>3'-r(CGU AUA GUG) | 27.0 | 38.5<br>(+6.0) | 39.0<br>(+6.0) | 38.5<br>(+6.0) | 41.5<br>(+7.0) |

Table 5 illustrates the results obtained from thermal denaturation studies of other particular disclosed embodiments. Oligonucleotides comprising compound W' result in small fluctuations in thermal affinity toward complementary single stranded DNA. In another interesting embodiment, oligonucleotides comprising compounds W', Q' or P' generally exhibit modest increases in thermal affinity toward complementary single stranded RNA.

TABLE 5

Thermal affinity values for α-L-LNA against complementary DNA and RNA

| Duplex | B = T | W' | Q' | P' |
|---|---|---|---|---|
| 5'-d(GCA TAT CAC)<br>3'-d(CGT ABA GTG) | 29.5 | 30.5<br>(+1.0) | 27.0<br>(-2.5) | 28.5<br>(-1.0) |
| 5'-d(GCA TAB CAC)<br>3'-d(CGT ATA GTG) | 29.5 | 29.0<br>(-0.5) | 19.5<br>(-10.0) | 19.0<br>(-10.5) |
| 5'-d(GCA BAT CAC)<br>3'-d(CGT ATA GTG) | 29.5 | 30.0<br>(+0.5) | 27.5<br>(-2.0) | 29.5<br>(0) |
| 5'-d(GCA BAB CAC)<br>3'-d(CGT ATA GTG) | 29.5 | nt | nt | 30.5<br>(+0.5) |
| 5'-r(GCA UAU CAC)<br>3'-d(CGT ABA GTG) | 27.0 | 30.5<br>(+3.5) | 28.0<br>(+1.0) | 28.5<br>(+1.5) |
| 5'-d(GCA TAB CAC)<br>3'-r(CGU AUA GUG) | 27.0 | 29.5<br>(+2.5) | 27.5<br>(+0.5) | 18.5<br>(-8.5) |
| 5'-d(GCA BAT CAC)<br>3'-r(CGU AUA GUG) | 27.0 | 29.5<br>(+2.5) | 26.5<br>(-0.5) | 29.5<br>(+2.5) |
| 5'-d(GCA BAB CAC)<br>3'-r(CGU AUA GUG) | 27.0 | nt | nt | 30.5<br>(+2.0) |

2. Double Stranded Nucleic Acid Targets

Disclosed embodiments concern the modulation of thermal affinity of C5- or C8-functionalized LNA and α-L-LNA triplex-forming oligonucleotides (TFOs) toward double stranded nucleic acid targets. (TC)-motif TFOs, which bind to polypurine regions in double stranded nucleic acid targets via Hoogsteen base pairs in the major groove, are the most widely studied nucleic acid-targeting agents. A drawback of the TFO-approach is the instability of triplexes at physiological pH due to electrostatic repulsion between the three strands and insufficient N3-protonation of cytosines results in weak Hoogsteen base pairing. Chemical modification of TFOs is therefore essential to increase triplex stability as well as to protect TFOs from enzymatic degradation.

Particular embodiments of the current compounds can be first incorporated into a (TC)-motif nucleic acid TFO sequence. A person of ordinary skill in the art will recognize that the number of nucleotides in the sequence can range from at least 2 to about 50; more typically, the number will range from at least 8 to about 25 nucleotides. Particular embodiments utilize a sequence comprising 15 nucleotides. The number of C5- or C8-functionalized LNA and/or α-L-LNA compounds that can be incorporated into the sequence can range from greater than 0 to 100 percent of the number of nucleotides in the sequence; more typically from greater than 0 to about 6. The modified TFOs can be synthesized using a DNA synthesizer. Particular embodiments were synthesized on a 0.2 mM scale, using standard conditions except for extended coupling (15 min, using 4,5-dicyanoimidazole as activator) and oxidation times (45 sec), which resulted in stepwise coupling yields of >98% for the LNA compounds. Certain embodiments utilize 5-methyldeoxycytidine rather than deoxycytidine monomers in order to ameliorate the normal pH dependence of (TC)-motif TFOs.

Figure 10:
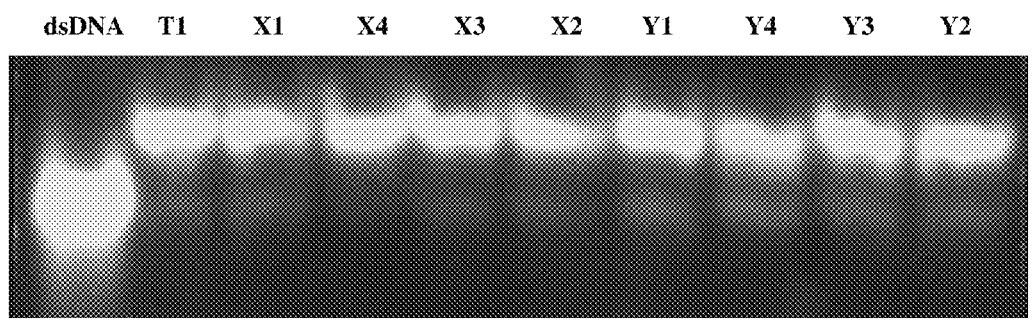
FIG. 10 is an image of results obtained from using non-denaturing polyacrylamide gel electrophoresis (PAGE) of a double stranded DNA target, and complexes formed between this target and reference DNA (T), conventional LNA (X1-X4), and a disclosed embodiment of β-D-LNA compound (Y1-Y4).
Figure 11:
FIG. 11 is an image of PAGE results illustrating incomplete complex formation between a disclosed embodiment of a β-D-LNA compound (V2-V4) and a dsDNA target.
Figure 12:
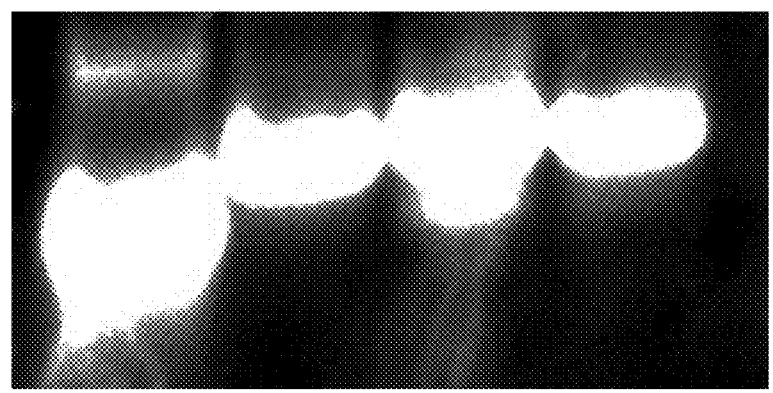
FIG. 12 is an image of PAGE results illustrating complete complex formation between a disclosed embodiment of a β-D-LNA compound (V2-V4) and a dsDNA target.

For particular working embodiments, stable triplexes between dsDNA and C5-functionalized LNA, conventional LNA, and unmodified nucleic acids targets were characterized by non-denaturing polyacrylamide gel electrophoresis (PAGE) using equimolar quantities of TFOs and the dsDNA target in a pH 7.2, 4-(2-hydroxyethyl)-1-piperazineethanesulfonic acid (HEPES) buffer containing $Mg^{2+}$. FIG. 10 is an electrophoresis gel illustrating the bands of complexes between reference DNA (T), conventional LNA (X1-X4), and a C5-functionalized LNA TFOs (Y1-Y4), and a dsDNA target (dsDNA). Triplex formation between C5-propargylamine functionalized LNA TFOs (V2-V4) and dsDNA target was incomplete as a band (~20-40% intensity) of identical mobility as the corresponding dsDNA target is observed in addition to the triplex band (V2-V4 series, FIG. 11). Triplex formation can be driven toward completion using a two-fold excess of C5-propargylamine functionalized LNA TFOs (FIG. 12).

Figure 13:
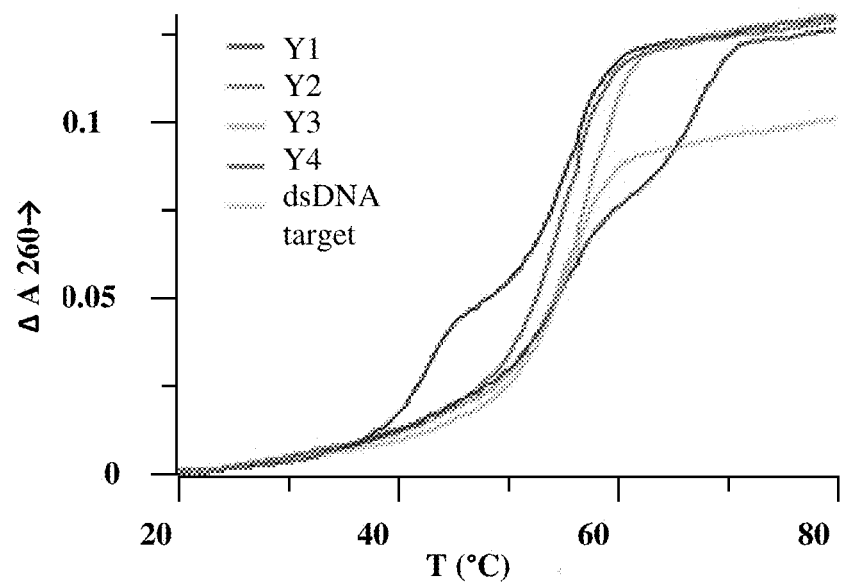
FIG. 13 is a graph of temperature in ° C. (x-axis) versus absorbance (y-axis) that illustrates the raw thermal denaturation profile obtained from denaturing triplexes between a dsDNA target and a disclosed embodiment of a β-D-LNA-modified triplex forming oligonucleotide (TFO).
Figure 14:
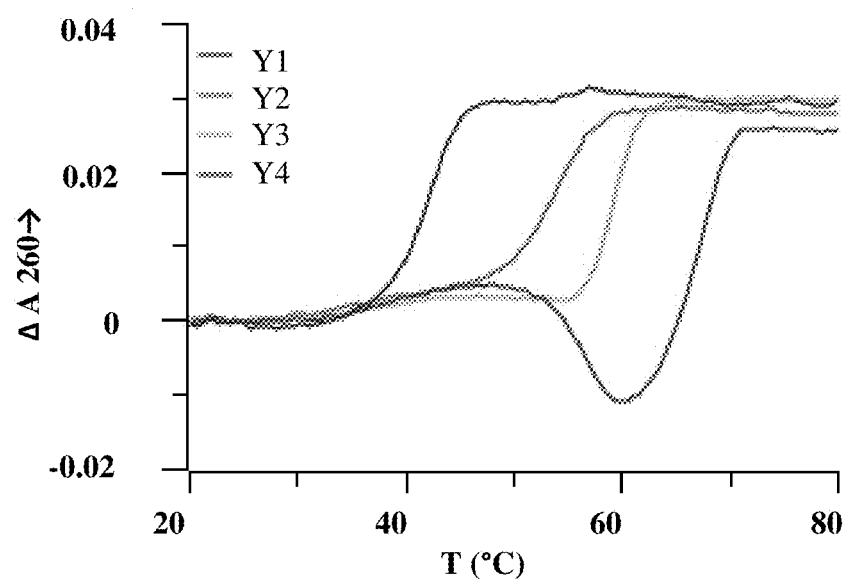
FIG. 14 illustrates the differential thermal denaturation profile obtained from denaturing triplexes between a dsDNA target and a disclosed embodiment of a β-D-LNA-modified TFO.
Figure 15:
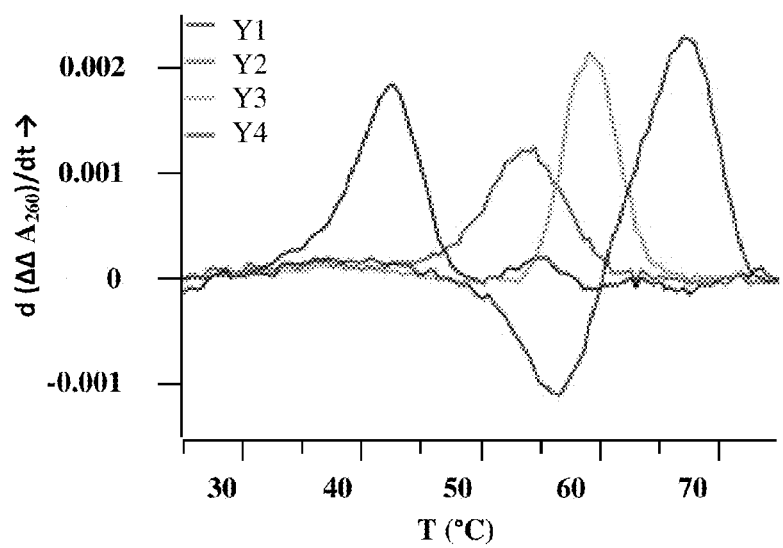
FIG. 15 illustrates the first derivative of the differential thermal denaturation profile obtained from denaturing triplexes between a dsDNA target and a disclosed embodiment of a β-D-LNA-modified TFO.

After triplex formation has been established, the thermal affinity of C5-functionalized LNA TFOs toward double stranded nucleic acid targets can be determined. The thermal affinity of nucleic acids modified with C5-functionalized LNA towards matched double stranded nucleic acid targets can be determined by any method known to a person of ordinary skill in the art to include denaturation of a triplex. Particular embodiments can be analyzed using UV thermal denaturation. UV thermal denaturation includes the denaturation of each strand by heating, followed by cooling and analysis using ultraviolet spectroscopy. The modified and unmodified triplexes are heated to a temperature effective to cause denaturation, which is herein referred to as $T_m$. $T_m$ values for C5-functionalized LNA TFOs can range from greater than 0° C. to about 100° C.; more typically the $T_m$ ranges from about 20° C. to about 80° C. Representative thermal denaturation curves for a disclosed embodiment and the double stranded nucleic acid target are provided by FIG. 13. To facilitate determination of triplex $T_m$'s, differential thermal denaturation curves were obtained by subtracting the denaturation curve of the double stranded nucleic acid target from the raw triplex denaturation curve for the modified nucleic acid (FIG. 14). FIG. 15 illustrates the first derivative graph of differential thermal denaturation curves of triplexes formed with working embodiment Y. The apparent melting temperatures during heating and cooling cycles of parallel duplexes formed by TC-motif TFOs and the polypurine strand of the double stranded nucleic acid target are shown in Table 6.

TABLE 6

Melting temperatures for LNA for duplexes formed between TFOs and dsDNA[a]

| | | $T_m/T_a$ (° C.) | | |
|---|---|---|---|---|
| ON Seq 5'→3' | B = | X | Y | V |
| B1 TTT TT$^m$C T<u>B</u>T $^m$CT$^m$C T$^m$CT | | 30.5/13.5<br>SEQ ID NO: 23 | 26.5/14.0<br>SEQ ID NO: 12 | 28.5/15.0<br>SEQ ID NO: 16 |
| B2 TTT T<u>B</u>$^m$C TT<u>B</u> $^m$CTmC <u>B</u>$^m$CT | | 42.0/19.0<br>SEQ ID NO: 20 | 45.0/22.0<br>SEQ ID NO: 13 | 34.0/23.0<br>SEQ ID NO: 17 |
| B3 TTT T<u>B</u>$^m$C T<u>B</u>T C<u>B</u>$^m$C T$^m$CT | | 42.5/18.5<br>SEQ ID NO: 21 | 40.0/20.5<br>SEQ ID NO: 14 | 37.0/26.5<br>SEQ ID NO: 18 |
| B4 TT<u>B</u> T<u>B</u>$^m$C <u>BTB</u> $^m$C<u>B</u>$^m$C <u>B</u>$^m$CT | | 50.0/32.0<br>SEQ ID NO: 22 | 53.0/41.5<br>SEQ ID NO: 15 | 51.5/50.5<br>SEQ ID NO: 19 |

[a]The denaturation curves ($A_{260}$ vs T) were recorded using 1.0 μM of each strand in a pH 7.0 phosphate buffer solution (adjusted with 10 mM NaH$_2$PO$_4$/5 mM Na$_2$HPO$_4$) containing 140 mM KCl at 0.5° C./min heating and cooling rates. The $T_m$'s and $T_a$'s were determined by first derivative of denaturation curves and are averages of two independent measurements within 1° C. For T1 (B = T) (SEQ ID NO: 1): Tm = 23.5° C., and Ta = 12.0° C., were observed. IUPAC names for the diphosphate-form of compounds X, Y, and V have been included in the sequence listing.

Singly modified C5-alkynyl functionalized LNA TFOs exhibit dramatically increased thermal affinity toward dsDNA targets relative to reference DNA TFO T1 ($\Delta T_m$~+13.5° C., B1-series, Table 7). A person of ordinary skill in the art will recognize that this increase in $T_m$ values for C5-LNA-modified TFOs is likely to be sequence specific; however, certain embodiments of C5-LNA-modified DNA strands, comprising from about 5 to about 50 nucleotides, can exhibit an increase in $T_m$ ranging from greater than 0° C. to about 15° C. as compared to unmodified DNA strands. Additional modification of TFOs with certain embodiments results in progressively more stabilized triplexes, although less pronounced $\Delta T_m$/mod-values are observed (e.g., compare data of B1-, B2- and B4-series, Table 7). C5-propargylamine functionalized LNAs (V-series) stabilize triplexes slightly more efficiently than the corresponding C5-ethynyl functionalized LNAs (Y-series). Without being limited to a theory of operation, it is currently believed that this difference is a result of reduced electrostatic repulsion between the triplex strands due to partial protonation of the propargylamino substituent, or from improved π-stacking with neighboring nucleobases.

TABLE 7

Thermal affinity for triplexes formed by LNA TFOs with dsDNA[a]

| | | $T_m[\Delta T_m$/mod] ° C. | | |
|---|---|---|---|---|
| ON Sequence 5' to 3' | B = | X | Y | V |
| B1 TTT TT$^m$C T<u>B</u>T $^m$CT$^m$C T$^m$CT | | 40.0 [+11.0]<br>SEQ ID NO: 23 | 42.5 [+13.5]<br>SEQ ID NO: 12 | 42.5 [+13.5]<br>SEQ ID NO: 16 |
| B2 TTT T<u>B</u>$^m$C TT<u>B</u> $^m$CT$^m$C <u>B</u>$^m$CT | | 48.5 [+6.5]<br>SEQ ID NO: 20 | 54.0 [+8.3]<br>SEQ ID NO: 13 | 57.0 [+9.3]<br>SEQ ID NO: 17 |
| B3 TTT T<u>B</u>$^m$C T<u>B</u>T $^m$C<u>B</u>$^m$C T$^m$CT | | 53.5 [+8.2]<br>SEQ ID NO: 21 | 59.5 [+10.2]<br>SEQ ID NO: 14 | 60.0 [+10.3]<br>SEQ ID NO: 18 |

TABLE 7-continued

Thermal affinity for triplexes formed by LNA TFOs with dsDNA[a]

| | | $T_m[\Delta T_m/mod]$ °C. | | |
|---|---|---|---|---|
| ON Sequence 5' to 3' | B = | X | Y | V |
| B4  TTB TB<sup><i>m</i></sup>C BTB <sup><i>m</i></sup>CB<sup><i>m</i></sup>C B<sup><i>m</i></sup>CT | | 61.0 [+5.3]<br>SEQ ID NO: 22 | 67.5 [+6.4]<br>SEQ ID NO: 15 | 74.5 [+7.6]<br>SEQ ID NO: 19 |

[a]$T_m$'s were determined as the first derivative of differential thermal denaturation curves ($A_{260}$ vs T), recorded in a pH 7.0 phosphate buffer solution (pH adjusted with 10 mM $NaH_2PO_4$/5 mM $Na_2HPO_4$) containing 140 mM KCl using 1.0 µM of each strand. $T_m$-values are averages of at least two independent measurements within 1° C. Data for DNA reference TFO T1 (B = T) (SEQ ID NO: 1): $T_m = 29.0$° C., $k_{on} = 4400$ $Lmol^{-1}s^{-1}$. <sup><i>m</i></sup>C = 5-methyldeoxycytidine monomers. dsDNA target sequence (TFO binding region underlined): 5'-GCT <u>AAAAAGAAAGAGA</u> TCG-3' (SEQ ID NO.: 2), 3'-CGA <u>TTTTTCTTTCTCT</u> ACG-5' (SEQ ID NO: 3). IUPAC names for the diphosphate-form of compounds X, Y, and V have been included in the sequence listing.

Figure 16:
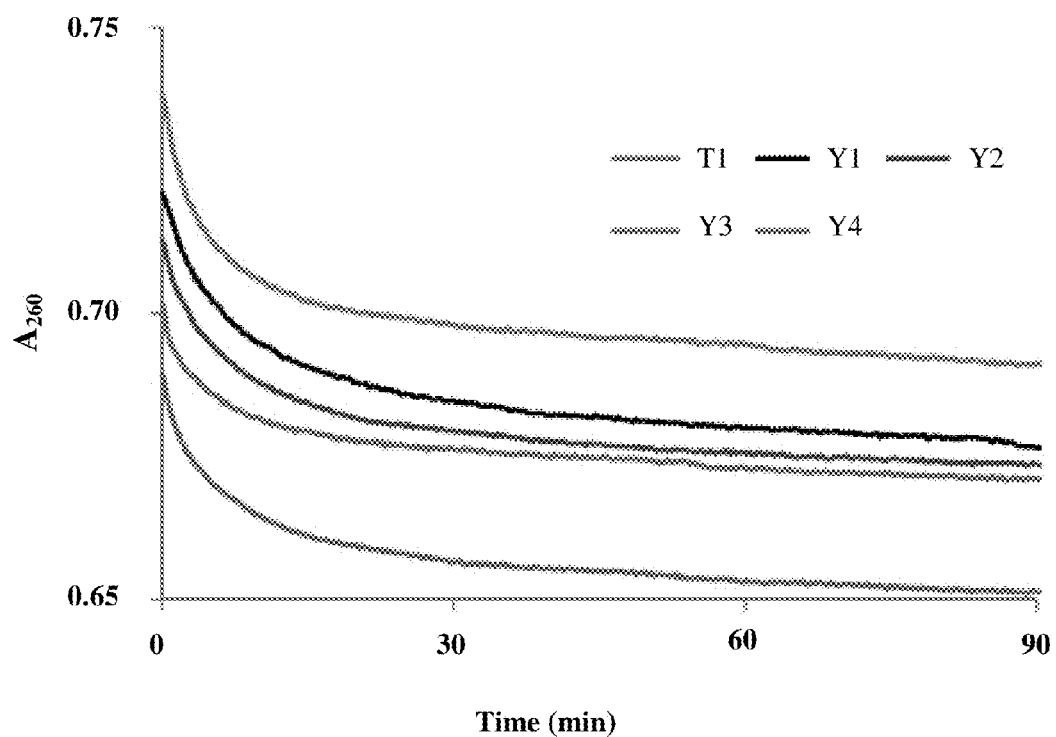
FIG. 16 is a graph of time in minutes (x-axis) versus absorbance (y-axis) illustrating the absorption decay profiles for triplexes formed between a dsDNA target and reference DNA TFO (T1) and a dsDNA target, and a disclosed embodiment of a β-D-LNA-modified TFO (Y1-Y4).
Figure 17:
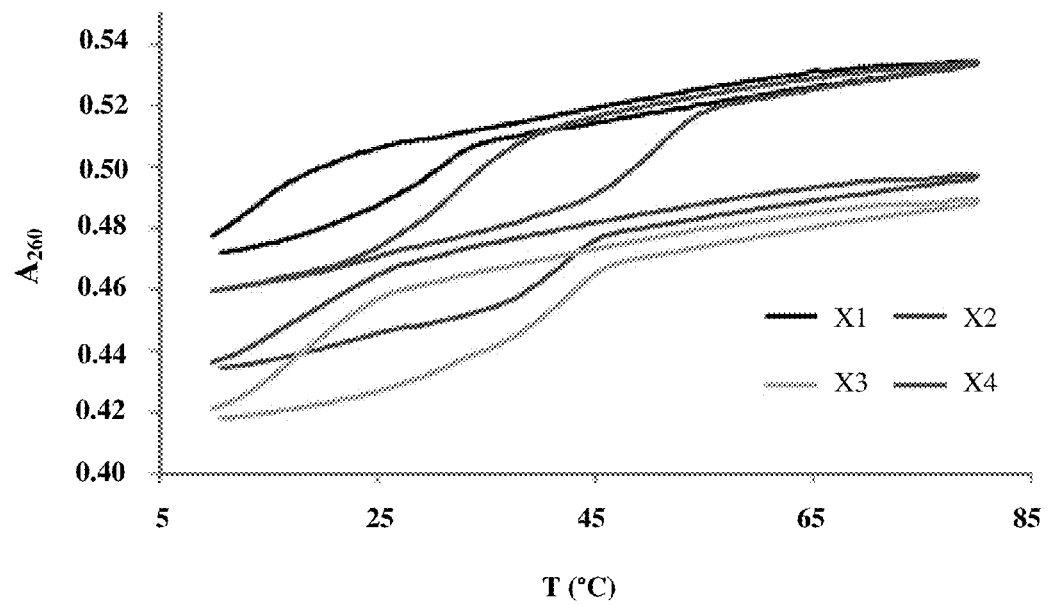
FIG. 17 is a graph of temperature in ° C. (x-axis) versus absorbance (y-axis) illustrating the hysteresis profiles for parallel duplex formation by a conventional LNA TFO (X1-X4).

Particular embodiments concern the evaluation of the influence of C5-functionalized LNA compounds on association kinetics of triplex formation. The association rate constant, $k_{on}$, can be determined for TFOs by fitting a second order rate equation to the $A_{260}$ decay curve obtained by mixing a pre-annealed double stranded nucleic acid target with equimolar quantities of TFOs (FIG. 16). Particular embodiments exhibited little variation in the $k_{on}$-values between DNA, conventional LNA, or C5-functionalized LNA TFOs, as illustrated in Table 8. These results indicate that LNA-type TFOs primarily influence triplex dissociation kinetics. Certain embodiments utilizing the C5-propargylamine functionalized LNA (V) exhibited faster triplex association kinetics. Without being limited to a theory of operation, it is currently believed that this result is due to the presence of partially positively charged 'patches' of the C5-propargylamine substituent. In addition, significant hysteresis was observed for parallel duplex formation involving denaturation of the triplex to three single strands for compound X (X1-X4, as illustrated in FIG. 17).

TABLE 8

Association rate constants for triplexes formed by LNA TFOs with ds DNA

| | | kon ($Lmol^{-1}s^{-1}$) | | |
|---|---|---|---|---|
| ON Sequence 5' to 3' | B = | X | Y | V |
| B1  TTT TT<sup><i>m</i></sup>C TBT <sup><i>m</i></sup>CT<sup><i>m</i></sup>C T<sup><i>m</i></sup>CT | | 3800<br>SEQ ID NO: 23 | 4400<br>SEQ ID NO: 12 | ND<br>SEQ ID NO: 16 |
| B2  TTT TB<sup><i>m</i></sup>C TTB <sup><i>m</i></sup>CT<sup><i>m</i></sup>C B<sup><i>m</i></sup>CT | | 3600<br>SEQ ID NO: 20 | 4000<br>SEQ ID NO: 13 | 3700<br>SEQ ID NO: 17 |
| B3  TTT TB<sup><i>m</i></sup>C TBT <sup><i>m</i></sup>CB<sup><i>m</i></sup>C T<sup><i>m</i></sup>CT | | 3900<br>SEQ ID NO: 21 | 4100<br>SEQ ID NO: 14 | 3900<br>SEQ ID NO: 18 |
| B4  TTB TB<sup><i>m</i></sup>C BTB <sup><i>m</i></sup>CB<sup><i>m</i></sup>C B<sup><i>m</i></sup>CT | | 4300<br>SEQ ID NO: 22 | 4400<br>SEQ ID NO: 15 | 5500<br>SEQ ID NO: 19 |

$k_{on}$'s were measured in pH 7.2 HEPES buffer. The listed values of $k_{on}$'s are average of at least three independent measurements. Data for DNA reference TFO T1 (B = T) (SEQ ID NO: 1): $T_m = 29.0$° C., $k_{on} = 4400$ $Lmol^{-1}s^{-1}$. <sup><i>m</i></sup>C = 5-methyldeoxycytidine monomers. dsDNA target sequence (TFO binding region underlined): 5'-GCT <u>AAAAAGAAAGAGA</u> TCG-3' (SEQ ID NO: 2), 3'-CGA <u>TTTTTCTTTCTCT</u> ACG-5' (SEQ ID NO: 3).

ND = not determined.

IUPAC names for the diphosphate-form of compounds X, Y, and V have been included in the sequence listing.

Triplex-forming oligonucleotides modified with one or more C5-functionalized α-L-LNA monomers can also modulate thermal affinity toward double stranded nucleic acid targets with complementary purine target regions (Hoogsteen base-pairing) relative to the TFOs. In particular embodiments, oligonucleotides comprising compounds Y' or V' result in dramatic increases in thermal affinity toward complementary double stranded nucleic acid targets ($\Delta T_m$/modification between +2.8° C. and +8.5° C., Table 9). These increases in thermal affinity are more pronounced than with reference α-L-LNA (X').

ing the increased thermal affinity as compared to unmodified DNA. Particular embodiments include C5-functionalized LNA compounds wherein the alkynyl linker is attached to a hydrogen atom or $CH_2X$, where X is selected from hydroxyl, sulfhydryl, phosphine, or amine. Incorporation of particular embodiments, such as C5-acetylene LNA Y and C5-propargylamine LNA V exhibit pronounced discrimination of RNA strands with a mismatched nucleotide opposite of the building block (Table 10). In certain embodiments, C5-functionalized LNAs can display an increased ability to discriminate amongst mismatched nucleic acid strands, as compared to

TABLE 9

Thermal affinity of triplexes formed by α-L-LNA TFOs with dsDNA

| ON Sequence 5'→3' | B = | X'[a] | Y' | V' |
|---|---|---|---|---|
| B1 TTT TT$^m$C T<u>B</u>T $^m$CT$^m$C T$^m$CT | | 35.5 [+6.5] SEQ ID NO: 37 | 37.5 [+8.5] SEQ ID NO: 38 | 37.0 [+8.0] SEQ ID NO: 39 |
| B2 TTT T<u>B</u>$^m$C TT<u>B</u> $^m$CT$^m$C <u>B</u>$^m$CT | | 43.5[+4.8] SEQ ID NO: 40 | 48.0[+6.3] SEQ ID NO: 43 | 46.0[+5.7] SEQ ID NO: 46 |
| B3 TTT T<u>B</u>$^m$C T<u>B</u>T $^m$C<u>B</u>$^m$C T$^m$CT | | 44.5[+5.2] SEQ ID NO: 41 | 50.0[+7.0] SEQ ID NO: 44 | 45.5[+5.5] SEQ ID NO: 47 |
| B4 TT<u>B</u> T<u>B</u>$^m$C <u>B</u>T<u>B</u> $^m$C<u>B</u>$^m$C <u>B</u>$^m$CT | | 37.5[+1.4] SEQ ID NO: 42 | 45.5[+2.8] SEQ ID NO: 45 | ND SEQ ID NO: 48 |

[a]IUPAC names for the diphosphate-form of compounds X', Y', and V' have been included in the sequence listing.

B. Modulation of Thermal Affinity Toward Mismatched, Single Stranded DNA/RNA Targets or Double Stranded DNA Targets.

The ability of C5- or C8-functionalized LNA and α-L-LNA compounds to modulate affinity toward mismatched, single stranded nucleic acid targets or double stranded nucleic acid targets can also be explored. Monomers of C5- or C8-functionalized LNA or α-L-LNA compounds can be incorporated into oligonucleotides such as by using a DNA synthesizer, as previously described. A person of ordinary skill in the art will understand that oligonucleotides can contain from two nucleotides to at least 300 nucleotides. Particular embodiments utilize oligonucleotides having from about 5 to about 50 nucleotides; more typically from about 8 to 35 nucleotides. Particular embodiments can be tested against unmodified reference strands, as well as reference strands modified with commercially available LNA thymidine phosphoramidite (Wengel et. al. *Tetrahedron*, 1998, 54, 3607-3630).

1. Mismatched Single Stranded Nucleic Acids

Thermal affinity of oligonucleotides modified with C5- or C8-functionalized LNA towards mismatched single stranded nucleic acid strands can be determined by any method known to a person of ordinary skill in the art to include denaturation of the oligonucleotide and its complement nucleic acid strand. Particular embodiments can be analyzed using UV thermal denaturation experiments.

Particular embodiments exhibit the ability to discriminate amongst mismatched DNA/RNA sequences, while maintainunmodified DNA. A person of ordinary skill in the art will understand that increases in $T_m$ likely depend on the specific mismatch being investigated, as well as the particular DNA sequence. Particular embodiments can exhibit increased mismatch discrimination in 9-mer sequences, as compared to unmodified DNA, ranging from less than 0 to about −5° C., where a cytosine has replaced an adenine; from less than 0 to about −12° C., where a guanine has replaced an adenine; and from less than 0 to about −7° C., where a uracil has replaced an adenine. Importantly, discrimination of the challenging U:rG mismatch (M=G) is markedly improved relative to DNA and LNA reference strands (compare $\Delta T_m$ for ON=Y1 and V1 with T1 and X1, Table 10).

Particular embodiments utilize C5-LNAs comprising a hydrophobic moiety at the C5 position. Certain embodiments have cholesterol or stearic acid appended to the C5 position via a functionalized alkyne linker C5-Functionalized LNA carrying hydrophobic substituents (W1 and Q1) exhibit excellent, while slightly lower than above disclosed embodiments, discrimination of mismatched targets (Table 10). The data demonstrate that introduction of C5-alkynyl substituents to the LNA skeleton not only maintains the Watson-Crick base pairing fidelity of LNA, but even can enhance it. Without being limited to a theory of operation, it is currently believed that the enhancement of Watson-Crick base pairing fidelity is attributed to restricted rotation of the glycosidic torsion angle (O4'-C1'-N1-C2) as imposed by steric interactions between H6 or the C5-substituent and the H3' of the LNA skeleton.

TABLE 10

Thermal Affinity of LNA compounds against mismatched RNA targets $T_m[\Delta T_m]$ (° C.)
RNA: 3'-CAC UBU ACG

| ON | Sequence | B = A | C | G | U |
|---|---|---|---|---|---|
| T1 | 5'-GTG A<u>T</u>A TGC | 27.0 | <10 (<-17.0) | 22.5 (-4.5) | <10 (<-17.0) |
| X1 | 5'-GTG A<u>X</u>A TGC | 36.5 | 17.5 (-19.0) | 28.5 (-8.0) | 18.0 (-18.5) |
| Y1 | 5'-GTG A<u>Y</u>A TGC | 38.0 | 17.5 (-20.5) | 24.5 (-13.5) | 16.0 (-22.0) |
| O1 | 5'-GTG A<u>O</u>A TGC | 37.0 | 18.0 (-19.0) | 27.0 (-10.0) | 16.5 (-20.5) |
| V1 | 5'-GTG A<u>V</u>A TGC | 40.0 | 21.5 (-18.5) | 28.5 (-11.5) | 17.5 (-22.5) |
| W1 | 5'-GTG A<u>W</u>A TGC | 31.0 | 11.5 (-19.5) | 21.0 (-10.0) | 11.0 (-20.0) |
| Q1 | 5'-GTG A<u>Q</u>A TGC | 25.0 | 10.0 (-15.0) | 16.0 (-9.0) | <10 (<-15.0) |
| P1 | 5'-GTG A<u>P</u>A TGC | 23.0 | <10 (<-13.0) | 12.5 (-10.5) | <10 (<-13.0) |
| β1 | 5'-GTG A<u>β</u>A TGC | 25.5 | 24.0 (-1.5) | <10 (<-15.5) | <10 (<-15.5) |
| γ1 | 5'-GTG A<u>γ</u>A TGC | 25.0 | <10 (<-15.0) | 17.0 (-8.0) | <10 (<-15.0) |
| α1 | 5'-GTG A<u>α</u>A TGC | 15.0 | <10 (<-5.0) | <10 (<-5.0) | <10 (<-5.0) |

Table 11 illustrates data obtained from thermal denaturation studies involving nucleic acid sequences comprising one or more C5-functionalized LNA monomers and single stranded DNA targets.

TABLE 11

Thermal Affinity of LNA compounds against mismatched DNA targets $T_m [\Delta T_m]$ (° C.)
DNA: 3'-CAC T<u>B</u>T ACG

| ON | Sequence | B = A | C | G | T |
|---|---|---|---|---|---|
| T1 | 5'-GTG A<u>T</u>A TGC | 29.5 | 13.0 (-16.5) | 21.5 (-8.0) | 14.0 (-15.5) |
| X1 | 5'-GTG A<u>X</u>A TGC | 34.5 | 16.5 (-18.0) | 23.5 (-11.0) | 18.5 (-16.0) |
| Y1 | 5'-GTG A<u>Y</u>A TGC | 36.5 | 16.5 (-20.0) | 21.0 (-15.5) | 18.0 (-18.5) |
| O1 | 5'-GTG A<u>O</u>A TGC | 36.0 | 16.5 (-19.5) | 25.0 (-11.0) | 18.0 (-18.0) |
| V1 | 5'-GTG A<u>V</u>A TGC | 37.5 | 18.5 (-19.0) | 25.5 (-12.0) | 20.0 (-17.5) |
| W1 | 5'-GTG A<u>W</u>A TGC | 30.5 | 12.5 (-18.0) | 17.5 (-13.0) | 14.0 (-16.5) |
| Q1 | 5'-GTG A<u>Q</u>A TGC | 24.0 | 12.5 (-11.5) | 14.0 (-10.0) | 13.0 (-11.0) |
| P1 | 5'-GTG A<u>P</u>A TGC | 23.0 | 15.5 (-7.5) | 13.0 (-10.0) | 15.5 (-7.5) |
| β1 | 5'-GTG A<u>β</u>A TGC | 24.0 | 14.0 (-10.0) | <10 (<-14.0) | 14.5 (-9.5) |
| γ1 | 5'-GTG A<u>γ</u>A TGC | 19.0 | 18.0 (-1.0) | 15.0 (-4.0) | 16.5 (-2.5) |
| α1 | 5'-GTG A<u>α</u>A TGC | 17.0 | 26.5 (+9.5) | 17.0 (0) | 23.0 (+6.0) |

Table 12 illustrates $T_m$ values obtained for oligonucleotides that have twice been modified with C5-functionalized LNA and conventional LNA monomers. These sequences can form duplexes with a nucleic acid strand, particularly DNA (Table 12) and RNA (Table 12) possessing a nucleobase that is a mismatch to that of the oligonucleotide comprising the C5-functionalized LNA monomer. The differences in $T_m$ for the singly mismatched sequences are also presented.

particular embodiments, oligonucleotides comprising compounds X', Y', O', V', W' or Q' exhibit dramatically more pronounced thermal discrimination of single stranded DNA or RNA targets with mismatched nucleotides opposite of the site of modification. The thermal discrimination of these oligonucleotides is pronounced than observed with reference

TABLE 12

Thermal Affinity of LNA compounds against mismatched DNA targets $T_m$ [$\Delta T_m$] (° C.)
DNA: 3'-CGT ABA GTG

| ON Sequence | B = | T | A | C | G |
|---|---|---|---|---|---|
| 5'-GCA TAT CAC | | 29.5 | <10 (<-19.5) | 13.0 (-16.5) | 22.0 (-7.5) |
| 5'-GCA XAX CAC | | 40.0 | 23.0 (-17.0) | 24.5 (-15.5) | 20.5 (-19.5) |
| 5'-GCA YAY CAC | | 40.5 | 28.0 (-12.5) | 26.5 (-14.0) | 28.0 (-12.5) |
| 5'-GCA OAO CAC | | 40.5 | 25.0 (-15.5) | 25.5 (-15.0) | 25.5 (-15.0) |
| 5'-GCA VAV CAC | | 45.5 | nt (<-35.5) | nt (<-35.5) | nt (<-35.5) |
| 5'-GCA PAP CAC | | 30.5 | nt (<-20.5) | 10.5 (-20.0) | <10 (<-20.5) |

Table 13 illustrates results obtained from denaturing duplexes formed between nucleic acid strands that are modified with particular embodiments of C5-functionalized LNA compounds and mismatched single stranded RNA targets.

α-L-LNA. In another embodiment, oligonucleotides containing an incorporation of monomer P' exhibit pronounced thermal discrimination of single stranded RNA targets with mismatched nucleotides opposite of the site of modification.

TABLE 13

Thermal Affinity of LNA compounds against mismatched RNA targets $T_m$ [$\Delta T_m$] (° C.)
RNA: 3'-CGU ABA GUG

| ON Sequence | B = | U | A | C | G |
|---|---|---|---|---|---|
| 5'-GCA TAT CAC | | 27.0 | 11.0 (-16.0) | 11.0 (-16.0) | 16.0 (-11.0) |
| 5'-GCA XAX CAC | | 43.0 | 23.0 (-20.0) | 27.5 (-15.5) | 27.0 (-16.0) |
| 5'-GCA YAY CAC | | 44.0 | 28.5 (-15.5) | 29.0 (-15.0) | 29.0 (-15.0) |
| 5'-GCA OAO CAC | | 43.5 | 25.0 (-18.5) | 29.0 (-14.5) | 27.5 (-16.0) |
| 5'-GCA VAV CAC | | 49.0 | 26.0 (-23.0) | 30.0 (-19.0) | 27.0 (-22.0) |
| 5'-GCA PAP CAC | | 30.5 | 11.0 (-19.5) | <10 (<-20.5) | 10.5 (-20.0) |

Oligonucleotides modified with one or more C5-functionalized α-L-LNA compounds allow differential discrimination of mismatched single stranded DNA/RNA targets relative to unmodified reference strands (Tables 14 and 15). In

TABLE 14

Thermal Affinity of α-L-LNA compounds against mismatched DNA targets

T$_m$ [ΔT$_m$/mod] (° C.)
DNA: 3'-CAC TBT ACG

| ON Sequence | B = | A | C | G | T |
|---|---|---|---|---|---|
| 5'-GTG ATA TGC | | 29.5 | 13.0 (−16.5) | 21.5 (−8.0) | 14.0 (−15.5) |
| 5'-GTG AX'A TGC | | 33.5 | 10.0 (−23.5) | 20.0 (−13.5) | 16.0 (−17.5) |
| 5'-GTG AY'A TGC | | 37.0 | 13.0 (−24.0) | 20.0 (−17.0) | 14.0 (−23.0) |
| 5'-GTG AO'A TGC | | 36.5 | 13.0 (−23.5) | 21.0 (−15.5) | 14.5 (−22.0) |
| 5'-GTG AV'A TGC | | 39.0 | 14.0 (−25.0) | 22.0 (−17.0) | 16.5 (−22.5) |
| 5'-GTG AW'A TGC | | 30.5 | 12.5 (−17.5) | 15.0 (−15.5) | 12.0 (−18.0) |
| 5'-GTG AQ'A TGC | | 27.0 | <10 (<47.0) | <10 (<−17.0) | <10 (<−17.0) |
| 5'-GTG AP'A TGC | | 28.5 | 15.0 (−13.5) | 15.0 (−13.5) | 20 (−8.5) |

Table 15 illustrates results obtained from denaturing duplexes formed between nucleic acid strands that are modified with particular embodiments of disclosed C5-functionalized α-L-LNA compounds and mismatched single stranded RNA targets.

TABLE 15

Thermal Affinity of α-L-LNA compounds against mismatched RNA targets

T$_m$ [ΔT$_m$/mod] (° C.)
RNA: 3'-CAC UBU ACG

| ON Sequence | B = | A | C | G | U |
|---|---|---|---|---|---|
| 5'-GTG ATA TGC | | 27.0 | <10 (<−17.0) | 22.5 (−4.5) | <10 (<−17.0) |
| 5'-GTG AX'A TGC | | 36.5 | 14.0 (−22.5) | 28.5 (−8.5) | 14.0 (−22.5) |
| 5'-GTG AY'A TGC | | 38.0 | 11.0 (−27.0) | 27.0 (−11.0) | 13.0 (−25.0) |
| 5'-GTG AO'A TGC | | 35.5 | 14.5 (−21.0) | 27.0 (−8.5) | 14.5 (−21.0) |
| 5'-GTG AV'A TGC | | 39.5 | 16.0 (−23.5) | 28.5 (−11.0) | 15.0 (−24.5) |
| 5'-GTG AW'A TGC | | 30.5 | 15.5 (−14.5) | 23.5 (−7.0) | 10.5 (−20.0) |
| 5'-GTG AQ'A TGC | | 28.0 | <10 (<−18.0) | 17.0 (−11.0) | <10 (<−18.0) |
| 5'-GTG AP'A TGC | | 28.5 | <10 (<−18.5) | 15.5 (−13.0) | <10 (<−18.5) |

In yet another embodiment, illustrated in Table 16, oligonucleotides comprising two compounds, selected from X', Y', O', V', and P', as next-nearest neighbors (e.g., 5'-V'BV'-3') exhibit pronounced thermal discrimination of single stranded DNA targets with certain mismatched nucleotides in the position between the two incorporations (e.g., opposite of "B" in 5'-V'BV'-3', see Table 16).

TABLE 16

Thermal Affinity of α-L-LNA compounds against mismatched DNA targets

T$_m$ [ΔT$_m$/mod] (° C.)
DNA: 3'-CGT ABA GTG

| ON Sequence | B = | T | A | C | G |
|---|---|---|---|---|---|
| 5'-GCA TAT CAC | | 29.5 | <10 (<−19.5) | 13.0 (−16.5) | 22.0 (−7.5) |
| 5'-GCA X'AX' CAC | | 37.0 | 14.0 (−23.0) | 19.0 (−18.0) | 20.0 (−17.0) |
| 5'-GCA Y'AY' CAC | | 37.0 | 19.0 (−18.0) | 20.5 (−16.5) | 24.5 (−12.5) |

TABLE 16-continued

Thermal Affinity of α-L-LNA compounds against mismatched DNA targets

| | | $T_m$ [$\Delta T_m$/mod] (° C.) DNA: 3'-CGT ABA GTG | | | |
|---|---|---|---|---|---|
| ON Sequence | B = | T | A | C | G |
| 5'-GCA O'AO' CAC | | 37.5 | 14.5 (-23.0) | 22.0 (-15.5) | 25.5 (-12.0) |
| 5'-GCA V'AV' CAC | | 42.0 | 20.5 (-21.5) | 20.5 (-21.5) | 27.5 (-14.5) |
| 5'-GCA P'AP' CAC | | 30.5 | <10 (<-20.5) | 15.0 (-14.5) | <10 (<-20.5) |

Table 17 illustrates results obtained from denaturing duplexes formed between nucleic acid strands that are modified with two particular embodiments of C5-functionalized α-L-LNA compounds and mismatched single stranded RNA targets.

TABLE 17

Thermal Affinity of α-L-LNA compounds against mismatched RNA targets

| | | $T_m$ [$\Delta T_m$/mod] (° C.) RNA: 3'-CGU ABA GUG | | | |
|---|---|---|---|---|---|
| ON Sequence | B = | U | A | C | G |
| 5'-GCA TAT CAC | | 27.0 | 11.0 (-16.0) | 11.0 (-16.0) | 16.0 (-11.0) |
| 5'-GCA X'AX' CAC | | 38.5 | 20.5 (-22.5) | 21.0 (-22.0) | 24.0 (-19.0) |
| 5'-GCA Y'AY' CAC | | 39.0 | 24.0 (-15.0) | 22.0 (-17.0) | 25.5 (-13.5) |
| 5'-GCA O'AO' CAC | | 38.5 | 24.5 (-14.0) | 23.0 (-15.5) | 24.5 (-14.0) |
| 5'-GCA V'AV' CAC | | 41.5 | 27.0 (-14.5) | 25.0 (-16.5) | 30.0 (-12.5) |
| 5'-GCA P'AP' CAC | | 30.5 | 15.0 (-15.5) | <10 (<-20.5) | 14.5 (-16.0) |

2. Mismatched Double Stranded DNA Targets.

Oligonucleotides modified with one or more C5-functionalized LNA building blocks allow differential discrimination of fully base-paired Hoogsteen mismatched double stranded DNA relative to reference triplex forming oligonucleotides. In particular embodiments, oligonucleotides comprising compounds X or Y exhibit dramatically improved thermal discrimination of fully base-paired double stranded DNA targets with Hoogsteen mismatches opposite of the site of modification, i.e., more negative $\Delta T_m$-values (see Table 18).

TABLE 18

Thermal affinity of LNA against matched and mismatched triplexes in the presence of $Mg^{2+}$ ions.

| | | A:T | Tm [ΔTm/mod]/° C. | | |
|---|---|---|---|---|---|
| ON | SEQ ID NO: | (match) | T:A | C:G | G:C |
| T1 | 1 | 37.0 | 10.0 [-27.0] | 19.5 [-17.5] | 13.5 [-23.5] |
| X1 | 23 | 49.0 | 10.0 [-39.0] | 28.5 [-20.5] | 24.0 [-25.0] |
| Y1 | 12 | 51.5 | 10.0 [-41.5] | 24.5 [-27.0] | 27.5 [-24.0] |
| V1 | 16 | 50.0 | 10.0 [-40.0] | 26.5 [-23.5] | 27.5 [-22.5] |

Oligonucleotides modified with one or more C5-functionalized α-L-LNA monomers exhibit differential discrimination of fully base-paired Hoogsteen mismatched double stranded DNA relative to reference triplex forming oligonucleotides. In particular embodiments, oligonucleotides comprising compounds X' or Y' exhibit markedly improved thermal discrimination of fully base-paired double stranded DNA targets with Hoogsteen mismatches opposite of the site of modification (see Table 19).

TABLE 19

Thermal affinity of α-L-LNA against matched and mismatched triplexes in the presence of $Mg^{2+}$ ions.

| | | A:T | $T_m[\Delta T_m]$ | | |
|---|---|---|---|---|---|
| ON | SEQ ID NO: | (match) | T:A | C:G | G:C |
| T1 | 1 | 37.0 | 10.0 [-27.0] | 19.5 [-17.5] | 13.5 [-23.5] |
| X1' | 37 | 45.0 | 10.0 (-35.0) | 15.5 (-29.5) | 22.5 (-22.5) |
| Y1' | 38 | 47.5 | 12.0 (-35.5) | 13.5 (-34.0) | 24.5 (-23.0) |
| V1' | 39 | 46.0 | 11.0 (-36.0) | 14.5 (-31.5) | 25.5 (-20.5) |

$^a T_m$-values ($\Delta T_m$ = change in $T_m$-value relative to matched triplex).
Buffers and conditions as described previously except for addition of 10 mM $MgCl_2$.
$T_m$-values are averages of at least two independent measurements.
dsDNA targets = 5'-GCT AAA AAG ABA GAG AGA TCG-3' (SEQ ID NO: 4):3'-CGA TTT TTC TB'T CTC TCT ACG-5' (SEQ ID NO: 5), where B:B' = A:T, T:A, C:G and G:C, respectively.

C. C5- or C8-Functionalized Locked Nucleic Acids as Building Blocks to Reduce Enzymatic Degradation.

Disclosed embodiments display increased stability against enzymatic degradation, as compared to unmodified nucleic acid strands. Enzymatic degradation is used herein to describe the cleavage of nucleic acid strands by an enzyme. The enzyme can be an exonuclease or an endonuclease, selected from any enzyme capable of cleaving a phosphodiester bond, typically a phosphodiesterase. Non-limiting examples of exonuclease and endonucleases include micrococcal nuclease, S1 nuclease, mung bean nuclease, P1 nuclease, snake venom phosphodiesterase, DNaseI, RNase H, exonucleaselll and Bal 31 nuclease. Particular embodiments utilize snake venom phosphodiesterase to illustrate enzymatic stability.

1. Stability of C5- or C8-Functionalized LNA Compounds

Figure 20:
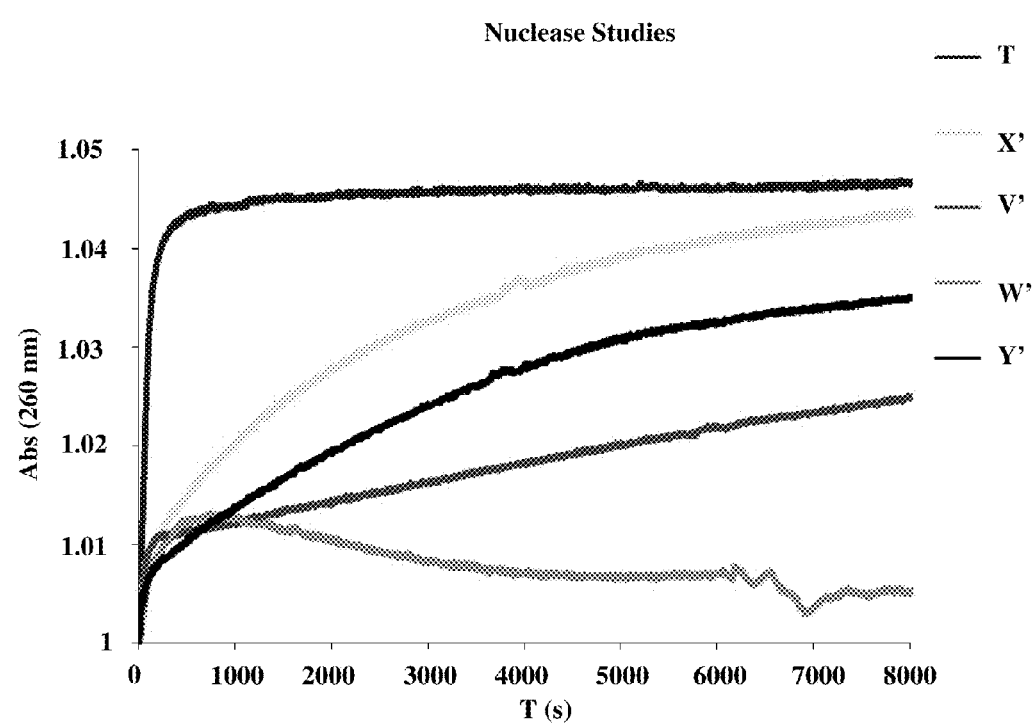
FIG. 20 is a graph of time measured in seconds (x-axis) versus absorbance (y-axis) illustrating exonuclease (SVPDE) degradation of singly modified oligonucleotides (modified with embodiments of α-L-LNA compounds) and a reference strand (T).

In particular embodiments, the stability of nucleic acid sequences, modified with C5- or C8-functionalized LNA and α-L-LNA compounds, against snake venom phosphodiesterase (SVPDE) was assessed. Particular working embodiments utilized nuclease degradation studies performed in magnesium buffer, but a person of ordinary skill in the art will recognize that any buffer capable of maintaining a pH of 9.0 can be used. The stability of the C5-functionalized LNA can be determined by measuring the change in absorbance at 260 nm over time, such as the examples illustrated in FIGS. 20-21.

Figure 18:
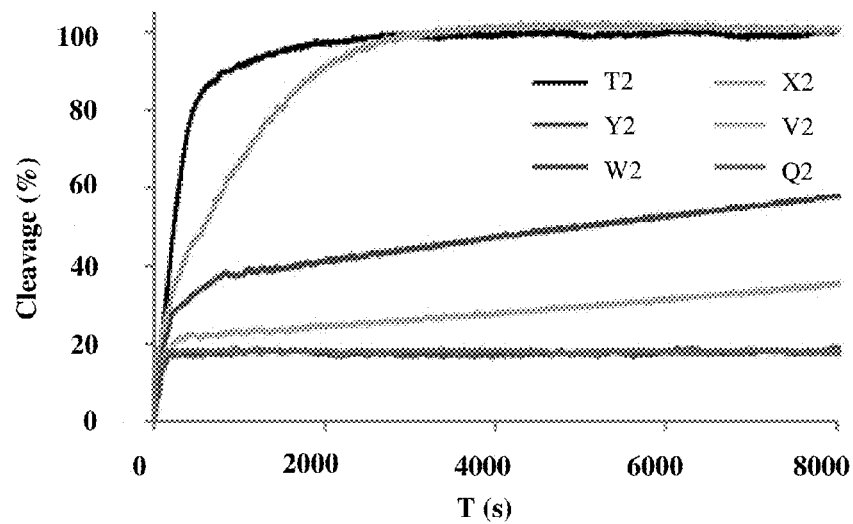
FIG. 18 is a graph of time measured in seconds (x-axis) versus cleavage percentage (y-axis) illustrating exonuclease (SVPDE) degradation of singly modified oligonucleotides (modified with embodiments of β-D-LNA compounds) and a reference DNA strand (T2).

Typically, the C5-LNAs were placed at a position not more than 3 nucleotides from the 3'-end. A person of ordinary skill in the art will recognize that a 5' exonuclease may be used, as can an endonuclease, and that the placement of the C5-LNA can be less than or more than 3 nucleotides away from the strand end. DNA strands modified with particular embodiments exhibit increase stability, compared to that of unmodified DNA strands. FIG. 18 illustrates the effects of an exonuclease on C5-functionalized LNA and a reference nucleic acid strand. According to FIG. 18, the reference strand (T) is rapidly degraded, as indicated by a high percentage of cleavage (Y-axis) in a short period of time (X-axis), whereas singly modified conventional LNA X (X2, as indicated in FIG. 18) offers moderate protection against enzymatic degradation, as indicated by a high percentage of cleavage in a period of time longer than that of the reference strand. FIG. 18 also indicates that C5-acetylene LNA Y and C5-propargylamine LNA V (Y2 and V2, respectively, as indicated in FIG. 18) are markedly more resistant toward exonuclease degradation (only ~55% and ~35% cleavage, respectively after 2 h). Interestingly, C5-alkynyl LNA carrying hydrophobic substituents (W2 and Q2, as indicated in FIG. 18) are, following a brief period of cleavage (~4 min), completely inert against further exonuclease-mediated cleavage (FIG. 18). Without being limited to a single theory of operation, it is currently believed that the steric bulk of the C5-substituents not only slows down enzymatic cleavage at the site of modification but also provides protection from degradation several nucleotides away from the site of incorporation.

Figure 19:
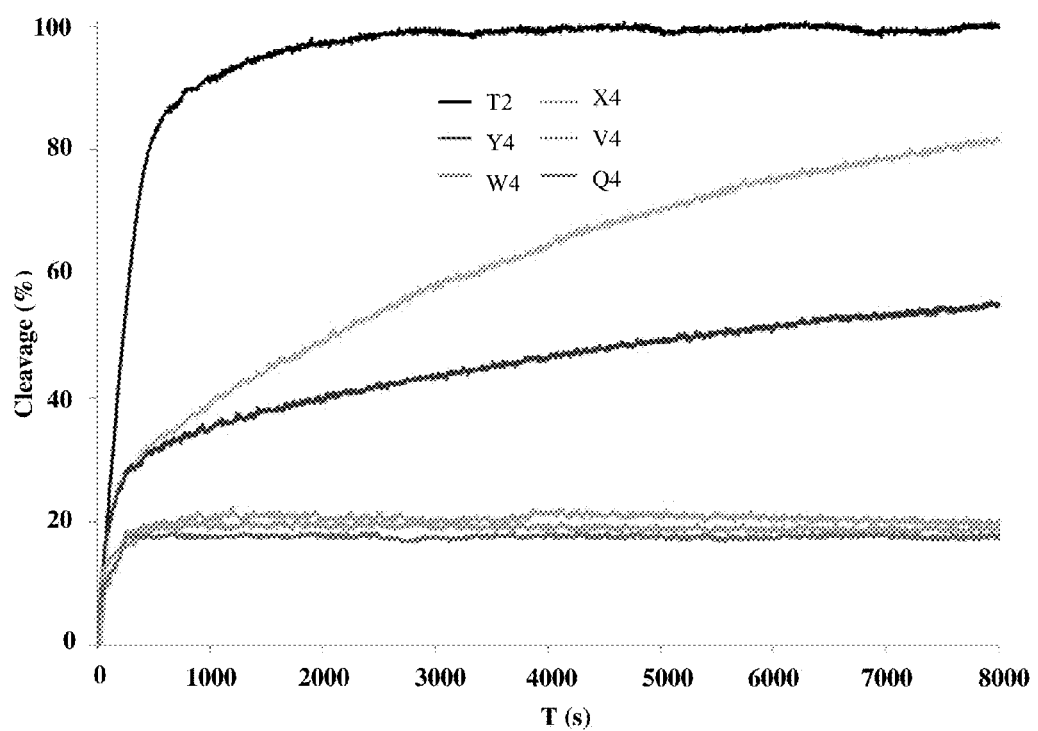
FIG. 19 is a graph of time measured in seconds (x-axis) versus cleavage percentage (y-axis) illustrating exonuclease (SVPDE) degradation of doubly modified oligonucleotides (modified with embodiments of β-D-LNA compounds) and a reference DNA strand (T2).

Particular embodiments comprise oligonucleotides that have been modified with at least two of the disclosed compounds. The effects of an exonuclease on these doubly-modified oligonucleotides was determined. Particular embodiments illustrate increased resistance to cleavage as compared with reference nucleic acid strands, whereas other embodiments, after a period of time (ranging from the time of exonuclease addition to about 10 minutes; more typically from the time of exonuclease addition to about 4 minutes), illustrate complete resistance to exonuclease-mediated cleavage. FIG. 19 illustrates that oligonucleotides comprising two Y compounds as next-nearest neighbors are markedly more resistant toward exonuclease activity (particularly SVPDE) than reference DNA strand, T, which exhibits a high percentage of cleavage in a shorter time period, or doubly modified conventional LNA (X). In another working embodiment, oligonucleotides comprising two compounds, selected from V, W or Q, as next-nearest neighbors are, following a brief period of cleavage (~4 min), completely inert against further SVPDE-mediated cleavage. Without being limited to a single theory of operation, it is currently believed that the steric bulk of the C5-substituents not only slows down enzymatic cleavage at the site of modification but also provides protection from degradation several nucleotides away from the incorporation.

2. Stability of C5- or C8-Functionalized α-L-LNA Compounds

Figure 21:
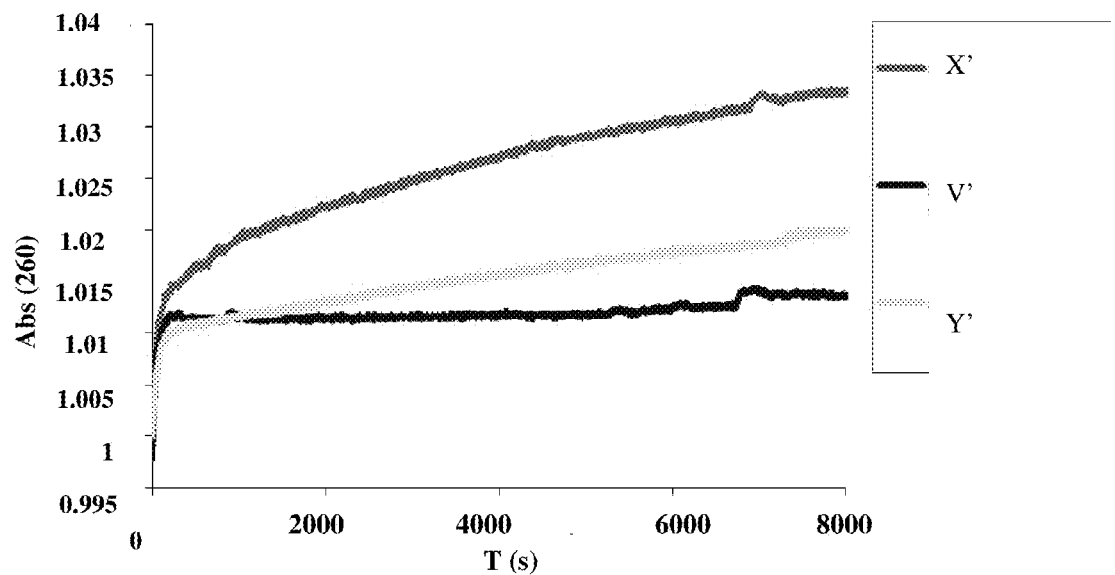
FIG. 21 is a graph of time measured in seconds (x-axis) versus absorbance (y-axis) illustrating exonuclease (SVPDE) degradation of doubly modified oligonucleotide (modified with embodiments of α-L-LNA compounds) and conventional α-L-LNA (X').

Certain embodiments concern the effects of exonuclease degradation on oligonucleotides modified with at least one C5-functionalized α-L-LNA compound. In particular embodiments, oligonucleotides comprising a single compound Y' or V' are markedly more resistant toward exonuclease degradation than reference strand T, which exhibits high percentage of cleavage after a shorter period of time than Y' or V', or singly modified α-L-LNA X. In certain disclosed embodiments, oligonucleotides comprising a single compound W' are, following a brief period of cleavage, completely inert against further SVPDE-mediated cleavage (FIG. 20) In yet another embodiment, oligonucleotides comprising two compounds Y' or V' as next-nearest neighbors are markedly more resistant toward SVPDE (only ~35% and ~15% cleavage, respectively after 2 h) than reference DNA strand T (>93% cleavage after 600 s) or doubly modified α-L-LNA X (~95% cleaved after 70 min) (FIG. 21). Without being limited to a theory of operation, it is currently believed that the steric bulk of the C5-substituents not only slows down enzymatic cleavage at the site of modification but also provides protection from degradation several nucleotides away from the incorporation. Disclosed embodiments provide the ability to maximize gene knock-down via non-endo/exonuclease mediated mechanisms, but rather through a steric block mechanism, while false positives and off-target effects that can arise from endo/exonuclease-mediated cleavage of non-target nucleic acids are minimized.

3. Stability of Triplex Forming C5- or C8-Functionalized LNA Compounds

Figure 22:
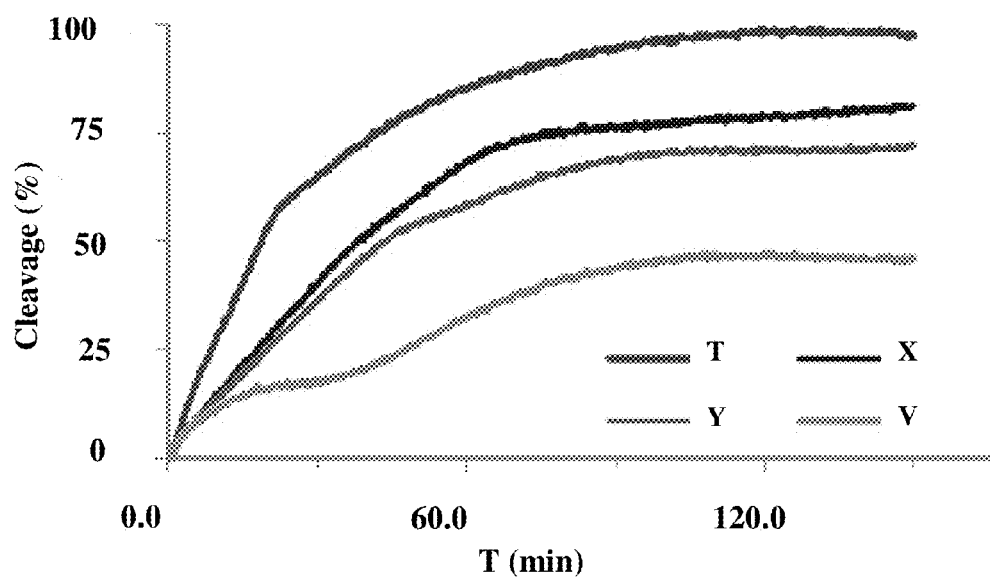
FIG. 22 is a graph of time measured in seconds (x-axis) versus cleavage percentage (y-axis) illustrating exonuclease (SVPDE) degradation of triplexes formed between singly modified oligonucleotide (modified with embodiments of β-D-LNA compounds) and a reference DNA strand (T).
Figure 23:
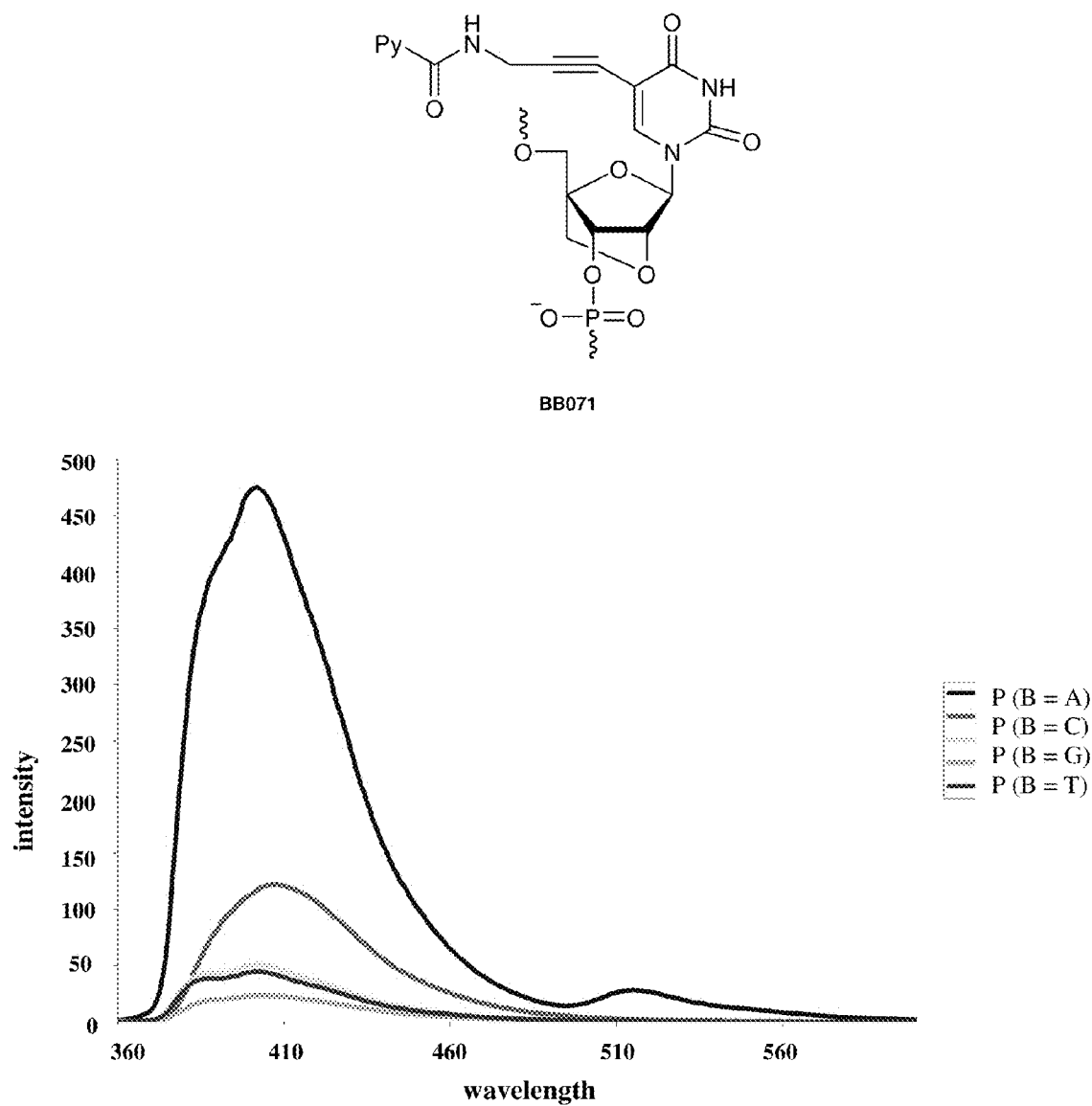
FIG. 23 is a steady-state fluorescence emission spectrum illustrating change in fluorescence intensity upon hybridization of oligonucleotides, modified with compound P, to single stranded DNA targets.
Figure 24:
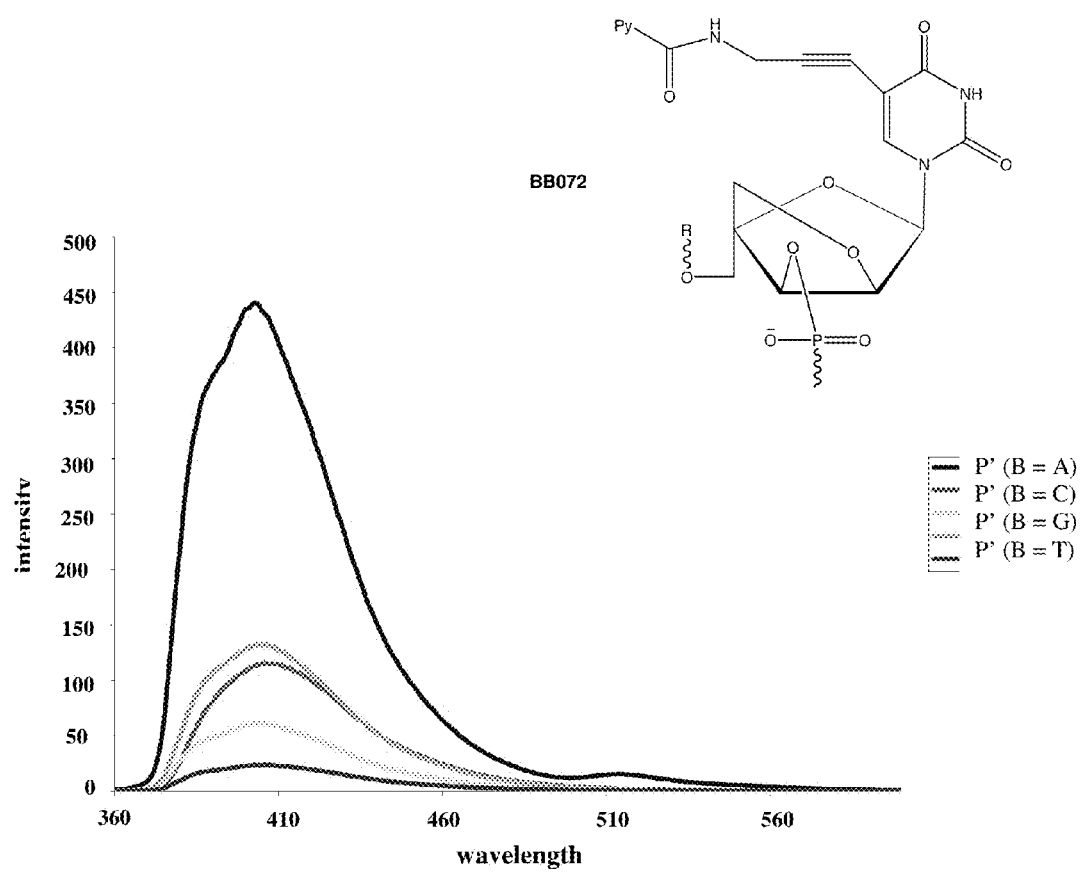
FIG. 24 is a steady-state fluorescence emission spectrum illustrating change in fluorescence intensity upon hybridization of oligonucleotides, modified with compound P', to single stranded DNA targets.
Figure 25:
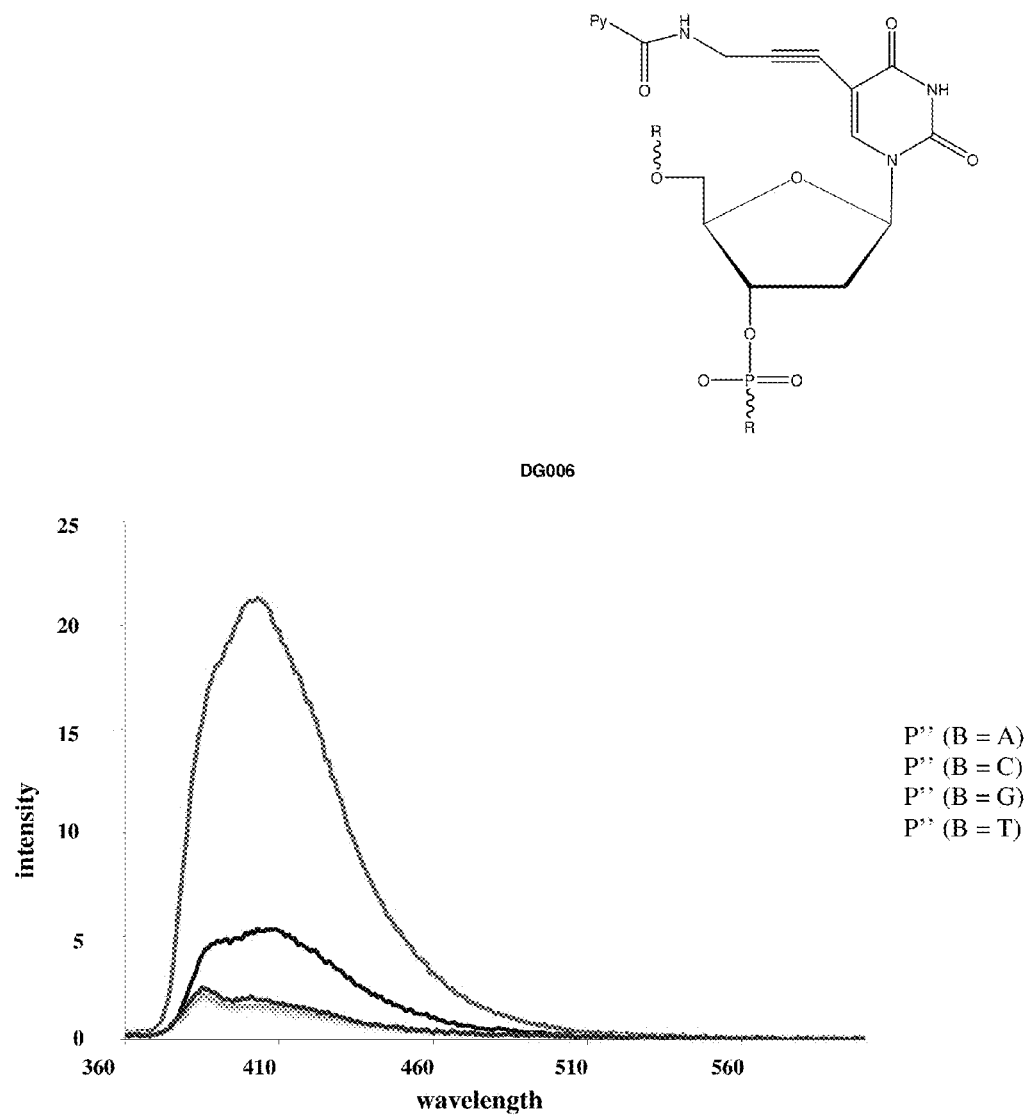
FIG. 25 is a steady-state fluorescence emission spectrum illustrating change in fluorescence intensity upon hybridization of oligonucleotides, modified with compound P''', to single stranded DNA targets.
Figure 26:
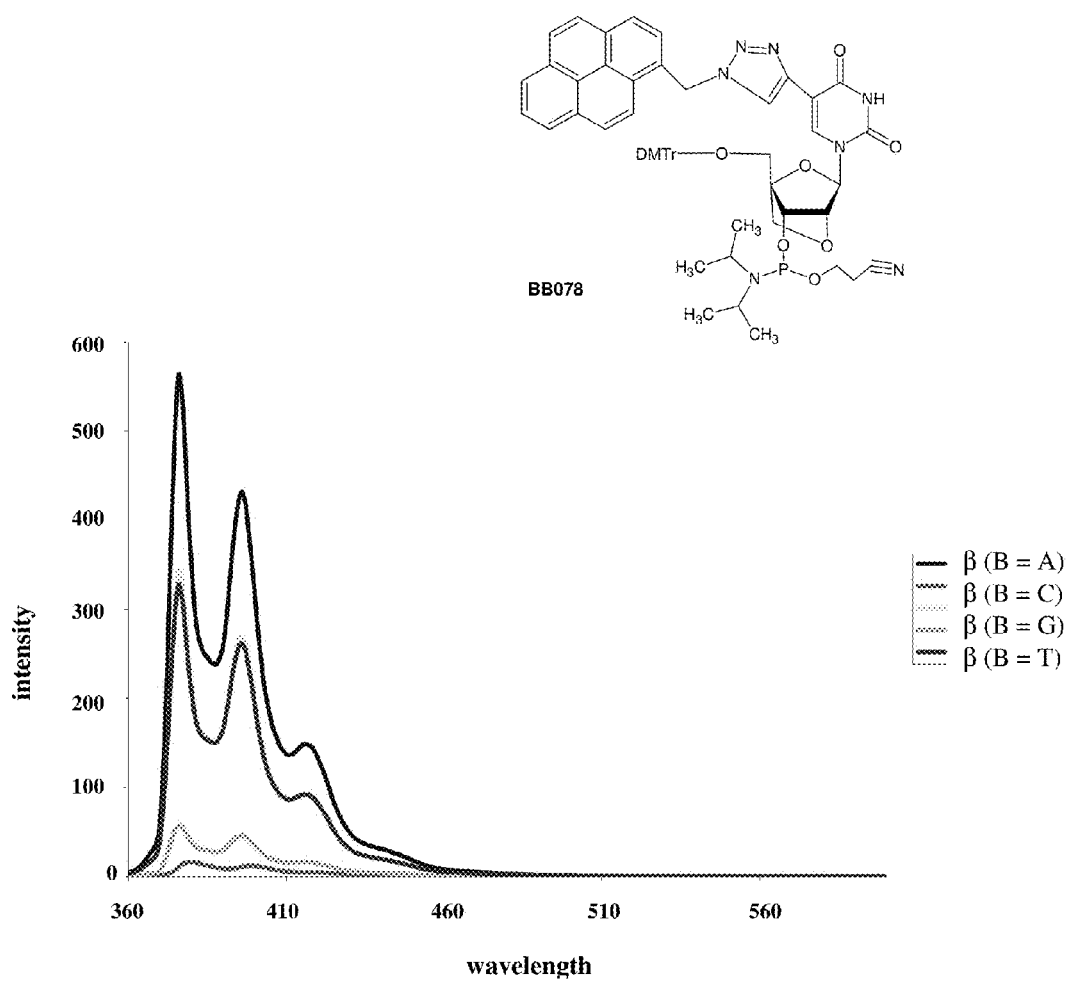
FIG. 26 is a steady-state fluorescence emission spectrum illustrating change in fluorescence intensity upon hybridization of oligonucleotides, modified with compound β, to single stranded DNA targets.
Figure 27:
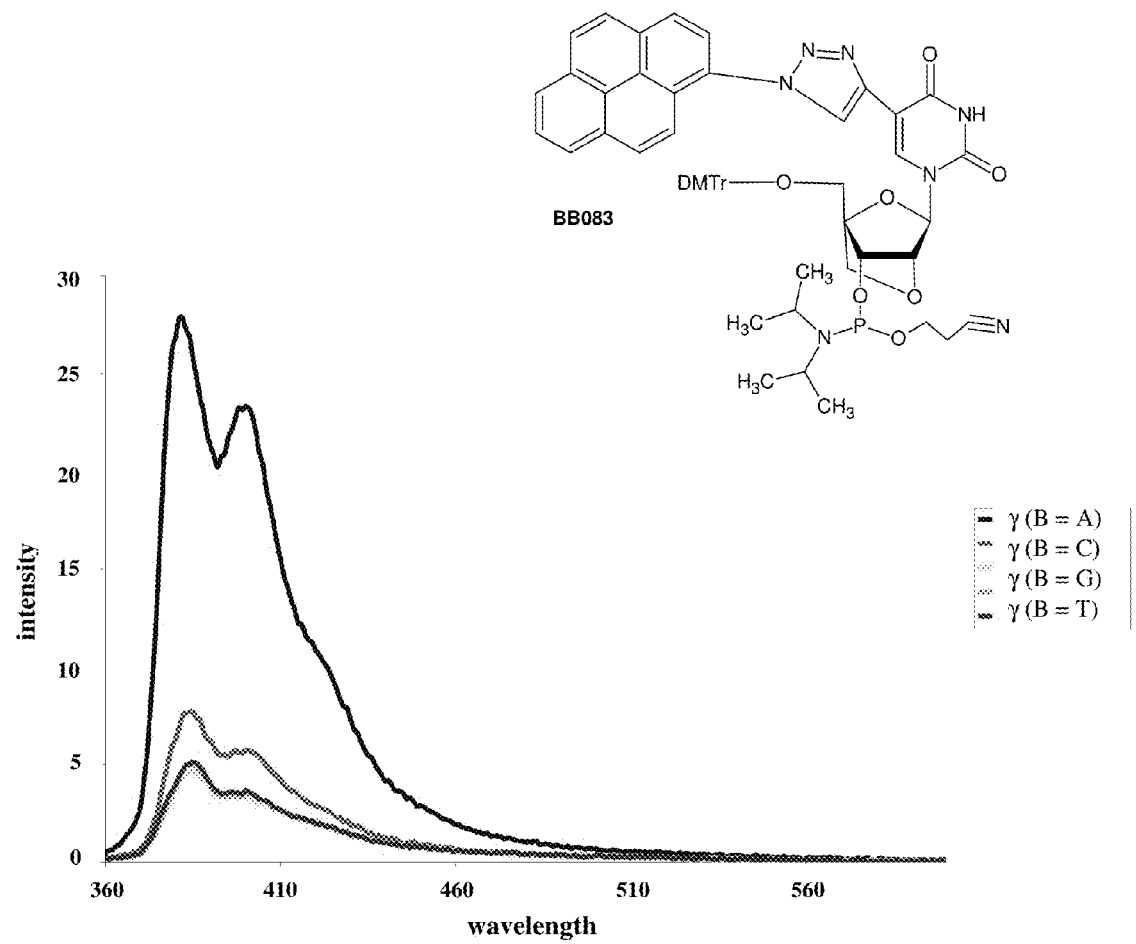
FIG. 27 is a steady-state fluorescence emission spectrum illustrating change in fluorescence intensity upon hybridization of oligonucleotides, modified with compound γ, to single stranded DNA targets.
Figure 28:
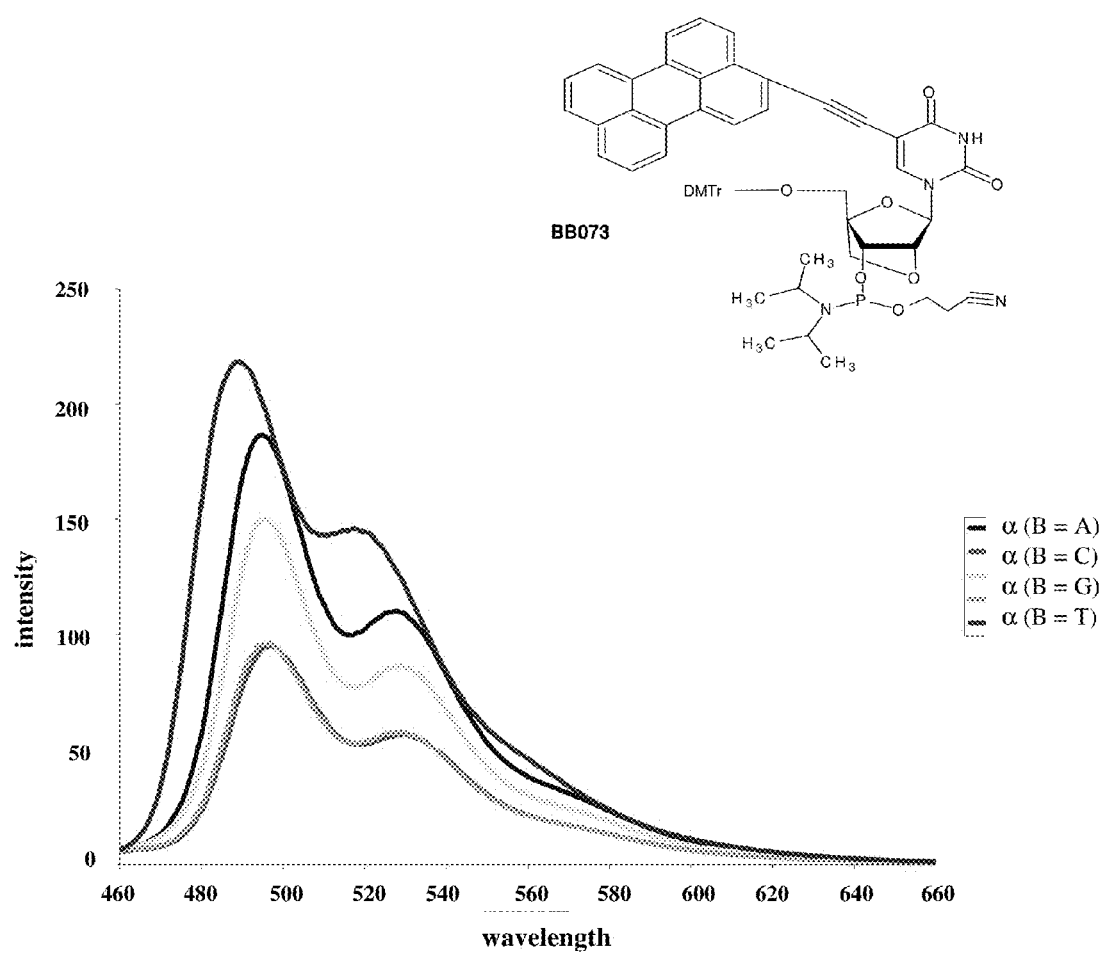
FIG. 28 is a steady-state fluorescence emission spectrum illustrating change in fluorescence intensity upon hybridization of oligonucleotides, modified with compound α, to single stranded DNA targets.

Certain embodiments concern the effects of exonuclease degradation on triplexes modified with at least one of the disclosed compounds. In particular working embodiments, the resistance of singly modified C5-functionalized LNA TFOs (utilizing a sequence comprising TTT TT$^m$C TBT $^m$CT$^m$C T$^m$CT, where B indicates the modified location) against degradation by an exonuclease, such as SVPDE, was evaluated. Particular working embodiments include oligonucleotides modified with C5-functionalized LNA compouds Y and V. FIG. 22 illustrates that oligonucleotides modified with conventional LNA compounds X illustrated some protection against exonuclease degradation, while C5-functionalized LNA compounds Y and V show considerably more resistance (Y ~60%, V ~35% after 1 h). These results strongly suggest that the C5-substituents act as an additional steric shield, to ensure greater biostability. Incorporation of the disclosed compounds into the so-called "gapmer" design can result in increased stability even following a RNaseH mediated RNA-degradation mechanism.

D. Fluorescence Studies

Disclosed embodiments of the current method utilize spectroscopy, such as fluorescence spectroscopy, to detect single nucleotide polymorphisms (SNPs). SNPs often result in phenotypic changes, and are accordingly important markers in disease genetics and pharmacogenomic studies. The most established SNP genotyping technologies are enzyme-based or rely on small differences in thermostability between duplexes of probes and complementary or SNP-containing targets. Moreover, these process-intensive, multi-step protocols often necessitate stringent control of assay conditions (e.g., temperature, ionic strength). As a result, there has been a substantial effort to develop alternative SNP-typing approaches, which are operationally more simple and costefficient. Particular embodiments of the current method concern using base discriminating fluorescent probes, which can be used for optical discrimination of complementary versus mismatched targets and potentiality for use in discrimination of SNPs in biological targets, such as human breast cancer cell lines.

Particular embodiments of the disclosed method exhibit hybridization of modified sequences to complementary DNA, which can result in hypochromic shifts in absorption and excitation maxima, hyperchromic shifts, and formation of duplexes that exhibit broad fluorescent emission maxima. Typically, the C5- or C8-linker of the LNA and α-L-LNA compounds was functionalized with a fluorophore. Particular embodiments concern fluorophores, such as pyrene or perylene; however, a person of ordinary skill in the art will recognize that any fluorophore amenable for coupling with or incorporation into a nucleotide can be used. Table 22 illustrates the thermal affinity values obtained for particular embodiments of the disclosed method.

-continued

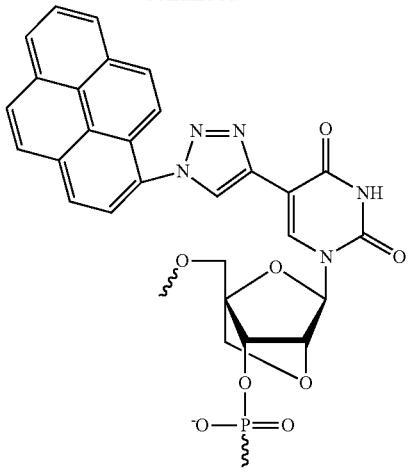

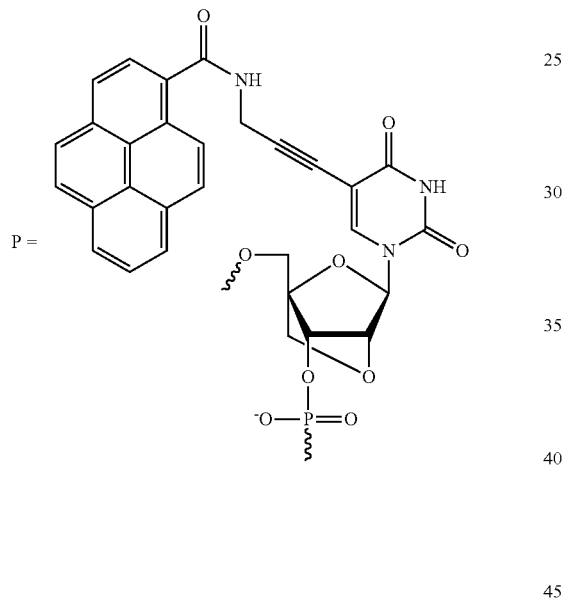

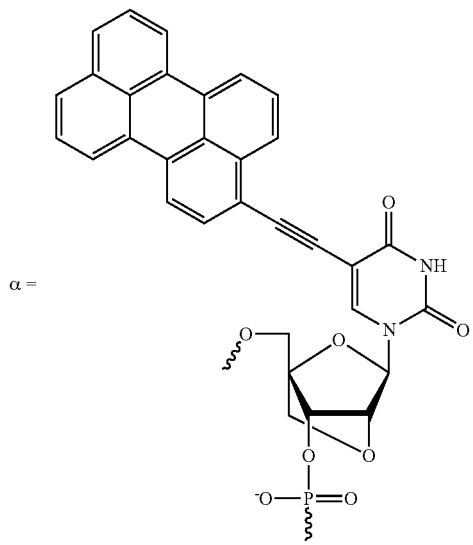

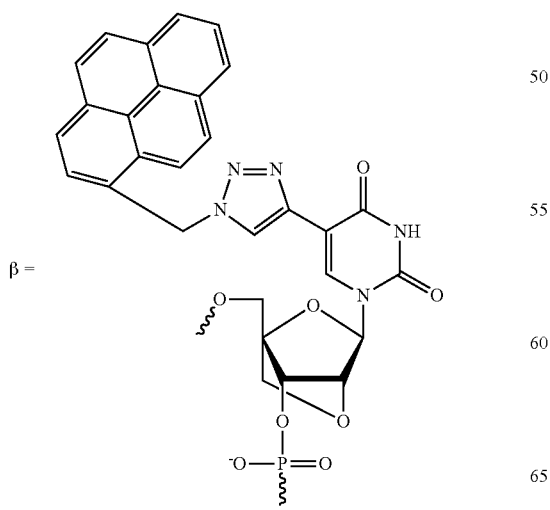

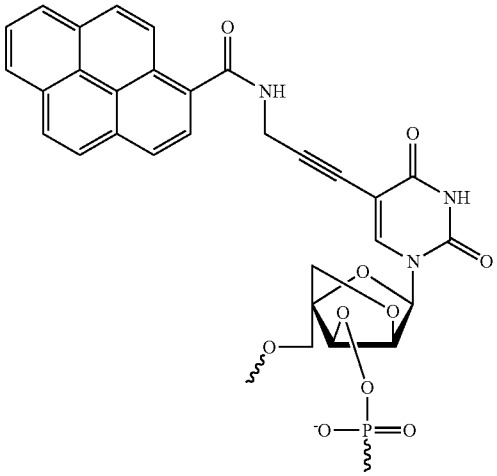

-continued

P″ = 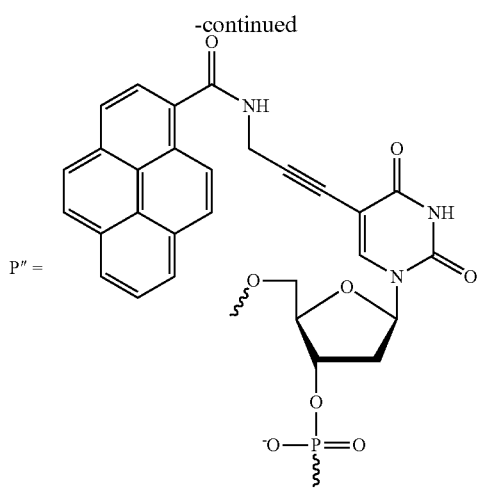

cence intensity. Thus, without being limited to a theory of operation, it is currently believed that a high level of fluorescence can only be observed when the C5-functionalized LNA or α-L-LNA compounds are engaged in correct Watson-Crick base pairing.

Figure 29:
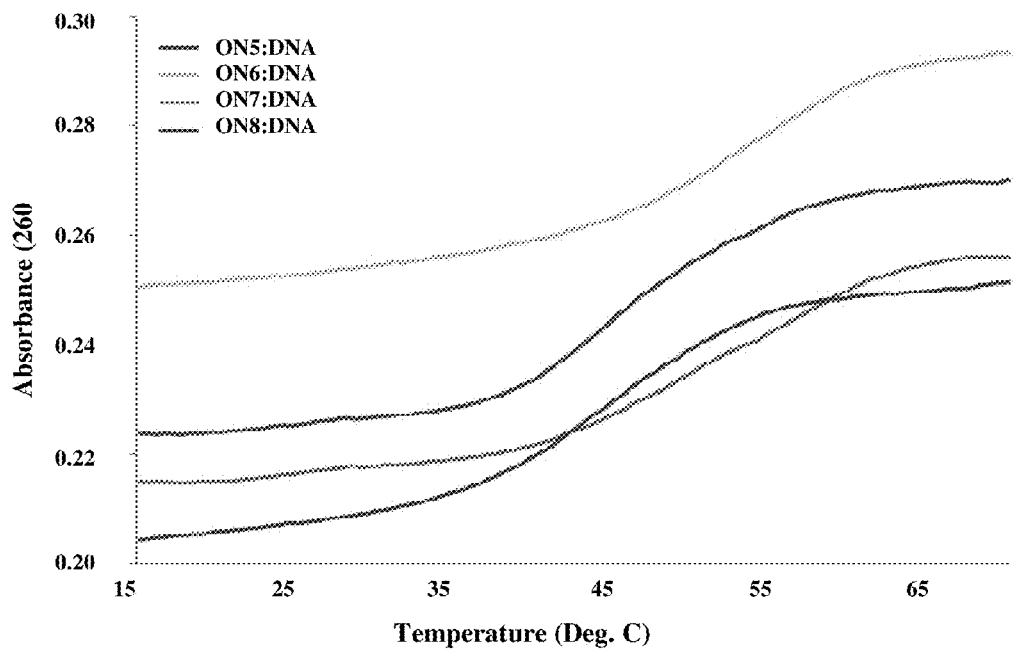
FIG. 29 is a graph of temperature in ° C. (x-axis) versus absorbance (y-axis) that illustrates the thermal denaturation curves for duplexes between oligonucleotides 5-8 and complementary DNA.
Figure 30:
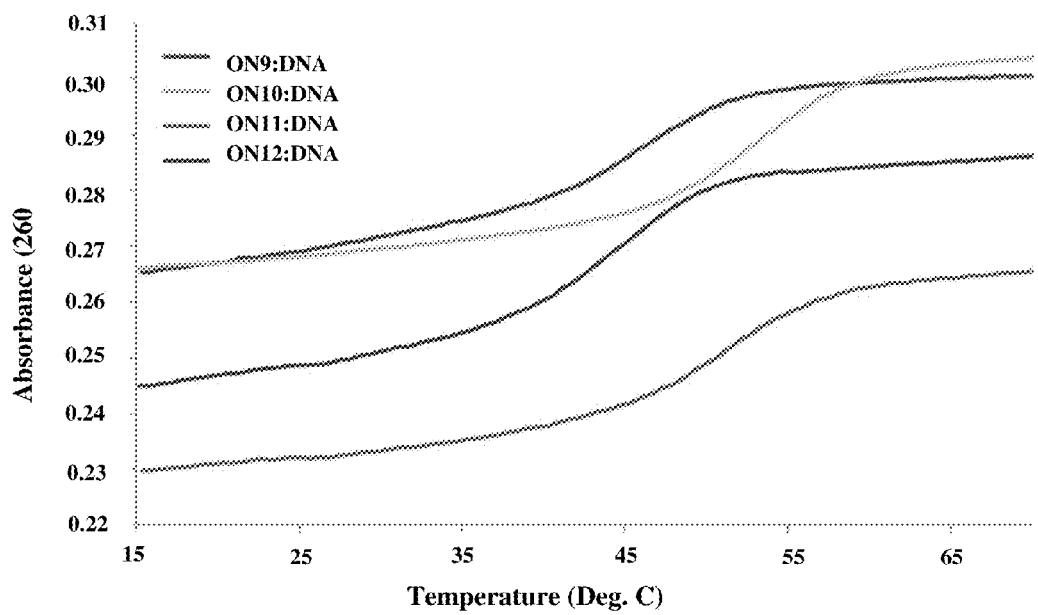
FIG. 30 is a graph of temperature in ° C. (x-axis) versus absorbance (y-axis) that illustrates the thermal denaturation curves for duplexes between oligonucleotides 9-12 and complementary DNA.
Figure 31:
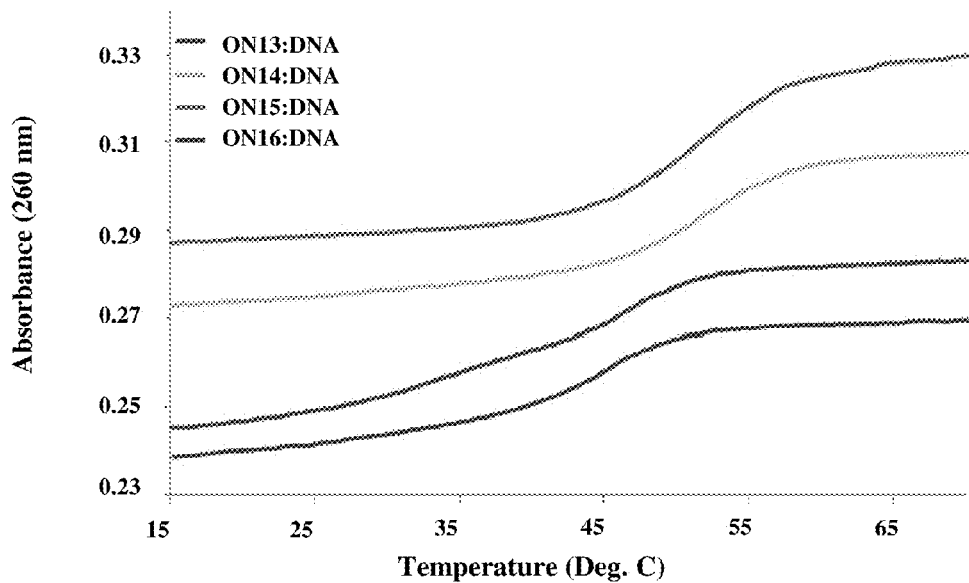
FIG. 31 is a graph of temperature in ° C. (x-axis) versus absorbance (y-axis) that illustrates the thermal denaturation curves for duplexes between oligonucleotides 13-16 and complementary DNA.

The thermostability of duplexes between complimentary or mismatched strands and oligonucleotides comprising at least one fluorescently labeled conventional LNA, DNA, or disclosed embodiment. Table 21 illustrates the results obtained from thermal denaturation of 16 different modified oligonucleotides and their complementary strand (B=A) or mismatched strands (B=C, G, or T). ON5-ON16 and complementary or mismatched nucleic acid targets were studied by UV thermal denaturation using medium salt buffer conditions ([Na⁺]=110 mM) and compared to the corresponding unmodified DNA duplexes. The UV thermal denaturation curves of all modified DNA duplexes exhibit smooth sigmoidal monophasic transitions, as illustrated in FIGS. 29-31. Less pronounced hyperchromicity was observed in duplexes modified with C5-functionalized LNA compound P(ON9-12,

TABLE 20

Thermal affinity for fluorophore-containing LNA and α-L-LNA with single stranded DNA.

| SEQ ID NO: | Sequence | B = | $T_m [\Delta T_m]$ (° C.) DNA: 3'-d(GCG TTG BGT TGC G) | | | |
|---|---|---|---|---|---|---|
| | | | A | C | G | T |
| 6 | 5'-d(CGC AAC TCA ACG C | | 55.5 | 42.0 (−13.5) | 48.5 (−7.0) | 46.5 (−9.0) |
| 7 | 5'-d(CGC AAC PCA ACG C | | 52.5 | 43.0 (−9.5) | 48.0 (−4.5) | 46.0 (−6.5) |
| 8 | 5'-d(CGC AAC P'CA ACG C | | 51.5 | 40.5 (−11.5) | 44.5 (−7.0) | 44.5 (−7.0) |
| 9 | 5'-d(CGC AAC βCA ACG C | | 56.5 | 43.0 (−13.0) | 46.5 (−10.0) | 48.5 (−8.0) |
| 10 | 5'-d(CGC AAC γCA ACG C | | 47.0 | 45.5 (−1.5) | 46.5 (−0.5) | 45.5 (−1.5) |
| 11 | 5'-d(CGC AAC αCA ACG C | | 44.5 | 43.0 (−1.5) | 46.0 (+1.5) | 45.0 (+0.5) |

Hybridization of oligonucleotides comprising one or more of the disclosed embodiments to a complementary single stranded DNA target can result in an increase in fluorescence intensity and formation of a visibly detectable fluorescent duplex with high quantum yields. For example, an oligonucleotide comprising working embodiments P, P', β, γ, and α can exhibit from about a 1 fold to about a 40 fold increase in intensity. More typically, from about a 2 fold to a 30 fold increase can be observed (FIGS. 23-28). FIGS. 23-28 illustrate that the duplexes, comprising complimentary strands, exhibit increased intensity compared to mismatched strands. A comparison of FIGS. 23, 24, 26-28 to FIG. 25 illustrates that incorporation of C5-functionalized LNA or α-L-LNA compounds produces increased fluorescence intensity than oligonucleotides modified with a fluorophore-containing DNA monomer. In other embodiments of the disclosed method, the hybridization of an oligonucleotide modified with a C5-functionalized LNA or α-L-LNA to a single stranded DNA target with a mismatched nucleotide opposite of C5-functionalized LNA or α-L-LNA compounds (violation of Watson-Crick base-pairing) under conditions where a duplex may or may not form, results in low levels of fluoresas referenced in FIG. 30) or α-L-LNA compound P' (ON13-16, as referenced in FIG. 31), which indicates less efficient π-π-stacking between nucleobases in the duplex. Incorporation of the known 5-[3-(1-pyrenecarboxamido)propynyl]-2'-deoxyuridine compound P‴ (Okamoto et al., *J. Am. Chem. Soc.* 2004, 126, 4820-4827) into oligonucleotides (ON5-ON8) significantly decreases thermal denaturation temperatures ($T_m$) of duplexes with DNA complements ($\Delta T_m$ between −1.5° C. to −6.0° C., Table 21). Interestingly, incorporation of the corresponding C5-functionalized LNA or α-L-LNA building blocks into ONs results in similar destabilization of duplexes; although with reduced sequence variability ($\Delta T_m$ between −2.0 to −4.5° C. for compound P, and −2.5 to −4.0° C. for compound P', Table 21). Thus, the well-established stabilizing effects of conventional LNA and α-L-LNA compounds appear to be fully compromised by the 3-(1-pyrenecarboxamido)propynyl moiety at the C5-position. This observation is in contrast to observed trends with C5-functionalized LNA carrying non-aromatic moieties, which generally are very well tolerated in nucleic acid duplexes.

Particular embodiments explore the Watson-Crick specificity of modified oligonucleotides with mismatched nucleic acid sequences. In particular embodiments, reference strands ON1-ON4 exhibit the expected specificity patterns, i.e., a) formation of duplexes with substantially reduced thermostability, and b) less efficient discrimination of T:G-mismatches compared to T:C- and T:T-mismatches (Table 21). Comparison with modified ON5-ON16 in the same sequence contexts reveals that the 3-(1-pyrenecarboxamido)propynyl moiety at the C5-position markedly decreases target specificity as the following order is observed: thymidine [highest specificity] >α-L-LNA compound P'>LNA compound P>DNA compound P''' (e.g., compare mismatch $\Delta T_m$-values for ON2, ON6, ON10 and ON14, Table 21). Without being limited to a single theory of operation, the data support the hypothesis that the pyrene moiety intercalates upon hybridization with mismatched targets, as decreased mismatch specificity often is observed for monomers with intercalating units. The improved mismatch discrimination of LNA compound P and α-L-LNA compound P' relative to DNA compound P''' is in line with the well-established enhanced mismatch discrimination of LNA (Wengel et al., *Tetrahedron* 1998, 54, 3607-3630 and Owczarzy et al. *Nucleic Acid Res.* 2006, 34, e60) and α-L-LNA (Wengel et al. *J. Org. Chem.* 2009, 74, 1070-1081 and Wengel et al. *J. Am. Chem. Soc.* 2002, 124, 2164-2176).

TABLE 21

Thermal denaturation temperatures of duplexes between fluorophore-containing oligonucleotides and complementary or mismatched DNA targets.[a]

| ON | SEQ ID NO: | Sequences | $T_m$ ($\Delta T_m$) [° C.][b] B = A[b] | mismatch $\Delta T_m$ [° C.][c] C[c] | G[c] | T[c] |
|---|---|---|---|---|---|---|
| 1 | 24 | 5'-CG CAA ATA AAC GC | 48.5 | -10.0 | -5.0 | -9.0 |
| 2 | 6 | 5'-CG CAA CTC AAC GC | 55.5 | -13.5 | -7.0 | -9.0 |
| 3 | 25 | 5'-CG CAA GTG AAC GC | 55.0 | -13.0 | -9.5 | -10.0 |
| 4 | 26 | 5'-CG CAA TTT AAC GC | 48.5 | -11.0 | -9.0 | -11.0 |
| 5 | 27 | 5'-CG CAA AP"A AAC GC | 45.0 (-3.5) | -4.5 | -2.0 | -3.0 |
| 6 | 28 | 5'-CG CAA CP"C AAC GC | 54.0 (-1.5) | -8.0 | -4.0 | -5.5 |
| 7 | 29 | 5'-CG CAA GP"G AAC GC | 49.0 (-6.0) | -3.5 | -7.0 | -4.5 |
| 8 | 30 | 5'-CG CAA TP"T AAC GC | 44.0 (-4.5) | -5.0 | -4.0 | -3.5 |
| 9 | 31 | 5'-CG CAA APA AAC GC | 45.5 (-3.0) | -5.5 | -3.5 | -4.5 |
| 10 | 7 | 5'-CG CAA CPC AAC GC | 53.5 (-2.0) | -9.0 | -4.5 | -7.0 |
| 11 | 32 | 5'-CG CAA GPG AAC GC | 51.5 (-3.5) | -3.5 | -11.5 | -6.5 |
| 12 | 33 | 5'-CG CAA TPT AAC GC | 44.0 (-4.5) | -7.5 | -6.5 | -6.0 |
| 13 | 34 | 5'-CG CAA AP'A AAC GC | 44.5 (-4.0) | -7.5 | -6.5 | -2.5 |
| 14 | 8 | 5'-CG CAA CP'C AAC GC | 52.5 (-3.0) | -11.0 | -6.5 | -6.0 |
| 15 | 35 | 5'-CG CAA GP'G AAC GC | 52.5 (-2.5) | -8.0 | -12.0 | -8.0 |
| 16 | 36 | 5'-CG CAA TP'T AAC GC | 45.0 (-3.5) | -9.5 | -10.0 | -3.0 |

[a]$T_m$'s measured as maximum of first derivative plot of melting curves ($A_{260}$ vs. T) recorded in medium salt buffer solution ([Na$^+$] = 110 mM, [Cl$^-$] = 100 mM, pH 7.0 (NaH$_2$PO$_4$/Na$_2$HPO$_4$), EDTA = 0.2 mM) using 1.0 µM concentrations of each strand. $T_m$'s are an average of at least two measurements.

[b]($\Delta T_m$) = change in $T_m$-value relative to unmodified reference duplex e.g. ON5: DNA vs. ON1: DNA.

[c]mismatch $\Delta T_m$ = difference in $T_m$-value between mismatched duplex and complementary duplex; mismatch sequences: 3'-GC GTT TBT TTG CG-5' (for ON1/ON5/ON9/ON13) (SEQ ID NOS: 24, 27, 31, 34), 3'-GC GTT GBG TTG CG-5' (for ON2/ON6/ON10/ON14) (SEQ ID NOS: 6, 38, 7, 8), 3'-GC GTT CBC TTG CG-5' (for ON3/ON7/ON11/ON15) (SEQ ID NOS: 25, 29, 32, 35) and 3'-GC GTT ABA TTG CG-5' (for ON4/ON8/ON12/ON16) (SEQ ID NOS: 26, 30, 33, 36) where B is A, C, G and T.

Particular embodiments of the disclosed compounds can be utilized as single nucleotide polymorphism probes. Three characteristics can be considered for the design of SNP probes: 1) the relative increase in fluorescence intensity upon hybridization to complementary nucleic acid targets (since excess probe cannot be washed out in homogeneous assays); 2) the brightness of the resulting target duplexes, defined as the product of the extinction coefficient of the fluorophore at the applied excitation wavelength E, and the fluorescence emission quantum yield $\Phi_F$ (since this influences detection limits); and 3) the optical discrimination of singly mismatched nucleic acid targets (since this determines the robustness of the SNP-typing method). To fully evaluate these characteristics and gain additional insight into the binding mode of the fluorophore, absorption, steady-state fluorescence emission, and fluorescence excitation spectra of single stranded probes (SSPs) and of the corresponding duplexes with complementary or mismatched DNA targets were obtained. Deoxygenation was deliberately not applied to the samples since the scope of the work was to determine fluorescence enhancement under aerated conditions prevailing in bioassays, but a person of ordinary skill in the art would recognize that deoxygenation is not precluded in the current method. In addition, cross-calibrated fluorescence emission quantum yields ($\Phi_F$) were determined relative to reference compounds that comprise fluorescent properties. Examples of reference compounds include, but are not limited to, pyrenebutanoic acid in methanol and 9,10-diphenylanthracene in cyclohexane following established protocols.

To fully evaluate the three previously mentioned characteristics and gain additional insight into the binding mode of the fluorophore, the absorption, steady-state fluorescence emission ($\lambda_{ex}$=344 nm) and fluorescence excitation ($\lambda_{em}$=404 nm) spectra of single stranded probes (SSPs) ON5-ON16 and of the corresponding duplexes with complementary or mismatched DNA targets were measured.

Figure 32:
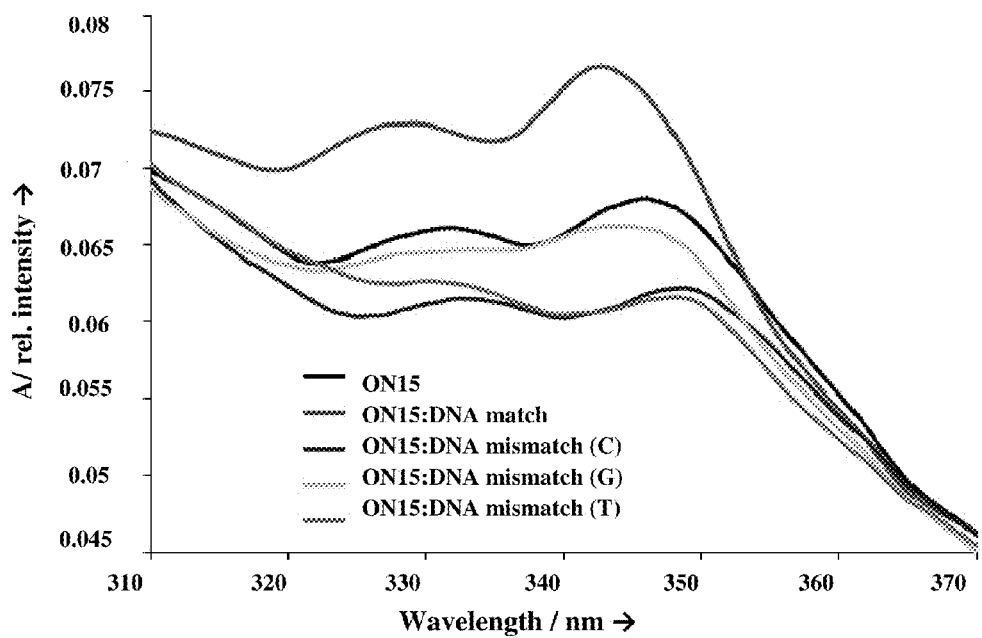
FIG. 32 is a graph of wavelength in nanometers (x-axis) versus relative intensity (y-axis) that illustrates the absorption spectra of oligonucleotide 15 and the duplexes formed between the oligonucleotide and matched or mismatched DNA targets (mismatched nucleotide opposite of incorporation site in parenthesis).
Figure 33:
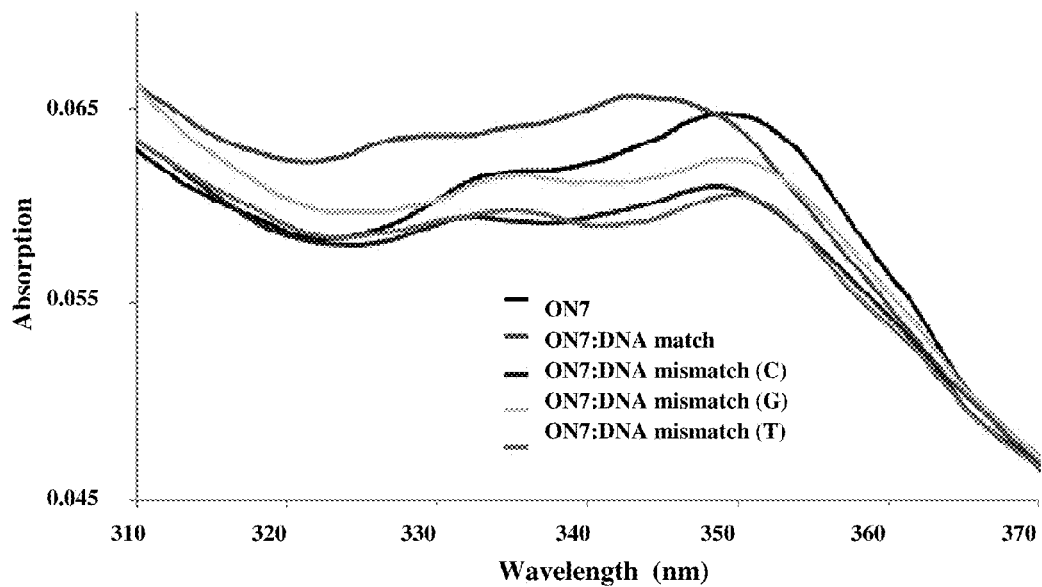
FIG. 33 is a graph of wavelength in nanometers (x-axis) versus absorption (y-axis) that illustrates the absorption spectra of oligonucleotide 7 in the absence or presence of matched or mismatched DNA targets (mismatched nucleotide opposite of incorporation site in parenthesis).
Figure 34:
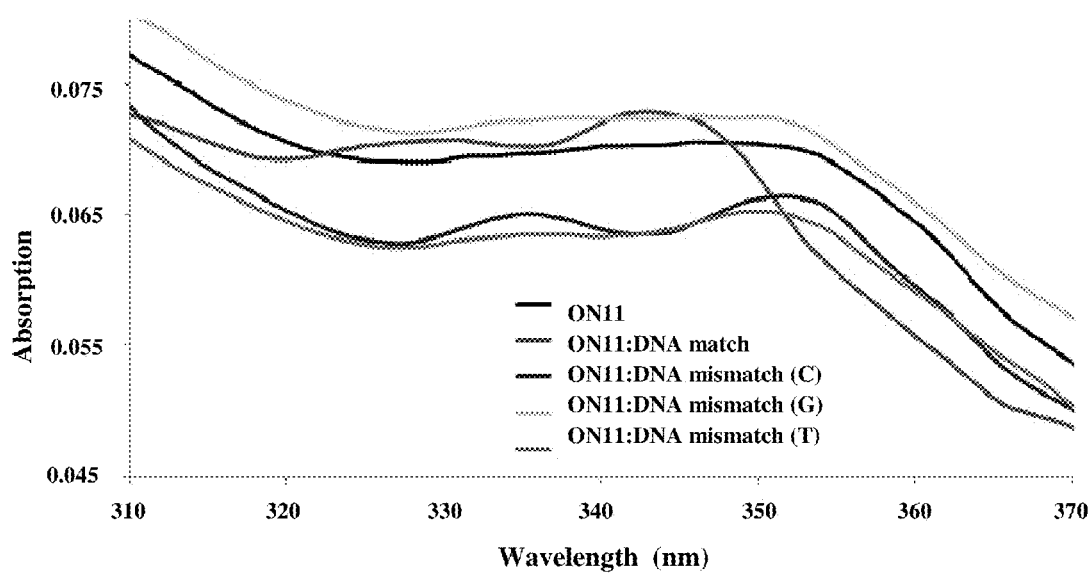
FIG. 34 illustrates the absorption spectra of oligonucleotide 11 in the absence or presence of matched or mismatched DNA targets (mismatched nucleotide opposite of incorporation site in parenthesis).

Hybridization of ON5-ON16 to complementary DNA can be accompanied by hypsochromic shifts in absorption and excitation maxima of the pyrene moiety of 3-7 nm from ~345-350 nm to ~342-346 nm. FIGS. 32-34 illustrate the absorption spectra obtained using particular embodiments of disclosed compounds to form duplexes between modified oligonucleotides and complimentary strands or mismatched strands. FIG. 32 illustrates the combined spectra for matched and mismatched duplexes formed with the P' compound (ON 15, as referenced in FIG. 32); FIG. 33 illustrates the combined spectra for matched and mismatched duplexes formed with the P''' compound (ON7, as referenced in FIG. 33); and FIG. 34 illustrates the combined spectra for matched and mismatched duplexes formed with the P compound (ON11, as referenced in FIG. 34). The values for the wavelength at which maximum absorption occurs are provided in Table 22.

TABLE 22

Absorption maxima $\lambda_{max}$ of single stranded (SSPs) and corresponding duplexes with matched or singly mismatched DNA targets[a]

| ON | SEQ ID NO: | Sequences | $\lambda_{max}$ nm | | | | |
|---|---|---|---|---|---|---|---|
| | | | SSP | B = A | C | G | T |
| 5 | 27 | 5'-CG CAA A<u>P"</u>A AAC GC | 349 | 345 | 349 | 349 | 349 |
| 6 | 28 | 5'-CG CAA C<u>P"</u>C AAC GC | 349 | 346 | 349 | 350 | 349 |
| 7 | 29 | 5'-CG CAA G<u>P"</u>G AAC GC | 350 | 344 | 349 | 349 | 349 |
| 8 | 30 | 5'-CG CAA T<u>P"</u>T AAC GC | 350 | 343 | 350 | 350 | 350 |
| 9 | 31 | 5'-CG CAA A<u>P</u>A AAC GC | 348 | 344 | 350 | 350 | 350 |
| 10 | 7 | 5'-CG CAA C<u>P</u>C AAC GC | 350 | 345 | 350 | 350 | 350 |
| 11 | 32 | 5'-CG CAA G<u>P</u>G AAC GC | 350 | 343 | 351 | 350 | 351 |
| 12 | 33 | 5'-CG CAA T<u>P</u>T AAC GC | 350 | 343 | 350 | 350 | 350 |
| 13 | 34 | 5'-CG CAA A<u>P'</u>A AAC GC | 349 | 342 | 349 | 349 | 349 |
| 14 | 8 | 5'-CG CAA C<u>P'</u>C AAC GC | 349 | 344 | 349 | 349 | 350 |
| 15 | 35 | 5'-CG CAA G<u>P'</u>G AAC GC | 347 | 343 | 349 | 345 | 349 |
| 16 | 36 | 5'-CG CAA T<u>P'</u>T AAC GC | 349 | 344 | 349 | 349 | 349 |

[a]Absorption spectra were recorded in $T_m$ buffer (see Table 1) using 1.0 μM concentrations of each strand. Absorption was recorded from 220 to 390 nm on a Cary 100 Bio UV/VIS spectrophotometer; each sample was scanned four times and the resulting averaged spectrum was smoothed using a filter size of nine.
Target sequences: 3'-GC GTT TBT TTG CG-5' (for ON5/ON9/ON13), 3'-GC GTT GBG TTG CG-5' (for ON6/ON10/ON14), 3'-GC GTT CBC TTG CG-5' (for ON7/ON11/ON15) and 3'-GC GTT ABA TTG CG-5' (for ON8/ON12/ON16) where B is A, C, G and T.

Figure 35:
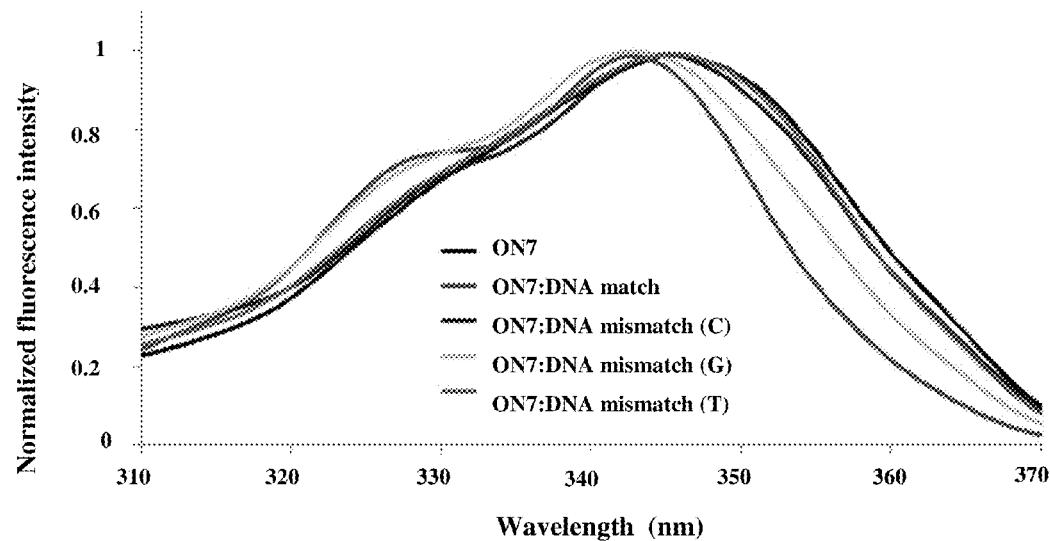
FIG. 35 is a graph of wavelength in nanometers (x-axis) versus normalized fluorescence intensity (y-axis) that illustrates the fluorescence excitation spectra of oligonucleotide 7 in the absence or presence of matched or mismatched DNA targets (mismatched nucleotide opposite of incorporation site in parenthesis).
Figure 36:
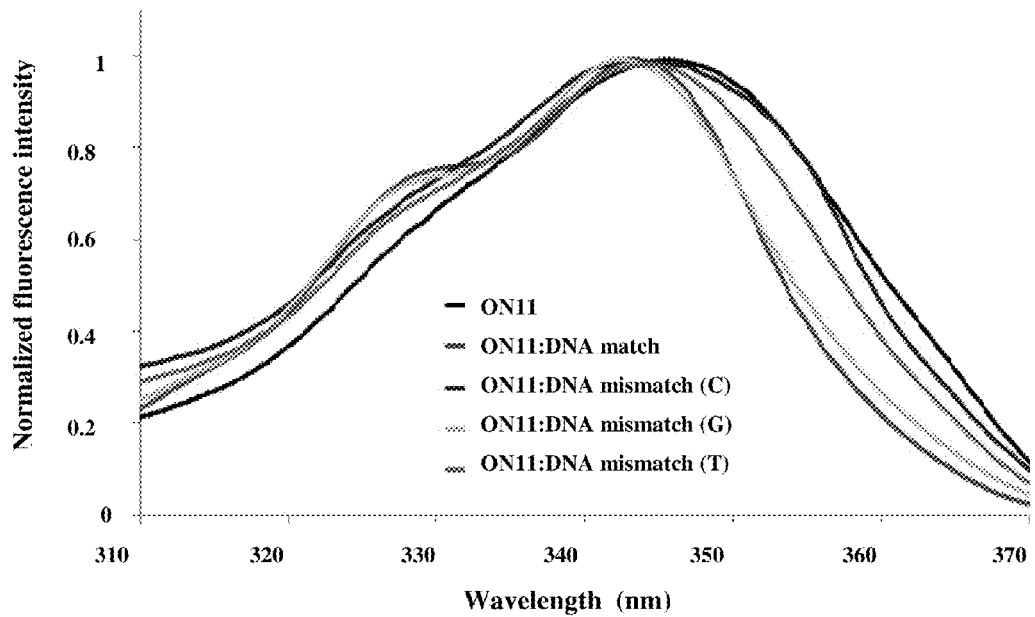
FIG. 36 illustrates the fluorescence excitation spectra of oligonucleotide 11 in the absence or presence of matched or mismatched DNA targets (mismatched nucleotide opposite of incorporation site in parenthesis).
Figure 37:
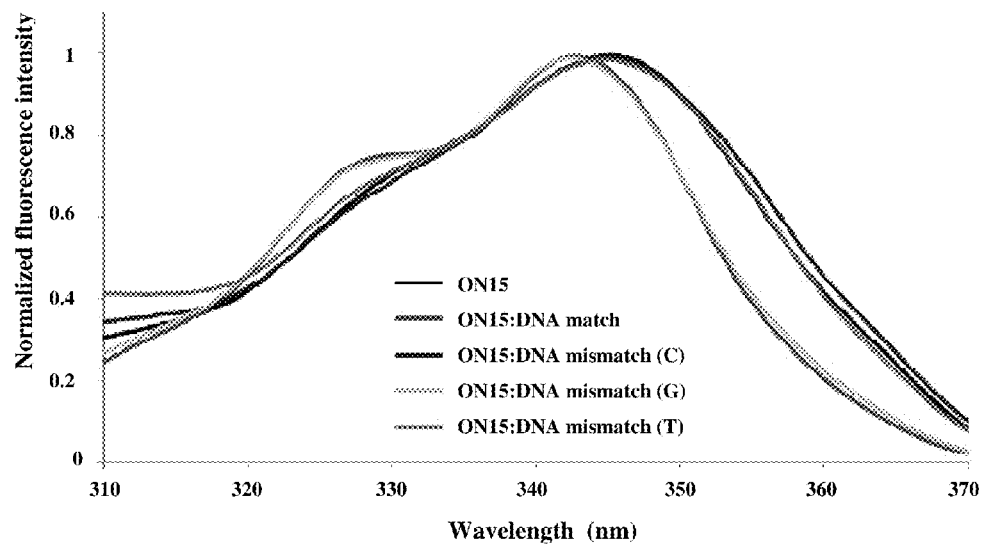
FIG. 37 illustrates the fluorescence excitation spectra of oligonucleotide 15 in the absence or presence of matched or mismatched DNA targets (mismatched nucleotide opposite of incorporation site in parenthesis).

FIGS. 35-37 illustrate the excitation spectra obtained using particular embodiments of disclosed compounds to form duplexes between modified oligonucleotides and complimentary strands or mismatched strands. The values for the wavelength at which maximum excitation occurs are provided in Table 23.

TABLE 23

Fluorescence excitation maxima $\lambda_{ex,max}$ in absence (SSP) or presence of matched or singly mismatched DNA targets ($\lambda_{em}$ = 404 nm).[a]

| ON | SEQ ID NO: | Sequences | SSP | $\lambda_{ex}$ max (nm) B = A | C | G | T |
|---|---|---|---|---|---|---|---|
| 5 | 27 | 5'-CG CAA AP"A AAC GC | 348 | 344 | 348 | 346 | 348 |
| 6 | 28 | 5'-CG CAA CP"C AAC GC | 347 | 344 | 344 | 343 | 343 |
| 7 | 29 | 5'-CG CAA GP"G AAC GC | 346 | 343 | 345 | 343 | 346 |
| 8 | 30 | 5'-CG CAA TP"T AAC GC | 349 | 343 | 349 | 349 | 349 |
| 9 | 31 | 5'-CG CAA APA AAC GC | 348 | 344 | 350 | 347 | 350 |
| 10 | 7 | 5'-CG CAA CPC AAC GC | 348 | 344 | 344 | 342 | 344 |
| 11 | 32 | 5'-CG CAA GPG AAC GC | 346 | 343 | 343 | 342 | 344 |
| 12 | 33 | 5'-CG CAA TPT AAC GC | 350 | 343 | 351 | 349 | 350 |
| 13 | 34 | 5'-CG CAA AP'A AAC GC | 348 | 343 | 347 | 346 | 347 |
| 14 | 8 | 5'-CG CAA CP'C AAC GC | 347 | 344 | 345 | 345 | 346 |
| 15 | 35 | 5'-CG CAA GP'G AAC GC | 345 | 342 | 345 | 342 | 345 |
| 16 | 36 | 5'-CG CAA TP'T AAC GC | 348 | 343 | 347 | 347 | 348 |

[a]Conditions as described in footnote of Table 21.
Target sequences: 3'-GC GTT TBT TTG CG-5' (for ON5/ON9/ON13), 3'-GC GTT GBG TTG CG-5' (for ON6/ON10/ON14), 3'-GC GTT CBC TTG CG-5' (for ON7/ON11/ON15) and 3'-GC GTT ABA TTG CG-5' (for ON8/ON12/ON16) where B is A, C, G and T.

Figure 38:
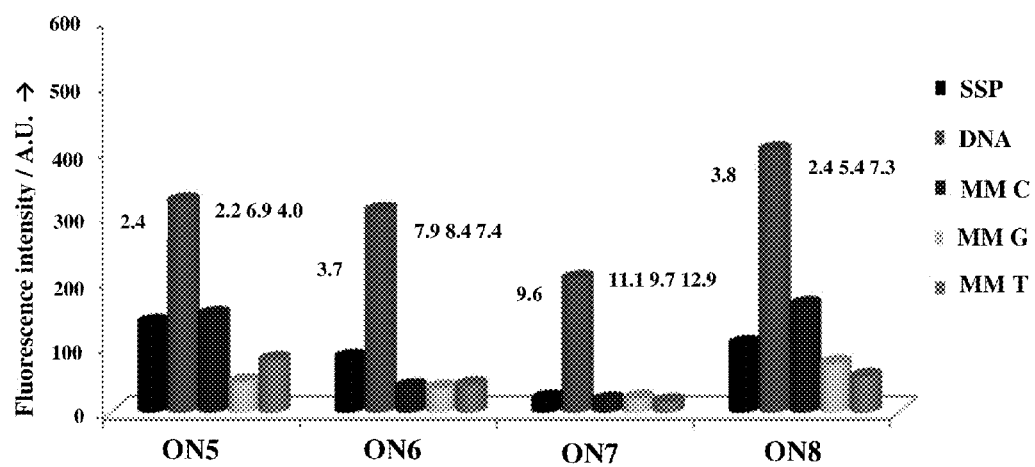
FIG. 38 is a chart illustrating the fluorescence intensities of oligonucleotides 5-8 in the absence (SSPs) or presence of complimentary DNA or mismatched DNA targets.
Figure 39:
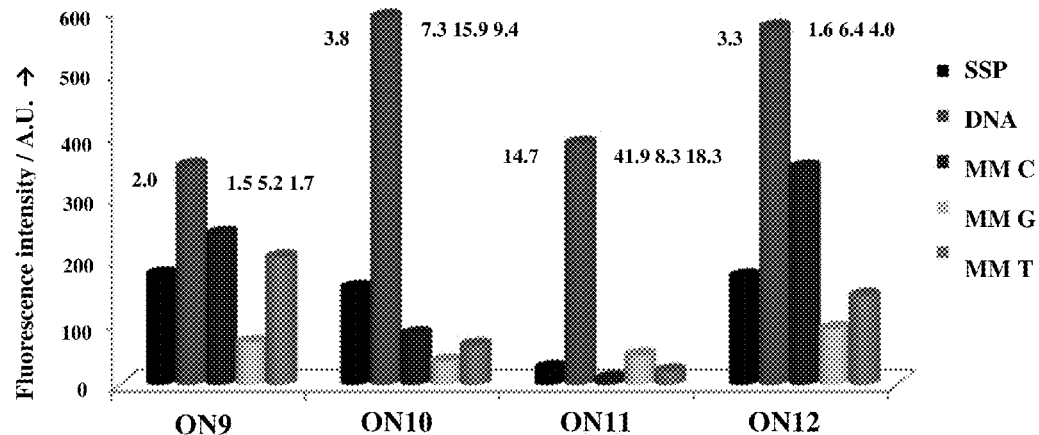
FIG. 39 is a chart illustrating the fluorescence intensities oligonucleotides 9-12 in the absence (SSPs) or presence of complimentary DNA or mismatched DNA targets.

Another important characteristic for developing single nucleotide polymorphism probes is the ability to achieve detectable fluorescence intensity. This characteristic can be evaluated by measuring the extinction coefficients and quantum yields of particular embodiments. Increases in extinction coefficients (hyperchromic shifts) appear to be most pronounced for α-L-LNA compound P' and least pronounced for DNA compound P''', as illustrated by the data provided in Table 24. Duplex formation between oligonucleotides modified with DNA compound P''' (ON5-ON8) and complementary DNA is accompanied with 2.4- to 9.6-fold increases in fluorescence intensity (FIG. 38) and high fluorescence quantum yields ($\Phi_F$=0.33-0.58, Table 24). In concert, these observations suggest decreased electronic interactions between pyrene and quenching nucleobase moieties upon duplex formation. Oligonucleotides modified with LNA compound P(ON9-ON12) display similar hybridization-induced increases in fluorescence intensity (FIG. 39) but form duplexes with even higher quantum yields, particularly in the CYC- and GYG-sequence contexts (ON10 and ON11, Table 24). Interestingly, oligonucleotides modified with α-L-LNA compound P' display larger hybridization-induced increases in fluorescence intensity in the AP'A- and TP'T-contexts (FIG. 40) than corresponding oligonucleotides modified with P''' or P compounds (e.g., compare ON8/ON12/ON16, FIGS. 38-40).

TABLE 24

Fluorescence quantum yields ($\Phi_F$) and extinction coefficients $\epsilon_{344}$ of fluorophore-containing oligonucleotides[a]

| ON | SEQ ID NO: | Sequences | SSP | $\epsilon_F$ (344 nm/cm$^{-1}$ mM$^{-1}$) B = A | C | G | T |
|---|---|---|---|---|---|---|---|
| 5 | 27 | 5'-CG CAA AP"A AAC GC | 0.21 (22) | 0.44 (24) | 0.31 (17) | 0.10 (17) | 0.16 (16) |
| 6 | 28 | 5'-CG CAA CP"C AAC GC | 0.16 (19) | 0.43 (24) | 0.08 (17) | 0.08 (16) | 0.09 (18) |
| 7 | 29 | 5'-CG CAA GP"G AAC GC | 0.04 (19) | 0.33 (20) | 0.04 (17) | 0.05 (15) | 0.03 (17) |
| 8 | 30 | 5'-CG CAA TP"T AAC GC | 0.17 (21) | 0.58 (23) | 0.32 (18) | 0.15 (17) | 0.12 (16) |
| 9 | 31 | 5'-CG CAA APA AAC GC | 0.32 (19) | 0.48 (23) | 0.47 (17) | 0.16 (15) | 0.45 (16) |
| 10 | 7 | 5'-CG CAA CPC AAC GC | 0.27 (20) | 0.67 (29) | 0.14 (18) | 0.09 (16) | 0.12 (17) |

TABLE 24-continued

Fluorescence quantum yields ($\phi_F$) and extinction coefficients $\epsilon_{344}$ of fluorophore-containing oligonucleotides[a]

| ON | SEQ ID NO: | Sequences | SSP | $\phi_F$ ($\lambda_{344\ nm}$/cm$^{-1}$ mM$^{-1}$) B = A | C | G | T |
|---|---|---|---|---|---|---|---|
| 11 | 32 | 5'-CG CAA GPG AAC GC | 0.04 (25) | 0.44 (29) | 0.02 (20) | 0.07 (20) | 0.04 (20) |
| 12 | 33 | 5'-CG CAA TPT AAC GC | 0.31 (20) | 0.61 (28) | 0.62 (17) | 0.17 (18) | 0.31 (16) |
| 13 | 34 | 5'-CG CAA AP'A AAC GC | 0.17 (11) | 0.53 (16) | 0.22 (8) | 0.25 (11) | 0.07 (9) |
| 14 | 8 | 5'-CG CAA CP'C AAC GC | 0.23 (20) | 0.61 (30) | 0.19 (17) | 0.24 (23) | 0.10 (14) |
| 15 | 35 | 5'-CG CAA GP'G AAC GC | 0.08 (23) | 0.50 (31) | 0.05 (20) | 0.27 (27) | 0.05 (16) |
| 16 | 36 | 5'-CG CAA TP'T AAC GC | 0.28 (12) | 0.80 (20) | 0.44 (9) | 0.40 (14) | 0.17 (9) |

[a]Conditions as described in footnote of Table 21. $\lambda_{ex}$ nm, T = 5° C. SSP = single stranded probes. The values in parentheses are the extinction coefficients of the fluorophore-containing oligonucleotides (measured at 344 nm).

Figure 41:
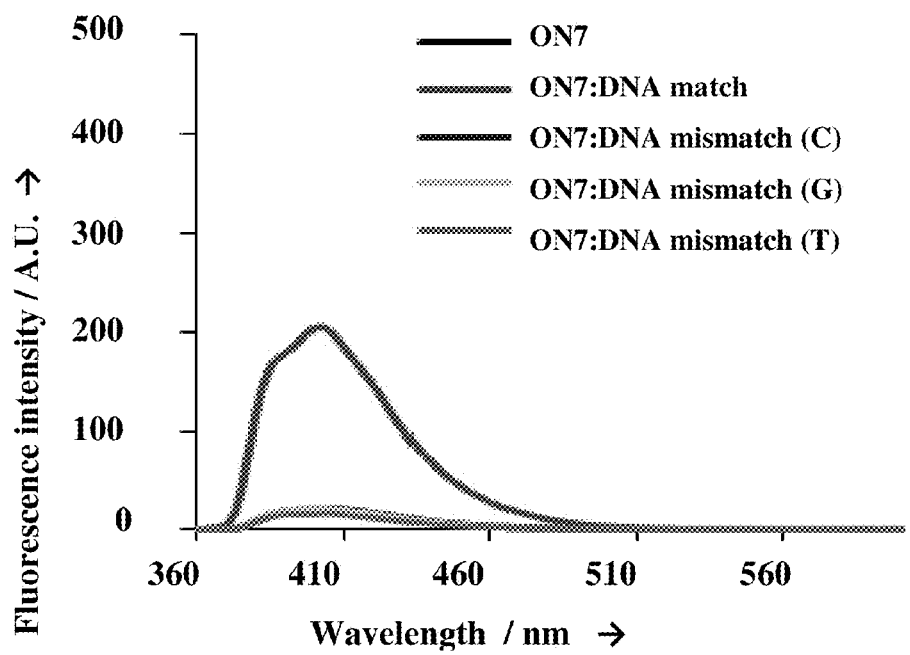
FIG. 41 is a graph of wavelength in nanometers (x-axis) versus fluoresence intensity (y-axis) that illustrates the steady state fluorescence spectra of oligonucleotide 7 in the absence or presence of matched or mismatched DNA targets (mismatched nucleotide opposite of incorporation site in parenthesis).
Figure 42:
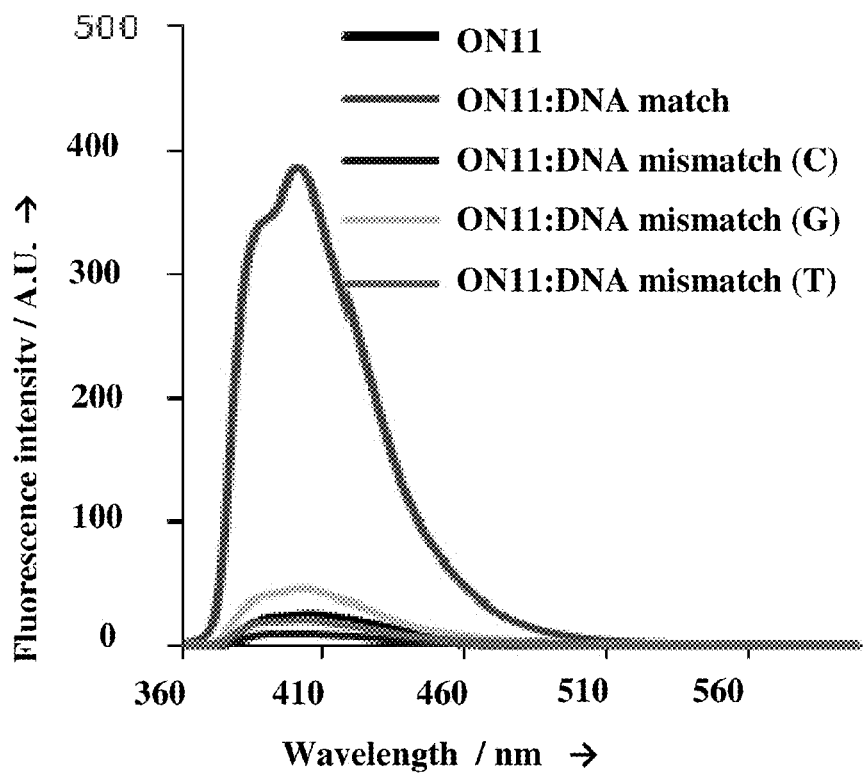
FIG. 42 illustrates the steady state fluorescence spectra of oligonucleotide 11 in the absence or presence of matched or mismatched DNA targets (mismatched nucleotide opposite of incorporation site in parenthesis).

Yet another important characteristic for developing single nucleotide polymorphism probes involves the formation of duplexes that allow for the optical discrimination of singly mismatched nucleic acid targets. Probes where DNA compound P" is incorporated between flanking cytosine or guanine moieties display excellent optical discrimination of SNPs, as illustrated in FIG. 41 (ON7) by the large decrease in intensity for those sequences in which the modified oligonucleotide forms a duplex with a mismatched target. The large discrimination factors, $I_m/I_{mm}$, are included in FIG. 38. $I_m/I_{mm}$ is the fluorescence intensity of duplexes with complementary DNA divided by the intensity of SSPs or duplexes with mismatched DNA. Less efficient discrimination is observed in AP"A- and TP"T-sequence contexts, which demonstrates the need for nearby guanine moieties to quench pyrene monomer fluorescence and ensure efficient SNP discrimination. Oligonucleotides modified with C5-functionalized LNA compound P generally display improved SNP discrimination in the CPC- and GPG-sequence contexts ($I_m/I_{mm}$=7.3-15.9 and 8.3-41.9 for ON10 and ON11, respectively, FIG. 39) but less efficient discrimination in the APA- and TPT-sequence contexts. The emission spectra for compound P are illustrated in FIG. 42 (ON 11, as referenced in FIG. 42). By contrast, oligonucleotides modified with α-L-LNA compound P' (ON13-ON16) display distinctly different fluorescence trends than ON5-ON12, e.g., the P':G-mismatches are the least efficiently discriminated mismatches. This behaviour is surprising given the aforementioned efficiency of guanine to quench pyrene monomer fluorescence and that other SNP-typing probes discriminate G-mismatches well. Moreover, improved SNP discrimination is observed in the challenging AP'A- and TP'T-contexts although higher discrimination factors, in particular with G-mismatches, would be desirable for practical diagnostic applications ($I_m/I_{mm}$=3.4-14.1 and 2.9-11.4 for ON13 and ON16, respectively, FIG.

Figure 43:
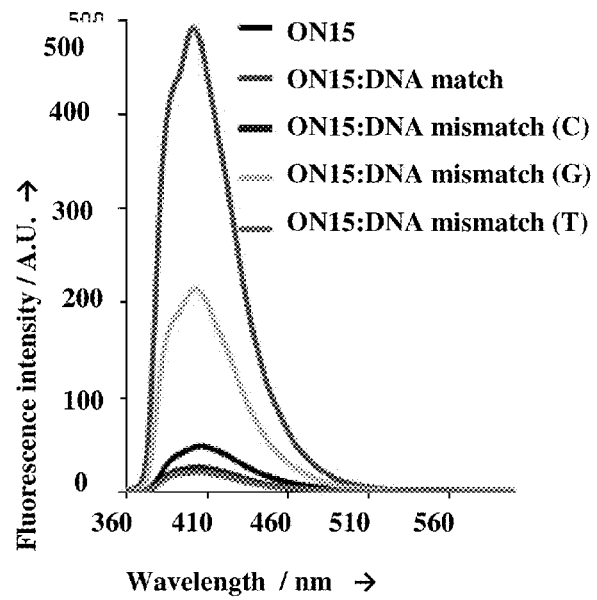
FIG. 43 illustrates the steady state fluorescence spectra of oligonucleotide 15 in the absence or presence of matched or mismatched DNA targets (mismatched nucleotide opposite of incorporation site in parenthesis).

40). The emission spectra for compound P' are illustrated in FIG. 43 (ON 15, as referenced in FIG. 43).

Figure 40:
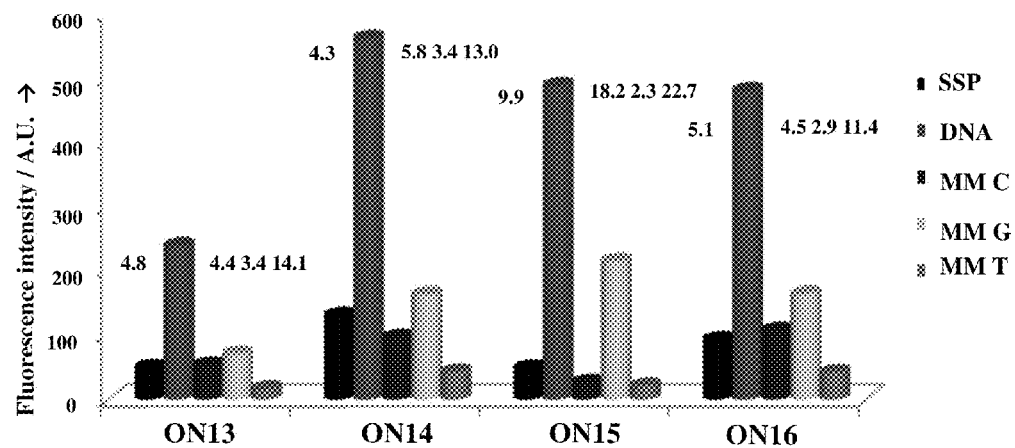
FIG. 40 is a chart illustrating the fluorescence intensities of oligonucleotides 13-16 in the absence (SSPs) or presence of complimentary DNA or mismatched DNA targets.

Interestingly, the observed intensity-based mismatch discrimination factors of ON5-ON16 are not fully accounted by the differences in quantum yields between matched and mismatched duplexes—e.g., compare $I_m/I_{mm}$=5.8 with $\Phi_{F,m}/\Phi_{F,mm}$=0.61/0.19~3.2 for ON14 vs. the C-mismatched target (FIG. 40 and Table 24, respectively). This reflects the fact that fluorescence brightness depends on the emission quantum yield $\Phi_F$ and the extinction coefficient (ε) of the fluorophore, which is markedly lower in mismatched duplexes than in matched duplexes (Table 24). Larger differences in extinction coefficients between matched and mismatched duplexes are observed for ON9-ON16 (LNA and α-L-LNA compounds P and P'). The results because all of the described embodiments demonstrate that a) decreased quantum yields in tandem with lower extinction coefficients of mismatched duplexes bring about the SNP discrimination of compounds P", P, and P', and b) without being limited to a single theory of operation, it is currently believed that conformational restriction of the furanose skeleton translates into altered emission output of polarity-sensitive fluorophores conjugated to the C5-position of pyrimidines.

A person of ordinary skill in the art will recognize that all the disclosed methods and compounds can be used with any nucleic acid, including RNA, in order to study the physical properties of duplexes between the disclosed probes and the particular nucleic acid target. In particular embodiments, the physical properties of duplexes between probes in the representative CBC- and TBT-sequence contexts and complementary or singly mismatched RNA targets can be analyzed. Similar trends in duplex thermostability, target specificity, excitation maxima, were observed compared to the corresponding studies with DNA targets, as illustrated in Tables 25, 26, and 27, respectively.

TABLE 25

Thermal denaturation temperatures of representative duplexes between probes and complementary (B = A) or mismatched RNA targets.[a]

| ON | SEQ ID NO: | Sequences | $T_m$ ($DT_m$) [° C.] B = A | mismatch $DT_m$ [° C.] C | G | U |
|---|---|---|---|---|---|---|
| 2  | 6  | 5'-CG CAA CTC AAC GC   | 51.5        | −15.5 | −3.0 | −13.5 |
| 6  | 28 | 5'-CG CAA CP"C AAC GC | 46.5 (−5.0) | −10.5 | −5.0 | −8.5  |
| 10 | 7  | 5'-CG CAA CPC AAC GC  | 49.5 (−2.5) | −14.0 | −5.5 | −11.5 |
| 14 | 8  | 5'-CG CAA CP'C AAC GC | 48.5 (−3.0) | −18.0 | −4.5 | −14.5 |
| 4  | 26 | 5'-CG CAA TTT AAC GC   | 40.0        | −19.0 | −5.0 | −18.0 |
| 8  | 30 | 5'-CG CAA TP"T AAC GC | 35.5 (−4.5) | −8.0  | −8.5 | −5.5  |
| 12 | 33 | 5'-CG CAA TPT AAC GC  | 34.5 (−5.5) | −12.0 | −8.5 | −10.5 |
| 16 | 36 | 5'-CG CAA TP'T AAC GC | 37.0 (−3.0) | −16.0 | −8.0 | −13.5 |

[a]For conditions see footnote of Table 21.

TABLE 26

Fluorescence quantum yields ($F_F$) of probes with complementary or mismatched RNA targets.[a]

| ON | SEQ ID NO: | Sequences | $F_F$ B = A | C | G | U |
|---|---|---|---|---|---|---|
| 6  | 28 | 5'-CG CAA CP"C AAC GC | 0.48 | 0.11 | 0.26 | 0.11 |
| 8  | 30 | 5'-CG CAA TP"T AAC GC | 0.44 | 0.23 | 0.27 | 0.19 |
| 10 | 7  | 5'-CG CAA CPC AAC GC  | 0.69 | 0.27 | 0.27 | 0.21 |
| 12 | 33 | 5'-CG CAA TPT AAC GC  | 0.51 | 0.36 | 0.30 | 0.24 |
| 14 | 8  | 5'-CG CAA CP'C AAC GC | 0.68 | 0.46 | 0.31 | 0.36 |
| 16 | 36 | 5'-CG CAA TP'T AAC GC | 0.50 | 0.18 | 0.39 | 0.14 |

[a]Conditions as described in footnote of Table 21.

TABLE 27

Fluorescence excitation maxima of probes in absence (SSP) or presence of complementary (B = A) or singly mismatched RNA targets ($l_{em}$ = 404 nm).[a]

| ON | SEQ ID NO: | Sequences | $\lambda_{ex\,max}$ max (nm) SSP | B = A | C | G | U |
|---|---|---|---|---|---|---|---|
| 6  | 28 | 5'-CG CAA CP"C AAC GC | 347 | 345 | 345 | 346 | 345 |
| 8  | 30 | 5'-CG CAA TP"T AAC GC | 349 | 345 | 350 | 349 | 350 |
| 10 | 7  | 5'-CG CAA CPC AAC GC  | 348 | 343 | 346 | 346 | 347 |
| 12 | 33 | 5'-CG CAA TPT AAC GC  | 350 | 345 | 350 | 348 | 350 |
| 14 | 8  | 5'-CG CAA CP'C AAC GC | 347 | 344 | 345 | 345 | 346 |
| 16 | 36 | 5'-CG CAA TP'T AAC GC | 348 | 346 | 348 | 348 | 348 |

[a]Conditions as described in footnote of Table 21.

Figure 44:
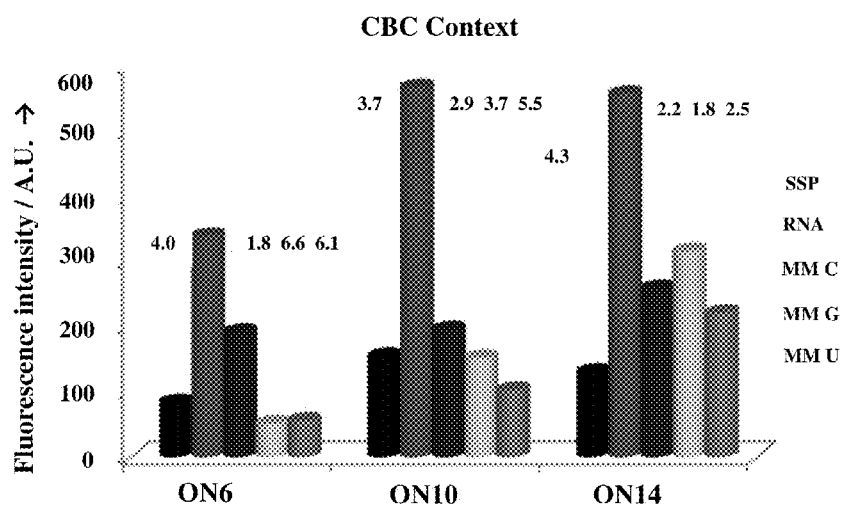
FIG. 44 is a chart illustrating fluorescence intensity of oligonucleotides 6, 10, and 14 in the absence or presence of complementary RNA or mismatched RNA targets for a CBC sequence context.
Figure 45:
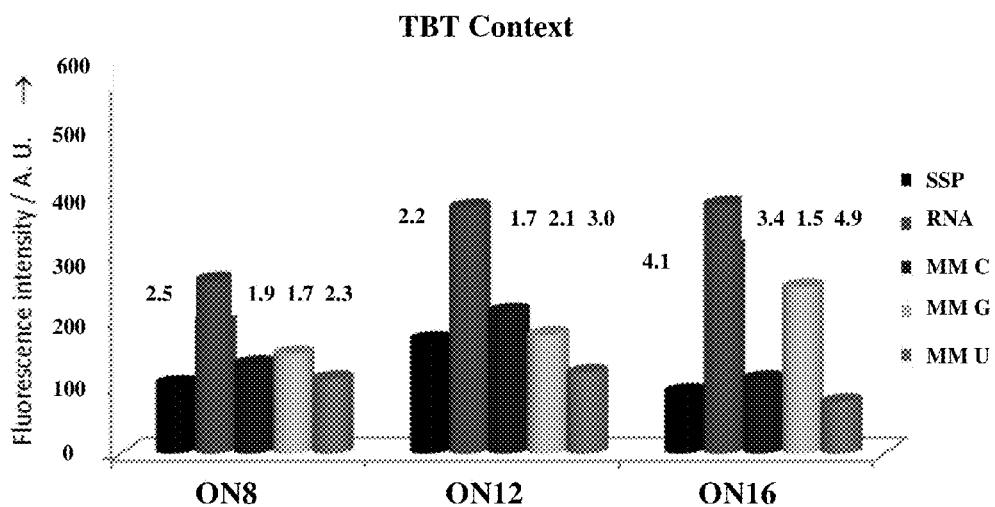
FIG. 45 is a chart illustrating fluorescence intensity oligonucleotides 8, 12, and 16 in the absence or presence of complementary RNA or mismatched RNA targets for a TBT sequence context.

As illustrated in FIGS. 44 (CBC-sequence context) and 45 (TBT-sequence context), hybridization-induced increases in fluorescence intensity were also observed compared to the corresponding studies with DNA targets; however, the optical discrimination of mismatched RNA targets is generally much lower which is accompanied by higher quantum yields for mismatched duplexes. These observations can possibly indicate less facile intercalation of the pyrene moiety in mismatched RNA duplexes, possibly due to the more compressed DNA:RNA duplex architectures, which leads to less efficient nucleobase-mediated quenching. Probes modified with compounds P'' or P display similar optical discrimination of RNA-mismatches, whereas compound P' modified probes display slightly improved discrimination in the TP'T-context (FIG. 45). Matched duplexes involving ONs modified with LNA compound P or α-L-LNA monomer P' exhibit higher quantum yields than with compound P''.

Figure 46:
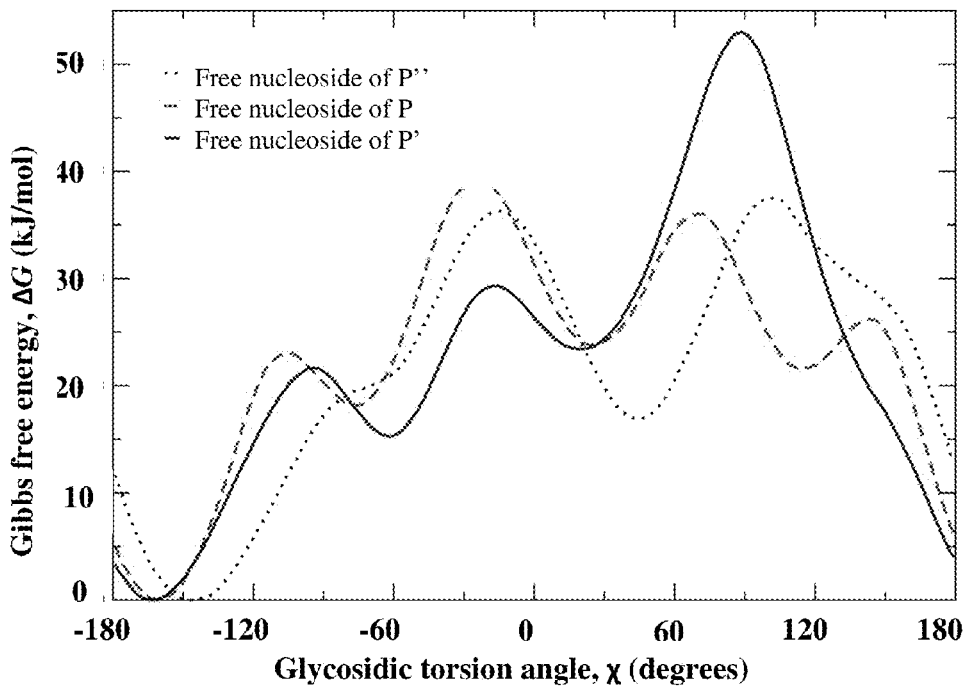
FIG. 46 is a graph of glycosidic torsion angle measured in degrees (x-axis) versus Gibbs free energy measured in kJ/mol (y-axis) for the free nucleosides of compounds P''', P, and P'.

Given the distinctly different fluorescent properties of ONs modified with compounds P'', P, P', the proposed importance of anti to syn rotation of the glycosidic torsion angle for SNP-discrimination by compound P'' ([a]M. Petersen, C. B. Nielsen, K. E. Nielsen, G. A. Jensen, K. Bondensgaard, S. K. Singh, V. K. Rajwanshi, A. A. Koshkin, B. M. Dahl, J. Wengel, J. P. Jacobsen, *J. Mol. Recognit.* 2000, 13, 44-53; [b] M. Petersen, A. E. Høkansson, J. Wengel, J. P. Jacobsen, *J. Am. Chem. Soc.* 2001, 123, 7431-7432), and that the extreme sugar puckering of LNA and α-L-LNA nucleotides[13] might influence the anti to syn rotational bather, it is possible to calcualte the Gibbs free energy as a function of the glycosidic angle for the corresponding O3',O5'-unprotected nucleosides of compounds P'', P, and P'. These Gibbs free energies were computed via the weighted histrogram analysis method known to those skilled in the art to include the method described by Kollman et al. (*J. Comput. Chem.* 1992, 13, 1011-1021) using all-atom molecular dynamics simulations in explicit solvent. FIG. 46 shows that the anti conformation is the global minimum of all three nucleosides, with a local minimum corresponding to the syn conformation (i.e., $25°<\chi<45°$. The syn conformation is the second lowest minimum for the 5-[3-(1-pyrenecarboxamido)propynyl]-2'-deoxyuridine and the difference between the anti and syn conformation is approximately 17 kJ/mol, thus the syn conformation is expected to be well populated. By contrast, the corresponding C5-functionalized LNA nucleoside has two additional minima at $-70°$ and $+115°$, while the C5-functionalized α-L-LNA nucleoside has one additional local minimum at $-60°$, all of which are of lower free energy than the syn conformation. The syn conformation of the C5-functionalized LNA and α-L-LNA nucleosides will therefore not be as highly populated as for the 5-[3-(1-pyrenecarboxamido)propynyl]-2'-deoxyuridine nucleoside. The results suggest that the bicyclic skeletons of the C5-functionalized LNA and α-L-LNA nucleosides influence the glycosidic torsional angle profile.

VI. Methods for Using C5- or C8-Functionalized LNA and α-L-LNA

The disclosed compounds can be used in a variety of biological applications. The disclosed compounds can be utilized in any application where the targeting of a nucleic acid is a component of the process, such as, but not limited to, therapeutics, diagnostics, prophylaxis, drug discovery, and research kits.

Therapeutic applications include the treatment of diseases of genetic origin or those caused by a single nucleotide polymorphism. Examples of diseases include, but are not limited to, viral infections, obesity, cancer, and hypertension. Disclosed compounds can be used for treatment of diseases characterized by the production of particular proteins. For example, any organism utilizing DNA-RNA transcription or RNA-protein translation can be contacted with an oligonucleotide modified with at least one of the disclosed compounds. In single stranded nucleic acids, this oligonucleotide can hybridize with the single stranded nucleic acid coding for the particular protein and prevent its production. Particular examples of therapeutic indications include diseases caused by viral, bacterial, or fungal agents, inflammatory disorders and cancers of the skin, and tumorigenesis. Typical examples of viral agents include human immunodeficiency virus (HIV), influenza virus, cytomegalovirus, Epstein-Barr virus, herpesvirus, and papillomavirus. Specific antisense compounds for these viral agents have been identified and may be used in combination with or replaced by disclosed embodiments, thereby eliciting prophylactic, palliative, or therapeutic relief from the diseases caused by these particular viral agents. Inflammatory disorders of the skin that can be treated using the disclosed compounds include allergic contact dermatitis and psoriasis. Cancers of the skin can include benign (warts and moles) and malignant (carcinomas, sarcomas, and melanomas) tumors.

The treatment of diseases using the disclosed compounds can be used in triple helical nucleic acids. In this method of use, an oligonucleotide, containing one or more of the disclosed compounds, can be targeted to the specific gene that codes for a disease-related protein and bind to the major groove of the double stranded target, thereby preventing transcription. Antigene techniques utilizing the disclosed compounds and methods can be used in anti-virus diseases, such as HIV, and anti-cancer diseases, such as those involving the HER2/neu gene or the human multidrug-resistance mdr1 gene.

Diagnostic applications utilizing the disclosed compounds and/or oligomers into which they have been inserted include certain methods of gene expression analysis. Particular methods of gene expression analysis include DNA and protein arrays or microarrays, serial analysis of gene expression, restriction enzyme amplification of digested cDNAs, total gene expression analysis, expressed gene sequence tag sequencing, subtractive RNA fingerprinting, subtractive cloning, differential display, comparative genomic hybridization, hybridization techniques (such as fluorescent in situ hybridization) and mass spectrometry methods. Typically, antisense oligonucleotides containing one or more of the disclosed compounds can be used to elucidate expression patterns of portions of or entire complements of certain expressed genes in cells and tissues.

An example of a diagnostic application utilizing the disclosed compounds concerns treating a sample, such as a cell or tissue, with one or more oligomers modified with one or more of the disclosed compounds. The expression patterns produced by this step can then be compared with patterns obtained in control samples (cells or tissues not treated with the modified oligomer) in order to detect differential levels of gene expression for areas including disease association, signaling pathways, cellular localization, expression level, size, structure, or function of the tested genes.

Oligomers modified with the disclosed compounds can also be used as primers or probes in gene amplification and/or detection techniques. The modified oligomers can act as probes, thereby identifying certain nucleic acid molecules that code for particular proteins. In addition, the modified oligomers can be used as primers for amplifying certain nucleic acid sequences in a polymerase chain reaction technique (PCR).

Hybridization techniques can also be employed using disclosed embodiments due to the high thermal affinity and specificity of particular embodiments. Oligonucleotides modified with certain disclosed embodiments can be used as probes that detect particular nucleic acid targets. In fluorescent in-situ hybridization techniques (FISH), these probes can comprise a fluorophore at one end of the oligonucleotide, while the other end comprises a quencher. The quencher will quench the fluorophore's signal until hybridization takes place at which point two possible alternatives can arise. The pre-hybridized hairpins (how the probe typically exists in solution) will unfold during hybridization, thus distancing the quencher from the fluorophore and allowing detection of fluorescence. Alternatively, hybridization of the oligonucleotide to the target will take place, followed by exonuclease or endonuclease-induced cleavage of the fluorophore or quencher, thereby allowing detection of fluorescence.

Disclosed embodiments comprehend the use of the disclosed compounds to produce modified oligomers that can be used in drug discovery determining how proteins influence or relate to a disease state, phenotype or condition. For example, an oligomer comprising one or more of the disclosed compounds can be added to a sample, tissue, cell, or organism in order to detect a target peptide. The levels of the nucleic acid or protein present at the target and the related phenotype can be measured after a certain time period. This measurement can then be compared with measurements obtained from samples, tissues, cells or organisms that have not been treated with a modified oligomer, or that have been treated with another modified oligomer (usually containing a different modification). Disclosed embodiments are not limited to this method, but can also be used in methods that are typically performed in parallel or combination in order to determine the function of unknown genes, which can aid in determining the validity of targeting a specific gene for the treatment or prevention of a particular disease, condition or phenotype.

Disclosed embodiments can be used to simultaneously analyze a nucleic acid target for multiple mutations. Oligonucleotides modified with one or more of the disclosed compounds can be immobilized in a set pattern on a solid support. A mutation in the nucleic acid sequence can then be detected because the mutation will hybridize at a certain predetermined position on the solid support. A similar solid support-based technique can be used to capture and purify natural or synthetic nucleic acids. For example, the natural or synthetic nucleic acid can be contacted with an oligomer that has been modified with one or more of the disclosed compounds, which have been immobilized on a solid surface. Hybridization of the modified oligomer with the nucleic acid can occur simultaneously with capture of the nucleic acid because the hybridized nucleic acid can be detected, characterized, quantified, and/or amplified directly on the surface. Alternatively, the captured nucleic acid can be released and undergo subsequent characterization and/or amplification upon exposure to denaturing conditions. Disclosed embodiments can be used in a kit that performs these functions, wherein the kit comprises a solid support and one or more modified oligonucleotides (either C5- or C8-functionalized LNA-modified or C5- or C8-functionalized α-L-LNA modified).

Examples of solid supports include polymer materials, such as polystyrene, polycarbonate, polyethylene, and polypropylene. The polymer material can be in the form of a plate, a stick, a pellet, a bead, a filter, a tube, a sheet, a film or the like. Attachment of the modified oligonucleotide can occur at either the 5' or 3' end of the nucleotide. Also, the modified oligonucleotide can be bound to the support via linkers. Typical chemical or photochemical methods can be used to bind the oligonucleotide to the support, such as immobilization or non-covalent coupling.

VII. Pharmaceutical Compositions and Methods for their Use

Disclosed embodiments can be used in biological media, both in vitro and in vivo, and exhibit desirable pharmacokinetic profiles, such as improved receptor-mediated or non-receptor-mediated cellular uptake when used without or with delivery agents, improved cellular compartmentalization of oligonucleotide probes, and altered biodistribution. The various moieties attached to the C5 or C8 position of the disclosed compounds can be manipulated in order to better facilitate particular pharmacokinetic aspects.

Another aspect of the disclosure includes pharmaceutical compositions prepared for administration to a subject and which include a therapeutically effective amount of one or more of the currently disclosed locked nucleic acids. The therapeutically effective amount of a disclosed locked nucleic acid will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed locked nucleic acids is understood by those of skill in the art.

Pharmaceutical compositions for administration to a subject can include carriers, thickeners, diluents, buffers, preservatives, surface active agents and the like in addition to the microbes/microbial enzymes of choice. Pharmaceutical compositions can also include one or more additional active ingredients such as anti-inflammatory agents, anesthetics, and the like.

Other ingredients include, for example, bulking agents, disintegrating agents, anti-adherents and glidants, lubricants, binding agents, flavoring agents, etc., including without limitation: bulking agents, such as microcrystalline cellulose (e.g., Avicel®, FMC Corp., Emcocel®, Mendell Inc.), mannitol, xylitol, dicalcium phosphate (eg. Emcompress, Mendell Inc.) calcium sulfate (e.g. Compactrol, Mendell Inc.) starches, lactose, sucrose (Dipac, Amstar, and Nutab, Ingredient Technology), dextrose (Emdex, Mendell, Inc.), sorbitol, cellulose powder (Elcema, Degussa, and Solka Floc, Mendell, Inc.), and combinations thereof; disintegrating agents, such as microcrystalline cellulose, starches, crospovidone (e.g., Polyplasdone XL, International Specialty Products), sodium starch glycolate (Explotab, Mendell Inc.), crosscarmellose sodium (e.g., Ac-Di-Sol, FMC Corp.), and combinations thereof; antiadherants and glidants, such as talc, corn starch, silicon dioxide, sodium lauryl sulfate, metallic stearates, and combinations thereof; lubricants, such as magnesium stearate, calcium stearate, sodium stearate, stearic acid, sodium stearyl fumarate, hydrogenated cotton seed oil (sterotex), talc, and waxes, including but not limited to, beeswax, carnauba wax, cetyl alcohol, glyceryl stearate, glyceryl palmitate, glyceryl behenate, hydrogenated vegetable oils, stearyl alcohol, and combinations thereof; and binding agents, such as polyvinyl pyrrollidone, starch, methylcellulose, hydroxypropyl methylcellulose, carboxymethyl cellulose, sucrose solution, dextrose solution, acacia, tragacanth, locust bean gum, and combinations thereof.

Pharmaceutical compositions comprising embodiments of the disclosed C5- or C8-functionalized locked nucleic acids may comprise a single active ingredient (e.g., a monomer), or may comprise plural active ingredients. Generally, but not necessarily, the active ingredient has a window of absorption. Additional examples of active ingredients can be selected from the group consisting of disease management agents, appetite stimulants, appetite suppressants, dietary supplements, enzymes, fatty acids, gastrointestinal agents, and mixtures thereof.

The disclosed compositions may include an enteric material. Examples, without limitation, of suitable enteric materials include cellulose acetate phthalate (CAP), hydroxypropyl methylcellulose phthalate (HPMCP), polyvinyl acetate phthalate (PVAP), hydroxypropylmethyl cellulose, hydroxypropyl methylcellulose acetate succinate (HPMCAS), cellulose acetate trimellitate, hydroxypropyl methylcellulose succinate, carboxymethyl cellulose, carboxymethyl ethyl cellulose, cellulose acetate phthalate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez E S series), ethyl methyacrylate-methylmethacrylate-chlorotrimethylammonium ethyl acrylate copolymer, polyvinyl acetate phthalate, natural resins such as zein, shellac and copal collophorium, commercially available enteric dispersion systems, including for example Eudragit L30D55, Eudragit FS30D, Eudragit L100, Eudragit S100, Kollicoat EMM30D, Estacryl 30D, Coateric, and Aquateric, and combinations of such materials.

Disclosed embodiments of the compositions may include other ingredients. For example, and without limitation, such other ingredients include bulking agents, disintegrating agents, anti-adherents and glidants, lubricants, and binding agents. These ingredients are known to persons of ordinary skill in the art. Typical bulking agents include, but are not limited to microcrystalline cellulose (e.g., Avicel®, FMC Corp., Emcocel®, Mendell Inc.), mannitol, xylitol, dicalcium phosphate (eg. Emcompress, Mendell Inc.) calcium sulfate (e.g. Compactrol, Mendell Inc.) starches, lactose, sucrose (Dipac, Amstar, and Nutab, Ingredient Technology), dextrose (Emdex, Mendell, Inc.), sorbitol, cellulose powder (Elcema, Degussa, and Solka Floc, Mendell, Inc.), and combinations thereof. The bulking agent may be present in the composition in any useful amount, which typically ranges from about 5 wt. % to about 90 wt. %, more typically from about 10 wt. % to about 50 wt. %.

Disintegrating agents that may be included in the composition include, but are not limited to, microcrystalline cellulose, starches, crospovidone (e.g., Polyplasdone XL, International Specialty Products), sodium starch glycolate (Explotab, Mendell Inc.), crosscarmellose sodium (e.g., Ac-Di-Sol, FMC Corp.), and combinations thereof. The disintegrating agent may be present in the composition in any useful amount, which typically is from about 0.5 wt. % to about 30 wt. %, more typically from about 1 wt. % to about 15 wt. %.

Antiadherants and glidants that may be used in the composition include, but are not limited to, talc, corn starch, silicon dioxide, sodium lauryl sulfate, metallic stearates, and combinations thereof. The antiadherant or glidant may be present in the composition in any useful amount, which typically ranges from about 0.2 wt. % to about 15 wt. %, more typically from about 0.5 wt. % to about 5 wt. %.

Lubricants that may be employed in the composition include, but are not limited to, magnesium stearate, calcium stearate, sodium stearate, stearic acid, sodium stearyl fumarate, hydrogenated cotton seed oil (sterotex), talc, and waxes, including but not limited to, beeswax, carnauba wax, cetyl alcohol, glyceryl stearate, glyceryl palmitate, glyceryl behenate, hydrogenated vegetable oils, stearyl alcohol, and combinations thereof. The lubricant may be present in any useful amount, which typically is from about 0.2 wt. % to about 20 wt. %, more typically from about 0.5 wt. % to about 5 wt. %.

Binding agents that may be employed include, but are not limited to, polyvinyl pyrrollidone, starch, methylcellulose, hydroxypropyl methylcellulose, carboxymethyl cellulose, sucrose solution, dextrose solution, acacia, tragacanth, locust bean gum, and combinations thereof. The binding agent may be present in any useful amount, which typically is from about 0.2 wt. % to about 10 wt. %, and more typically from about 0.5 wt. % to about 5 wt. %.

Pharmaceutical formulations also can include additional components, such as carriers. The pharmaceutically acceptable carriers useful for these formulations are conventional. Remington's Pharmaceutical Sciences, by E. W. Martin, Mack Publishing Co., Easton, Pa., 19th Edition (1995), describes compositions and formulations suitable for pharmaceutical delivery of the formulations herein disclosed. In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sorbitan monooleate.

The therapeutically effective amount of a pharmaceutical composition comprising a locked nucleic acid administered can vary depending upon the desired effects and the factors noted above. Embodiments of the locked nucleic acid disclosed herein may be administered orally and may be administered in dosage unit formulations containing conventional non-toxic pharmaceutically acceptable carriers, adjuvants and vehicles.

VIII. Examples

The following examples are provided to illustrate certain features of working embodiments of the present invention. A person of ordinary skill in the art will appreciate that the scope of the invention is not limited to the features of these working examples.

General Experimental Section for Method of Making C5-Functionalized LNA and aL-LNA Compounds:

All reagents and solvents were of analytical grade and obtained from commercial suppliers and used without further purification. Petroleum ether of the distillation range 60-80° C. was used. $CH_3CN$ was dried through storage over activated 3 Å molecular sieves. THF was dried by distillation over sodium metal, and subsequently stored over 4 Å molecular sieves. Anhydrous DMF was used as obtained from commercial suppliers. $CH_2Cl_2$, DCE, DCM, $ET_3N$ and DIPEA were dried through storage over 4 Å molecular sieves. The water content of anhydrous solvents was checked by Karl-Fischer apparatus. Reactions were conducted under an atmosphere of argon whenever anhydrous solvents were used. All reactions were monitored by thin layer chromatography (TLC) using silica gel coated plates with a fluorescence indicator ($SiO_2$-60, F-254) which were visualized under UV light and/or by dipping in 5% conc. $H_2SO_4$ in absolute ethanol (v/v) followed by heating. Silica gel column chromatography was performed with silica gel 60 (particle size 0.040-0.063 mm) using moderate pressure (pressure ball). Silica gel columns were generally built with an initial starting eluent containing 1% (v/v) of pyridine whenever the DMT-protected nucleosides were purified. Evaporation of solvents was carried out under reduced pressure at a temperature below 50° C. After column chromatography, appropriate fractions were pooled, evaporated and dried at high vacuum for at least 12 h to give the obtained products in high purity. $^1$H, $^{13}$C, $^{31}$P NMR spectra were recorded at 500 Mhz, 125.5 MHz, 121.5 MHz respectively, unless otherwise stated. Chemical shifts are reported in parts per million (ppm) relative to deutrated solvents or other internal standards (trimethylsilane, 80% phosphoric acid for $^1$H and $^{31}$P NMR). Exchangeable protons were detected by disappearance of peaks upon $D_2O$ addition. Assignments of NMR spectra are based on 2D spectra (COSY, HSQC) and follow standard carbohydrate/nucleoside nomenclature. Quaternary carbons in $^{13}$C NMR were only assigned if HSQC and DEPT spectra indicated their presence (absence of signals in DEPT). The carbon atom of C4'-substituents is numbered as C5". Similar conventions apply for the corresponding hydrogen atoms. Assignments of $^1$H NMR signals of H5'H5"/CH$_2$Ph and the corresponding $^{13}$C NMR signals are interchangeable. FAB-HRMS were recorded in positive ion mode on a jeol JMS-AX505HA mass spectrometer using 3-nitrobenzyl alcohol as a matrix and PEG as a calibration compound. ES$^+$-HRMS were recorded on a Micromass Q-T of Premier mass spectrometer, in solution form. Desired compound was dissloved in a solution of concentrated solution of NaCl in anhydrous CH$_3$CN.

Example 1

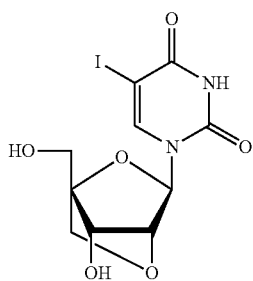 [SMILES: O=c1[nH]c(=O)n([C@@H]2O[C@@]3(CO)COC2[C@H]3O)cc1I]

5-iodo-LNA-U Diol

To a solution of the nucleoside precursor (Kumar 2008) (200 mg, 0.78 mmol) in glacial AcOH (10 mL) was added iodine (119 mg, 0.47 mmol) and ceric ammonium nitrate (CAN, 213 mg, 0.39 mmol), and the reaction mixture was stirred at 80° C. for 50 min. After cooling to rt, the mixture was evaporated to dryness and the resulting crude purified by column chromatography (0-15% MeOH/CH$_2$Cl$_2$, v/v) to afford the iodinated nucleoside (0.26 g, 87%) as white solid powder. R$_f$=0.4 (10% MeOH/CH$_2$Cl$_2$, v/v); FAB-HRMS m/z 382.9732 ([M+H]$^+$, C$_{10}$H$_{11}$IN$_2$O$_6$.H$^+$, Calcd 382.9735); $^1$H NMR (DMSO-d$_6$) δ 11.69 (s, 1H, ex, NH), 8.13 (s, 1H, H6), 5.65 (d, 1H, ex, J=4.5 Hz, 3'-OH), 5.40 (s, 1H, H1'), 5.27 (t, 1H, ex, J=5.4 Hz, 5'-OH), 4.13 (s, 1H, H2'), 3.91 (d, 1H, J=4.5 Hz, H3'), 3.79-3.82 (d, 1H, J=8.5 Hz, H5"), 3.68-3.75 (m, 2H, H5'), 3.58-3.62 (d, 1H, J=8.5 Hz, H5"); $^{13}$C NMR (DMSO-d$_6$) δ 160.5, 149.6, 143.5 (C6), 88.8, 86.4 (C1'), 78.5 (C2'), 70.8 (C5"), 68.4, 68.2 (C3'), 55.3 (C5').

Example 2

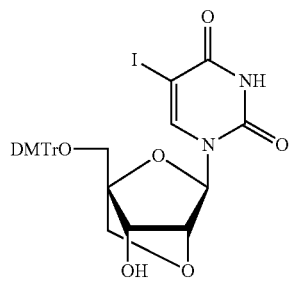

5-iodo-5'-ODMT-LNA-U

The diol product from above (200 mg, 0.52 mmol) was coevaporated with anhydrous pyridine (10 mL) and redissolved in anhydrous pyridine (10 mL). To this was added 4,4'-dimethoxytrityl chloride (DMTr-Cl, 230 mg, 0.68 mmol) and the reaction mixture was stirred at rt for 16 h, whereupon it was diluted with sat. aq. NaHCO$_3$ (20 mL) and CH$_2$Cl$_2$ (25 mL). The phases were separated and the organic phase was washed with sat. aq. NaHCO$_3$ (20 mL). The aqueous phase was back-extracted with CH$_2$Cl$_2$ (2×20 mL), and the combined organic phase was dried (Na$_2$SO$_4$), evaporated to near dryness, and coevaporated with toluene:abs. EtOH (2×30 mL, 1:2, v/v). The resulting crude was purified by column chromatography (0-4.5% MeOH in CH$_2$Cl$_2$, v/v) to afford the DMTr-protected iodide (0.28 g, 76%) as a slightly yellow solid material. R$_f$=0.5 (5% MeOH in CH$_2$Cl$_2$, v/v); FAB-HRMS m/z 684.0977 ([M]$^+$, C$_{31}$H$_{29}$IN$_2$O$_8$$^+$, Calcd 684.0969); $^1$H NMR (DMSO-d$_6$) δ 11.74 (s, 1H, ex, NH), 7.96 (s, 1H, H6), 7.23-7.45 (m, 9H, Ar), 6.91 (d, 4H, J=8.5 Hz, Ar), 5.70 (d, 1H, ex, J=4.5 Hz, 3'-OH), 5.44 (s, 1H, H1'), 4.24 (s, 1H, H2'), 4.07 (d, 1H, J=4.5 Hz, H3'), 3.74-3.76 (m, 8H, 2×OCH$_3$, 2×H5"), 3.39-3.42 (d, 1H, J=11.0 Hz, H5'), 3.28-3.31 (d, 1H, J=11.0 Hz, H5', overlap with H$_2$O); $^{13}$C NMR (DMSO-d$_6$) δ 160.5, 158.1, 158.0, 149.7, 144.6, 142.7 (C6), 135.3, 135.2, 129.7 (Ar), 129.6 (Ar), 127.9 (Ar), 127.5 (Ar), 126.6 (Ar), 113.3 (Ar), 87.5, 86.9 (C1'), 85.6, 78.8 (C2'), 71.3 (C5"), 69.4 (C3'), 68.9, 58.9 (C5'), 55.0 (CH$_3$O).

Representative Protocol for Sonogashira Coupling Reactions.

The vinyl iodide from the previous example, Pd(PPh$_3$)$_4$, CuI, and alkyne were added to anhydrous DMF [quantities and volumes specified below] and the reaction chamber was degassed and placed under an argon atmosphere. To this was added Et$_3$N and the reaction mixture was stirred in the dark until analytical TLC indicated full conversion of the starting material [reaction time and temperature specified below], whereupon solvents were evaporated off. The resulting residue was taken in up in EtOAc (100 mL) and sequentially washed with brine (2×50 mL) and sat. aq. NaHCO$_3$ (50 mL). The combined aqueous phase was back-extracted with EtOAc (100 mL), and the combined organic phase was dried (Na$_2$SO$_4$), evaporated to dryness and the resulting crude residue purified by column chromatography (0-5% MeOH in $CH_2Cl_2$ (v/v) to afford the desired product.

Example 3

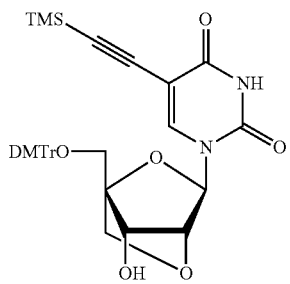

C-5 TMS Ethynyl LNA-U.

After setting up the vinyl iodide from the previous experiment (0.68 g, 1.00 mmol), $Pd(PPh_3)_4$ (120 mg, 0.10 mmol), CuI (40 mg, 0.20 mmol), trimethylsilylacetylene (294 mg, 0.42 mL, 3.x mmol), and $Et_3N$ (0.60 mL, 4.27 mmol) in DMF (10 mL) as described in the representative Sonogashira protocol, the reaction mixture was stirred at rt for 12 h. After workup and purification, the TMS acetylene (0.56 g, 85%) was obtained as a brown solid material. $R_f$=0.5 (5% MeOH in $CH_2Cl_2$, v/v); ESI-HRMS m/z 677.2297 ([M+Na]$^+$, $C_{36}H_{38}N_2O_8SiNa^+$, Calcd 677.2290); $^1$H NMR (DMSO-$d_6$) δ 11.68 (s, 1H, ex, NH), 7.85 (s, 1H, H6), 7.20-7.44 (m, 9H, Ar), 6.89 (d, 4H, J=8.5 Hz, Ar), 5.71 (d, 1H, ex, J=4.5 Hz, 3'-OH), 5.38 (s, 1H, H1'), 4.27 (s, 1H, H2'), 4.07 (d, 1H, J=4.5 Hz, H3'), 3.75-3.79 (m, 2H, 2×H5"), 3.73 (s, 6H, 2×OCH$_3$), 3.40-3.42 (d, 1H, J=11.0 Hz, H5'), 3.30-3.32 (d, 1H, J=11.0 Hz, H5', overlap with $H_2O$ signal), −0.04 (s, 9H, $Me_3Si$); $^{13}$C NMR (DMSO-$d_6$) δ 161.5, 158.05, 158.03, 148.9, 144.5, 142.4 (C6), 135.4, 135.1, 129.6 (Ar), 129.5 (Ar), 127.8 (Ar), 127.5 (Ar), 126.5 (Ar), 113.1 (Ar), 97.8, 97.4, 96.8, 87.7, 87.0 (C1'), 85.4, 78.6 (C2'), 71.3 (C5"), 69.4 (C3'), 58.8 (C5'), 55.0 ($CH_3O$), −0.47 ($Me_3Si$).

Example 4

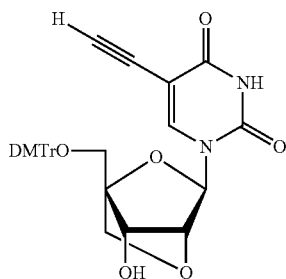

C-5 Ethynyl LNA-U.

To a solution of the TMS acetylene (0.53 g, 0.81 mmol) in THF (20 mL) was added tetrabutylammonium fluoride in THF (TBAF, 1M, 1.2 mL, 1.2 mmol) and the reaction mixture was stirred at rt for 2 h. At this point EtOAc (50 mL) was added and the organic phase sequentially washed with brine (2×30 mL) and $H_2O$ (30 mL). The aqueous phase was back-extracted with EtOAc (30 mL). The combined organic phase was dried ($Na_2SO_4$), evaporated to dryness, and the resulting crude residue purified by column chromatography (0-5% MeOH in $CH_2Cl_2$, v/v) to afford the pure desilylated acetylene (0.37 g, 78%). $R_f$=0.4 (5% MeOH/$CH_2Cl_2$, v/v); ESI-HRMS m/z 621.1666 ([M+K]$^+$, $C_{33}H_{30}N_2O_8^+K$, Calcd 621.1634); $^1$H NMR (DMSO-$d_6$) δ 11.70 (s, 1H, ex, NH), 7.88 (s, 1H, H6), 7.21-7.45 (m, 9H, Ar), 6.89 (d, 4H, J=9.0 Hz, Ar), 5.70 (d, 1H, ex, J=4.5 Hz, 3'-OH), 5.45 (s, 1H, H1'), 4.27 (s, 1H, H2'), 4.04 (d, 1H, J=4.5 Hz, H3'), 3.95 (s, 1H, CH), 3.76 (s, 2H, 2×H5"), 3.75 (s, 6H, 2×$CH_3O$), 3.43-3.45 (d, 1H, J=11.0 Hz, H5'), 3.28-3.30 (d, 1H, J=11.0 Hz, H5', overlap with $H_2O$ signal); $^{13}$C NMR (DMSO-$d_6$) δ 161.7, 158.0, 149.0, 144.6, 142.2 (C6), 135.3, 135.2, 129.7 (Ar), 129.6 (Ar), 127.9 (Ar), 127.6 (Ar), 126.7 (Ar), 113.3 (Ar), 97.2, 87.5, 86.9 (C1'), 85.7, 83.6, 78.9 (C2'), 76.2, 71.4 (C5"), 69.4 (C3'), 59.0 (C5'), 55.0 ($CH_3O$).

Example 5

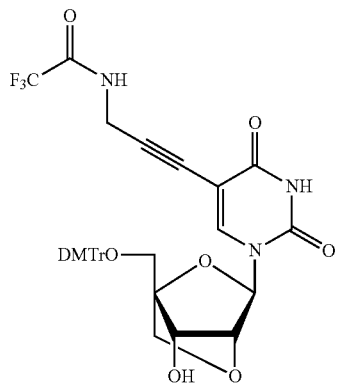

C-5 TFA Protected Propargylamine LNA-U.

After setting up the vinyl iodide from above (0.50 g, 0.73 mmol), $Pd(PPh_3)_4$ (90 mg, 0.07 mmol), CuI (30 mg, 0.14 mmol), 2,2,2-trifluoro-N-(prop-2-ynyl)acetamide$^r$ (180 mg, 1.46 mmol), and $Et_3N$ (0.40 mL, 2.84 mmol) in DMF (10 mL) as described in the representative Sonogashira protocol, the reaction mixture was stirred at rt for 12 h. After workup and purification, the TFA-protected propargyl amine (0.41 g, 80%) was obtained as a brown solid material. $R_f$=0.5 (5% MeOH in $CH_2Cl_2$, v/v); FAB-HRMS Submitted; $^1$H NMR (DMSO-$d_6$) δ 11.69 (s, 1H, ex, NH), 9.95 (t, 1H, ex, J=5.5 Hz, $NHCH_2$), 7.78 (s, 1H, H6), 7.22-7.46 (m, 9H, Ar), 6.89 (dd, 4H, J=9.0 Hz, 3.5 Hz, Ar), 5.72 (d, 1H, ex, J=4.5 Hz, 3'-OH), 5.41 (s, 1H, H1'), 4.24 (s, 1H, H2'), 3.97-4.10 (m, 3H, H3', $CH_2NH$), 3.79-3.83 (2d, 2H, J=x.x Hz, 2×H5"), 3.74 (s, 6H, 2×$CH_3O$), 3.56-3.58 (d, 1H, J=11.0 Hz, H5'), 3.26-3.28 (d, 1H, J=11.0 Hz, H5'); $^{13}$C NMR (DMSO-$d_6$) δ 161.6, 158.1, 158.0, 155.9 (q, J=36.1 Hz, $COCF_3$), 149.0, 144.6, 142.1 (C6), 135.4, 134.9, 129.8 (Ar), 129.6 (Ar), 127.8 (Ar), 127.5 (Ar), 126.6 (Ar), 115.6 (q, J=287.3 Hz, $CF_3$), 113.3 (Ar), 113.2 (Ar), 97.2, 87.6, 87.2, 86.9 (C1'), 85.6, 78.7 (C2'), 75.4, 71.3 (C5"), 69.6 (C3'), 59.1 (C5'), 55.0 ($CH_3O$), 29.4 ($CH_2NH$).

Example 6

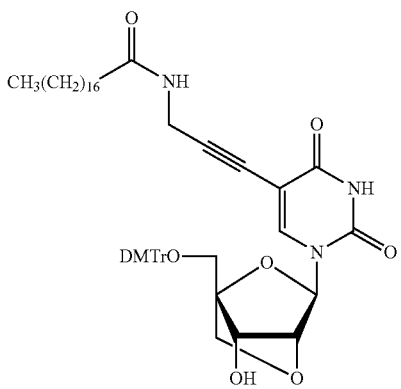

C-5 C$_{18}$ Protected Propargylamine LNA-U.

After setting up the vinyl iodide from above (0.34 g, 0.50 mmol), Pd(PPh$_3$)$_4$ (60 mg, 0.05 mmol), CuI (20 mg, 0.10 mmol), N-(prop-2-ynyl)stearamide (0.28 g, 1.00 mmol), and Et$_3$N (0.30 mL, 2.13 mmol) in DMF (10 mL) as described in the representative Sonogashira protocol, the reaction mixture was stirred at 40° C. for 6 h. After workup and purification, the C$_{18}$ protected propargylamine (0.29 g, 68%) was obtained as a brown solid material. R$_f$=0.5 (5% MeOH in CH$_2$Cl$_2$, v/v); FAB-HRMS 877.4844 ([M]$^+$, C$_{52}$H$_{67}$N$_3$O$_9$$^+$, Calcd 877.4877); $^1$H NMR (CDCl$_3$) δ 9.45 (bs, 1H, ex, NH), 8.05 (s, 1H, H6), 7.22-7.50 (m, 9H, Ar), 6.86-6.88 (dd, 4H, J=9.0 Hz, 1.5 Hz, Ar), 5.56-5.59 (m, 2H, 1 ex, H1', NHCH$_2$), 4.52 (s, 1H, H2'), 4.29 (s, 1H, H3'), 3.78-4.00 (m, 10H, 2×H5", CH$_2$NH, 2×CH$_3$O), 3.53-3.56 (d, 1H, J=11.0 Hz, H5'), 3.49-3.51 (d, 1H, J=11.0 Hz, H5'), 3.35 (bs, 1H, ex, 3'-OH), 1.85-1.88 (m, 2H, CH$_2$CONH), 1.44-1.51 (m, 2H, CH$_2$—CH$_2$CONH), 1.24-1.26 (m, 28H, SA-CH$_2$), 0.88 (t, 3H, J=x.x Hz, CH$_3$); $^{13}$C NMR (CDCl$_3$) δ 172.7, 162.1, 158.69, 158.67, 148.6, 144.6, 141.9 (C6), 135.5, 135.4, 130.02 (Ar), 130.01 (Ar), 128.1 (Ar), 128.0 (Ar), 127.0 (Ar), 113.44 (Ar), 113.43 (Ar), 99.1, 89.9, 88.4, 87.4 (C1'), 86.6, 79.1 (C2'), 74.2, 71.8 (C5"), 70.5 (C3'), 58.5 (C5'), 55.2 (CH$_3$O), 36.1 (CH$_2$CONH), 31.9 (CH$_2$), 29.9 (CH$_2$NH), 29.69 (CH$_2$), 29.68 (CH$_2$), 29.66 (CH$_2$), 29.64 (CH$_2$), 29.5 (CH$_2$), 29.38 (CH$_2$), 29.34 (CH$_2$), 29.33 (CH$_2$), 25.4 (CH$_2$—CH$_2$CONH), 22.7 (CH$_2$), 14.1 (CH$_3$).

Example 7

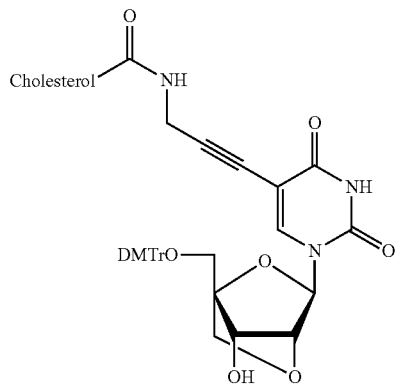

C-5 Cholesterol Protected Propargylamine LNA-U.

After setting up the vinyl iodide from above (0.34 g, 0.50 mmol), Pd(PPh$_3$)$_4$ (60 mg, 0.05 mmol), CuI (20 mg, 0.10 mmol), cholesteryl-prop-2ynyl-carbamate (0.47 g, 1.00 mmol), and Et$_3$N (0.30 mmol, 2.13 mmol) in DMF (8 mL) as described in the representative Sonogashira protocol, the reaction mixture was stirred at rt for 12 h. After workup and purification, the cholesterol-protected propargylamine (0.27 g, 53%) was obtained as a brown solid material. R$_f$=0.5 (5% MeOH in CH$_2$Cl$_2$, v/v); FAB-HRMS m/z 1046.5560 ([M+Na]$^+$, C$_{62}$H$_{77}$N$_3$O$_{10}$.Na$^+$, Calcd 1046.5507); $^1$H NMR (CDCl$_3$) δ 9.40 (bs, 1H, ex, NH), 7.97 (s, 1H, H6), 7.22-7.49 (m, 9H, Ar), 6.87 (d, 4H, J=9.0 Hz, Ar), 5.57 (s, 1H, H1'), 5.34 (d, 1H, J=5.0 Hz, HC=C-chol), 4.96 (bs, 1H, ex, NHCH$_2$), 4.53 (s, 1H, H2'), 4.40-4.46 (m, 1H, OCH-chol) 4.29 (bs, 1H, H3'), 3.83-3.98 (m, 4H, 2×H5", CH$_2$NH), 3.79 (s, 6H, 2×CH$_3$O), 3.58-3.61 (d, 1H, J=11.0 Hz, H5'), 3.51-3.53 (d, 1H, J=11.0 Hz, H5'), 3.27 (bs, 1H, ex, 3'-OH) 0.87-2.29 (m, 40H, chol), 0.69 (s, 3H, CH$_3$-chol); $^{13}$C NMR (CDCl$_3$) δ 162.1, 158.63, 158.60, 155.5, 148.7, 144.5, 141.8 (C6), 139.8, 135.44, 135.39, 130.0 (Ar), 128.1 (Ar), 128.0 (Ar), 127.0 (Ar), 122.5 (=CH, chole), 113.4 (Ar), 99.2, 90.1, 88.4, 87.4 (C1'), 86.6, 79.1 (C2'), 74.7 (OCH-chol), 74.1, 71.9 (C5"), 70.6 (C3'), 58.6 (C5'), 56.7 (CH-chol), 56.2 (CH-chol), 55.2 (CH$_3$O), 50.0 (CH-chol), 42.3, 39.8 (CH$_2$-chol), 39.5 (CH$_2$-chol), 38.5 (CH$_2$-chol), 37.0 (CH$_2$-chol), 36.5, 36.2 (CH$_2$-chol), 35.8 (CH-chol), 31.9 (CH-chol & CH$_2$NH), 28.2 (CH$_2$-chol), 28.1 (CH$_2$-chol), 28.0 (CH-chol), 24.3 (CH$_2$-chol), 23.8 (CH$_2$-chol), 22.8 (CH$_3$-chol), 22.5 (CH$_3$-chol), 21.0 (CH$_2$-chol), 19.3 (CH-chol), 18.7 (CH-chol), 11.4 (CH$_3$-chol).

Example 8

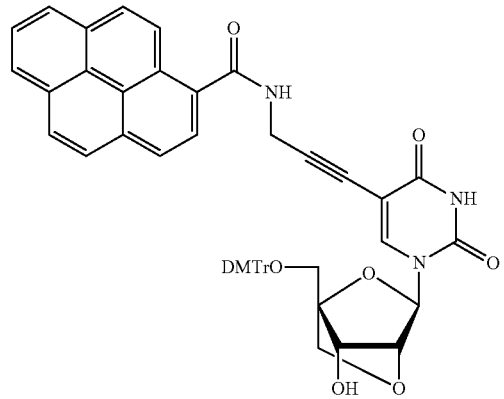

C-5 Pyrenecarboxamide Propargylamine LNA-U.

After setting up the vinyl iodide from above (0.50 g, 0.73 mmol), Pd(PPh$_3$)$_4$ (90 mg, 0.07 mmol), CuI (30 mg, 0.14 mmol), N-(prop-2-ynyl)pyrene-1-carboxamides (0.28 g, 1.00 mmol), and Et$_3$N (0.40 mL, 2.84 mmol) in DMF (10 mL) as described in the representative Sonogashira protocol, the reaction mixture was stirred at rt for 12 h. After workup and purification, the pyrenecarboxamide propargylamine (0.45 g, 74%) was obtained as a brown solid material. R$_f$=0.5 (5% MeOH in CH$_2$Cl$_2$, v/v); ESI-HRMS m/z 862.2778 ([M+Na]$^+$, C$_{51}$H$_{41}$N$_3$O$_9$.Na$^+$, Calcd 862.2735); $^1$H NMR (DMSO-d$_6$) δ 11.71 (s, 1H, ex, NH), 9.10 (t, ex, 1H, J=5.5 Hz, NHCH$_2$), 8.52-8.54 (d, 1H, J=9.5 Hz, Ar), 8.21-8.36 (m, 6H, Ar), 8.09-8.13 (m, 2H, Ar), 7.84 (s, 1H, H6), 7.23-7.46 (m, 9H, Ar), 6.90 (dd, 4H, J=9.0 Hz, 3.5 Hz, Ar), 5.73 (d, 1H, ex, J=4.5 Hz, 3'-OH), 5.45 (s, 1H, H1'), 4.23-4.34 (m, 3H, H2', CH₂NH), 4.07 (d, 1H, J=4.5 Hz, H3'), 3.82 (ap bs, 2H, 2×H5"), 3.73 (s, 3H, CH₃O), 3.72 (s, 3H, CH₃O) 3.57-3.59 (d, 1H, J=11.0 Hz, H5'), 3.29-3.31 (d, 1H, J=11.0 Hz, H5', overlap with H₂O); ¹³C NMR (DMSO-d₆) δ 168.5, 161.8, 158.12, 158.07, 149.0, 144.7, 141.6 (C6), 135.5, 134.9, 131.7, 131.0, 130.7, 130.1, 129.9 (Ar), 129.6 (Ar), 128.3 (Ar), 128.1 (Ar), 127.90 (Ar), 127.89 (Ar), 127.5 (Ar), 127.1 (Ar), 126.7 (Ar), 126.5 (Ar), 125.8 (Ar), 125.6, 125.2 (Ar), 124.6 (Ar), 124.3 (Ar), 123.7, 123.6, 113.26 (Ar), 113.24 (Ar), 97.8, 89.4, 87.6, 87.0 (C1'), 85.6, 78.8 (C2'), 74.6, 71.4 (C5"), 69.7 (C3'), 59.1 (C5'), 54.98 (CH₃O), 54.97 (CH₃O), 29.5 (CH₂NH).

Example 9

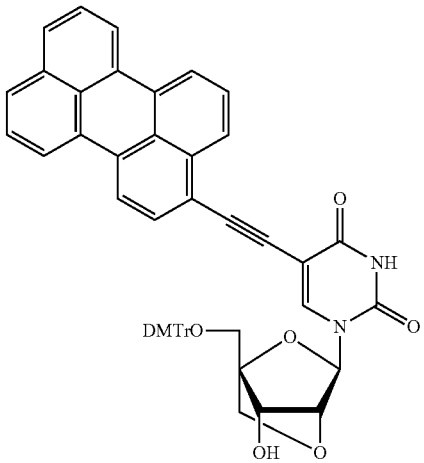

C-5 Ethynylperylene LNA-U.

After setting up the vinyl iodide from above (0.50 g, 0.73 mmol), Pd(PPh₃)₄ (90 mg, 0.07 mmol), CuI (30 mg, 0.14 mmol), 3-ethynylperylener (0.27 g, 1.00 mmol), and Et₃N (0.40 mmol, 2.84 mmol) in DMF (10 mL) as described in the representative Sonogashira protocol, the reaction mixture was stirred at rt for 12 h. After workup and purification, the ethynyl perylene compound (0.49 g, 80%) was obtained as a brown solid material. R_f=0.5 (5% MeOH in CH₂Cl₂, v/v); FAB-HRMS Submitted; ¹H NMR (DMSO-d₆) δ 11.86 (s, 1H, ex, NH), 8.35-8.39 (m, 3H, Ar), 8.22 (d, 1H, J=8.5 Hz, Ar), 8.12 (s, 1H, H6), 8.01 (d, 1H, J=8.5 Hz, Ar), 7.79-7.84 (m, 2H, Ar), 7.53-7.57 (m, 2H, Ar), 7.48-7.50 (m, 2H, Ar), 7.09-7.37 (m, 9H, Ar), 6.83-6.87 (m, 4H, Ar), 5.77 (d, 1H, ex, J=4.5 Hz, 3'-OH), 5.51 (s, 1H, H1'), 4.33 (s, 1H, H2'), 4.22 (d, 1H, J=4.5 Hz, H3'), 3.77-3.83 (m, 2H, 2×H5"), 3.59 (s, 3H, OCH₃), 3.56 (s, 3H, OCH₃), 3.48-3.50 (d, 1H, J=11.0 Hz, H5'), 3.35-3.39 (d, 1H, J=11.0 Hz, H5'); ¹³C NMR (DMSO-d₆) δ 161.7, 158.05, 158.00, 149.0, 144.4, 141.2 (C6), 135.43, 135.37, 134.2, 133.6, 130.9, 130.7, 130.4 (Ar), 130.1, 129.9, 129.6 (Ar), 129.5 (Ar), 128.5 (Ar), 128.2 (Ar), 127.9 (Ar), 127.7 (Ar), 127.60, 127.57, 127.47 (Ar), 127.0 (Ar), 126.9 (Ar), 126.7 (Ar), 125.7 (Ar), 121.5 (Ar), 121.2, 121.1 (Ar), 120.0 (Ar), 119.4, 113.2 (Ar), 98.1, 90.9, 88.5, 87.7, 87.1 (C1'), 85.6, 78.8 (C2'), 71.4 (C5"), 69.4 (C3'), 58.7 (C5'), 54.80 (CH₃O), 54.75 (CH₃O).

Example 10

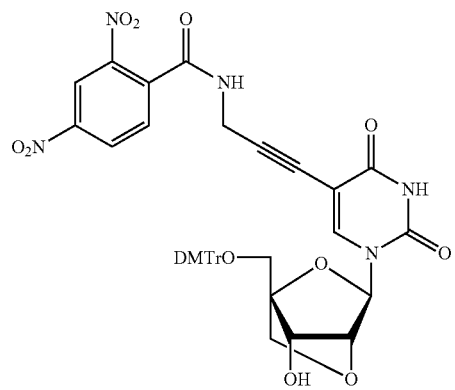

C-5 2,4-Dinitrobenzoic Acid Protected Propargylamine LNA-U.

After setting up the vinyl iodide from above (200 mg, 0.29 mmol), Pd(PPh₃)₄ (40 mg, 0.03 mmol), CuI (13 mg, 0.06 mmol), prop-2-ynyl benzoate^r (180 mg, 1.12 mmol), and Et₃N (0.16 mL, 1.15 mmol) in DMF (5 mL) as described in the representative Sonogashira protocol, the reaction mixture was stirred at rt for 12 h. After workup and purification, the 2,4-dinitrobenzoic acid-protected propargylamine (150 mg, 63%) was obtained as a light brown solid material. R_f=0.5 (5% MeOH in CH₂Cl₂, v/v); FAB-HRMS Submitted; ¹H NMR (DMSO-d₆) δ 11.69 (s, 1H, ex, NH), 9.33 (t, ex, 1H, J=5.0 Hz, NHCH₂), 8.74 (d, 1H, J=2.0 Hz, Ar), 8.56 (dd, 1H, J=8.0 Hz, J=2.0 Hz, Ar), 7.81-7.82 (m, 2H, H6, Ar), 7.23-7.44 (m, 9H, Ar), 6.89 (dd, 4H, J=9.0 Hz, 1.5 Hz, Ar), 5.72 (d, 1H, ex, J=4.5 Hz, 3'-OH), 5.43 (s, 1H, H1'), 4.25 (s, 1H, H2'), 4.07-4.18 (m, 2H, CH₂NH), 4.03 (d, 1H, J=4.5 Hz, H3'), 3.81 (s, 2H, 2×H5"), 3.73 (s, 6H, 2×OCH₃), 3.57-3.59 (d, 1H, J=11.0 Hz, H5'), 3.27-3.30 (d, 1H, J=11.0 Hz, H5', overlap with H₂O); ¹³C NMR (DMSO-d₆) δ 163.5, 161.6, 158.10, 158.05, 149.0, 147.9, 146.8, 144.7, 141.9 (C6), 136.7, 135.4, 134.9, 130.8 (Ar), 129.8 (Ar), 129.6 (Ar), 128.1 (Ar), 127.9 (Ar), 127.5 (Ar), 126.6 (Ar), 119.6 (Ar), 113.2 (Ar), 97.4, 88.0, 87.6, 86.9 (C1'), 85.6, 79.1, 78.8 (C2'), 75.4, 71.4 (C5"), 69.6 (C3'), 59.1 (C5'), 55.0 (CH₃O), 29.6 (CH₂NH).

Example 11

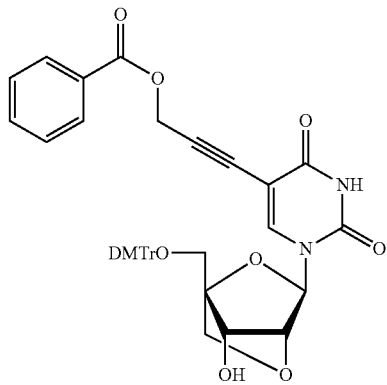

C-5 Benzoyl Protected Propargylalcohol LNA-U.

After setting up the vinyl iodide from above (0.50 g, 0.73 mmol), Pd(PPh$_3$)$_4$ (90 mg, 0.07 mmol), CuI (30 mg, 0.14 mmol), prop-2-ynyl benzoate (180 mg, 1.12 mmol), and Et$_3$N (0.40 mL, 2.84 mmol) in DMF (10 mL) as described in the representative Sonogashira protocol, the reaction mixture was stirred at rt for 12 h. After workup and purification, the benzoyl-protected propargyl alcohol (0.37 g, 70%) was obtained as a light brown solid material. R$_f$=0.5 (5% MeOH in CH$_2$Cl$_2$, v/v); ESI-HRMS m/z 739.2289 ([M+Na]$^+$, C$_{41}$H$_{36}$N$_2$O$_{10}$·Na, Calc 739.2262); $^1$H NMR (DMSO-d$_6$) δ11.72 (s, 1H, ex, NH), 7.91-7.93 (m, 2H, Ar), 7.89 (s, 1H, H6), 7.66-7.69 (m, 1H, Ar), 7.50-7.53 (m, 2H, Ar), 7.18-7.44 (m, 9H, Ar), 6.89 (dd, 4H, J=9.0 Hz, 3.0 Hz, Ar), 5.74 (d, 1H, ex, J=4.5 Hz, 3'-OH), 5.42 (s, 1H, H1'), 4.93-4.96 (d, 1H, J=16.0 Hz, CH$_2$OBz), 4.86-4.89 (d, 1H, J=16.0 Hz, CH$_2$OBz) 4.25 (s, 1H, H2'), 4.10 (d, 1H, J=4.5 Hz, H3'), 3.79-3.81 (d, 1H, J=8.0 Hz, H5"), 3.75-3.76 (d, 1H, J=8.0 Hz, H5"), 3.71 (s, 6H, 2×CH$_3$O), 3.53-3.55 (d, 1H, J=11.0 Hz, H5'), 3.27-3.29 (d, 1H, J=11.0 Hz, H5', partial overlap with H$_2$O); $^{13}$C NMR (DMSO-d$_6$) δ 164.9, 161.6, 158.1, 158.0, 149.0, 144.6, 142.7 (C6), 135.4, 135.0, 133.5 (Ar), 129.7 (Ar), 129.6 (Ar), 129.2 (Ar), 129.0, 128.7 (Ar), 127.8 (Ar), 127.5 (Ar), 126.6 (Ar), 113.20 (Ar), 113.17 (Ar), 96.8, 87.6, 86.9 (C1'), 86.3, 85.6, 79.2, 78.7 (C2'), 71.3 (C5"), 69.4 (C3'), 58.7 (C5'), 54.9 (CH$_3$O), 53.1 (CH$_2$OBz).

Example 12

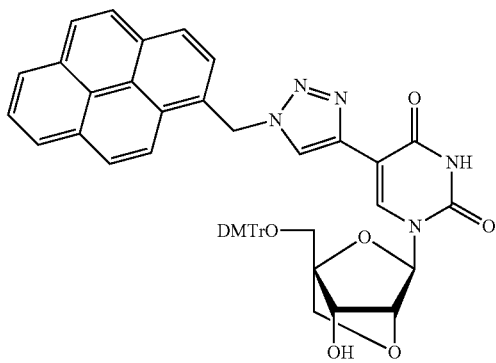

Click of 5-ethynyl-5'DMT-LNA-U with Pyrenemethylazide.

To a solution of the desilylated acetylene compound (0.33 g, 0.56 mmol) and pyrenemethyazider (200 mg, 0.78 mmol) in THF:H$_2$O:t-BuOH (10 mL, 3:1:1, v/v/v), was added aq. sodium ascorbate (1M, 1.00 mL, 1.00 mmol) and aq. CuSO$_4$ (7.5%, w/v, 1.00 mL, 0.30 mmol). The solution was stirred at rt for 2 h, whereupon it was diluted with EtOAc (50 mL) and brine (50 mL) and the phases were separated. The organic phase was washed with sat. aq. NaHCO$_3$ (50 mL), and the combined aqueous phase was back-extracted with EtOAc (50 mL). The combined organic phase was dried (Na$_2$SO$_4$), evaporated to dryness, and the resulting crude purified by column chromatography (0-75% EtOAc in petroleum ether, v/v) to afford the triazole (0.43 g, 91%) as a slightly yellow solid material. R$_f$=0.4 (70% EtOAc in petroleum ether, v/v); ESI-HRMS m/z 862.2869 ([M+Na]$^+$, C$_{50}$H$_{41}$N$_5$O$_8$·Na, Calc 862.2847); $^1$H NMR (DMSO-d$_6$) δ11.69 (s, 1H, ex, NH), 8.55-8.58 (d, 1H, J=9.0 Hz, Ar), 8.44 (s, 1H, H-triazole), 8.29-8.36 (m, 5H, H6, Ar), 8.20-8.23 (d, 1H, J=9.0 Hz, Ar), 8.16-8.20 (d, 1H, J=9.0 Hz, Ar), 8.11 (t, 1H, J=8.0 Hz, Ar), 8.06-8.08 (d, 1H, J=8.0 Hz, Ar), 7.09-7.40 (m, 9H, Ar), 6.88 (d, 4H, J=8.0 Hz, Ar), 6.40 (s, 2H, CH$_2$N), 5.68 (d, 1H, ex, J=4.5 Hz, 3'-OH), 5.55 (s, 1H, H1'), 4.32 (s, 1H, H2'), 3.91-3.95 (m, 2H, H3', H5"), 3.81-3.84 (d, 1H, J=8.0 Hz, H5"), 3.69 (s, 3H, CH$_3$O), 3.68 (s, 3H, CH$_3$O), 3.50-3.54 (d, 1H, J=11.0 Hz, H5"), 3.25-3.27 (d, 1H, J=11.0 Hz, H5'); $^{13}$C NMR (DMSO-d$_6$) δ 161.2, 158.1, 158.0, 149.2, 144.7, 138.9, 135.1, 134.2 (C6), 131.0, 130.7, 130.1, 129.7 (Ar), 129.6 (Ar), 129.1, 128.4, 128.2 (Ar), 127.8 (Ar), 127.6 (Ar), 127.5 (Ar), 127.2 (Ar), 126.52 (Ar), 126.45 (Ar), 125.7 (Ar), 125.5 (Ar), 125.0 (Ar), 124.0, 123.7, 122.7 (Ar), 122.4 (CH-triazole), 113.3 (Ar), 113.2 (Ar), 104.5, 87.5, 87.1 (C1'), 85.6, 79.0 (C2'), 71.5 (C5"), 70.0 (C3'), 59.8 (C5'), 54.9 (CH$_3$O), 54.8 (CH$_3$O), 50.7 (CH$_2$N).

Example 13

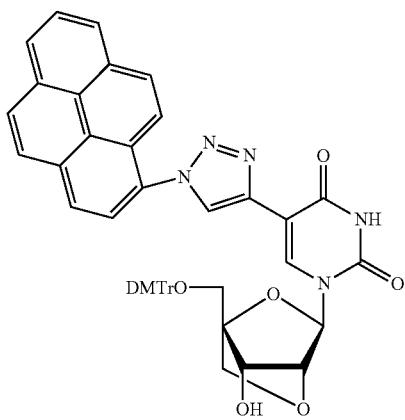

Click of 5-ethynyl-5'DMT-DNA-U with Pyreneazide.

To a solution of the desilylated acetylyene (0.25 g, 0.36 mmol) and pyreneazide$^r$ (110 mg, 0.45 mmol) in THF:H$_2$O:t-BuOH (10 mL, 3:1:1, v/v/v) was added aq. sodium ascorbate (1M, 0.70 mL, 0.70 mmol), and aq. CuSO$_4$ (7.5%, w/v, 0.65 mL, 0.19 mmol). The solution was stirred at rt for 2 h, whereupon it was diluted with EtOAc (50 mL) and brine (50 mL) and the phases were separated. The organic phase was washed with sat. aq. NaHCO$_3$ (50 mL), and the combined aqueous phase was back-extracted with EtOAc (50 mL). The combined organic phase was dried (Na$_2$SO$_4$), evaporated to dryness, and the resulting crude residue purified by column chromatography (0-75% EtOAc in petroleum ether, v/v) to afford the triazole (23×mg, 76%) as a slightly yellow solid material. R$_f$=0.4 (70% EtOAc in petroleum ether, v/v); ESI-HRMS m/z 848.2712 ([M+Na]$^+$, C$_{49}$H$_{39}$N$_5$O$_8$·Na$^+$, Calcd 848.2691); $^1$H NMR (DMSO-d$_6$) δ11.85 (s, 1H, ex, NH), 8.84 (s, 1H, H-triazole), 8.58 (s, 1H, H6), 8.28-8.49 (m, 6H, Ar), 8.16-8.20 (overlapping d+t, 2H, Ar), 7.79 (d, 1H, J=8.0 Hz, Ar), 7.09-7.40 (m, 9H, Ar), 6.88 (dd, 4H, J=9.0 Hz, J=2.0 Hz, Ar), 5.78 (d, 1H, ex, J=4.5 Hz, 3'-OH), 5.64 (s, 1H, H1'), 4.43 (s, 1H, H2'), 4.13 (d, 1H, J=4.5 Hz, H3'), 3.94-3.96 (d, 1H, J=9.0 Hz, H5"), 3.87-3.89 (d, 1H, J=9.0 Hz, H5"), 3.68 (s, 3H, CH$_3$O), 3.67 (s, 3H, CH$_3$O), 3.57-3.60 (d, 1H, J=11.0 Hz, H5'), 3.34-3.37 (m, 1H, J=11.0 Hz, H5'); $^{13}$C NMR (DMSO-d$_6$) δ 161.3, 158.05, 158.02, 149.4, 144.6, 139.4, 135.3, 135.2, 135.0 (C6), 131.6, 130.6, 130.14, 130.09, 129.7 (Ar), 129.6 (Ar), 129.5 (Ar), 128.7 (Ar), 127.8 (Ar), 127.6 (Ar), 127.0 (Ar), 126.6 (Ar), 126.5 (Ar), 126.1 (Ar), 125.3, 125.1 (CH-triazole), 124.8 (Ar), 124.0, 123.7 (Ar), 123.3, 120.9

(Ar), 113.24 (Ar), 113.19 (Ar), 104.3, 87.6, 87.2 (C1'), 85.6, 79.0 (C2'), 71.5 (C5"), 70.0 (C3'), 59.5 (C5'), 54.9 (CH$_3$O).

Representative procedure for O3'-phosphitylation:

The free alcohols described above were dried by the coevaporation with anhydrous 1,2-dichloroethane (2×10 mL) and dissolved in anhydrous CH$_2$Cl$_2$. To this was added DIPEA and 2-cyanoethyl N,N-diisopropylchlorophosphoramidite (PCl-reagent) [quantities and volumes specified below] and the reaction was stirred at rt until analytical TLC indicated complete conversion (2 h unless otherwise mentioned). The reaction mixture was diluted with CH$_2$Cl$_2$ (25 mL), washed with aq. NaHCO$_3$ (2×10 mL), and the combined aqueous phase back-extracted with CH$_2$Cl$_2$ (2×10 mL). The combined organic phase was dried (Na$_2$SO$_4$), evaporated to dryness, and the resulting crude residue purified by column chromatography (typically 0-4% MeOH/CH$_2$Cl$_2$, v/v) and subsequent trituration from CH$_2$Cl$_2$ and petroleum ether to provide the desired phosphoramidites.

Example 14

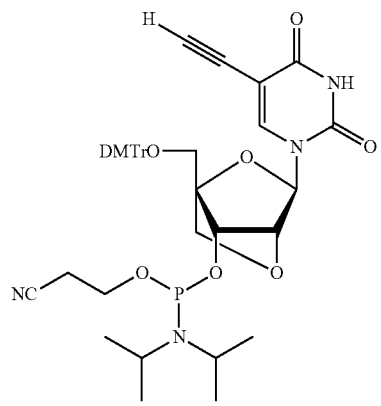

C-5 ethynyl LNA-U phosphoramidite. The C5-ethynyl compound (0.34 g 0.58 mmol), DIPEA (0.50 mL, 2.9×mmol), and PCl-reagent (0.20 mL, 0.87 mmol) in anhydrous CH$_2$Cl$_2$ (10 mL) were mixed, reacted, worked up and purified as described in the representative phosphitylation protocol to provide the phosphoramidite product (0.38 g, 83%) as a white foam. R$_f$=0.5 (2% MeOH in CH$_2$Cl$_2$, v/v); ESI-HRMS m/z 805.2973 ([M+Na]$^+$, C$_{42}$H$_{47}$N$_4$O$_9$P.Na$^+$, Calcd 805.2958); $^{31}$P NMR (CDCl$_3$) δ 149.8, 149.3.

Example 15

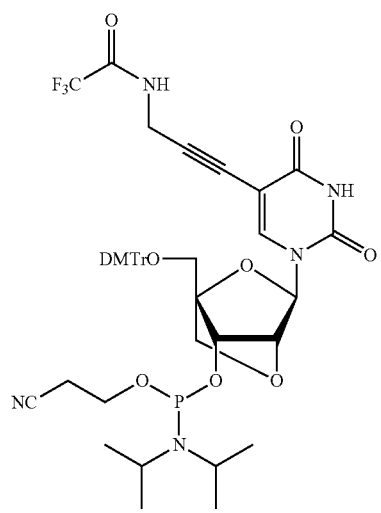

C-5 TFA Protected Propargylamine LNA-U Phosphoramidite.

The TFA-protected propargylamine (0.37 g 0.52 mmol), DIPEA (0.44 mL, 2.6 mmol), and PCl-reagent (0.18 mL, 0.78 mmol) in anhydrous CH$_2$Cl$_2$ (10 mL) were mixed, reacted, worked up and purified as described in the representative phosphitylation protocol to provide the phosphoramidite product (0.39 g, 80%) as a white foam. R$_f$=0.5 (2% MeOH in CH$_2$Cl$_2$, v/v); ESI-HRMS m/z 930.3068 ([M+Na]$^+$, C$_{45}$H$_{49}$F$_3$N$_5$O$_{10}$P.Na$^+$, Calcd 930.3061); $^{31}$P NMR (CDCl$_3$) δ 149.7, 149.1.

Example 16

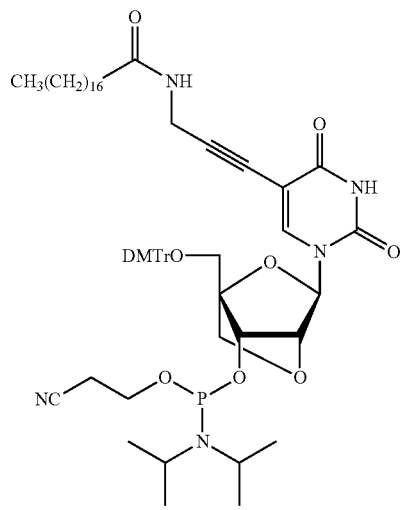

C-5 C18 Protected Propargylamine LNA-U Phosphoramidite.

The C$_{18}$-protected propargylamine (0.25 g, 0.28 mmol), DIPEA (0.18 mL, 1.4×mmol), and PCl-reagent 0.10 mL, 0.42 mmol) in anhydrous CH$_2$Cl$_2$ (10 mL) were mixed, reacted, worked up and purified as described in the representative phosphitylation protocol to provide the phosphoramidite product (180 mg, 60%) as a white foam. R$_f$=0.5 (2% MeOH in CH$_2$Cl$_2$, v/v); ESI-HRMS 1100.5836 ([M+Na]$^+$, C$_{61}$H$_{84}$N$_5$O$_{10}$P.Na$^+$, Calcd 1100.5848); $^{31}$P NMR (CDCl$_3$) δ 149.8, 149.2.

Example 17

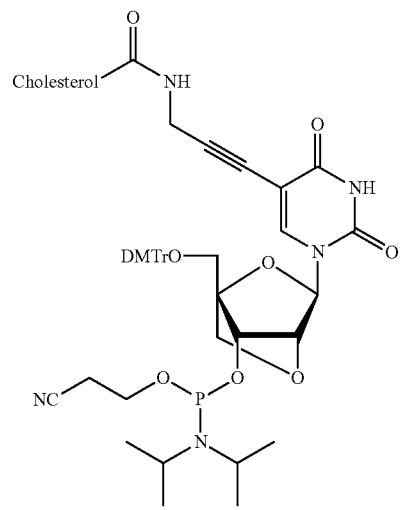

C-5 cholesterol protected propargylamine LNA-U phosphoramidite. The cholesterol-protected propargylamine (240 mg, 0.23 mmol), DIPEA (0.19 mL, 1.5×mmol), and PCl-reagent (0.08 mL, 0.34 mmol) in anhydrous CH$_2$Cl$_2$ (10 mL) were mixed, reacted, worked up and purified as described in the representative phosphitylation protocol to provide the phosphoramidite product (190 mg, 66%) as a white foam. R$_f$=0.5 (2% MeOH in CH$_2$Cl$_2$, v/v); ESI-HRMS m/z 1246.6571 ([M+Na]$^+$, C$_{71}$H$_{94}$N$_5$O$_{11}$P.Na$^+$, Calcd 1246.6579); $^{31}$P NMR (CDCl$_3$) δ 149.8, 149.3.

Example 18

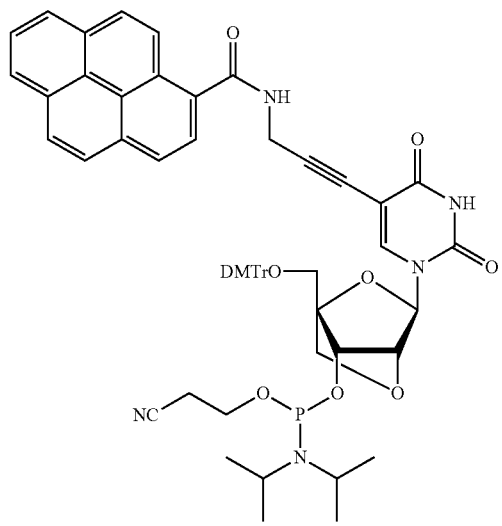

C-5 pyrene-carboxamide LNA-U phosphoramidite. The pyrene-carboxamide (0.25 g, 0.29 mmol), DIPEA (0.19 mL, 1.5×mmol), and PCl-reagent (0.09 mL, 0.38 mmol) in anhydrous CH$_2$Cl$_2$ (10 mL) were mixed, reacted, worked up and purified as described in the representative phosphitylation protocol to provide the phosphoramidite product (190 mg, 61%) as a white foam. R$_f$=0.5 (2% MeOH in CH$_2$Cl$_2$, v/v); ESI-HRMS m/z 1062.3807 ([M+Na]$^+$, C$_{60}$H$_{58}$N$_5$O$_{10}$P.Na$^+$, Calcd 1062.3814); $^{31}$P NMR (CDCl$_3$) δ 149.7, 149.2.

Example 19

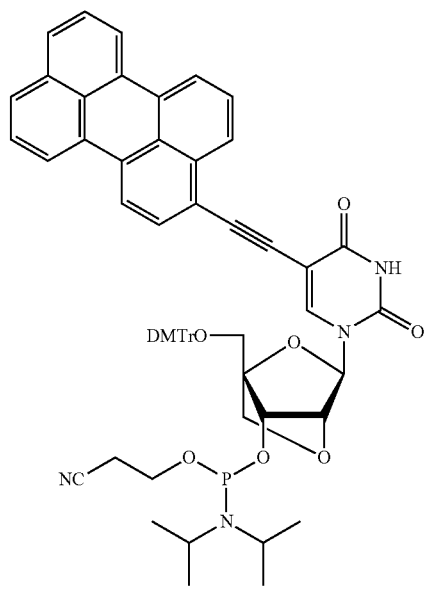

C5-perylene LNA Phosphoramidite.
The C5-perylene (0.47 g, 0.56 mmol), DIPEA (0.40 mL, 2.26 mmol), and PCl-reagent (165 µL, 0.73 mmol) in anhydrous CH$_2$Cl$_2$ (4 mL) were mixed, reacted (3 h), worked up and purified as described in the representative phosphitylation protocol to provide the phosphoramidite product (0.43 g, 78%) as a yellow foam. R$_f$=0.4 (4% MeOH in CH$_2$Cl$_2$, v/v); ESI-HRMS m/z 1055.3751 ([M+Na]$^+$, C$_{62}$H$_{57}$N$_4$O$_9$P.Na$^+$, Calcd 1055.3763); $^{31}$P NMR (CDCl$_3$) δ 149.7, 149.3

Example 20

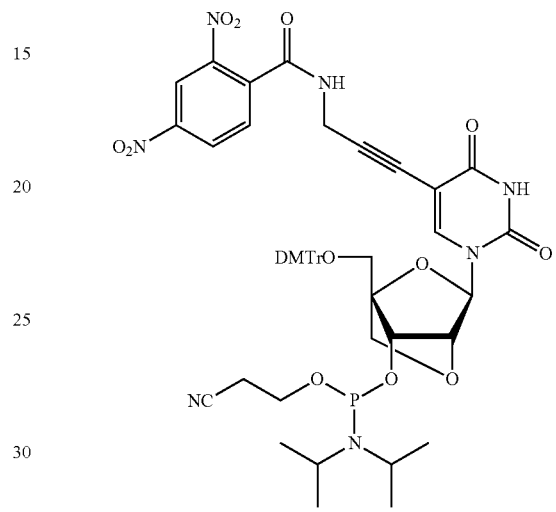

C5-dinitrobenzene LNA Phosphoramidite.
The 2,4-dinitrobenzoic acid-protected propargylamine (100 mg, 0.12 mmol), DIPEA (90 µL, 0.50 mmol), and PCl-reagent (36 µL, 0.16 mmol) in anhydrous CH$_2$Cl$_2$ (3 mL) were mixed and reacted (5.5 h) as described in the representative phosphitylation protocol. The reaction mixture was then evaporated to dryness and the resulting crude purified as described in the protocol to provide the phosphoramidite product (41 mg, 33%) as a white foam. R$_f$=0.2 (3% MeOH in CH$_2$Cl$_2$, v/v); ESI-HRMS m/z 1028.3193 ([M+Na]$^+$, C$_{50}$H$_{52}$N$_7$O$_{14}$P.Na$^+$, Calcd 1028.3202); $^{31}$P NMR (CDCl$_3$) δ 149.8, 148.7.

Example 21

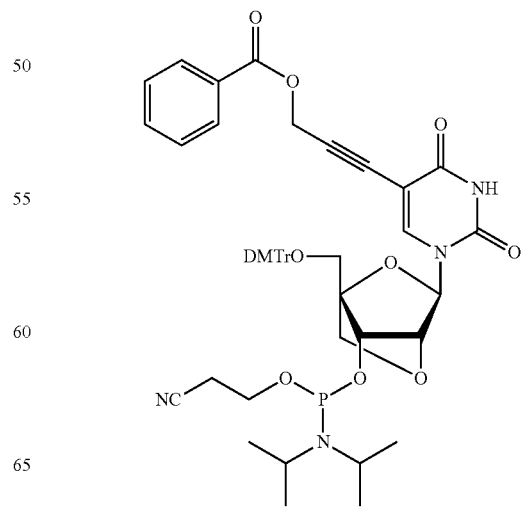

C5-Bz-propargylalcohol LNA Phosphoramidite.

The benzoyl-protected propargylalcohol (0.30 g, 0.42 mmol), DIPEA (300 µL, 1.67 mmol), and PCl-reagent (121 µL, 0.54 mmol) in anhydrous $CH_2Cl_2$ (5 mL) were mixed and reacted (5 h) as described in the representative phosphitylation protocol. At this point the reaction mixture was concentrated to ⅓ volume, diluted with diethyl ether (100 mL) and the organic phase sequentially washed with $H_2O$ (35 mL), $H_2O$:DMF (70 mL, 1:1, v/v), $H_2O$ (35 mL) and brine (35 mL). The organic phase was evaporated to dryness and the resulting crude purified as described in the protocol to provide the phosphoramidite product (150 mg, 43%) as a white foam. $R_f$=0.6 (5% MeOH in $CH_2Cl_2$, v/v); ESI-HRMS m/z 939.3356 ([M+Na]$^+$, $C_{50}H_{53}N_4O_{11}P.Na^+$, Calcd 939.3341); $^{31}P$ NMR ($CDCl_3$) δ 149.8, 149.3.

Example 22

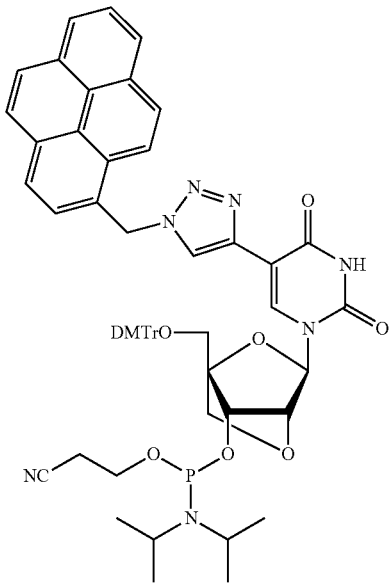

C5-pyrenylmethyltriazole (PyCH2Tz) LNA Phosphoramidite.

The triazole (0.41 g, 0.49 mmol), DIPEA (345 µL, 1.95 mmol), and PCl-reagent (165 µL, 0.73 mmol) in anhydrous $CH_2Cl_2$ (5 mL) were mixed, reacted (2.5 h), worked up and purified as described in the representative phosphitylation protocol to provide the phosphoramidite product (190 mg, 40%) as a white foam. $R_f$=0.5 (3% MeOH in $CH_2Cl_2$, v/v); ESI-HRMS m/z 1062.3909 ([M+Na]$^+$, $C_{59}H_{58}N_7O_9P.Na^+$, Calcd 1062.3934); $^{31}P$ NMR ($CDCl_3$) δ 149.6, 149.1.

Example 23

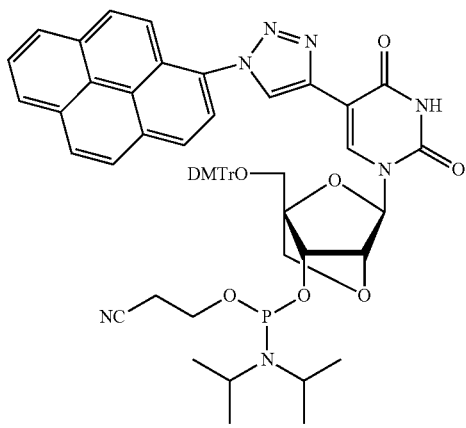

C5-pyrenyltriazole (PyTz) LNA Phosphoramidite.

The triazole (180 mg, 0.22 mmol), DIPEA (160 µL, 0.88 mmol), and PCl-reagent (63 µL, 0.28 mmol) in anhydrous $CH_2Cl_2$ (1.5 mL) were mixed and reacted (2.5 h) as described in the representative phosphitylation protocol, whereupon the reaction mixture was diluted with EtOAc (20 mL) and washed with $H_2O$ (2×25 mL). The organic phase was dried ($Na_2SO_4$), evaporated to dryness and purified as described in the protocol to provide the phosphoramidite product (184 mg, 82%) as a white foam. $R_f$=0.7 (5% MeOH in $CH_2Cl_2$, v/v); ESI-HRMS m/z 1048.3789 ([M+Na]$^+$, $C_{58}H_{56}N_7O_9P.Na^+$, Calcd 1048.3769); $^{31}P$ NMR ($CDCl_3$) δ 149.8, 149.1.

Example 24

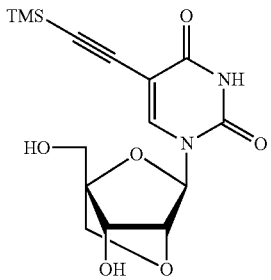 [SMILES: C[Si](C)(C)C#Cc1cn([C@@H]2O[C@@]3(CO)COC2[C@H]3O)c(=O)[nH]c1=O]

Representative Example of Alternate Route—Synthesis of TMS-Protected Acetylene.

A mixture of the vinyl iodide intermediate illustrated above (1.20 g, 3.14 mmol), $PdP(PPh_3)_4$ (380 mg, 0.319 mmol) and CuI (387 mg, 0.64 mmol) in anhydrous DMF (10 mL) was degassed, and to this was added $Et_3N$ (0.96 mL) followed by the addition of trimethylsilylacetylene (2.30 mL, 16.12 mmol). The reaction mixture was stirred at 55° C. in the dark for 21 h, whereupon the reaction mixture was concentrated under vacuum. MeOH (30 mL) was added to the residue, and the mixture was stirred for 20 minutes, filtered, and washed with MeOH (50 mL). The combined filtrate was concentrated at reduced pressure to afford a crude residue, which was purified by column chromatography (0-4% MeOH in DCM, v/v) to furnish the desired TMS acetylene (680 mg, 62%). FAB-HRMS m/z 352.1081 ([M]$^+$, $C_{15}H_{20}N_2O_6Si$, Calcd 352.1091) $^1H$ NMR (DMSO-d6, 500 MHz) δ 11.60 (bs, ex, 1H), 8.00 (s, 1H), 5.64 (d, 1H, ex, J=4.4 Hz), 5.39 (s, 1H), 5.24 (t, 1H, ex, J=5.2 Hz), 4.15 (s, 1H), 3.91 (d, 1H, J=4.4 Hz), 3.80 (d, 1H, J=7.7 Hz), 3.72 (d, 2H, J=5.2 Hz), 3.60 (d, 1H, J=7.7 Hz), 0.19 (s, 9H); $^{13}C$ (DMSO-d6, 500 MHz): δ 161.4, 148.8, 143.1, 98.0, 97.5, 96.7, 88.8, 86.4, 78.5, 70.7, 68.2, 55.3, −0.1.

Example 25

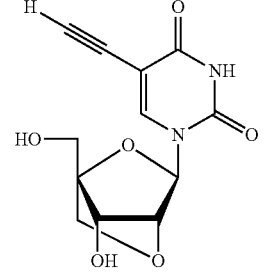 [SMILES: C#Cc1cn([C@@H]2O[C@@]3(CO)COC2[C@H]3O)c(=O)[nH]c1=O]

C-5 Ethynyl LNA-U.

The TMS-protected acetylene above (100 mg, 0.28 mmol) was dissolved in THF (10 mL) and a 1M solution of tetrabutylammonium fluoride in THF (0.3 mL, 0.3 mmol) was added and reaction mixture was stirred at room temperature for 2 h, whereupon the solvent was removed under reduced pressure and the residue was purified by column chromatography (0-10% MeOH in $CH_2Cl_2$, v/v) to afford the pure desilylated acetylene (55 mg, 69%). FAB-HRMS m/z 280.070 ([M]$^+$, $C_{15}H_{20}N_2O_6Si$, Calcd 280.0695). $^1$H NMR (DMSO-d6, 300 MHz) δ 11.64 (bs, ex, 1H), 8.03 (s, 1H), 5.63 (d, 1H, ex, J=4.4 Hz), 5.40 (s, 1H), 5.23 (t, 1H, ex, J=5.2 Hz), 4.16 (s, 1H), 4.06 (s, 1H), 3.91 (d, 1H, J=4.4 Hz), 3.81 (d, 1H, J=7.9 Hz), 3.73 (d, 2H, J=5.2 Hz), 3.60 (d, 1H, J=7.9 Hz).

Example 26

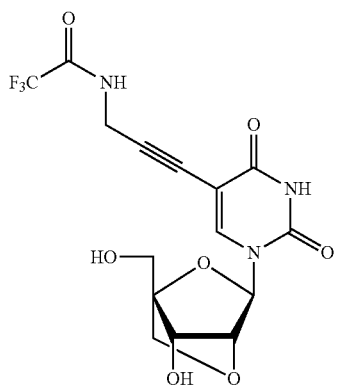

C-5 TFA Protected Propargylamine LNA-U.

A mixture of nucleoside 2 (191 mg, 0.5 mmol), Pd(PPh$_3$)$_4$ (30 mg, 0.025 mmol) and CuI (10 mg, 0.05 mmol) was dissolved in anhydrous DMF (5 mL) and degassed. To this was added Et$_3$N (0.15 mL) followed by addition of 2,2,2-trifluoro-N-(prop-2-ynyl)acetamide (260 mg, 16.12 mmol). The reaction mixture was stirred at 40° C. in the dark for 14 h, whereupon solvents were removed under vacuum. MeOH (20 mL) was added to residue and the mixture was stirred for 20 minutes, whereupon it was filtered and washed with MeOH (50 mL). The combined filtrate was concentrated under reduced pressure to afford a crude residue, which was purified by column chromatography (0-5% MeOH/CH$_2$Cl$_2$, v/v) to give desired product 8c (105 mg, 52%). $^1$H NMR (DMSO-d6, 300 MHz) δ 11.67 (bs, ex, 1H), 10.04 (t, ex, 1H, J=5.2 Hz), 7.96 (s, 1H), 5.62 (d, ex, 1H, J=4.4 Hz), 5.40 (s, 1H), 5.22 (t, ex, 1H, J=5.5 Hz), 4.23 (d, J=5.2 Hz, 2H), 4.17 (s, 1H), 3.90 (d, 1H, J=4.4 Hz), 3.82 (d, 1H, J=7.9 Hz), 3.74 (d, 2H, J=5.5 Hz), 3.62 (d, 1H, J=7.9 Hz).

Example 27

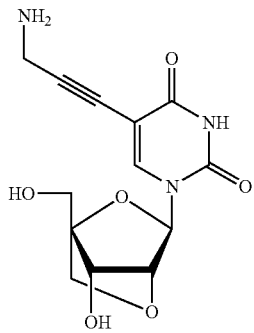 [SMILES: NCC#Cc1cn([C@@H]2O[C@@]3(CO)COC2[C@H]3O)c(=O)[nH]c1=O]

Propargylamine LNA-U.

The TFA-protected propargylamine (150 mg) was dissolved in sat. methanolic ammonia (20 mL), and the mixture was stirred for 2 h, whereupon the solvents were evaporated give a crude residue, which was purified by column chromatography (0-30% MeOH/CH$_2$Cl$_2$, v/v) to afford the free propargylamine (75 mg, 65%). FAB-HRMS m/z 310.1032 ([M+H]$^+$, $C_{13}H_{16}N_3O_6$ Calcd 310.1032). $^1$H NMR (DMSO-d6, 300 MHz) δ 7.91 (s, 1H), 5.63 (br s, ex, 1H), 5.41 (s, 1H), 5.22 (br s, ex, 1H), 4.16 (s, 1H), 3.90 (s, 1H), 3.82 (d, 1H, J=7.9 Hz), 3.74 (s, 2H), 3.62 (d, 1H, J=7.9 Hz), 3.45 (d, 2H, J=5.2 Hz).

General Procedure for Synthesis and Purification of Oligodeoxyribonucleotides:

0.2 mol scale synthesis of oligodeoxyribonucleotides (ONs) C5-alkynyl functionalized LNA monomers was performed on an Expedite 8909 Synthesizer using succinyl linked LCAA-CPG (long chain alkyl amine controlled pore glass) columns with a pore size of 500 Å. Standard protocols for incorporation of DNA phosphoramidites were used, except for extended coupling times (15 min with DCI as activator, or 15 min with activator-42) and oxidations (45 sec). Cleavage from solid support and removal of protecting groups was accomplished by treatment with aq. ammonia (55° C., 24 h). Purification of all C5-functionalized LNA was performed to minimum 80% purity using either of two methods: a) overall synthesis yield >80%: cleavage of DMT using 80% aq. AcOH, followed by precipitation from acetone (-18° C. for 12-16 h) and washing with acetone, or b) overall synthesis yield <80%: purification of ONs by RP-HPLC as described below (Table Si), followed by detritylation and precipitation as outlined under a.

Purification of the crude ONs was performed on a Varian Prostar HPLC system equipped with an XTerra MS C18 pre-column (10 µm, 7.8×10 mm) and a XTerra MS C18 column (10 µm, 7.8×150 mm) using the representative gradient protocol depicted in Table 21. The composition of all synthesized ONs were verified by MALDI-MS analysis (Table 22) recorded in positive mode on a Quattro II, Waters Micromass LTD., U. K., mass spectrometer using anthranilic acid as a matrix, while purity (>80%) was verified by RP-HPLC (Table S1).

TABLE 25

Representative RP-HPLC gradient protocol.[a]

| Time/min | Buffer A/(v %) | Buffer B/(v %) |
|---|---|---|
| 0 | 100 | 0 |
| 2 | 100 | 0 |
| 50 | 30 | 70 |
| 64 | 0 | 100 |
| 69 | 0 | 100 |
| 71 | 100 | 0 |
| 80 | 100 | 0 |

[a]Buffer A is 0.05M TEAA (triethylammonium acetate) pH 7.4, while buffer B is 75% MeCN in H$_2$O v/v. A flow rate of 1.2 mL/min was used.

TABLE 26

MALDI-MS of synthesized ONs for C5-functionalized LNAs.

| ON | Sequence | Found m/z [M]+ | Calc. m/z [M]+ |
|---|---|---|---|
| X1 | 3'-CGT AXA GTG | 2780.5 | 2781.9 |
| X2 | 5'-GCA TAX CAC | 2709.5 | 2710.9 |
| X3 | 5'-GCA XAT CAC | 2709.5 | 2710.9 |
| X4 | 5'-GCA XAX CAC | 2737.5 | 2738.9 |
| Y1 | 3'-CGT AYA GTG | 2791.9 | 2791.2 |
| Y2 | 5'-GCA TAY CAC | 2719.5 | 2720.4 |
| Y3 | 5'-GCA YAT CAC | 2719.5 | 2720.4 |
| Y4 | 5'-GCA YAY CAC | 2757.5 | 2758.4 |
| V1 | 3'-CGT AVA GTG | 2820.5 | 2820.7 |
| V2 | 5'-GCA TAV CAC | 2749.5 | 2749.7 |
| V3 | 5'-GCA VAT CAC | 2749.5 | 2749.7 |
| V4 | 5'-GCA VAV CAC | 2817.5 | 2816.8 |
| W1 | 3'-CGT AWA GTG | 3087.2 | 3086.5 |
| W2 | 5'-GCA TAW CAC | 3014.8 | 3015.8 |
| W3 | 5'-GCA WAT CAC | 3014.8 | 3015.9 |
| W4 | 5'-GCA WAW CAC | 3348.0 | 3349.1 |
| Q1 | 3'-CGT AQA GTG | 3231.8 | 3233.1 |
| Q2 | 5'-GCA TAQ CAC | 3159.8 | 3161.5 |
| Q3 | 5'-GCA QAT CAC | 3159.8 | 3161.9 |
| Q4 | 5'-GCA QAQ CAC | 3638.2 | 3640.8 |
| O1 | 3'-CGT AOA GTG | n/a | 2820.5 |
| O2 | 5'-GCA TAO CAC | n/a | 2749.3 |
| O3 | 5'-GCA OAT CAC | n/a | 2749.3 |
| O4 | 5'-GCA OAO CAC | n/a | 2817.5 |
| α1 | 3'-CGT AαA GTG | n/a | 3040.5 |
| α2 | 5'-GCA TAα CAC | n/a | 2970.5 |
| α3 | 5'-GCA αAT CAC | n/a | 2970.5 |
| α4 | 5'-GCA αAα CAC | n/a | 3257.6 |
| β1 | 3'-CGT AβA GTG | n/a | 3047.5 |
| β2 | 5'-GCA TAβ CAC | n/a | 2976.5 |
| β3 | 5'-GCA βAT CAC | n/a | 2976.5 |
| β4 | 5'-GCA βAβ CAC | n/a | 3271.6 |
| γ1 | 3'-CGT AγA GTG | n/a | 3033.5 |
| γ2 | 5'-GCA TAγ CAC | n/a | 2962.5 |
| γ3 | 5'-GCA γAT CAC | n/a | 2962.5 |
| γ4 | 5'-GCA γAγ CAC | n/a | 3243.6 |

TABLE 26-continued

MALDI-MS of synthesized ONs for C5-functionalized LNAs.

| ON | Sequence | Found m/z [M]+ | Calc. m/z [M]+ |
|---|---|---|---|
| P1 | 3'-CGT APA GTG | 3048.8 | 3048.5 |
| P2 | 5'-GCA TAP CAC | 2977.8 | 2977.5 |
| P3 | 5'-GCA PAT CAC | 2977.8 | 2977.5 |
| P4 | 5'-GCA PAP CAC | 3272.8 | 3272.7 |

Synthesis of C5-functionalized-α-L-LNA

Example 28

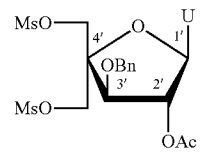

1-[2-O-Acetyl-3-O-benzyl-5-O-(methanesulfonyl)-4-C-(methanesulfonyloxymethyl)-α-L-threo-pento-furanosyl]uracil The di-mesylate starting material of Scheme 7 (6.10 g, 12.0 mmol) and uracil (2.70 g, 24.0 mmol) were coevaporated with anhydrous CH$_3$CN (100 mL) and resuspended in anhydrous CH$_3$CN (150 mL). To this was added N,O-bis-trimethylsilylacetamide (BSA, 10.4 mL, 41.9 mmol) and the solution was refluxed until becoming homogeneous. After cooling to rt, trimethylsilyltriflate (TMSOTf, 5.5 mL, 29.9 mmol) was added and the reaction mixture was refluxed for 28 h, whereupon it was concentrated to ear dryness. The resulting residue was taken up in EtOAc (200 mL), washed with sat. aq. NaHCO$_3$ (2×100 mL) and brine (100 mL). The aqueous phase was back-extracted with EtOAc (100 mL) and the combined organic phase dried (Na$_2$SO$_4$) and evaporated to dryness. The resulting residue was purified by silica gel column chromatography (0-2% MeOH in CH$_2$Cl$_2$, v/v) to afford the uracil-coupled nucleoside (4.80 g, 85%) as a white foam. R$_f$=0.5 (2% MeOH in CH$_2$Cl$_2$, v/v); FAB-HRMS 563.0998 ([M+H]+, C$_{21}$H$_{25}$N$_2$O$_{12}$S$_2$.H+, Calcd 563.1005; $^1$H NMR (DMSO-d$_6$) δ11.40 (d, 1H, ex, J=2.0 Hz, NH), 7.76 (d, 1H, J=8.0 Hz, H6), 7.35-7.38 (m, 5H, Ph), 6.09 (d, 1H, J=6.0 Hz, H1'), 5.68 (dd, 1H, J=8.0 Hz, 2.0 Hz, H5), 5.53 (t, 1H, J=6.0 Hz, H2'), 4.68-4.71 (d, 1H, J=12.0 Hz, CH$_2$Ph) 4.65-4.67 (d, 1H, J=12.0 Hz CH$_2$Ph), 4.59 (d, 1H, J=11.0 Hz, H5'), 4.39-4.46 (m, 4H, H3', H5', 2×H5"), 3.26 (s, 3H, CH$_3$SO$_2$), 3.20 (s, 3H, CH$_3$SO$_2$), 2.02 (s, 3H, CH$_3$); $^{13}$C NMR (DMSO-d$_6$) δ 169.5, 162.7, 150.3, 140.2 (C6), 137.1, 128.3 (Ar), 127.9

(Ar), 127.8 (Ar), 102.6 (C5), 84.6 (C1'), 81.8, 80.6 (C3'), 77.2 (C2'), 72.4 (CH$_2$Ph), 68.3 (C5''), 67.8 (C5'), 36.7 (CH$_3$SO$_2$), 36.5 (CH$_3$SO$_2$), 20.3 (CH$_3$).

Example 29

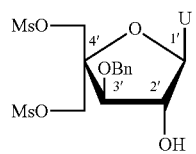

1-[3-O-Benzyl-5-O-(methylsulfonyl)-4-C-(methane-sulfonyloxymethyl)-α-L-threo-pentofuranosyl]uracil Method A.

HCl in MeOH (1M, 50 mL) was added to a solution of the uracil-coupled nucleoside from the previous example (2.81 g, 5.00 mmol) in MeOH (30 mL), and after stirring the reaction mixture at rt for 24 h, the solvent was removed at reduced pressure. The residue was dissolved in CH$_2$Cl$_2$ (100 mL), washed with sat. aq. NaHCO$_3$ (2×100 mL) and the aqueous phase back-extracted with CH$_2$Cl$_2$ (2×50 mL). The combined organic phase was dried (Na$_2$SO$_4$) and evaporated to dryness to afford analytically the pure free alcohol (2.52 g, 97%) as a white solid material. R$_f$=0.4 (4% MeOH in CH$_2$Cl$_2$, v/v); FAB-HRMS m/z 521.0900 ([M+H]$^+$, C$_{19}$H$_{24}$N$_2$O$_{11}$S$_2$.H$^+$, Calcd 521.0894; $^1$H NMR (DMSO-d$_6$) δ11.41 (d, 1H, ex, J=2.0 Hz, NH), 7.76 (d, 1H, J=8.0 Hz, H6), 7.29-7.40 (m, 5H, Ph), 6.11 (d, 1H, ex, J=5.0 Hz, 2' OH), 5.91 (d, 1H, J=7.5 Hz, H1'), 5.67 (dd, 1H, J=8.0 Hz, 2.0 Hz, H5), 4.74-4.77 (d, 1H, J=12.0 Hz, CH$_2$Ph), 4.67-4.69 (d, 1H, J=12.0 Hz, CH$_2$Ph), 4.33-4.52 (m, 5H, H2', 2×H5', 2×H5''), 4.19 (d, 1H, J=6.5 Hz, H3'), 3.26 (s, 3H, CH$_3$SO$_2$), 3.20 (s, 3H, CH$_3$SO$_2$); $^{13}$C NMR (DMSO-d$_6$) δ 162.7, 150.7, 140.4 (C6), 137.5, 128.3 (Ar), 127.9 (Ar), 127.8 (Ar), 102.5 (C5), 85.9 (C1'), 82.7 (C3'), 80.8 (C4'), 75.7 (C2'), 72.3 (CH$_2$Ph), 68.9 (C5''), 68.2 (C5'), 36.6 (CH$_3$SO$_2$), 36.5 (CH$_3$SO$_2$).

Method B.

To a solution of the uracil-coupled nucleoside from the previous example (1.50 g, 2.66 mmol) in MeOH (50 mL) was added sat. methanolic ammonia (50 mL). The solution was stirred for 2 h at rt whereupon solvents were evaporated off. The resulting crude was purified by column chromatography (0-3% MeOH in CH$_2$Cl$_2$, v/v) to afford the free alcohol (1.11 g, 80%) as a white solid material with physical data as reported above.

Example 30

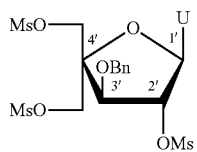

Trimesylate.

The free alcohol from the previous example (10.00 g, 19.2 mmol) was coevaporated with anhydrous pyridine (2×75 mL) and redissolved in anhydrous pyridine (120 mL). To this was added methanesulfonyl chloride (MsCl, 1.8 mL, 23.3 mmol) and the reaction mixture was stirred for 4 h at rt whereupon it was poured into sat. aq. NaHCO$_3$ (200 mL) and extracted with CH$_2$Cl$_2$ (2×200 mL). The organic phase was dried (Na$_2$SO$_4$) and concentrated to dryness to afford analytically the pure trimesylate product (11.26 g, 98%) as a slightly brown solid material. R$_f$=0.4 (2% MeOH in CH$_2$Cl$_2$, v/v); FAB-HRMS 599.0675 ([M+H]$^+$, C$_{20}$H$_{26}$N$_2$O$_{13}$S$_3$.H+, Calcd 599.0670); $^1$H NMR (DMSO-d$_6$) δ 11.47 (d, 1H, ex, J=2.0 Hz, NH), 7.76 (d, 1H, J=8.0 Hz, H6), 7.34-7.42 (m, 5H, Ph), 6.24 (d, 1H, J=7.5 Hz, H1'), 5.70 (dd, 1H, J=8.0 Hz, 2.0 Hz, H5), 5.54 (t, 1H, J=7.0 Hz, H2'), 4.71 (s, 2H, CH$_2$Ph), 4.61 (d, 1H, J=11.0 Hz, H5'), 4.59 (d, 1H, J=7.0 Hz, H3), 4.41-4.48 (m, 3H, H5' Hz, 2×H5''), 3.27 (s, 3H, CH$_3$), 3.24 (s, 3H, CH$_3$), 3.18 (s, 3H, CH$_3$); $^{13}$C NMR (DMSO-d$_6$) δ 162.7, 150.4, 140.3 (C6), 136.8 (Ar), 128.3 (Ar), 128.1 (Ar), 128.0 (Ar), 102.7 (C5), 83.5 (C1'), 81.0 (C2'), 80.9 (C4'), 80.7 (C3'), 72.9 (CH$_2$Ph), 68.4 (C5''), 67.6 (C5'), 37.7 (CH$_3$SO$_2$) 36.7 (CH$_3$SO$_2$), 36.6 (CH$_3$SO$_2$).

Example 31

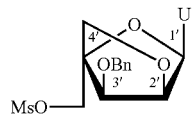

1-(3-O-Benzyl-5-O-methanesulfonyl-2-O,4-C-methylene-α-L-ribofuranosyl)uracil

To a solution of the trimesylate from the previous example (9.87 g, 16.5 mmol) in 1,4-dioxane:H$_2$O (60 mL, 1:1, v/v) was added NaOH (2M, 50 mL, 0.10 mol). After stirring at rt for 4 h, the reaction mixture was neutralized by 10% aq. AcOH, diluted with EtOAc (300 mL) and the phases separated. The organic phase was sequentially washed with sat. aq. NaHCO$_3$ (100 mL) and H$_2$O (100 mL), dried (Na$_2$SO$_4$) and evaporated to dryness to afford analytically the pure bicycle product (7.00 g, quant.) as slightly brown solid material. R$_f$=0.5 (80% EtOAc in petroleum ether, v/v); FAB-HRMS m/z 425.1018 ([M+H]$^+$, C$_{18}$H$_{20}$N$_2$O$_8$S.H$^+$, Calcd 425.1013; $^1$H NMR (DMSO-d$_6$) δ 11.39 (s, 1H, ex, NH), 7.79 (d, 1H, J=8.0 Hz, H6), 7.30-7.38 (m, 5H, Ph), 5.97 (s, 1H, H1'), 5.62 (d, 1H, J=8.0 Hz, H5), 4.50-4.70 (m, 6H, H2', H3', 2×CH$_2$Ph, 2×H5'), 4.05-4.06 (d, 1H, J=8.5 Hz, H5''), 3.99-4.01 (d, 1H, J=8.5 Hz, H5''), 3.23 (s, 3H, CH$_3$); $^{13}$C NMR (DMSO-d$_6$) δ 163.0, 150.2, 140.3 (C6), 137.5 (Ar), 128.2 (Ar), 127.6 (Ar), 127.4 (Ar), 100.5 (C5), 86.6 (C1'), 86.5, 79.2 (C2'), $^r$ 76.3 (C3'), 71.8 (C5''), 71.2 (CH$_2$Ph), 65.3 (C5') 36.8 (CH$_3$SO$_2$). A trace impurity of 1,4-dioxane was identified and the compound was used as such in next step without further purification.

Example 32

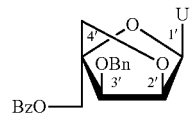

α-LNA-U-Bz.

To a solution of the pure bicycle product from the previous example (7.00 g, 16.5 mmol) in anhydrous DMF (300 mL) was added NaOBz (7.00 g, 48.6 mmol) and the reaction mixture was stirred at 90° C. for 20 h, whereupon it was cooled to rt and poured into ice cold water (500 mL). The solution was extracted with EtOAc (2×300 mL) and the organic phase sequentially washed with $H_2O$ (2×150 mL) and brine (100 mL). The combined organic phase was dried ($Na_2SO_4$) and concentrated to dryness to afford analytically the benzoylated bicycle product (7.24 g, 98%) as a slightly brown solid material. $R_f$=0.6 (80% EtOAc in petroleum ether, v/v); FAB-HRMS m/z 451.1505 ([M+H]$^+$, $C_{24}H_{22}N_2O_7.H^+$, Calcd 451.1500; $^1$H NMR (DMSO-$d_6$) δ 11.38 (s, 1H, ex, NH), 7.97-7.99 (m, 2H, Ar), 7.82 (d, 1H, J=8.0 Hz, H6), 7.66-7.70 (m, 1H, Ar), 7.51-7.54 (m, 2H, Ar), 7.26-7.36 (m, 5H, Ph), 6.00 (s, 1H, H1'), 5.62 (d, 1H, J=8.0 Hz, H5), 4.54-4.75 (m, 6H, H2', H3', $CH_2Ph$, 2×H5'), 4.14-4.16 (d, 1H, J=8.5 Hz, H5"), 4.07-4.09 (d, 1H, J=8.5 Hz, H5"); $^{13}$C NMR (DMSO-$d_6$) δ 165.2, 163.0, 150.2, 140.7 (C6), 137.5 (Ar), 133.5 (Ar), 129.3 (Ar), 129.0 (Ar), 128.7 (Ar), 128.2 (Ar), 127.6 (Ar), 127.4 (Ar), 100.5 (C5), 86.9 (C1'), 86.5, 79.2 (C2'), 76.2 (C3'), 72.1 (C5"), 71.1 ($CH_2Ph$), 59.8 (C5').

Example 33

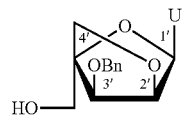

Debenzoylated Product.

Method A.

To a solution of the benzoylated bicycle from the previous example (5.00 g, 11.1 mmol) dissolved in MeOH (100 mL) was added sat. methanolic ammonia (100 mL). The reaction mixture was stirred at rt for 14 hr whereupon the solvent was evaporated off and the resulting residue purified by column chromatography (0-7% MeOH in $CH_2Cl_2$) to afford the debenzoylated product (3.66 g, 95%) as a white solid material. $R_f$=0.4 (7% MeOH in $CH_2Cl_2$, v/v); FAB-HRMS m/z 347.1230 ([M+H]$^+$, $C_{17}H_{18}N_2O_6.H^+$, Calcd 347.1243); $^1$H NMR (DMSO-$d_6$) δ 11.36 (s, 1H, ex, NH), 7.80 (d, 1H, J=8.0 Hz, H6), 7.30-7.36 (m, 5H, Ph), 5.88 (s, 1H, H1'), 5.62 (d, 1H, J=8.0 Hz, H5), 5.05 (t, 1H, ex, J=5.5 Hz, 5'-OH), 4.67-4.69 (d, 1H, J=12.0 Hz, $CH_2Ph$), 4.64-4.66 (d, 1H, J=12.0 Hz, $CH_2Ph$), 4.52 (s, 1H, H2'), 4.33 (s, 1H, H3'), 3.95-3.97 (d, 1H, J=8.5 Hz, H5"), 3.92-3.94 (d, 1H, J=8.5 Hz, H5"), 3.74 (d, 2H, J=5.5 Hz, 2×H5'); $^{13}$C NMR (DMSO-$d_6$) δ 163.1, 150.2, 140.4 (C6), 137.8, 128.2 (Ar), 127.5 (Ar), 127.3 (Ar), 100.3 (C5), 90.1 (C4'), 86.5 (C1'), 79.2 (C3'), 76.3 (C2'), 72.3 (C5"), 71.0 ($CH_2Ph$), 57.1 (C5').

Method B.

To a solution of the benzoylated bicycle product from the previous example (1.50 g, 3.33 mmol) in THF:$H_2O$ (25 mL, 1:1, v/v) was added aq. NaOH (2M, 10 mL, 20 mmol) and the reaction mixture was stirred at rt for 4 hr, whereupon it was carefully neutralized with 10% aq. AcOH at 0° C. and diluted with EtOAc (50 mL). The organic phase was washed with sat. aq. $NaHCO_3$ (50 mL) and the combined aqueous phase extracted with EtOAc (2×50 mL). The combined organic phase was dried ($Na_2SO_4$) and concentrated to dryness to afford the debenzoylated product (1.05 g, 91%) as a slightly brown solid of adequate purity to proceed in the next step without further purification.

Example 34

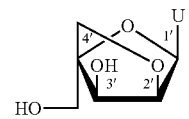

α-LNA-U-diol.

To a solution of the debenzoylated product (1.50 g, 4.32 mmol) in THF:MeOH (100 mL, 9:1, v/v), was added Pd(OH)$_2$/C (20 wt %, 0.60 g) and 88% aq. formic acid (2.3 mL, 61.1 mmol). The reaction mixture was refluxed for 24 h whereupon it was cooled to rt. The catalyst was filtered off, washed with excess MeOH, and the combined filtrates concentrated to dryness. The resulting crude residue was purified by silica gel column chromatography (0-16% MeOH in $CH_2Cl_2$, v/v) to afford the diol product (0.94 g, 85%) as a white solid material. $R_f$=0.4 (15% MeOH in $CH_2Cl_2$, v/v); FAB-HRMS m/z 257.0760 ([M+H]$^+$, $C_{10}H_{12}N_2O_6.H^+$, Calcd 257.0768); $^1$H NMR (DMSO-$d_6$) δ 11.34 (s, 1H, ex, NH), 7.79 (d, 1H, J=8.0 Hz, H6), 5.87 (s, 1H, H1'), 5.85 (d, ex, J=4.0 Hz, 3'-OH), 5.63 (d, 1H, J=8.0 Hz, H5), 4.92 (t, ex, J=5.5 Hz, 5'-OH), 4.26 (d, 1H, J=4.0 Hz, H3'), 4.21 (s, 1H, H2'), 3.92-3.93 (d, 1H, J=8.5 Hz, H5"), 3.88-3.90 (d, 1H, J=8.5 Hz, H5"), 3.72 (d, 2H, J=5.5 Hz, 2×H5'); $^{13}$C NMR (DMSO-$d_6$) δ 163.1, 150.2, 140.4 (C6), 100.1 (C5), 90.9, 86.4 (C1'), 78.7 (C2'), 72.4 (C3'), 71.8 (C5"), 57.3 (C5').

The stereochemistry of final diol was assigned on the basis of ROESY as it showed in space coupling between H6 and H5", and also between H5' and H3'. Beside this absence of in space coupling between H2' and H5 further confirms the reported structure.

Example 35

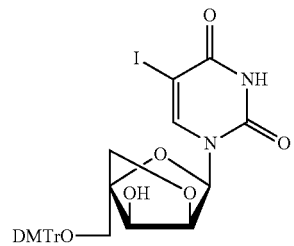

5-iodo-5'DMT-α-L-LNA U $Ac_2O$ (0.21 mL, 2.20 mmol) was added to a solution of the diol from the previous example (0.25 g, 1.00 mmol) in pyridine (10 mL) and the reaction mixture was stirred at 60° C. for 14 h. After cooling to rt, the reaction mixture was diluted with sat. aq. $NaHCO_3$ (30 mL) and $CH_2Cl_2$ (30 mL) and the phases were separated. The organic phase was washed with sat. aq. $NaHCO_3$ (20 mL) and the combined aqueous phase subsequently back-extracted with $CH_2Cl_2$ (2×20 mL). The combined organic phase was dried ($Na_2SO_4$), evaporated to dryness, and coevaporated with toluene:abs EtOH (2×30 mL, 1:2, v/v). The resulting crude, tentatively assigned as the O3',O5'-diacetylated nucleoside, was used in next step without further purification [$R_f$=0.5 (2% MeOH in $CH_2Cl_2$, v/v); FAB-MS m/z 341 ([M+H]$^+$); $^1$H NMR (DMSO-$d_6$, 300 MHz) δ 11.40 (s, 1H), 7.78 (d, 1H, J=8.1 Hz), 5.63 (d, 1H, J=8.1 Hz), 6.07 (s, 1H), 5.36 (s, 1H), 4.57 (s, 1H), 4.37-4.39 (m, 2H), 4.09-4.12 (d, 1H, J=9.0 Hz), 3.95-3.98 (d, 1H, J=9.0 Hz), 2.11 (s, 3H), 2.07 (s, 3H)].

To a solution of the crude O3',O5'-diacetylated α-L-LNA uridine in glacial AcOH (10 mL) was added iodine (160 mg, 0.62 mmol) and ceric ammonium nitrate (CAN, 235 mg, 0.50 mmol) and the reaction mixture was stirred at 80° C. for 50 min. After cooling to rt, the reaction mixture was evaporated to dryness, and taken up in $CH_2Cl_2$ (50 mL). The organic phase was sequentially washed with sat. aq. NaHCO$_3$ (2×20 mL) and H$_2$O (20 mL). The combined aqueous phase was back-extracted with $CH_2Cl_2$ (2×20 mL), and the combined organic phase dried (Na$_2$SO$_4$) and evaporated to dryness. This resulting crude, tentatively assigned as the C5-iodo-O3', O5'-diacetylated nucleoside, was used in next step without further purification. [$R_f$=0.5 (3% MeOH in $CH_2Cl_2$, v/v); FAB-HRMS m/z 466.9966 ([M+1$^{-1}$]$^+$, $C_{14}H_{15}IN_2O_8$.H+, Calcd 466.9946); $^1$H NMR (DMSO-$d_6$) δ11.75 (s, 1H), 8.06 (s, 1H), 6.02 (s, 1H), 5.34 (s, 1H), 4.58 (s, 1H), 4.44-3.47 (d, 1H, J=8.8 Hz), 4.36-4.39 (d, 1H, J=8.8 Hz), 3.98-4.02 (m, 2H), 2.14 (s, 3H), 2.07 (s, 3H)].

The crude C5-iodo-O3',O5'-diacetylated nucleoside was dissolved in sat. methanolic ammonia (30 mL) and stirred in a sealed flask at rt for 12 h. The reaction mixture was evaporated to dryness affording a crude residue that was tentatively assigned as the C5-iodo α-L-LNA diol and used in next step without further purification. [$R_f$=0.4 (15% MeOH in $CH_2Cl_2$, v/v); FAB-HRMS m/z 382.9735 ([M+H]$^+$, $C_{10}H_{11}IN_2O_6$.H+, Calcd 382.9740); $^1$H NMR (DMSO-$d_6$) δ 11.75 (s, 1H, ex), 8.08 (s, 1H), 5.87 (d, 1H, ex, J=4.5 Hz), 5.83 (s, 1H), 4.97 (t, 1H, ex, J=5.4 Hz), 4.24 (d, 1H, J=4.5 Hz), 4.22 (s, 1H), 3.93-3.95 (d, 1H, J=8.5 Hz), 3.78-3.80 (d, 1H, J=8.5 Hz), 3.72-3.74 (m, 2H)].

The crude C5-iodo α-L-LNA diol was dried by coevaporation with anhydrous pyridine (10 mL) and redissolved in anhydrous pyridine (10 mL). To this was added 4,4'-dimethoxytrityl chloride (DMTrCl, 0.40 g, 1.20 mmol) and the reaction mixture was stirred at rt for 16 h, whereupon it was diluted with sat. aq. NaHCO$_3$ (20 mL) and $CH_2Cl_2$ (25 mL). The phases were separated, and the organic phase washed with sat. aq. NaHCO$_3$ (20 mL). The aqueous phase was back-extracted with $CH_2Cl_2$ (2×20 mL), and the combined organic phase dried (Na$_2$SO$_4$), evaporated to near dryness, and coevaporated with toluene:abs. EtOH (2×30 mL, 1:2, v/v). The resulting residue was purified by column chromatography (0-4.5% MeOH in $CH_2Cl_2$, v/v) to afford the DMTr-protected nucleoside product (0.48 g, 70%, over four steps) as a light yellow solid material. $R_f$=0.5 (5% MeOH in $CH_2Cl_2$, v/v); FAB-HRMS m/z 684.0980 ([M]$^+$, $C_{31}H_{29}IN_2O_8$, Calcd 684.0969); $^1$H NMR (DMSO-$d_6$) δ 11.77 (s, 1H, ex, NH), 8.15 (s, 1H, H6), 7.23-7.42 (m, 9H, Ar), 6.91 (d, 4H, J=8.5 Hz, Ar), 5.91 (d, 1H, ex, J=4.5 Hz, 3'-OH), 5.89 (s, 1H, H1'), 4.34 (d, 1H, J=4.5 Hz, H3'), 4.27 (s, 1H, H2'), 3.99-4.01 (d, 1H, J=8.5 Hz, H5") 3.93-3.94 (d, 1H, J=8.5 Hz, H5"), 3.74 (s, 6H, 2×OCH$_3$), 3.34-3.36 (d, 1H, J=10.5 Hz, H5'), 3.28-3.31 (d, 1H, J=10.5 Hz, H5'); $^{13}$C NMR (DMSO-$d_6$) δ 160.5, 158.1, 158.0, 149.9, 144.6, 144.2 (C6), 135.2, 135.0, 129.6 (Ar), 129.6 (Ar), 127.9 (Ar), 127.5 (Ar), 126.7 (Ar), 113.2 (Ar), 89.3, 87.2 (C1'), 85.2, 78.7 (C2'), 72.8 (C3'), 72.2 (C5"), 67.6, 60.0 (C5'), 55.0 (CH$_3$O).

Example 36

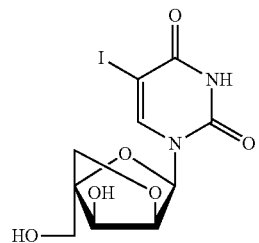 [SMILES: O=c1[nH]c(=O)n([C@@H]2O[C@]3(CO)COC2[C@@H]3O)cc1I]

5-iodo-α-L-LNA U

To a solution of the diol product from the previous example (200 mg, 0.78 mmol) in glacial AcOH (10 mL) was added iodine (119 mg, 0.47 mmol) and ceric ammonium nitrate (213 mg, 0.39 mmol), and the reaction mixture was stirred at 80° C. for 50 min. After cooling to rt, the mixture was evaporated to dryness, and the resulting crude purified by column chromatography (0-16% MeOH/CH$_2$Cl$_2$, v/v) to afford the vinyl iodide product (240 mg, 80%) as white solid material. $R_f$=0.4 (15% MeOH in $CH_2Cl_2$, v/v); FAB-HRMS m/z 382.9735 ([M+H]$^+$, $C_{10}H_{11}IN_2O_6$.H+, Calcd 382.9740); $^1$H NMR (DMSO-$d_6$) δ11.75 (s, 1H, ex, NH), 8.08 (s, 1H, H6), 5.87 (d, 1H, ex, J=4.5 Hz, 3'-OH), 5.83 (s, 1H, H1'), 4.97 (t, 1H, ex, J=5.4 Hz, 5'-OH), 4.24 (d, 1H, J=4.5 Hz, H3'), 4.22 (s, 1H, H2'), 3.93-3.95 (d, 1H, J=8.5 Hz, H5"), 3.78-3.80 (d, 1H, J=8.5 Hz, H5"), 3.72-3.74 (m, 2H, 2×H5'); $^{13}$C NMR (DMSO-$d_6$) δ 160.4, 149.9, 144.2 (C6), 91.1, 87.0 (C1'), 78.6 (C2'), 72.4 (C3'), 72.0 (C5"), 67.6, 57.4 (C5').

Example 37

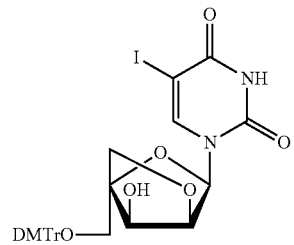

5-iodo-5'DMT-α-L-LNA U

The vinyl iodide product from the previous example (200 mg, 0.52 mmol) was coevaporated with anhydrous pyridine (10 mL) and redissolved in anhydrous pyridine (10 mL). To this was added 4,4'-dimethoxytrityl chloride (DMTrCl, 230 mg, 0.68 mmol) and the reaction mixture was stirred at rt for 16 h, whereupon it was diluted with sat. aq. NaHCO$_3$ (20 mL) and $CH_2Cl_2$ (25 mL). The phases were separated, and theorganic phase was washed with sat. aq. NaHCO$_3$ (20 mL).

The aqueous phase was back-extracted with CH₂Cl₂ (2×20 mL), and the combined organic phase was dried (Na₂SO₄), concentrated to near dryness, and coevaporated with toluene: abs. EtOH (2×30 mL, 1:2, v/v). The resulting crude was purified by column chromatography (0-4.5% MeOH in CH₂Cl₂, v/v) to afford the DMTr-protected vinyl iodide product (250 mg, 70%) as a light yellow solid material with identical physical data as described above.

Representative Protocol for Sonogashira Coupling Reactions:

The DMTr-protected vinyl iodide from the previous example, Pd(PPh₃)₄, CuI, and alkyne were added to anhydrous DMF [quantities and volumes specified below], and the reaction chamber was degassed and placed under an argon atmosphere. To this was added Et₃N and the reaction mixture was stirred in the dark at rt f whereupon solvents were evaporated off. The resulting residue was taken in up in EtOAc (100 mL) and sequentially washed with brine (2×50 mL) and sat. aq. NaHCO₃ (50 mL). The combined aqueous phase was back-extracted with EtOAc (100 mL), and the combined organic phase was dried (Na₂SO₄), evaporated to dryness and the crude residue purified by column chromatography (0-5% MeOH in CH₂Cl₂ (v/v) to afford the coupled products.

Example 38

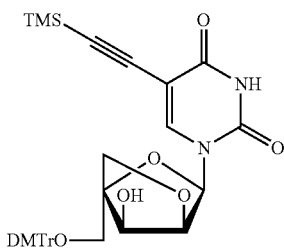

C-5 TMS Ethynyl-5'DMT-α-L-LNA U.

After setting up the DMTr-protected vinyl iodide (0.68 g, 1.00 mmol), Pd(PPh₃)₄ (120 mg, 0.10 mmol), CuI (40 mg, 0.20 mmol), trimethylsilylacetylene (0.42 mL, 3.00 mmol) and Et₃N (0.60 mL, 4.27 mmol) in DMF (10 mL) as described in the representative Sonogashira protocol, the reaction mixture was stirred at rt for 12 h. After workup and purification, the TMS-protected acetylene (0.55 g, 84%) was obtained as a slightly brown solid material. $R_f$=0.5 (5% MeOH in CH₂Cl₂, v/v); FAB-HRMS 655.2462 ([M+H]⁺, C₃₆H₃₈N₂O₈Si.H⁺, Calcd 655.2476); ¹H NMR (DMSO-d₆) δ 11.75 (s, 1H, ex, NH), 7.92 (s, 1H, H6), 7.21-7.41 (m, 9H, Ar), 6.89 (d, 4H, J=8.5 Hz, Ar), 5.93 (d, 1H, ex, J=4.5 Hz, 3'-OH), 5.91 (s, 1H, H1'), 4.38 (d, 1H, J=4.5 Hz, H3'), 4.26 (s, 1H, H2'), 3.99-4.01 (d, 1H, J=8.5 Hz, H5"), 3.93-3.95 (d, 1H, J=8.5 Hz, H5"), 3.74 (s, 6H, 2×OCH₃), 3.34 (s, 2H, H5'), 0.23 (s, 9H, SiMe₃); ¹³C NMR (DMSO-d₆) δ 161.3, 158.1, 149.1, 144.6, 143.6 (C6), 135.2, 135.1, 129.66 (Ar), 129.63 (Ar), 127.8 (Ar), 127.5 (Ar), 126.6 (Ar), 113.2 (Ar), 97.8, 97.1, 96.9, 89.4, 87.3 (C1'), 85.3, 78.5 (C2'), 72.7 (C3'), 72.3 (C5"), 60.0 (C5'), 54.9 (CH₃O), −0.11 (Si(CH₃)₃).

Example 39

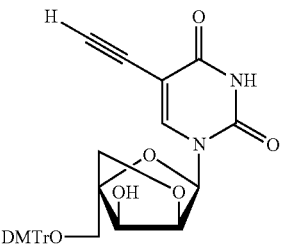

C-5-ethynyl-5'DMT-α-L-LNA U. To a solution of the TMS-protected acetylene (0.53 g, 0.81 mmol) in THF (20 mL), was added TBAF in THF (1M, 1.2 mL, 1.2 mmol) and the reaction mixture was stirred at rt for 2 h. EtOAc (50 mL) was added and the solution was sequentially washed with brine (2×30 mL) and H₂O (30 mL), and the combined aqueous phase back-extracted with EtOAc (30 mL). The combined organic phase was dried (Na₂SO₄), concentrated to dryness, and the resulting crude residue purified by column chromatography (0-5% MeOH in CH₂Cl₂, v/v) to afford the pure desilylated acetylene (0.37 g, 78%) as a light brown solid material. $R_f$=0.5 (5% MeOH in CH₂Cl₂, v/v); ESI-HRMS m/z 605.1918 ([M+Na]⁺, C₃₃H₃₀N₂O₈.Na, Calc 605.1894); ¹H NMR (DMSO-d₆) δ 11.74 (s, 1H, ex, NH), 8.02 (s, 1H, H6), 7.23-7.41 (m, 9H, Ar), 6.89 (d, 4H, T=8.5 Hz, Ar), 5.92 (m, 2H, 1 ex, H1',3'-OH), 4.39 (s, 1H, HCC), 4.27 (s, 1H, H3'), 4.18 (s, 1H, H2'), 4.01-4.03 (d, 1H, T=8.5 Hz, H5"), 3.91-3.92 (d, 1H, T=8.5 Hz, H5"), 3.74 (s, 6H, 2×CH₃O), 3.32 (s, 2H, H5'); ¹³C NMR (DMSO-d₆) δ 161.6, 158.1, 149.1, 144.6, 143.6 (C6), 135.2, 135.1, 129.6 (Ar), 128.8 (Ar), 127.8 (Ar), 127.5 (Ar), 126.6 (Ar), 113.2 (Ar), 96.4, 89.4, 87.2 (C1'), 85.2, 83.3, 78.7 (C2'), 76.3 (C3'), 72.7 (HCC), 72.2 (C5"), 59.8 (C5'), 54.9 (CH₃O).

Example 40

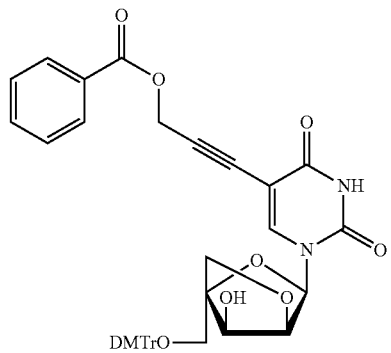

C-5 Benzoylprotected Propargylalcohol α-L-oxy-LNA-U.
After setting up the DMTr-protected vinyl iodide (0.50 g, 0.73 mmol), Pd(PPh₃)₄ (90 mg, 0.07 mmol), CuI (30 mg, 0.14 mmol), prop-2-ynyl benzoate (180 mg, 1.12 mmol), and Et₃N (0.40 mL, 2.84 mmol) in DMF (10 mL) as described in the representative Sonogashira protocol, the reaction mixture was stirred at rt for 12 h. After workup and purification, the benzoyl-protected propargylalcohol (0.40 g, 76%) was obtained as a slightly brown solid material. $R_f$=0.5 (5% MeOH in $CH_2Cl_2$, v/v); ESI-HRMS m/z 739.2234 ([M+Na]$^+$, $C_{41}H_{36}N_2O_{10}$.Na, Calc 739.2262); $^1$H NMR (DMSO-$d_6$) δ 11.78 (s, 1H, ex, NH), 8.03 (s, 1H, H6), 7.97-7.99 (m, 2H, Ar), 7.65-7.69 (m, 1H, Ar), 7.50-7.53 (m, 2H, Ar), 7.17-7.42 (m, 9H, Ar), 6.90 (d, 4H, J=9.0 Hz, Ar), 5.93 (bs, 2H, 1 ex, H1',3'-OH), 5.20 (s, 2H, $CH_2OBz$), 4.41 (d, 1H, J=4.5 Hz, H3'), 4.27 (s, 1H, H2'), 4.01-4.03 (d, 1H, J=8.0 Hz, H5"), 3.91-3.92 (d, 1H, J=8.0 Hz, H5"), 3.72 (s, 6H, 2×$OCH_3$), 3.29 (s, 2H, H5'); $^{13}$C NMR (DMSO-$d_6$) δ 165.0, 161.4, 158.1, 149.1, 144.6, 144.0 (C6), 135.1, 135.0, 133.5, 129.68 (Ar), 129.66 (Ar), 129.2 (Ar), 128.9, 128.7 (Ar), 127.7 (Ar), 127.5 (Ar), 126.6 (Ar), 113.2 (Ar), 96.1, 89.3, 87.2 (C1'), 86.5, 85.2, 79.1, 78.6 (C2'), 72.7 (C3'), 72.3 (C5"), 59.7 (C5'), 54.9 ($CH_3O$), 53.1 ($CH_2OBz$).

Example 41

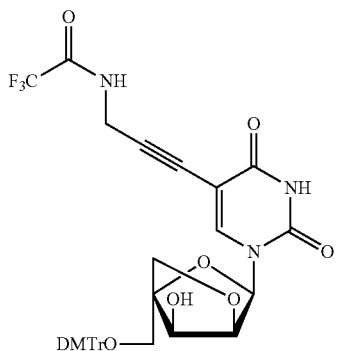

C5 TFA Protected Propargylamine 5'DMT-α-L-LNA U.

After setting up the DMTr-protected vinyl iodide (0.50 g, 0.73 mmol), Pd(PPh$_3$)$_4$ (90 mg, 0.07 mmol), CuI (30 mg, 0.14 mmol), 2,2,2-trifluoro-N-(prop-2-ynyl)acetamide (180 mg, 1.46 mmol), and Et$_3$N (0.4 mL, 2.84 mmol) in DMF (10 mL) as described in the representative Sonogashira protocol, the reaction mixture was stirred at rt for 12 h. After workup and purification, the TFA-protected propargylamine (0.43 g, 84%) was obtained as a slightly brown solid material. $R_f$=0.5 (5% MeOH in $CH_2Cl_2$, v/v); $^1$H NMR (DMSO-$d_6$) δ 11.76 (s, 1H, ex, NH), 10.04 (t, ex, 1H, J=5.5 Hz, NHCH$_2$), 7.94 (s, 1H, H6), 7.22-7.41 (m, 9H, Ar), 6.90 (d, 4H, J=9.0 Hz, Ar), 5.94-5.95 (m, 2H, 1 ex, HP, 3'-OH), 4.43 (d, 1H, J=4.0 Hz, H3'), 4.26-4.27 (m, 3H, H2', CH$_2$NH), 3.98-4.00 (d, 1H, J=8.5 Hz, H5"), 3.92-3.93 (d, 1H, J=8.5 Hz, H5"), 3.74 (s, 6H, 2×$OCH_3$), 3.32 (s, 2H, H5'); $^{13}$C NMR (DMSO-$d_6$) δ 161.5, 158.1, 156.0 (q, J=36.3 Hz, COCF$_3$) 149.1, 144.7, 143.4 (C6), 135.1, 135.0, 129.7 (Ar), 129.6 (Ar), 127.8 (Ar), 127.5 (Ar), 126.6 (Ar), 115.7 (q, J=287 Hz, CF$_3$), 113.2 (Ar), 96.5, 89.3, 87.3, 87.1 (C1'), 85.3, 78.6 (C2'), 75.3, 72.6 (C3'), 72.2 (C5"), 69.6, 59.7 (C5'), 54.9 (CH$_3$O), 29.4 (CH$_2$NH).

Example 42

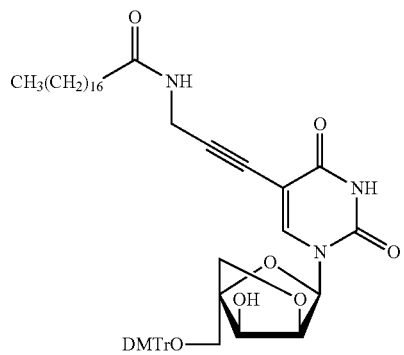

C5 $C_{18}$ Protected Propargylamine 5'DMT-α-L-LNA U (10×).

After setting up the DMTr-protected vinyl iodide (0.34 g, 0.50 mmol), Pd(PPh$_3$)$_4$ (60 mg, 0.05 mmol), CuI (20 mg, 0.10 mmol), N-(prop-2-ynyl)stearamide (0.28 g, 1.00 mmol), and Et$_3$N (0.30 mL, 2.13 mmol) in DMF (10 mL) as described in the representative Sonogashira protocol, the reaction mixture was stirred at 40° C. for 6 h. After workup and purification, the $C_{18}$-protected propargylamine (0.24 g, 55%) was obtained as a brown solid material. $R_f$=0.5 (5% MeOH in $CH_2Cl_2$, v/v); ESI-HRMS m/z 900.4813 ([M+Na]$^+$, $C_{52}H_{67}N_3O_9$.Na, Calc 900.4770); $^1$H NMR (CDCl$_3$) δ 7.89 (s, 1H, H6), 7.25-7.45 (m, 9H, Ar), 6.87 (d, 4H, J=9.0 Hz, Ar), 5.97 (s, 1H, H1'), 5.88 (t, ex, 1H, J=5.0 Hz, NHCH$_2$), 4.54 (s, 1H, H2'), 4.48 (s, 1H, H3'), 4.27-4.28 (m, 2H, CH$_2$NH), 4.09-4.13 (d, 1H, J=9.0 Hz, H5"), 3.97-4.01 (d, 1H, J=9.0 Hz, H5"), 3.81 (s, 6H, 2×CH$_3$O), 3.54-3.57 (d, 1H, J=11.0 Hz, H5'), 3.50-3.53 (d, 1H, J=11.0 Hz, H5'), 2.16-2.19 (m, 2H, CH$_2$CONH), 1.61-1.63 (m, 2H, CH$_2$—CH$_2$CONH), 1.26-1.27 (m, 26H, 13×CH$_2$), 1.12-1.13 (m, 2H, CH$_2$), 0.89 (t, 3H, J=7.0 Hz, CH$_3$CH$_2$); $^{13}$C NMR (CDCl$_3$) δ 172.7, 161.6, 158.77, 158.76, 149.0, 144.2, 142.7 (C6), 135.22, 135.20, 130.03 (Ar), 130.02, (Ar), 128.0 (Ar), 127.9 (Ar), 127.1 (Ar), 113.3 (Ar), 98.5, 89.8, 89.5, 87.9 (C1'), 86.6, 78.8 (C2'), 74.4, 74.3 (C3'), 72.7 (C5"), 59.4 (C5'), 55.2 (CH$_3$O), 36.4 (CH$_2$CONH), 31.9 (CH$_2$), 30.0 (CH$_2$NH), 29.69 (CH$_2$), 29.68 (CH$_2$), 29.66 (CH$_2$), 29.65 (CH$_2$), 29.63 (CH$_2$), 29.5 (CH$_2$), 29.4 (CH$_2$), 29.35 (CH$_2$), 29.33 (CH$_2$), 25.5 (CH$_2$—CH$_2$CONH), 22.7 (CH$_2$), 14.1 (CH$_3$).

Example 43

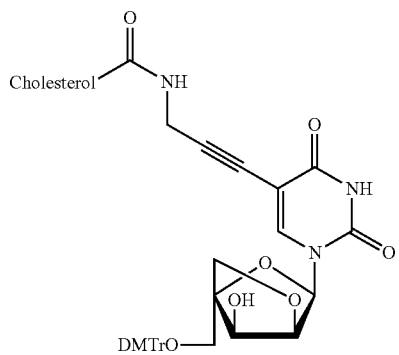

C5 Cholesterol Protected Propargylamine 5'DMT-α-L-LNA U.

After setting up the DMTr-protected vinyl iodide (0.34 g, 0.50 mmol), Pd(PPh$_3$)$_4$ (60 mg, 0.05 mmol), CuI (20 mg, 0.10 mmol), cholesteryl-prop-2-ynyl-carbamate amine$^r$ (0.47 g, 1.00 mmol) and Et$_3$N (0.30 mL, 2.13 mmol) in DMF (8 mL) as described in the representative Sonogashira protocol, the reaction mixture was stirred at rt for 12 h. After workup and purification, the cholesterol-protected propargylamine (0.39 g, 76%) was obtained as a slightly yellow solid material. R$_f$=0.5 (5% MeOH in CH$_2$Cl$_2$, v/v); ESI-HRMS m/z 1046.5533 ([M+Na]$^+$, C$_{62}$H$_{77}$N$_3$O$_{10}$.Na, Calc 1046.5501); $^1$H NMR (CDCl$_3$) δ 8.92 (bs, 1H, ex, NH), 7.88 (s, 1H, H6), 7.27-7.45 (m, 9H, Ar), 6.86 (d, 4H, J=9.0 Hz, Ar), 5.97 (s, 1H, H1'), 5.36 (d, 1H, J=5.0 Hz, HC=C-chol), 5.11 (t, ex, 1H, J=5.0 Hz, NHCH$_2$), 4.55 (s, 1H, H2'), 4.50-4.53 (m, 1H, OCH-chol), 4.48 (s, 1H, H3'), 4.19 (d, 2H, J=5.0 Hz, CH$_2$NH), 4.11-4.15 (d, 1H, J=9.0 Hz, H5"), 3.98-4.02 (d, 1H, J=9.0 Hz, H5"), 3.80 (s, 6H, 2×CH$_3$O), 3.50-3.58 (2d, 2H, J=11.0 Hz, H5'), 0.87-2.36 (m, 34H, H-Chol), 0.69 (s, 3H, CH$_3$-chol); $^{13}$C NMR (CDCl$_3$) δ 161.5, 158.74, 158.73, 155.6, 149.0, 144.3, 142.6 (C6), 139.7, 135.28, 135.26, 132.1 (Ar), 132.0 (Ar), 130.04 (Ar), 130.03 (Ar), 128.5 (Ar), 128.4 (Ar), 128.02 (Ar), 128.00 (Ar), 127.0 (Ar), 122.5 (CH=C-chol), 113.3 (Ar), 98.5, 89.8, 87.9 (C1'), 86.6, 78.9 (C2'), 74.9 (OCH-chol), 74.4, 74.2 (C3'), 72.8 (C5"), 59.4 (C5'), 56.7 (CH-chol), 56.1 (CH-chol), 55.2 (CH$_3$O), 50.0 (CH-chol), 42.3, 39.7 (CH$_2$-chol), 39.5 (CH$_2$-chol), 38.5 (CH$_2$-chol), 36.9 (CH$_2$-chol), 36.5, 36.2 (CH$_2$-chol), 35.7 (CH-chol), 31.9 (CH$_2$NH and CH$_2$-chol overlap), 31.8 (CH-chol), 28.2 (CH$_2$-chol), 28.1 (CH$_2$-chol), 28.0 (CH-chol), 24.2 (CH$_2$-chol), 23.8 (CH$_2$-chol), 22.7 (CH$_3$-chol), 22.5 (CH$_3$-chol), 21.0 (CH$_2$-chol), 19.3 (CH$_3$-chol), 18.7 (CH$_3$-chol), 11.8 (CH$_3$-chol).

Example 44

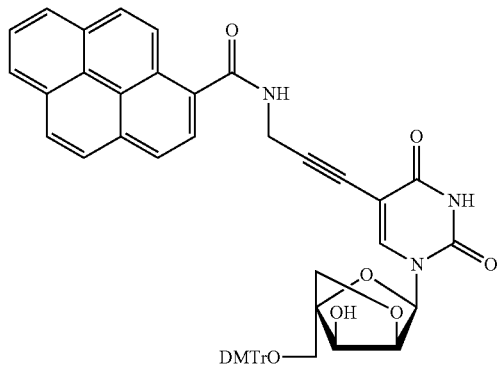

C5 Pyrenecarboxamide Propargylamine 5'DMT-α-L-LNA U.

After setting up the DMTr-protected vinyl iodide (0.50 g, 0.73 mmol), Pd(PPh$_3$)$_4$ (90 mg, 0.07 mmol), CuI (30 mg, 0.14 mmol), N-(prop-2-ynyl)pyrene-1-carboxamide (280 mg, 1.00 mmol), and Et$_3$N (0.40 mL, 2.84 mmol) in DMF (10 mL) as described in the representative Sonogashira protocol, the reaction mixture was stirred at rt for 12 h. After workup and purification, the pyrene carboxamide (0.47 g, 79%) was obtained as a slightly yellow solid material. R$_f$=0.5 (5% MeOH in CH$_2$Cl$_2$, v/v); ESI-HRMS m/z 862.2756 ([M+Na]$^+$, C$_{52}$H$_4$IN$_3$O$_9$.Na, Calc 862.2735); $^1$H NMR (DMSO-d$_6$) δ 11.77 (s, 1H, ex, NH), 9.23 (t, 1H, ex, J=5.5 Hz, NHCH$_2$), 8.54-8.55 (d, 1H, J=9.5 Hz, Ar), 8.19-8.35 (m, 6H, Ar), 8.10-8.14 (m, 2H, Ar), 7.99 (s, 1H, H6), 7.13-7.40 (m, 9H, Ar), 6.88 (d, 4H, J=9.0 Hz, Ar), 5.98 (s, 1H, H1'), 5.95 (d, 1H, ex, J=4.5 Hz, 3'-OH), 4.49 (d, 2H, J=5.5 Hz, CH$_2$NH), 4.43 (d, 1H, J=4.5 Hz, H3'), 4.28 (s, 1H, H2'), 4.03-4.05 (d, 1H, J=8.5 Hz, H5"), 3.95-3.97 (d, 1H, J=8.5 Hz, H5"), 3.69 (s, 6H, 2×CH$_3$O), 3.32 (s, 2H, H5'); $^{13}$C NMR (DMSO-d$_6$) δ 168.5, 161.6, 158.0, 149.2, 144.6, 142.9 (C6), 135.1, 135.0, 131.6, 131.0, 130.7, 130.1, 129.69 (Ar), 129.67 (Ar), 128.3 (Ar), 128.1 (Ar), 127.9 (Ar), 127.8 (Ar), 127.5 (Ar), 127.1 (Ar), 126.6 (Ar), 126.5 (Ar), 125.8 (Ar), 125.5 (Ar), 125.1 (Ar), 124.5 (Ar), 124.3 (Ar), 123.7, 123.5, 113.2 (Ar), 97.0, 89.5, 89.3, 87.1 (C1'), 85.3, 78.6 (C2'), 74.5, 72.7 (C3'), 72.3 (C5"), 59.7 (C5'), 54.9 (CH$_3$O), 29.5 (CH$_2$NH).

Representative Protocol for Phosphitylation:

The coupled products described above (α-series) were dried by coevaporation with anhydrous 1,2-dichloroethane (2×10 mL) and dissolved in anhydrous CH$_2$Cl$_2$. To this was added EtN(iPr)$_2$ (DIPEA) and 2-cyanoethyl N,N'-(diisopropyl)-phosphoramidochloridite (PCl-reagent) and the reaction mixture was stirred at rt until analytical TLC showed full conversion of the starting material (2-3 h) [quantities and volumes specified below]. The reaction mixture was diluted with CH$_2$Cl$_2$ (25 mL), washed with 5% aq. NaHCO$_3$ (2×10 mL), and the combined aqueous phase back-extracted with CH$_2$Cl$_2$ (2×10 mL). The combined organic phase was dried (Na$_2$SO$_4$), evaporated to dryness and the resulting residue purified by column chromatography (0-3% MeOH in CH$_2$Cl$_2$, v/v) and subsequent trituration from CH$_2$Cl$_2$ and petroleum ether to provide phosphoramidite products.

Example 45

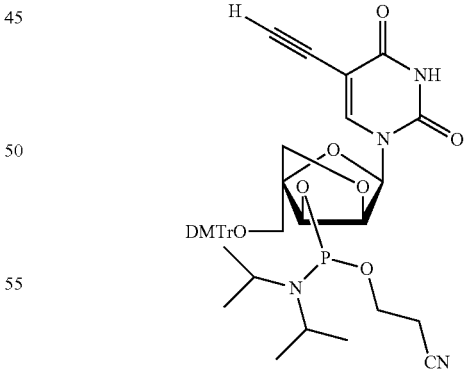

C5 Ethynyl α-L-LNA-U Phosphoramidite.

The desilylated acetylene product (0.35 g 0.60 mmol), DIPEA (0.50 mL, 2.88 mmol), and PCl-reagent (0.20 mL, 0.87 mmol) in anhydrous CH$_2$Cl$_2$ (10 mL) were reacted, worked up and purified as described in the representative phosphitylation protocol to provide the phosphoramidite compound (0.39 mg, 83%) as a white foam. R$_f$=0.5 (2%

MeOH in CH$_2$Cl$_2$, v/v); ESI-HRMS m/z 805.2943 ([M+Na]$^+$, C$_{42}$H$_{47}$N$_4$O$_9$P.Na$^+$, Calcd 805.2958); $^{31}$P NMR (CDCl$_3$) δ 150.2, 149.9.

Example 46

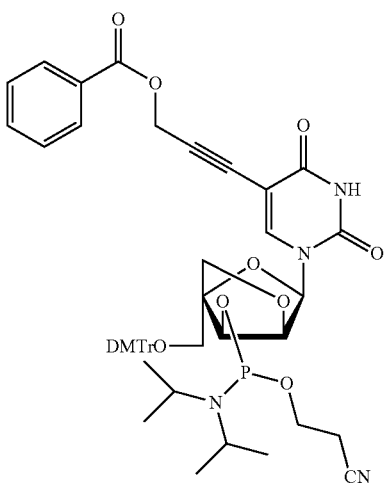

C5 Propargylalcohol α-L-LNA-U Phosphoramidite.

The benzoyl-protected propargylalcohol (0.35 g, 0.49 mmol) was co-evaporated with anhydrous 1,2-dichloroethane (2×7 mL) and redissolved in anhydrous CH$_2$Cl$_2$ (7 mL). To this was added DIPEA (425 μL, 2.44 mmol) and N-methylimidazole (31 μL, 0.39 mmol), followed by dropwise addition of the PCl-reagent (220 μL, 0.98 mmol). The reaction mixture was stirred at rt for 3 h, whereupon it was evaporated to near dryness, purified via column chromatography (0-3% MeOH in CH$_2$Cl$_2$), and subsequent trituration from CH$_2$Cl$_2$ and petroleum ether to provide the phosphoramidite compound (0.28 g, 62%) a white foam. R$_f$=0.5 (3% MeOH in CH$_2$Cl$_2$); ESI-HRMS m/z 939.3332 ([M+Na]$^+$, C$_{50}$H$_{53}$N$_4$O$_{11}$P.Na$^+$, Calcd 939.3341); $^{31}$P NMR (CDCl$_3$) δ 150.1, 149.8.

Example 47

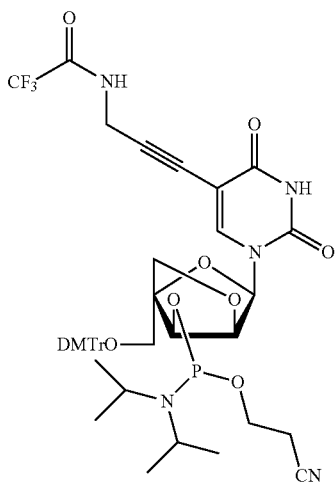

C5 TFA Protected Propargylamine α-L-LNA-U Phosphoramidite.

The TFA-protected propargylamine (0.25 g 0.35 mmol), DIPEA (0.30 mL, 1.7 mmol), PCl-reagent (0.10 mL, 0.45 mmol) in anhydrous CH$_2$Cl$_2$ (10 mL) were reacted, worked up and purified as described in the representative phosphitylation protocol to provide the phosphoramidite compound (0.27 g, 84%) as a white foam. R$_f$=0.5 (2% MeOH in CH$_2$Cl$_2$, v/v); ESI-HRMS m/z 930.3068 ([M+Na]$^+$, C$_{45}$H$_{49}$F$_3$N$_5$O$_{10}$P.Na$^+$, Calcd 930.3080); $^{31}$P NMR (CDCl$_3$) δ 150.2, 149.9.

Example 48

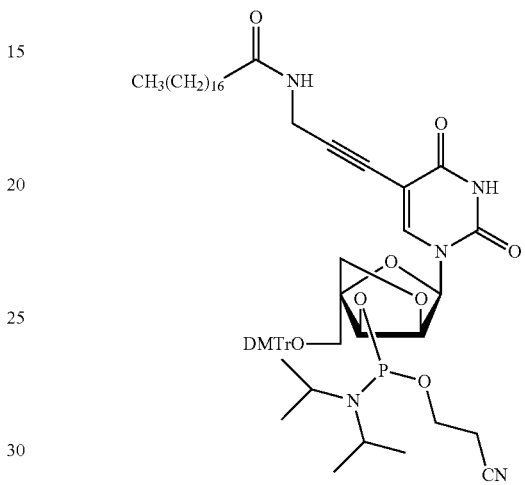

C5 C$_{18}$ protected propargylamine α-L-LNA U PA.

The C$_{18}$-protected propargylamine (170 mg, 0.19 mmol), DIPEA (145 μL, 0.83), and PCl-reagent (61 μL, 0.27 mmol) in anhydrous CH$_2$Cl$_2$ (2 mL) were mixed and reacted as described in the representative phosphitylation protocol. After stirring at rt for 3 h, the mixture was diluted with EtOAc (20 mL) and washed with H$_2$O (2×30 mL). The organic phase was dried (Na$_2$SO$_4$), evaporated to dryness, and the resulting crude residue purified by column chromatography (0-70% EtOAc in petroleum ether, v/v) and subsequent trituration from CH$_2$Cl$_2$ and petroleum ether to provide the phosphoramidite compound (107 mg, 52%) as a white foam. R$_f$=0.4 (5% MeOH in CH$_2$Cl$_2$, v/v); ESI-HRMS m/z 1100.5859 ([M+Na]$^+$, C$_{61}$H$_{84}$N$_5$O$_{10}$P.Na$^+$, Calcd 1100.5848); $^{31}$P NMR (CDCl$_3$) δ 150.2, 149.9.

Example 49

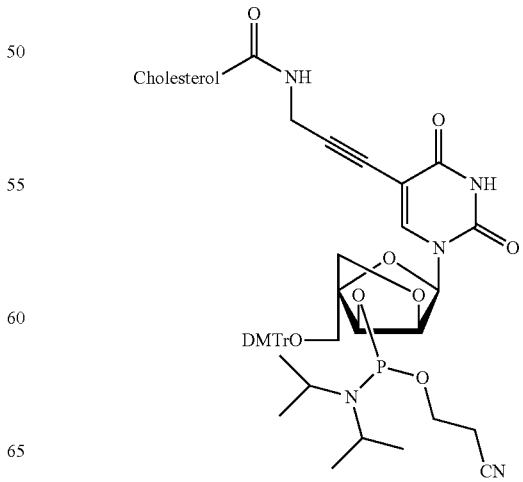

C5 Cholesterol Protected Propargylamine α-L-LNA U PA.

The cholesterol-protected propargylamine (150 mg, 0.15 mmol), DIPEA (105 μL, 0.59 mmol), and PCl-reagent (50 μL, 0.21 mmol) in anhydrous $CH_2Cl_2$ (1.5 mL) were mixed and reacted as described in the representative phosphitylation protocol. After stirring at rt for 3 h, the reaction mixture was diluted with EtOAc (20 mL) and washed with $H_2O$ (2×30 mL). The organic phase was dried ($Na_2SO_4$), evaporated to dryness, and the resulting crude residue purified by column chromatography (0-70% EtOAc in petroleum ether, v/v) and subsequent trituration from $CH_2Cl_2$ and petroleum ether to provide the phosphoramidite compound (102 mg, 57%) as a white foam. $R_f$=0.4 (5% MeOH in $CH_2Cl_2$, v/v); ESI-HRMS m/z 1246.6519 ([M+Na]+, $C_{71}H_{94}N_5O_{11}P·Na^+$, Calcd 1246.6579); $^{31}P$ NMR ($CDCl_3$) δ 150.2, 149.9.

Example 50

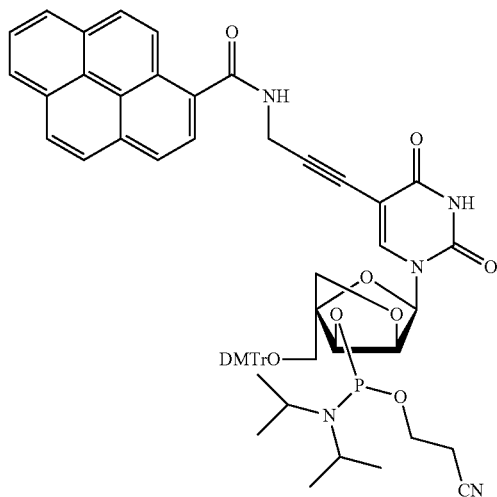

C5 pyrene-propargylamine α-L-LNA-U phosphoramidite. The pyrene carboxamide (0.44 g, 0.52 mmol), DIPEA (0.46 mL, 2.6 mmol), PCl-reagent (0.18 mL, 0.78 mmol) in anhydrous $CH_2Cl_2$ (10 mL) were reacted, worked up and purified as described in the representative phosphitylation protocol to provide nucleoside the phosphoramidite compound (190 mg, 61%) as a white foam. $R_f$=0.5 (2% MeOH in $CH_2Cl_2$, v/v); ESI-HRMS 1062.3790 ([M+Na]+, $C_{60}H_{58}N_5O_{10}P·Na^+$, Calcd 1062.3814); $^{31}P$ NMR ($CDCl_3$) δ 150.2, 149.8.

Example 51

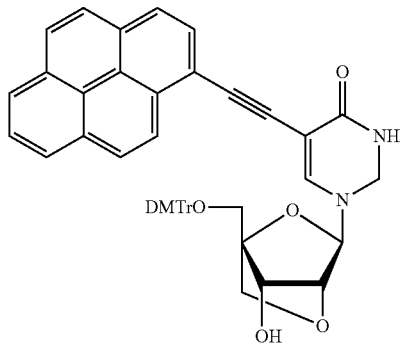

5-[2-(1-Pyrenyl)ethynyl]-5'-O-(4,4'-dimethoxytrityl) LNA uridine 5-iodo-5'-ODMTr LNA U (0.34 g, 0.50 mmol), Pd(PPh$_3$)$_4$ (60 mg, 0.05 mmol), CuI (20 mg, 0.10 mmol) and pyrene-1-ethynyl (0.28 g, 1.00 mmol) were added to anhydrous DMF (10 mL) and the resulting mixture was degassed and placed under argon. To this was added Et$_3$N (0.30 mL, 2.84 mmol) and the reaction mixture was stirred at rt for 12 h whereupon solvents were evaporated off. The resulting residue was taken up in EtOAc (100 mL) and sequentially washed with brine (50 mL) and sat. aq. NaHCO$_3$ (50 mL). The combined aqueous phase was back-extracted with EtOAc (100 mL), and the combined organic phase was dried (Na$_2$SO$_4$), evaporated to dryness and the resulting crude residue purified by column chromatography (0-5% MeOH in CH$_2$Cl$_2$ (v/v) to afford the desired nucleoside (0.31 g, 80%) as a yellow solid. $R_f$=0.5 (5% MeOH in CH$_2$Cl$_2$, v/v); $^1$H NMR (DMSO-d$_6$) δ 11.89 (s, 1H, ex, NH), 8.36-8.08 (m, 8H, Ar), 7.93 (d, 1H, J=9.0 Hz, Ar), 7.67 (d, 1H, J=8.0 Hz, Ar), 7.50-7.49 (m, 2H, Ar), 7.37-7.33 (m, 4H, Ar), 7.30-7.26 (m, 2H, Ar), 7.06-7.03 (m, 1H, Ar), 6.83 (d, 2H, J=9.0 Hz, Ar), 6.80 (d, 2H, J=9.0 Hz, Ar), 5.79 (d, 1H, ex, J=4.5 Hz, 3'-OH), 5.53 (s, 1H, H1'), 4.34 (s, 1H, H2'), 4.24 (d, 1H, J=4.5 Hz, H3'), 3.81-3.82 (d, 1H, J=7.5 Hz, H5''), 3.78-3.80 (d, 1H, J=7.5 Hz, H5''), 3.50 (s, 3H, OCH$_3$), 3.48 (d, 1H, J=11.0 Hz, H5'), 3.49 (s, 3H, OCH$_3$), 3.39 (d, 1H, J=11.0 Hz, H5'); $^{13}$C NMR (DMSO-d$_6$) δ 161.7, 158.0, 157.9, 149.5, 149.0, 144.4, 141.3, 135.4, 130.7, 130.6, 130.5, 130.3, 129.58, 129.50, 128.8, 128.2, 128.0, 127.8, 127.6, 127.1, 126.6, 126.5, 125.7, 125.6, 124.7, 124.4, 123.4, 123.2, 116.8, 113.17, 113.15, 98.2, 91.3, 88.1, 87.7, 87.1, 85.5, 78.7, 69.3, 58.7, 54.7, 54.6.

Example 52

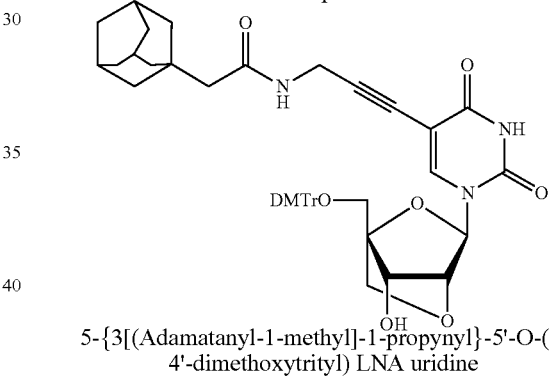

5-{3[(Adamatanyl-1-methyl]-1-propynyl}-5'-O-(4,4'-dimethoxytrityl) LNA uridine 5-iodo-5'-ODMTr LNA U (0.50 g, 0.73 mmol), Pd(PPh$_3$)$_4$ (90 mg, 0.05 mmol), CuI (30 mg, 0.10 mmol) and adamantane (220 mg, 1.00 mmol) were added to anhydrous DMF (10 mL) and the resulting mixture was degassed and placed under argon. To this was added Et$_3$N (0.50 mL) and the reaction mixture was stirred at rt for 12 h whereupon solvents were evaporated off. The resulting residue was taken up in EtOAc (100 mL) and sequentially washed with brine (50 mL) and sat. aq. NaHCO$_3$ (50 mL). The combined aqueous phase was back-extracted with EtOAc (100 mL), and the combined organic phase was dried (Na$_2$SO$_4$), evaporated to dryness and the resulting crude residue purified by column chromatography (0-5% MeOH in CH$_2$Cl$_2$ (v/v) to afford the desired nucleoside PK-10-10 (0.43 g, 76%) as a yellow solid. $R_f$=0.5 (5% MeOH in CH$_2$Cl$_2$, v/v); HRMS required 773.3676 Submitted $^1$H NMR (DMSO-d$_6$) δ 11.66 (s, 1H, ex, NH), 8.08 (t, 1H, ex, J=5.5 Hz, NHCO), 7.74 (s, 1H, H6), 7.42-7.44 (m, 2H, Ar), 7.28-7.34 (m, 6H, Ar), 7.23-7.25 (m, 1H, Ar), 6.91 (dd, 4H, J=9.0 Hz, 3.5 Hz, Ar), 5.71 (d, 1H, ex, J=4.5 Hz, 3'-OH), 5.42 (s, 1H, H1'), 4.24 (s, 1H, H2'), 4.01 (d, 1H, J=4.5 Hz, H3'), 3.92-3.86 (m, 2H, CH$_2$), 3.80-3.82 (m, 2H, H5''), 3.75 (s, 3H, OCH$_3$), 3.74 (s, 3H, OCH$_3$), 3.54-3.56 (d, 1H, J=11.0 Hz, H5'), 3.27-3.29 (d, 1H, J=11.0 Hz, H5'); $^{13}$C NMR (DMSO-d$_6$) 169.5, 161.6, 158.1, 158.0, 148.9, 144.6, 141.4, 135.4, 134.8, 129.8, 129.5, 127.8, 127.5, 126.6, 113.24, 113.22, 97.7, 89.5, 87.5, 86.9, 85.5, 78.7, 74.2, 71.3, 69.6, 59.0, 54.9, 49.4, 41.9, 36.3, 32.2, 28.4, 27.9.

Example 53

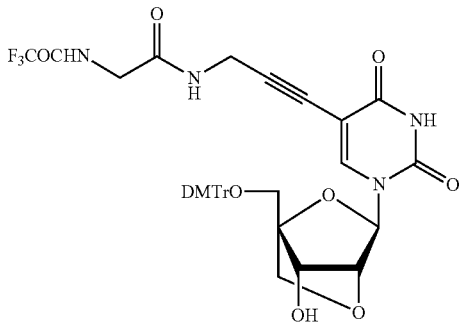

5-[3-{2-(2,2,2-Trifluoroacetylamino)acetyl}-1-propynyl)-5'-O-(4,4'-dimethoxytrityl] LNA uridine A solution of 2-(2,2,2-trifluoroacetamido)acetic acid (90 mg, 0.58 mmol), O—(N-Succinimidyl)-1,1,3,3-tetramethyluronium tetrafluoroborate (TSTU, 190 mg, 0.63 mmol) and DIPEA (0.25 mL, 1.47 mmol) in DMF (10 mL) was stirred at room temperature for 30 minutes whereupon C5-propargylamine-5'-ODMTr LNA U (0.30 g, 0.49 mmol) was added to it. The reaction mixture stirred for 2 h at rt. Whereupon solvents were removed at reduced pressure and the residue was taken in EtOAc (50 mL) and washed with NaHCO$_3$ (2×50 mL) followed by brine (50 mL). The organic phase was dried over Na$_2$SO$_4$ and evaporated to dryness to afford crude which was purified by column chromatography (0-5% MeOH/DCM) to afford desired nucleoside (180 mg, 48%) as slight brown solid material. R$_f$=0.4 (5% MeOH in CH$_2$Cl$_2$, v/v); $^1$H NMR (DMSO-d$_6$) δ 11.68 (s, 1H, ex, NH), 9.61 (t, 1H, ex, J=5.5 Hz, NHCO), 8.49 (t, 1H, ex, J=5.0 Hz, NHCO), 7.77 (s, 1H, H6), 7.42-7.44 (m, 2H, Ar), 7.28-7.34 (m, 6H, Ar), 7.24-7.26 (m, 1H, Ar), 6.91 (dd, 4H, J=9.0 Hz, 2.5 Hz, Ar), 5.72 (d, 1H, ex, J=5.0 Hz, 3'-OH), 5.42 (s, 1H, H1'), 4.24 (s, 1H, H2'), 4.03 (d, 1H, J=5.0 Hz, H3'), 3.86-3.98 (m, 2H, CH$_2$), 3.80-3.82 (m, 4H, CH$_2$, 2×H5"), 3.74 (s, 6H, 2×OCH$_3$), 3.55-3.57 (d, 1H, J=11.0 Hz, H5'), 3.26-3.29 (d, 1H, J=11.0 Hz, H5'); $^{13}$C NMR (DMSO-d$_6$) δ 166.6, 161.8, 158.1, 158.0, 156.6, 148.9, 144.6, 141.8, 135.4, 134.9, 129.7, 129.5, 127.8, 127.5, 126.6, 115.0, 113.25, 113.23, 97.5, 88.8, 87.5, 86.9, 85.5, 78.7, 74.7, 71.3, 69.6, 59.0, 54.9, 41.6, 28.7.

Example 54

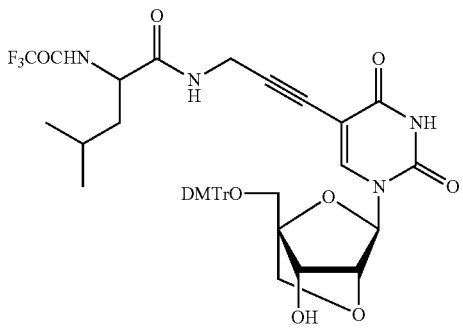

5-[3-{2-(2,2,2-Trifluoroacetylamino)-4-methylpentanoyl}-1-propynyl)-5'-O-(4,4'-dimethoxytrityl]LNA uridine A Solution of (S)-2-(2,2,2-trifluoroacetamido)-4-methylpentanoic acid (100 mg, 0.44 mmol), O—(N-Succinimidyl)-1,1,3,3-tetramethyluronium tetra-fluoroborate (TSTU, 160 mg, 0.53 mmol), DIPEA (0.21 mL, 1.2 mmol) was stirred at room temperature for 30 minutes whereupon C5-propargylamine-5'-ODMTr LNA U (0.25 g, 0.40) was added. The reaction mixture was stirred for 2 h at rt whereupon solvents were removed at reduced pressure and the residue was taken in EtOAc (50 mL) and washed with NaHCO$_3$ (2×50 mL) followed by brine. The organic phase was dried over Na$_2$SO$_4$ and evaporated to dryness to afford crude which was purified by column chromatography (0-5% MeOH/DCM) to afford desired nucleoside (170 mg, 49%) as brown solid material. $^1$H NMR (DMSO-d$_6$) δ 11.68 (s, 1H, ex, NH), 9.54 (d, 1H, ex, J=8.5 Hz, NH), 8.58-8.60 (m, 1H, ex, NHCO), 7.77 (s, 1H, H6), 7.42-7.44 (m, 2H, Ar), 7.28-7.34 (m, 6H, Ar), 7.22-7.25 (m, 1H, Ar), 6.90 (dd, 4H, J=9.0 Hz, 2.5 Hz, Ar), 5.72 (m, 1H, ex), 5.43 (s, 1H, H1'), 4.36-4.40 (m, 1H), 4.24 (s, 1H, H2'), 4.02-4.04 (m, 1H), 3.86-3.98 (m, 2H, CH$_2$), 3.80-3.82 (m, 2H, 2×H5"), 3.74 (s, 6H, 2×OCH$_3$), 3.55-3.57 (d, 1H, J=11.0 Hz, H5'), 3.26-3.29 (d, 1H, J=11.0 Hz, H5'), 1.63-1.66 (m, 1H, CH), 11.45-1.53 (m, 2H, CH$_2$), 0.81-0.88 (m, 6H); $^{13}$C NMR (DMSO-d$_6$) 170.1, 161.8, 158.1, 158.0, 156.2 (q, $^2$J$_{CF}$=36.3 Hz), 148.9, 144.6, 141.7, 135.4, 134.9, 129.8, 129.5, 127.8, 127.5, 126.6, 115.7 (q, $^1$J$_{CF}$=287.6 Hz), 113.2, 97.5, 88.8, 87.5, 86.9, 85.5, 74.7, 71.3, 69.6, 59.1, 54.9, 51.5, 28.9, 24.2, 22.8, 20.9.

Example 55

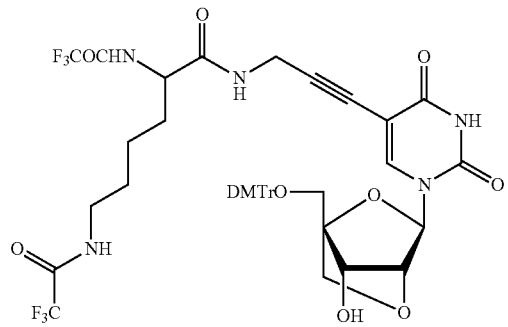

5-[3-{2,6-bis(2,2,2-Trifluoroacetylamino)hexanoyl}-1-propynyl)-5'-O-(4,4'-dimethoxytrityl]LNA uridine A Solution of (S)-2,6-bis(2,2,2-trifluoroacetamido)hexanoic acid (0.27 g, 0.8 mmol), O—(N-Succinimidyl)-1,1,3,3-tetramethyluronium tetrafluoroborate (TSTU, 320 mg, 1.06 mmol), DIPEA (0.42 mL, 2.4 mmol) was stirred at room temperature for 30 minutes whereupon C5-propargylamine-5'-ODMTr LNA U (0.5 g, 0.8 mmol) was added at 0° C. The reaction mixture was slowly allowed to attain room temperature and stirred for another 1 h at rt whereupon solvents were removed at reduced pressure and the residue was taken in EtOAc (100 mL) and washed with NaHCO$_3$ (2×50 mL) followed by brine (50 mL). The organic phase was dried over Na$_2$SO$_4$ and evaporated to dryness to afford crude which was purified by column chromatography (0-5% MeOH in DCM, v/v) to afford desired nucleoside (0.44 mg, 58%) as slight brown solid material. $R_f$=0.5 (5% MeOH in $CH_2Cl_2$, v/v); $^1$H NMR (DMSO-$d_6$) δ 11.67 (s, 1H, ex, NH), 9.49 (m, 1H, ex, NH), 9.30 (t, 1H, ex, J=5.0 Hz), 8.54-8.56 (m, 1H, ex), 7.77 (s, 1H, H6), 7.42-7.44 (m, 2H, Ar), 7.28-7.34 (m, 6H, Ar), 7.22-7.24 (m, 1H, Ar), 6.90 (dd, 4H, J=9.0 Hz, 3.0 Hz, Ar), 5.72 (d, 1H, ex, J=5.0 Hz, 3'-OH), 5.43 (s, 1H, H1'), 4.36-4.40 (m, 1H), 4.24 (s, 1H, H2'), 4.03 (d, 1H, J=5.0 Hz, H3'), 3.86-3.98 (m, 2H, $CH_2$), 3.80-3.82 (m, 4H, $CH_2$, 2×H5''), 3.74 (s, 6H, 2×$OCH_3$), 3.55-3.57 (d, 1H, J=11.0 Hz, H5'), 3.26-3.29 (d, 1H, J=11.0 Hz, H5'), 3.13-3.17 (m, 2H, $CH_2$), 1.66-1.71 (m, 2H, $CH_2$), 1.41-1.48 (m, 2H, $CH_2$), 1.20.1.29 (m, 2H, $CH_2$).

argon. The reaction mixture was stirred at room temperature for 2 h, at which point the reaction was quenched with ice-cold EtOH (1 mL) and the solvent was evaporated under reduced pressure. The crude mixture was purified via column chromatography (0-2.5% MeOH/$CH_2Cl_2$, v/v) to afford phosphoramidite X (118.6 mg, 64% yield). $R_f$=0.3 (5% MeOH in $CH_2Cl_2$, v/v). $^{31}$P NMR ($CDCl_3$, 300 MHz) δ 149.916, 148.77.

Example 57

Example 56

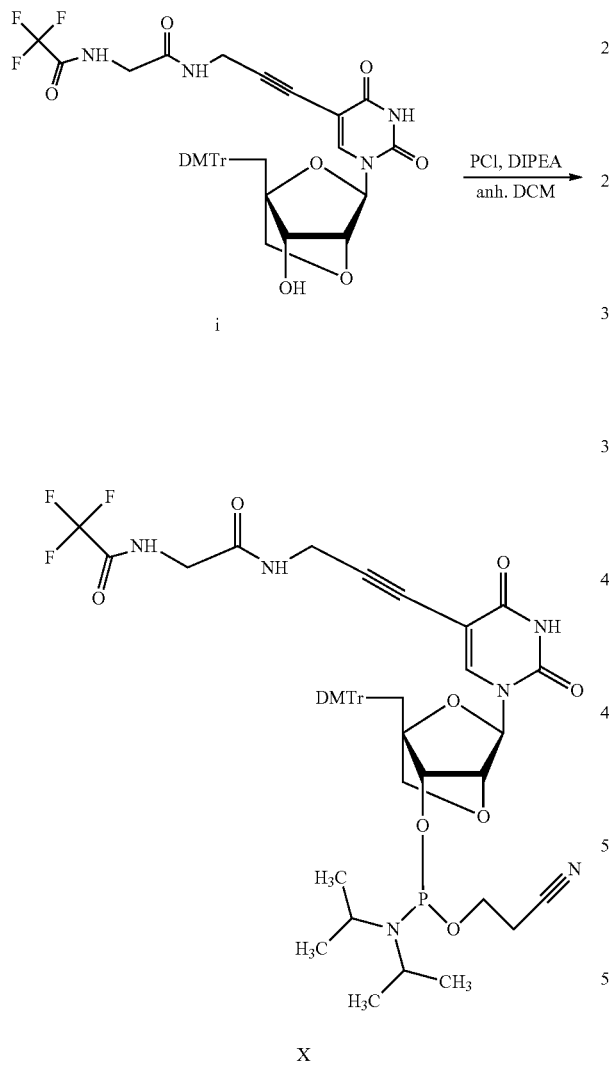

X

C5-TFA Protected Glysine LNA-U Phosphoramidite

The nucleoside i (146 mg, 0.19 mmol) was dried by coevaporation with anhydrous 1,2-dichloroethane (3×5 mL) under reduced pressure and dissolved in anhydrous $CH_2Cl_2$ (4 mL). To this solution, DIPEA (137 μL, 0.78 mmol) was added, followed by dropwise addition of 2-cyanoethyldiiso-propylchlorophosphoramidite (66 μL, 0.29 mmol), under

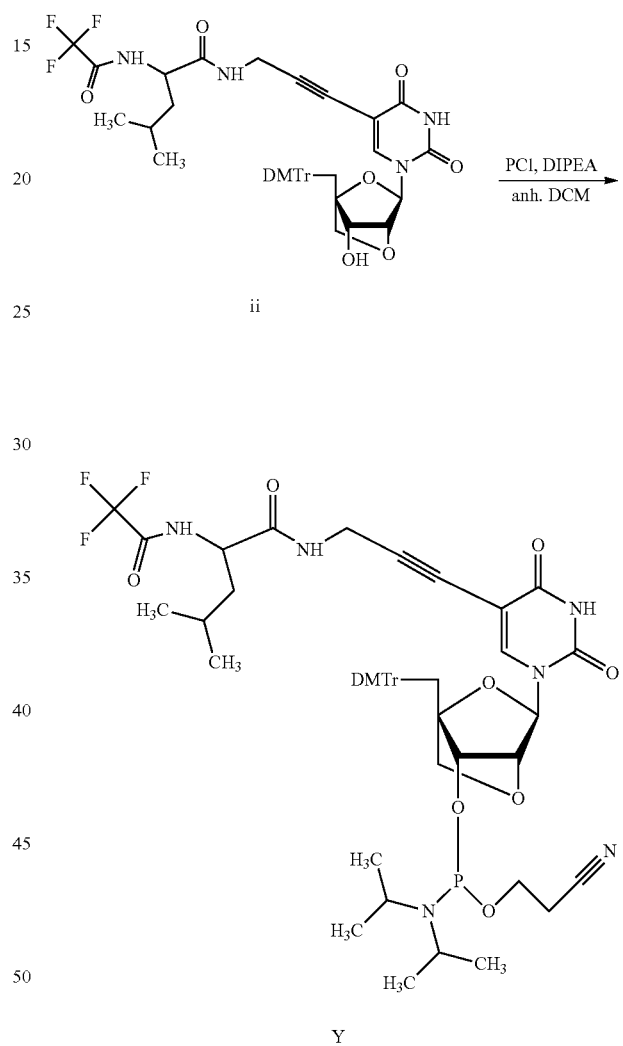

Y

C5-TFA Protected Leucine LNA-U Phosphoramidite

The nucleoside ii (83 mg, 0.10 mmol) was dried by coevaporation with anhydrous 1,2-dichloroethane (3×5 mL) under reduced pressure and dissolved in anhydrous $CH_2Cl_2$ (3 mL). To this solution, DIPEA (71 μL, 0.41 mmol) was added, followed by drop wise addition of 2-cyanoethyldiiso-propylchlorophosphoramidite (41 μL, 0.18 mmol), under argon. The reaction mixture was stirred at room temperature for 2 h, at which point the reaction was quenched with ice-cold EtOH (1 mL) and the solvent was evaporated under reduced pressure. The crude mixture was purified via column chromatography (0-2.5% MeOH/$CH_2Cl_2$, v/v) to afford phosphoramidite Y (38 mg, 37% yield/70% conversion).

$R_f$=0.3 (5% MeOH in CH$_2$Cl$_2$, v/v). $^{31}$P NMR (CDCl$_3$, 300 MHz) δ 149.783, 148.846.

Example 58

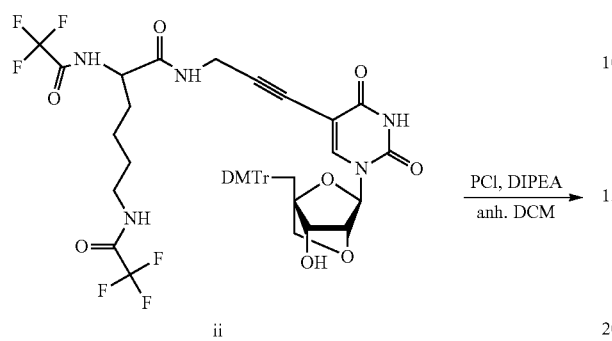

ii

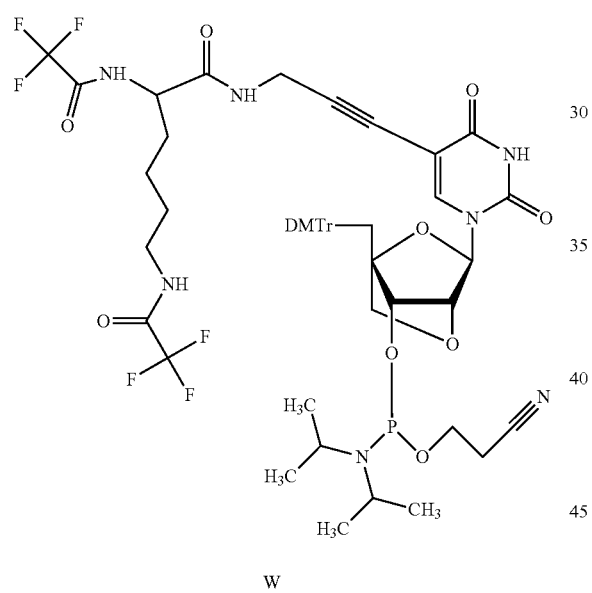

W

C5-TFA Protected Lysine LNA-U Phosphoramidite

The nucleoside iii (154 mg, 0.16 mmol) was dried by coevaporation with anhydrous 1,2-dichloroethane (3×5 mL) under reduced pressure and dissolved in anhydrous CH$_2$Cl$_2$ (4 mL). To this solution, DIPEA (112 μL, 0.65 mmol) was added, followed by drop wise addition of 2-cyanoethyldiisopropylchlorophosphoramidite (72 μL, 0.32 mmol), under argon. The reaction mixture was stirred at room temperature for 2 h, at which point the reaction was quenched with ice-cold EtOH (1 mL) and the solvent was evaporated under reduced pressure. The crude mixture was purified via column chromatography (0-2.5% MeOH/CH$_2$Cl$_2$, v/v) to afford phosphoramidite Z (82.7 mg, 45% yield). $R_f$=0.4 (5% MeOH in CH$_2$Cl$_2$, v/v). $^{31}$P NMR (CDCl$_3$, 300 MHz) δ 149.969, 149.914, 148.824, 148.658.

Example 59

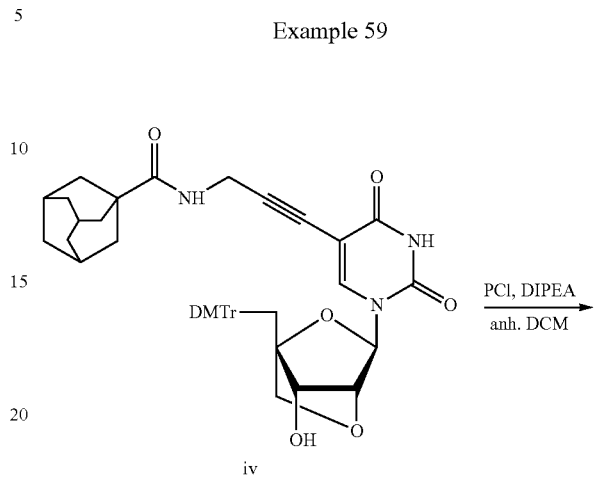

iv

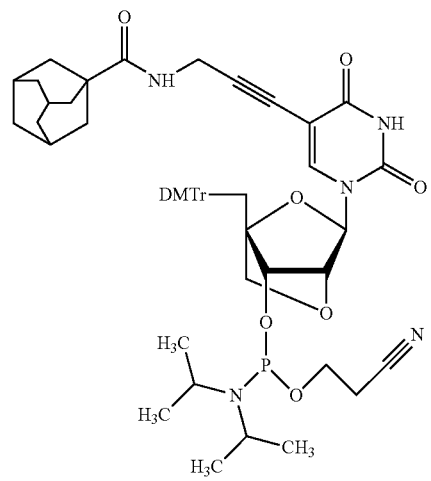

W

C5-Adamantane LNA-U Phosphoramidite

The nucleoside iv (204 mg, 0.26 mmol) was dried by coevaporation with anhydrous 1,2-dichloroethane (3×5 mL) under reduced pressure and dissolved in anhydrous CH$_2$Cl$_2$ (4 mL). To this solution, DIPEA (184 μL, 1.1 mmol) was added, followed by drop wise addition of 2-cyanoethyldiisopropylchlorophosphoramidite (106 μL, 0.48 mmol), under argon. The reaction mixture was stirred at room temperature for 2 h, at which point the reaction was quenched with ice-cold EtOH (1 mL) and the solvent was evaporated under reduced pressure. The crude mixture was purified via column chromatography (0-2.5% MeOH/CH$_2$Cl$_2$, v/v) to afford phosphoramidite W (190 mg, 74% yield). $R_f$=0.4 (5% MeOH in CH$_2$Cl$_2$, v/v). $^{31}$P NMR (CDCl$_3$, 300 MHz) δ 149.809, 149.165.

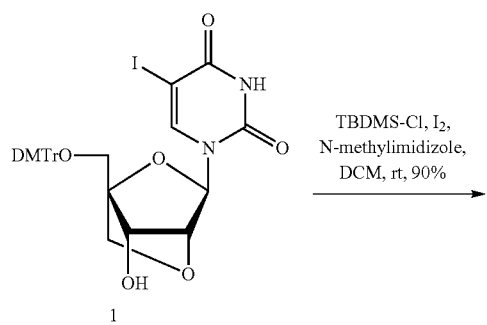

1

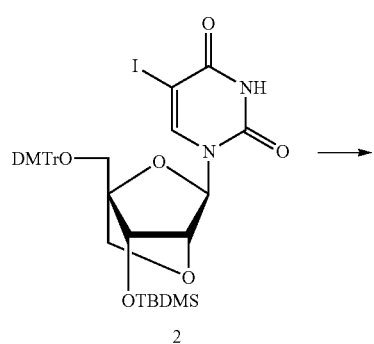

2

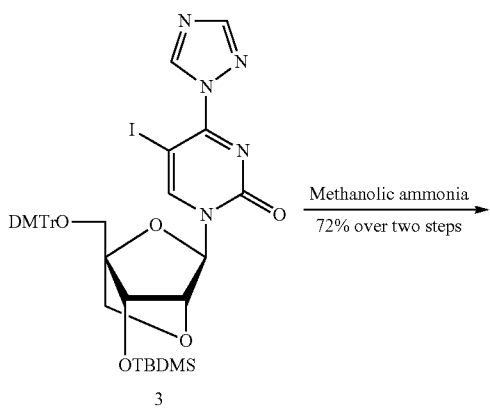

3

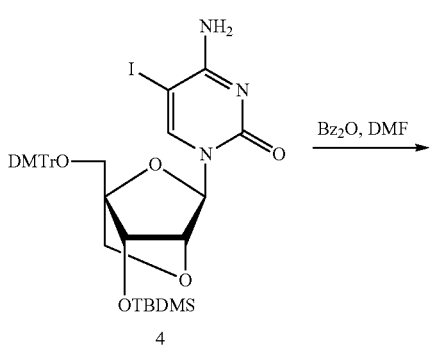

4

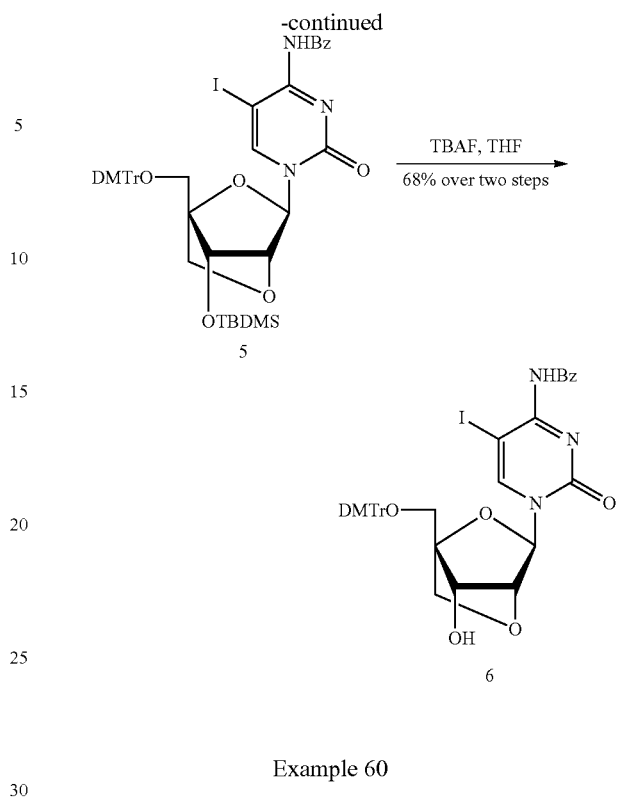

Example 60

Synthesis of 5-iodo-5'-ODMTr-3'-OTBDMS LNA uridine (2)

To a solution of Nucleoside 1 (3.2 g, 4.67 mmol), $I_2$ (3.5 g, 14.0 mmol) and N-methylimidazole (1.2 mL, 14.0 mmol) in dry DCM (50 mL) was added a TBDMS-Cl (1M in DCM, 5.6 mL, 5.6 mmol). Reaction mixture was stirred for 4 h whereupon it was diluted with DCM (100 mL) aq. sat. solution of sodium thiosulfate (100 mL). Phases were separated out and the organic layer was washed with aq. sat. solution of sodium thiosulfate (2×200 mL). The combined aq. phase was back extracted with DCM (100 mL). The combined organic phase was dried over $Na_2SO_4$ and evaporated to afford crude which was purified by column chromatography (0-40% Ethylacetate in Pet ether) to afford nucleoside 2 (3.3 g, 90%) as slight yellow solid. $R_f$=0.5 (40% Ethylacetate in Pet ether). $^1$H NMR (DMSO-$d_6$) δ 11.74 (s, 1H, ex, NH), 8.04 (s, 1H, H6), 7.42-7.44 (m, 2H, Ar), 7.28-7.34 (m, 6H, Ar), 7.22-7.24 (m, 1H, Ar), 6.89 (d, 4H, J=8.5 Hz, Ar), 5.47 (s, 1H, H1'), 4.26 (s, 2H, H2', H3'), 3.72-3.73 (m, 7H, 2×OCH$_3$, H5"), 3.66 (d, 1H, J=8.0 Hz, H5"), 3.33-3.36 (d, 1H, J=11.0 Hz, H5'), 3.21-3.23 (d, 1H, J=11.0 Hz, H5'), 0.71 (s, 9H, 3×CH$_3$), 0.03 (s, 3H, CH$_3$), −0.03 (s, 3H, CH$_3$); $^{13}$C NMR (DMSO-$d_6$) δ 160.7, 158.1, 158.0, 149.7, 144.5, 143.0 (C6), 135.19, 135.17, 129.6 (Ar), 129.5 (Ar), 127.9 (Ar), 127.4 (Ar), 126.6 (Ar), 113.27 (Ar), 113.24 (Ar), 87.5, 87.1 (C1'), 85.5, 78.4 (C2'), 71.5 (C5"), 70.4 (C3'), 69.0, 58.4 (C5'), 54.9 (OCH$_3$), 25.3 (CH$_3$), 17.3 (C), −4.8 (CH$_3$), −5.4 (CH$_3$).

Example 61

Synthesis of 5-iodo-5'-ODMTr-3'-OTBDMS LNA cytidine (4)

To a stirred cold suspension of 1,24-triazole (4.65 g, 67.27 mmol), in acetonitrile (25 mL) was added POCl$_3$ (1.5 mL, 60 mmol). The mixture was stirred for 15 minutes, whereupon triethyamine (11.0 mL, 79.20 mmol) was added, after stirring for another 30 minutes, a solution of nucleoside 2 (1.6 g, 2 mmol) in acetonitrile was added. The reaction mixture was stirred for 3 h whereupon solvents were removed under reduced pressure and the resulting residue was taken up in ethylacetate (100 mL) and water (100 mL). The phases were separated out, organic phase was washed with NaHCO$_3$ (2×100 mL) and the combined aq. phase was back extracted with ethylacetate (100 mL). The combined organic phase was dried over Na$_2$SO$_4$ and evaporated to dryness to afford 3 which was directly dissolved in methanolic ammonia (150 mL) and the resulting solution was stirred for overnight at room temperature whereupon solvents were removed and the resulting residue was purified by column chromatography (0-2% MeOH in DCM) to afford 4 (1.15 g 72%) as slight yellow solid material. R$_f$=0.4 (2% MeOH in DCM); $^1$H NMR (DMSO-d$_6$) δ 8.06 (s, 1H, H6), 7.90 (s, 1H, ex, NH), 7.43-7.45 (m, 2H, Ar), 7.28-7.35 (m, 6H, Ar), 7.22-7.25 (m, 1H, Ar), 6.89 (dd, 4H, J=9.0 Hz, 1.0 Hz, Ar), 6.67 (s, 1H, ex, NH), 5.47 (s, 1H, H1'), 4.25 (s, 1H, H2'), 4.20 (s, 1H, H2'), 3.72-3.73 (m, 7H, 2×OCH$_3$, H5"), 3.64-3.66 (d, 1H, J=8.0 Hz, H5"), 3.34-3.37 (d, 1H, J=11.0 Hz, H5'), 3.18-3.20 (d, 1H, J=11.0 Hz, H5'), 0.71 (s, 9H, 3×CH$_3$), 0.04 (s, 3H, CH$_3$), −0.06 (s, 3H, CH$_3$); $^{13}$C NMR (DMSO-d$_6$) δ 164.0, 158.1, 153.4, 145.3, 144.5, 135.26, 135.21, 129.6, 129.5, 127.9, 127.5, 126.6, 113.28, 113.25, 87.4, 87.3, 85.6, 78.5, 71.4, 70.2, 58.5, 56.6, 54.9 (OCH$_3$), 25.3 (CH3), 17.3, −4.9 (CH$_3$), −5.3 (CH$_3$).

Example 62

Synthesis of 6

To a solution of nucleoside 4 (1.5 g, 1.91 mmol) in anhydrous DMF (7 mL) was added benzoic anhydride (0.65 g, 2.88 mmol). The resultin reaction mixture was stirred at rt for 24 h, whereupon solvents were removed at reduced pressure and the resulting residue was taken up in ethylacetate (100 mL) and washed with NaHCO$_3$ (2×100 mL) and brine (100 mL). The ethylacetate layer was dried over Na$_2$SO$_4$ and evaporated under reduced pressure to afford crude which was purified by column chromatography (0-1% MeOH in DCM) to afford nucleoside 5 which was directly dissolved in THF (5 mL). To this solution was added tetrabutylammonium fluoride (TBAF, 1M solution in THF, 2.2 mL, 2.2 mmol). The resulting reaction mixture was stirred at rt for 3 h whereupon it was diluted with EtOAc (100 mL) and washed with NaHCO$_3$ (100 mL) and brine (100 mL). The ethylacetate layer was dried over Na$_2$SO$_4$ and evaporated under reduced pressure to afford crude which was purified by column chromatography (0-2% MeOH in DCM) to afford nucleoside 6. $^1$H-NMR: (500 MHz, DMSO-d$_6$) δ 12.98 (s, 1H), 8.32 (s, 1H), 8.6-8.2 (m, 2H), 7.63-7.46 (m, 5H), 7.41-7.26 (m, 10H), 6.95-6.92 (d, 4H), 5.79 (d, 1H), 5.52 (s, 1H), 4.32 (s, 1H), 4.14-4.13 (d, 1H), 3.80 (s, 2H), 3.77-3.74 (s, 6H), 3.43 (d, 1H), 3.35-3.32 (d, 1H).

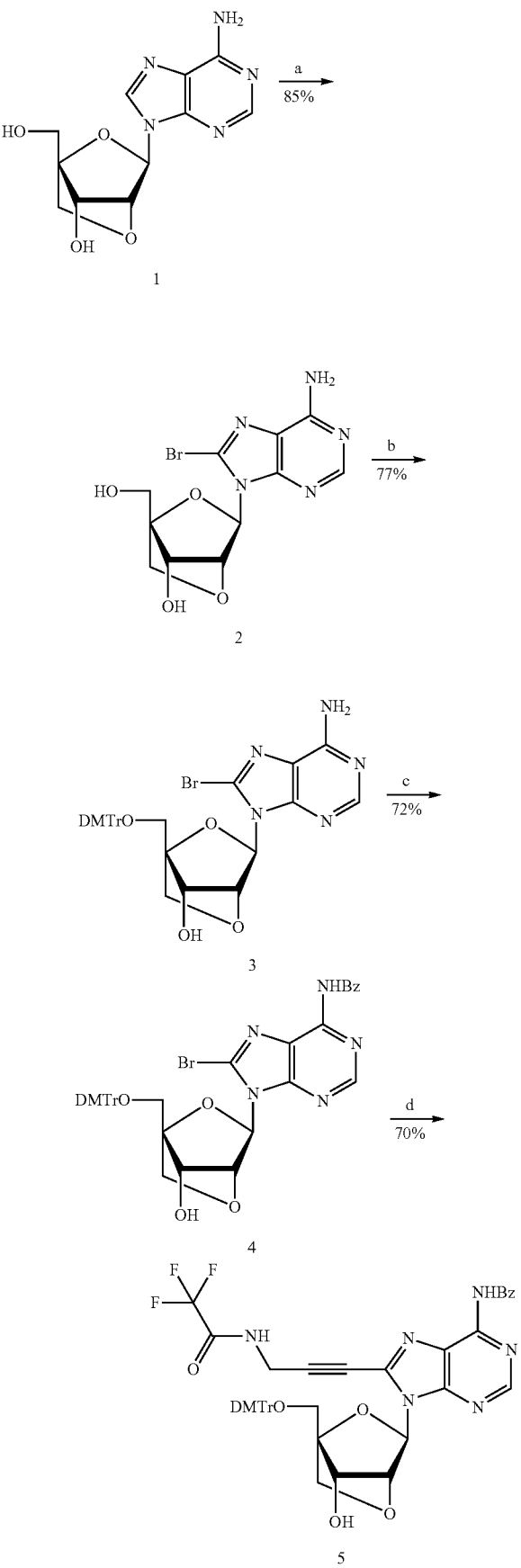

Example 63

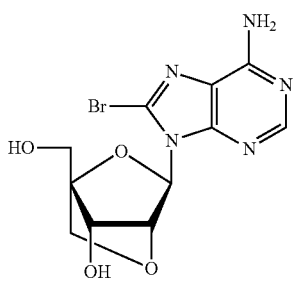 [SMILES: Nc1ncnc2c1nc(Br)n2[C@@H]1O[C@@]2(CO)COC1[C@H]2O]

8-Bromo LNA-A

A solution of known diol 1 (1.13 gm, 4.05 mmol) in dioxane:sodium acetate buffer (0.5 M, 23.2 ml), (pH=4.5) was obtained on gentle heating. To this was added a solution of $Br_2$ (0.28 ml, 5.07 mmol), in dioxane dropwise at rt. The reaction mixture was allowed to stir overnight, whereupon excess of $Br_2$ was decolorized using $Na_2S_2O_3$ and carefully neutralized to pH 7.0 using aq. solution of NaOH (0.5N). The content was reduced to half and allowed to stand overnight at +5.0° C. The solid obtained was filtered and washed with cold $H_2O$: dioxane mixture (1:1 v/v) to obtain 85% of C-8 bromo LNA 2 as a slightly pale yellow solid. Physical data for compound 2: $R_f$=0.5 (10% MeOH in $CH_2Cl_2$, v/v); $^1$H-NMR (500 MHz, DMSO-$d_6$) δ 8.12 (s, 1H, H2), 7.43 (bs, ex, 2H, $NH_2$), 5.76 (s, 1H, H-1'), 5.73-5.74 (d, ex, 1H, T=4.5 Hz, 3'-OH), 4.95 (t, ex, J=6.0 Hz, 1H, 5'-OH), 4.83 (s, 1H, H-2'), 4.68-4.69 (d, 1H, J=4.0 Hz H-3'), 3.96-3.97 (d, 1H, J=8.0 Hz, H-5"), 3.78-3.76 (d, 1H, J=8.0 Hz, H-5"), 3.72 (d, 2H, T=6.0 Hz 2×H-5'); $^{13}$C NMR (125 MHz, DMSO-$d_6$) δ 154.9 (C), 152.4 (C2), 149.9 (C), 126.4 (C), 119.0 (C), 88.4 (C), 87.5 (C1'), 79.4 (C2'), 71.9 (C3'), 71.5 (C5'), 57.1 (C5").

Example 64

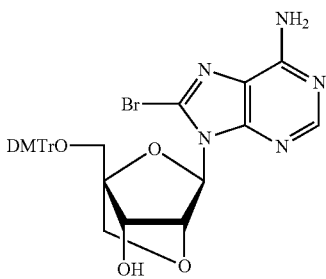

8-Bromo-(4,4'-dimethoxytrityl)LNA-A

Nucleoside 1 (0.5 g, 1.4 mmol), was co evaporated with anhydrous pyridine (10 ml) and redissolved in anhydrous pyridine (15 mL). To this solution of nucleic acid DMAP (10 mg, mmol), and DMTr-Cl (0.62 g, 1.81 mmol) were added under Ar, and the mixture was stirred at rt for 6 h. The reaction mixture was quenched with methanol and evaporated to obtain crude which was partitioned between $CH_2Cl_2$ and aq. $NaHCO_3$ solution. The organic phase was washed with aq. $NaHCO_3$ and the aqueous layer was back extracted with $CH_2Cl_2$. Combined organic layers were dried and concentrated. The residue was purified by silica gel chromatography (0-5% MeOH/$CHCl_3$) to obtain 77% of the pure product. Physical data of compound 3: $R_f$=0.5 (5% MeOH in $CH_2Cl_2$, v/v); MALDI-HRMS m/z 682.1277 ([M+Na]$^+$, C, Calcd 682.1277); $^1$H-NMR (500 MHz, DMSO-$d_6$) 8.11 (s, 1H, H2), 7.426 (bs, ex, 2H, $NH_2$), 7.33-7.35 (d, J=7.5 Hz, 2H, Ar), 7.19-7.27 (m, 7H, Ar), 6.83-6.85 (m, 4H, Ar), 5.85 (s, 1H, H-1'), 5.74-5.78 (d, ex, 1H, J=5.0 Hz, 3'-OH), 5.05 (s, 1H, H-2'), 4.64-4.63 (d, 1H, J=5.0 Hz, H-3'), 4.02-4.00 (d, 1H, J=8.0 Hz, H-5"), 3.98-4.02 (d, 1H, J=8.0 Hz, H-5") 3.73-3.72 (d, 6H, J=2.0 Hz, $OCH_3$) 3.33-3.30 (d, 1H, J=11.0 Hz, H-5'), 3.23-3.21 (d, 1H, J=11.0 Hz, H-5'); $^{13}$C-NMR (125 MHz, DMSO-$d_6$) δ 158.0 (C), 154.9 (C), 152.5 (C2), 149.8 (C), 135.4, 135.3 (C), 129.6-126.5 (Ar), 118.9 (C), 113.1 (C), 87.1 (Cl'), 86.6 (C), 85.2 (C), 78.8 (C2'), 72.7 (C3'), 72.0 (C5"), 60.1 (C5'), 55.0 (—$OCH_3$)

Example 65

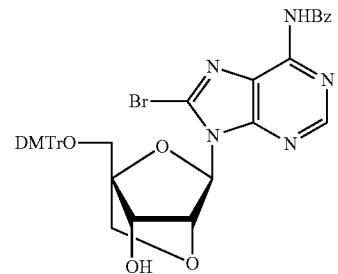

6-N-Benzoyl,
8-Bromo-(4,4'-dimethoxytrityl)LNA-A

To a solution of 5'-O DMT-protected nucleoside 3 (1.0 mmol), dried two times with pyridine and suspended in 5 mL of pyridine was added trimethylchlorosilane (3.0 mmol). After 30 min, (5.0 mmol) of benzoyl chloride was added and the reaction mixture was stirred at rt for 5 h. The mixture was then cooled to 0° C. and treated with water. After stirring for 15 min, 29% aq. NH3 (7 mL) was added and the suspension was stirred at rt for 30 min. The mixture was evaporated to obtain crude which was dissolved in DCM and washed with 5% aq.NaHCO3 (twice). The organic layer was evaporated to dryness and the residue was purified using silica gel chromatography (0-3% MeOH/DCM) to obtain 72% of the pure product. Physical data of compound 3: $R_f$=0.5 (3% MeOH in $CH_2Cl_2$, v/v) $^1$H-NMR: (500 MHz, DMSO-$d_6$) δ 11.26 (s, 1H), 8.71 (s, 1H), 8.06-8.03 (d, 2H), 7.59-7.56 (d, 2H), 7.35-7.21 (m, 8H), 6.87-6.85 (m, 4H), 5.94 (s, 1H), 5.88-5.87 (d, 1H), 5.17 (s, 1H), 4.64-4.62 (d, 1H), 4.07-4.04 (dd, 2H), 3.73 (s, 6H), 3.39 (d, 1H), 3.26 (d, 1H).

Example 66

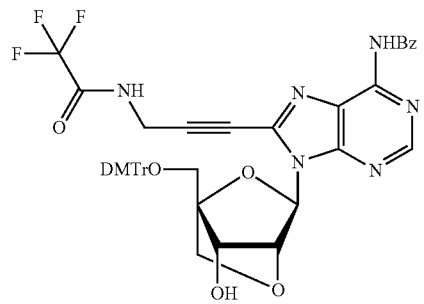

6-N-benzoyl,8-[3-(trifluoroacetylamino)-1-propynyl]-5'-O-(4,4'-dimethoxytrityl)-LNA-A (5)

Nucleoside 4 (0.37 g, 0.5 mmol), in CuI (20 mg, 0.1 mmol), Pd(PPh$_3$)$_4$ (60 mg, 0.05 mmol), 2,2,2-trifluoro-N-(2-propynyl)acetimide (100 mg, 1.0 mmol) were added to DMF (8.0 mL) and the resulting mixture was degassed and placed under argon. To this was added Et$_3$N (0.3 mL) and the reaction mixture was stirred at 50° C. for 12 h whereupon solvents were evaporated off. The resulting residue was taken up in ethyl actetate (15 mL) and subsequently washed with brine and sat. aq.NaHCO$_3$. The organic phase was dried (Na$_2$SO$_4$), evaporated to dryness and the resulting residue was purified by silica gel chromatography (0-5% MeOH—CH$_2$Cl$_2$) to obtain 70% of the pure product. Physical data of compound: R$_f$=0.5 (2% MeOH in CH$_2$Cl$_2$, v/v); $^1$H-NMR (500 MHz, DMSO-d$_6$) δ 8.70 (s, 1H, H-2), 8.01-7.99 (d, 2H, Ar), 7.65-7.52 (m, 4H, —NH, Ar), 7.36-7.18 (m, 9H, Ar), 6.85-6.82 (m, 4H, Ar), 6.10 (s, 1H, H-1'), 5.86-5.85 (m, 1H, 3'-OH), 5.28 (s, 1H, H-2'), 4.85 (d, 1H, H-3'), 4.81 (d, 1H, H-5"), 4.5 (d, 1H, H-5"), 4.05-4.02 (m, 2H, CH2), 3.71-3.70 (d, 6H, 2-OCH$_3$), 3.46-3.44 (d, 1H, H-5'), 3.29-3.26 (d, 1H, H-5'); $^{13}$C-NMR (125 MHz, DMSO-d$_6$) δ 151.2, 132.3, 129.6, 129.5, 128.4, 127.7, 127.5, 126.6, 126.5, 113.1, 86.6, 78.8, 72.1, 72.0, 59.9, 54.9, 25.8; $^{19}$F NMR (282.4 MHz, DMSO-d6) δ −65.16, −65.23.

Example 67

Thermal Affinity of Oligonucleotides Modified with C5-Functionalized Pyrimidine LNA Monomers Toward Complementary Single Stranded DNA/RNA Targets and Mismatched Single Stranded DNA/RNA Targets General Experimental Procedures for Thermal Denaturation Studies:

This example concerns the thermal affinity of oligonucleotides modified with C5-functionalized LNA or C5-functionalized α-L-LNA monomers toward complementary single stranded DNA/RNA targets and mismatched single stranded DNA/RNA targets.

Concentrations of ONs were estimated using the following extinctions coefficients for DNA (OD/µmol): G (12.01), A (15.20), T (8.40), C (7.05); for RNA (OD/µmol): G (13.70), A (15.40), U (10.00), C (9.00); ONs (1.0 µmol of each strand) were thoroughly mixed, denatured by heating and subsequently cooled to the starting temperature of the experiment. Quartz optical cells with a pathlength of 1.0 cm were used. Thermal denaturation temperatures [T$_m$-values/° C.; Mergny, J. L.; Lacroix, *Oligonucleotides* 13:515-537 (2003)] were measured on a Cary 100 UV/VIS spectrophotometer equipped with a 12-cell Peltier temperature controller and determined as the maximum of the first derivative of the thermal denaturation curve (A$_{260}$ versus temperature) recorded in medium salt buffer (T$_m$-buffer: 100 mM NaCl, 0.1 mM EDTA, and pH 7.0 adjusted with 10 mM Na$_2$HPO$_4$/5 mM Na$_2$HPO$_4$). The temperature of the denaturation experiments ranged from at least 15° C. below T$_m$ to 20° C. above T$_m$ (although not below 1° C.). A temperature ramp of 0.5° C./min was used in all experiments. Reported thermal denaturation temperatures are an average of two experiments within ±1.0° C.

Example 68

Thermal Affinity of Oligonucleotides Modified with C5-Functionalized LNA TFOs Toward Double Stranded DNA Targets General Experimental Procedure for Thermal Denaturation Studies:

Concentrations of all TFOs were determined using the extinction coefficient of 118500 L×(mol×cm)-1. 1 mL solution containing 1.0 nmol of each strand was denatured by heating and subsequently cooled to the starting temperature of the experiment in quartz optical cells with a path-length of 1.0 cm. Thermal denaturation profiles were recorded on a Cary 100 UV/VIS spectrophotometer equipped with a 12-cell Peltier temperature controller using a ramp of 0.5° C./min. Thermal denaturation temperatures (Tm) for triplex to duplex transitions were determined as the first derivative of difference thermal denaturation profiles (dA260 vs. T), which were obtained by subtracting the thermal denaturation profile of the dsDNA target (always included as one of the samples in multicell holder of UV-Vis spectrophotometer) from the raw thermal denaturation profile of the TFO+dsDNA (FIG. 13). Reported Tm-values are an average of at least two experiments within ±1.0° C.

General Experimental Procedure for Association Kinetics Studies:

Association rate constants (kon) for triplex formation were determined by fitting second order rate equations to the absorption (A260) decay profile upon association of TFOs with dsDNA target (FIG. 16). Profiles were recorded at 20° C. in pH 7.2 HEPES buffer (50 mM HEPES, 150 mM NaCl, 10 mM MgCl$_2$, 10% sucrose, 1 mg/mL spermine tetra-HCl). 0.5 nmol preannealed dsDNA target duplex in 100 µL buffer was mixed with 0.5 nmol TFO in 400 µL buffer (both dsDNA and TFOs were equilibrated at 20° C. before mixing).

General Experimental Procedure for 3'-Exonuclease Studies:

SVPDE (snake venom phosphordiesterase) was purchased from Worthington Biochemical Corporation. The change in absorbance at 260 nm as a function of time was monitored for 2 nmol of TFO in 500 µL Tris buffer (50 mM Tris.HCl, 10 mM MgC12, pH 9.0) at 37° C., to which SVPDE dissolved in H2O was added (0.43 µg in 10 µL).

Example 69

Detection of Complementary Single Stranded DNA/RNA Targets and/or Optical Discrimination of Mismatched Single Stranded DNA/RNA Targets Using Changes in Fluorescence Signal Output and C5-Functionalized LNA and/or C5-Functionalized α-L-LNA Compounds General Experimental Procedure for Thermal Denaturation Studies:

Concentrations of unmodified ONs were estimated using the following extinctions coefficients for DNA (OD/µmol): G (12.01), A (15.20), T (8.40), C (7.05); for RNA (OD/µmol): G (13.70), A (15.40), U (10.00), C (9.00). Concentrations of modified ONs (ON5-ON16) were determined by titration with complementary DNA; a progressive increase in steady-state fluorescence emission intensity was observed until a plateau was reached, at which point a 1:1 stoichiometry was assumed. This approach was crossvalidated by comparison with conventional methods for concentration determination of pyrene-functionalized ONs which assume an ε$_{260}$ of 22.4 OD/µmol for the pyrene moiety.[10b] The two methods gave concentration determinations within ±10%. ONs (1.0 μmol of each strand) were thoroughly mixed, denatured by heating and subsequently cooled to the starting temperature of the experiment. Quartz optical cells with a pathlength of 1.0 cm were used. Thermal denaturation temperatures ($T_m$ values [° C.]) were measured on a Cary 100 UV/VIS spectrophotometer equipped with 12-cell Peltier temperature controller and determined as the maximum of the first derivative of the thermal denaturation curve ($A_{260}$ vs. T) recorded in medium salt buffer ($T_m$ buffer: 110 mM NaCl, 0.1 mM EDTA, pH adjusted with 10 mM $Na_2HPO_4/NaH_2PO_4$). The temperature of the denaturation experiments ranged from at least 15° C. below $T_m$ to 20° C. above $T_m$ (although not below 1° C.). A temperature ramp of 0.5° C./min was used in all experiments. Reported thermal denaturation temperatures are an average of at least two experiments within ±1.0° C.

General Procedure for Fluorescence Studies:

Steady state fluorescence emission spectra were recorded using a Cary Eclipse fluorimeter using the same buffers and ON concentrations as in thermal denaturation studies. Fluorescence emission spectra of single stranded probes (SSP) and corresponding duplexes with complementary or mismatched targets were measured at 5° C. to ensure maximal hybridization. Deoxygenation was deliberately not applied to the samples since the scope of the work was to determine fluorescence under aerated condition prevailing in bioassays. Solutions were heated to 80° C. over 10 min, cooled to 5° C. over 15 min, and equilibrated at this temperature for more than 5 min. Steady state fluorescence emission spectra (360-600 nm range) were obtained as an average of five scans using an excitation wavelength of 344 nm, excitation slit 5.0 nm, emission slit 5.0 nm and a scan speed of 600 nm/min. The fluorescence quantum yield $\Phi_F$ of pyrenebutanoic acid (PBA) in MeOH in this experimental setting was measured to be 0.069 relative to 9,10-diphenylanthracene in cyclohexene ($\Phi_F$=0.95),[17] which is in excellent agreement with the reported value of 0.065[18]. Emission quantum yields $\Phi_F$ (ON) of single stranded ON9-ON12 and the corresponding duplexes with DNA/RNA targets were determined according to: $\Phi_F(ON)=\Phi_F(PBA)\times[A(ON)/A_{344}(ON)]\times[1/\alpha(PBA)]\times[n(H_2O)^2/n(MeOH)^2]$ where $\phi_F(PBA)$ is the cross-calibrated value for the fluorescence quantum yield of PBA in MeOH, A(ON) is the area of the fluorescence emission spectrum of the sample from 360 to 600 nm, $A_{344}$ (ON) is the absorbance of the sample at the excitation wavelength (344 nm), a (PBA) is the slope of the fluorescence emission vs. $A_{344}$ (ON) calibration curve for PBA and $n(H_2O)$ and n(MeOH) are the refractive indexes of water (1.3328) and methanol (1.3288), respectively. The reported quantum yields are an average of at least two measurements within ±10%, although low quantum yields ($\Phi_F$<10%) may be associated with considerably larger error.

Fluorescence excitation spectra were recorded using the same buffer and concentrations as for the thermal denaturation studies at T=5° C. 402 nm was used as the emission wavelength and excitation intensity was scanned from 300 to 400 nm.

Fluorescence Studies:

Concentrations of ONs were estimated using the following extinctions coefficients for DNA (OD/μmol): G (12.01), A (15.20), T (8.40), C (7.05); for RNA (OD/μmol): G (13.70), A (15.40), U (10.00), C (9.00). ONs (1.0 μmol of each strand) were thoroughly mixed, denatured by heating and subsequently cooled to the starting temperature of the experiment. Steady-state fluorescence emission spectra were recorded in medium salt buffer ($T_m$-buffer: 100 mM NaCl, 0.1 mM EDTA, and pH 7.0 adjusted with 10 mM $Na_2HPO_4$/5 mM $Na_2HPO_4$) at 5° C. on a Varian, Cary Eclipse Fluorescence spectrophotometer in the range 360-600 nm (for C5-pyrene-functionalized LNA/α-L-LNA derivatives) and in the range of 460-660 nm (for C5-perylene-functionalized LNA/α-L-LNA derivatives), using a quartz cell with a 1 cm path length nitrogen atmosphere. All measurements were carried out at medium salt concentration at pH 7 and 1.0 μM ON concentration at 5° C.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a formula

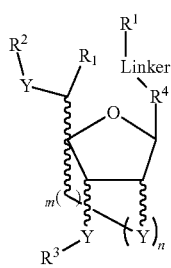

or a pharmaceutically acceptable salt, a hydrate, a solvate, or combinations thereof, where:

$R^1$ is selected from aliphatic, heteroaliphatic, aryl, heteroaryl, charged moieties, or metal complexes;

$R^2$ is selected from hydrogen, aliphatic, heteroaliphatic, aryl, heteroaryl, functional group protecting groups, oligonucleotides, a phosphorous-containing compound, a sulfur-containing compound, a nitrogen-containing compound, an oxygen-containing compound, a metal-containing compound, or a selenium-containing compound;

$R^3$ is selected from hydrogen, oligonucleotides, a phosphorous-containing compound, a sulfur-containing compound, a nitrogen-containing compound, an oxygen-containing compound, a metal-containing compound, or a selenium-containing compound;

$R^4$ is selected from

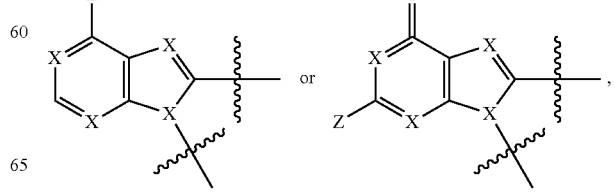

wherein each X is independently nitrogen, carbon, or any combination thereof; Y is selected from oxygen, sulfur, or $N(R^5)$ where $R^5$ is selected from hydrogen, aliphatic, aryl, heteroaliphatic, or heteroaryl; Z is selected from ether, thioether, hydroxyl, sulfhydryl or $N(R^5)_2$ where each $R^5$ is independently selected from hydrogen, aliphatic, aryl, heteroaliphatic, heteroaryl, or any combination thereof;

linker is selected from aliphatic, aryl, heteroaliphatic, or heteroaryl;

each Y is independently selected from oxygen, sulfur, or $NR^5$ where $R^5$ is selected from hydrogen, aliphatic, aryl, heteroaliphatic, or heteroaryl, or any combination thereof; and m+n=2 to 4.

2. The compound according to claim 1 having a formula selected from

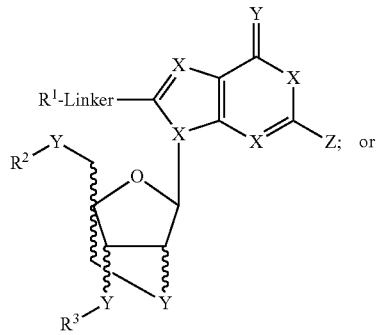

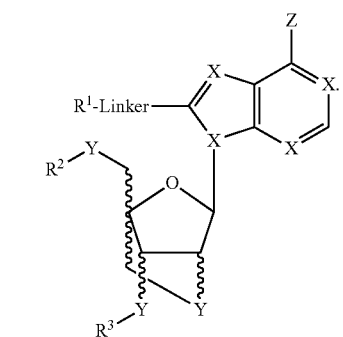

3. The compound according to claim 1 having a formula selected from

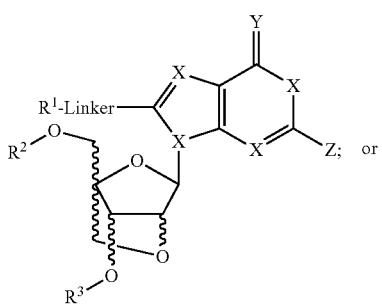

4. The compound according to claim 1 having a formula selected from

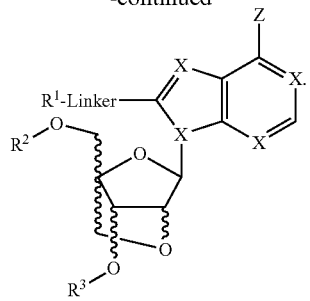

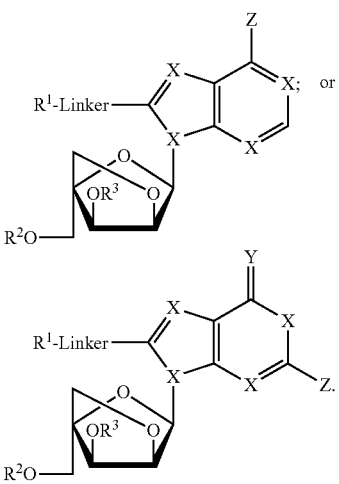

5. The compound according to claim 1 having a formula selected from

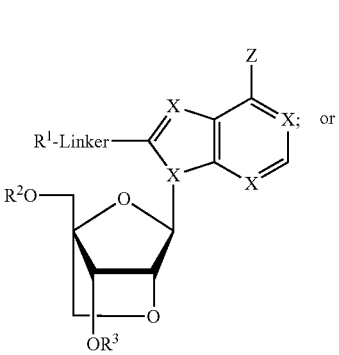

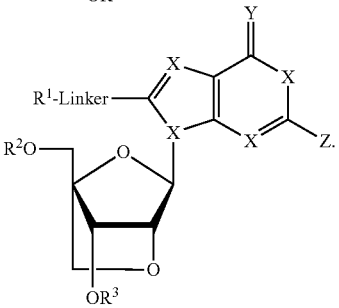

6. The compound according to claim 1 where $R^1$ is selected from ether, carbonyl, nitrile, disulfide, thioether, amine, amino acid, aminoglycoside, carbohydrate, fluorophores, nucleosides, nucleotides, oligonucleotides, peptides, intercalators, lipidoids, porphyrins, proteins, or vitamins.

7. The compound according to claim 1 where $R^2$ is selected from carbonyl, sulfonyl, benzyl, benzoyl, or alkyl.

8. The compound according to claim 1 where $R^2$ is selected from hydrogen, 4,4'-dimethoxytrityl, trityl, or 9-arylthioxanthenyl.

9. The compound according to claim 1 wherein each of $R^2$ and $R^3$ independently is

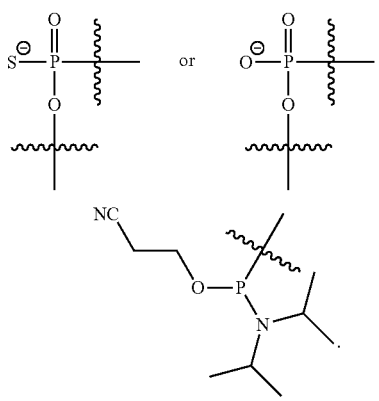

10. The compound according to claim 1 having an $R^1$-linker moiety selected from

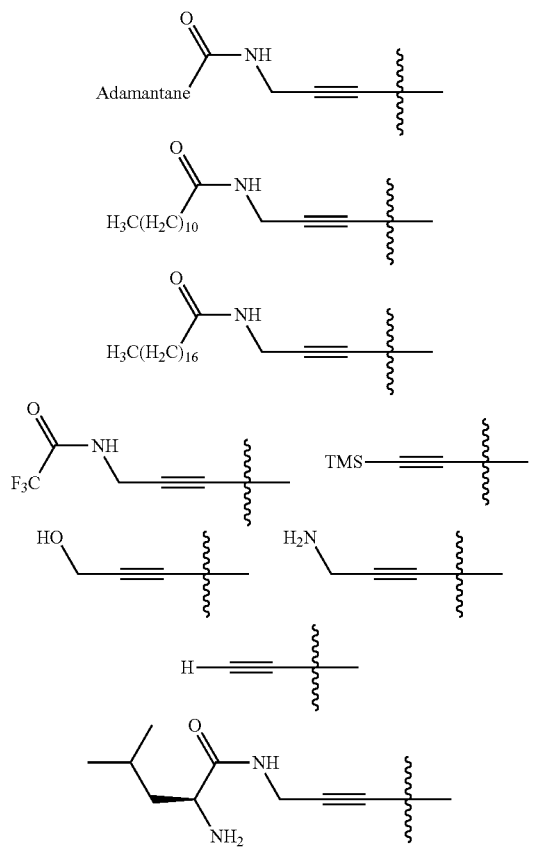

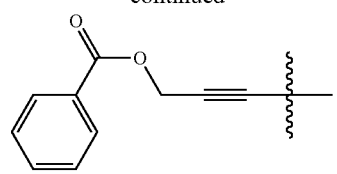

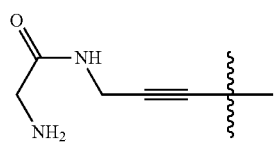

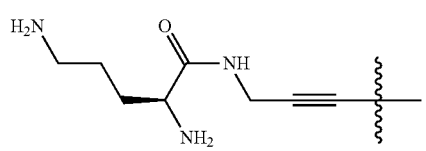

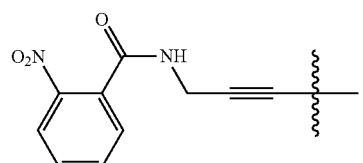

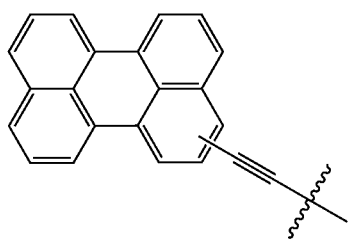

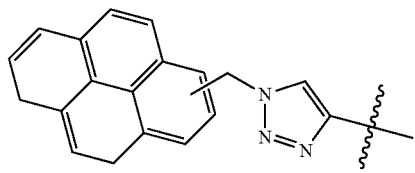

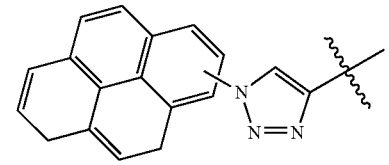

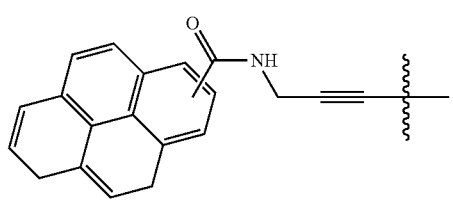

-continued

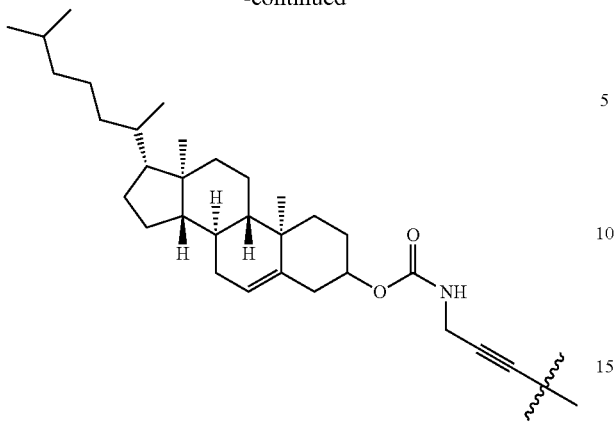

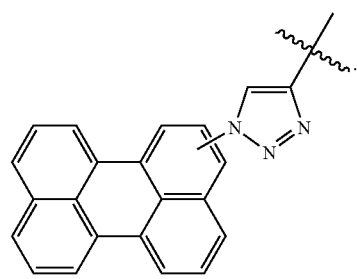

11. The compound according to claim 1 wherein the compound is selected from 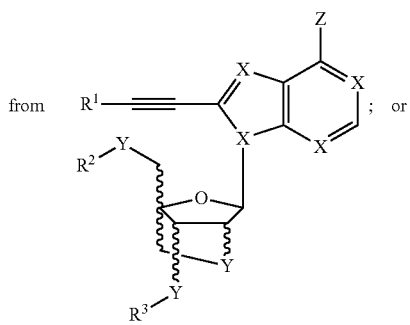

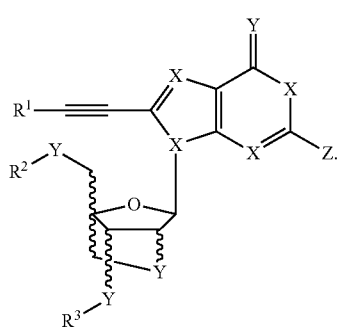

12. The compound according to claim 1 wherein the compound is selected from

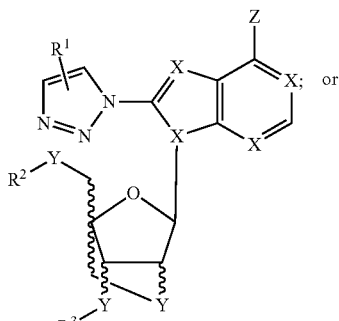

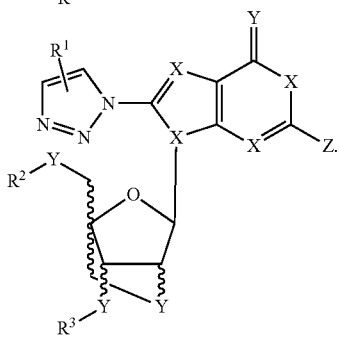

13. The compound according to claim 1 where the compound is

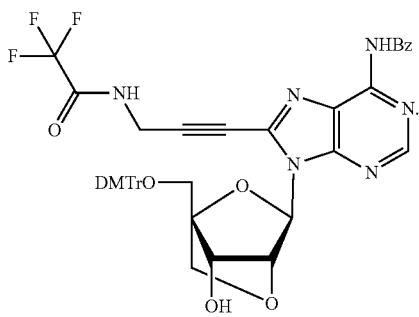

14. A probe on a solid support, the probe comprising at least one compound having a formula according to claim 1.

15. The probe according to claim 14 wherein the probe is configured to detect a target in a nucleic acid.

16. A method for detecting a target in a nucleic acid, comprising:
  providing a compound having a formula according to claim 1; and
  contacting the nucleic acid with the compound in a manner effective to detect the target.

17. The method according to claim 16 wherein the target is selected from HER2, EGFR gene, MET gene, CMYC gene, IGF1R, D5S271, KRAS, TYMS, lipoprotein lipase gene, RB1, p53, N-MYC, CHOP, FUS, FKHR, ALK, Ig heavy chain, CCND1, BCL2, BCL6, AP1, TOP2A, TMPRSS2, ERG, ETV1, EWS, FLI1, PAX3, PAX7, PTEN, AKT2, MYCL1, REL, or CSF1R.

18. The method according to claim 16 for detecting a single nucleotide polymorphism.

19. The method according to claim 16 wherein contacting comprises modifying the nucleic acid with the compound, thereby increasing thermal affinity of the nucleic acid by greater than 0° C. to about 15° C. compared to the thermal affinity of an unmodified nucleic acid.

20. A kit for isolating, purifying, amplifying, detecting, identifying or quantifying a nucleic acid, comprising at least one compound according to claim 1.

* * * * *